(12) United States Patent
Ma et al.

(10) Patent No.: US 10,985,324 B2
(45) Date of Patent: Apr. 20, 2021

(54) NITROGEN-CONTAINING COMPOUND, ORGANIC ELECTROLUMINESCENT DEVICE AND PHOTOELECTRIC CONVERSION DEVICE

(71) Applicant: Shaanxi Lighte Optoelectronics Material Co., Ltd., Shaanxi (CN)

(72) Inventors: Tiantian Ma, Xi'an (CN); Qiqi Nie, Xi'an (CN); Hongyan Li, Xi'an (CN); Zhen Feng, Xi'an (CN); Zhanyi Sun, Xianyang (CN); Yalong Wang, Xi'an (CN); Xunshan Sha, Xi'an (CN)

(73) Assignee: Shaanxi Lighte Optoelectronics Material Co., Ltd., Shaanxi (CN)

( * ) Notice: Subject to any disclaimer, the term of this patent is extended or adjusted under 35 U.S.C. 154(b) by 0 days.

(21) Appl. No.: 16/872,748

(22) Filed: May 12, 2020

(65) Prior Publication Data

US 2020/0395544 A1 Dec. 17, 2020

(30) Foreign Application Priority Data

| Jun. 14, 2019 | (CN) | 201910515733.1 |
| Aug. 15, 2019 | (CN) | 201910755507.0 |
| Aug. 19, 2019 | (CN) | 201910765403.8 |

(51) Int. Cl.
*C07C 211/54* (2006.01)
*C07C 211/61* (2006.01)
(Continued)

(52) U.S. Cl.
CPC .......... *H01L 51/006* (2013.01); *C07C 211/54* (2013.01); *C07C 211/61* (2013.01);
(Continued)

(58) Field of Classification Search
CPC .... C07C 211/54; C07C 211/61; H01L 51/006
See application file for complete search history.

(56) References Cited

FOREIGN PATENT DOCUMENTS

| CN | 103108859 A | 5/2013 |
| CN | 104583176 A | 4/2015 |

(Continued)

OTHER PUBLICATIONS

Machine-generated English-language translation of CN107459466A to Lee et al. (Year: 2017).*

(Continued)

*Primary Examiner* — Vu A Nguyen
(74) *Attorney, Agent, or Firm* — Qinghong Xu

(57) ABSTRACT

A nitrogen-containing compound, an organic electroluminescent device, and a photoelectric conversion device are provided, which relates to the technical field of electronic components. The nitrogen-containing compound has a structure represented by Chemical Formula 1. The organic electroluminescent device using the nitrogen-containing compound and the photoelectric conversion device using the nitrogen-containing compound can be improved.

Chemical Formula 1

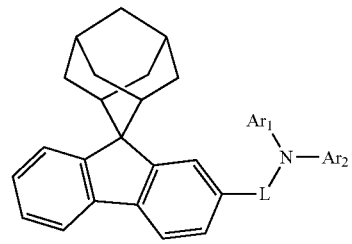

14 Claims, 1 Drawing Sheet

(51) Int. Cl.
  H01L 51/00    (2006.01)
  H01L 51/50    (2006.01)
  H01L 51/42    (2006.01)
  C07D 307/91   (2006.01)
  C07D 209/86   (2006.01)
  C07D 333/76   (2006.01)

(52) U.S. Cl.
  CPC ........ *C07D 209/86* (2013.01); *C07D 307/91* (2013.01); *C07D 333/76* (2013.01); *H01L 51/0061* (2013.01); *C07C 2603/18* (2017.05); *C07C 2603/97* (2017.05); *H01L 51/0056* (2013.01); *H01L 51/0072* (2013.01); *H01L 51/0073* (2013.01); *H01L 51/0074* (2013.01); *H01L 51/42* (2013.01); *H01L 51/5064* (2013.01); *H01L 51/5088* (2013.01)

(56) References Cited

FOREIGN PATENT DOCUMENTS

| | | |
|---|---|---|
| CN | 106008424 A | 10/2016 |
| CN | 10745466 A | 12/2017 |
| CN | 107459466 A | 12/2017 |
| CN | 109438350 A | 3/2019 |
| CN | 110128279 A | 8/2019 |
| CN | 110467536 A | 11/2019 |
| KR | 20190035567 A | 4/2019 |
| KR | 20190118515 A | 10/2019 |
| KR | 102020037732 A | 4/2020 |
| KR | 1020200037732 A | 4/2020 |
| WO | 2020050023 A1 | 3/2020 |
| WO | 2020050623 A1 | 3/2020 |
| WO | 2020060271 A1 | 3/2020 |
| WO | 2020080849 A1 | 4/2020 |

OTHER PUBLICATIONS

SciFinder Search (Year: 2020).*
Search Report for corresponding PCT App. No. PCT/CN2020/094957; dated Aug. 14, 2020.
Written Opinion for corresponding PCT App. No. PCT/CN2020/094957; dated Aug. 14, 2020.
First Office Action for corresponding JP Pat. App. No. 2020-101272; dated Oct. 6, 2020.
International Search Report regarding related PCT App. No. PCT/CN2020/089879; dated Jun. 14, 2019.
First Office Action regarding related CN Application No. 201910765403.8; dated Dec. 31, 2019.
Chen, Ching-Hsin; Shen, Wen-Jian, Jakka, Kavitha, Shu, Ching-Fong; Synthesis and characterization of spiro (adamantane-2,9-fluorene)-based triaryldiamines: thermally stable hole-transporting materials; Department of Applied Chemistry, National Chiao Tung University, accepted Dec. 4, 2003; Synthetic Metals 143 (2004) 215-220.

* cited by examiner

NITROGEN-CONTAINING COMPOUND, ORGANIC ELECTROLUMINESCENT DEVICE AND PHOTOELECTRIC CONVERSION DEVICE

CROSS-REFERENCE TO RELATED APPLICATIONS

The present disclosure claims the priorities of Chinese Patent Application No. 201910515733.1 filed on Jun. 14, 2019, Chinese Patent Application No. 201910755507.0 filed on Aug. 15, 2019 and Chinese Patent Application No. 201910765403.8 filed on Aug. 19, 2019, the entireties of which are herein incorporated by reference.

TECHNICAL FIELD

The present disclosure relates to the technical field of electronic components, and in particular relates to a nitrogen-containing compound, an organic electroluminescent device using the nitrogen-containing compound, and a photoelectric conversion device using the nitrogen-containing compound.

BACKGROUND

With the development of electronic technology and the progress of material science, the application range of electronic components for realizing electroluminescence or photoelectric conversion becomes more and more extensive. Such electronic components generally include a cathode and an anode disposed opposite to each other, and a functional layer disposed between the cathode and the anode. The functional layer is composed of multiple organic or inorganic film layers and generally includes an energy conversion layer, a hole transport layer between the energy conversion layer and the anode, and an electron transport layer between the energy conversion layer and the cathode.

Taking an organic electroluminescent device as an example, the organic electroluminescent device generally includes an anode, a hole transport layer, an electroluminescent layer as an energy conversion layer, an electron transport layer and a cathode, which are sequentially stacked. When voltage is applied to the anode and the cathode, an electric field is generated between the two electrodes, electrons on the cathode side move to the electroluminescent layer and holes on the anode side also move to the luminescent layer under the action of the electric field, the electrons and the holes are combined in the electroluminescent layer to form excitons, and the excitons are in an excited state and release energy outwards, so that the electroluminescent layer emits light outwards.

In the prior art, KR1020190035567A, CN107459466A, CN106008424A, CN104583176A, CN103108859A and the like disclose materials that can be used to prepare hole transport layers in organic electroluminescent devices. However, there is still a need to develop new materials to further improve the performance of electronic components.

SUMMARY

The purpose of the present disclosure is to provide a nitrogen-containing compound, an organic electroluminescent device using the nitrogen-containing compound, and a photoelectric conversion device using the nitrogen-containing compound, the nitrogen-containing compound is used to improve the performance of the organic electroluminescent device and the photoelectric conversion device.

In order to achieve the purpose, the technical solutions adopted by the present disclosure are as follows:

According to a first aspect of the present disclosure, there is provided a nitrogen-containing compound having a structure represented by Chemical Formula 1:

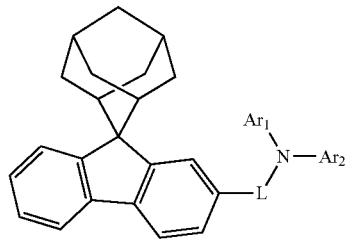

Chemical Formula 1 wherein L is selected from a single bond, a substituted or unsubstituted C6 to C30 arylene group, and a substituted or unsubstituted C1 to C30 heteroarylene group;

$Ar_1$ and $Ar_2$ are each independently selected from a substituted or unsubstituted C1 to C35 alkyl group, a substituted or unsubstituted C2 to C35 alkenyl group, a substituted or unsubstituted C2 to C35 alkynyl group, a substituted or unsubstituted C3 to C35 cycloalkyl group, a substituted or unsubstituted C2 to C35 heterocycloalkyl group, a substituted or unsubstituted C7 to C30 aralkyl group, a substituted or unsubstituted C2 to C30 heteroaralkyl group, a substituted or unsubstituted C6 to C30 aryl group, and a substituted or unsubstituted C1 to C30 heteroaryl group;

the substituents of $Ar_1$, $Ar_2$ and L are each independently selected from deuterium, a cyano group, a nitro group, a halogen, a hydroxyl group, a substituted or unsubstituted C1 to C40 alkyl group, a substituted or unsubstituted C3 to C40 cycloalkyl group, a substituted or unsubstituted C2 to C40 alkenyl group, a substituted or unsubstituted C2 to C40 alkynyl group, a substituted or unsubstituted C2 to C40 heterocycloalkyl group, a substituted or unsubstituted C7 to C40 aralkyl group, a substituted or unsubstituted C2 to C40 heteroaralkyl group, a substituted or unsubstituted C6 to C40 aryl group, a substituted or unsubstituted C1 to C40 heteroaryl group, a substituted or unsubstituted C1 to C40 alkoxy group, a substituted or unsubstituted C1 to C40 alkylamino group, a substituted or unsubstituted C6 to C40 arylamino group, a substituted or unsubstituted C1 to C40 alkylthio group, a substituted or unsubstituted C7 to C40 aralkylamino group, a substituted or unsubstituted C1 to C24 heteroarylamino group, a substituted or unsubstituted C1 to C45 alkylsilyl group, a substituted or unsubstituted C6 to C50 arylsilyl group, a substituted or unsubstituted C6 to C30 aryloxy group, and a substituted or unsubstituted C6 to C30 arylthio group.

In the present disclosure, $Ar_1$ is not 9,9-diphenylfluorene, and $Ar_2$ is not 9,9-diphenylfluorene.

According to a second aspect of the present disclosure, there is provided an organic electroluminescent device including an anode and a cathode disposed opposite to each other, and a functional layer disposed between the anode and the cathode, and the functional layer includes the above nitrogen-containing compound.

According to a third aspect of the present disclosure, there is provided a photoelectric conversion device including an anode and a cathode disposed opposite to each other, and a functional layer disposed between the anode and the cathode, and the functional layer includes the above nitrogen-containing compound.

In the nitrogen-containing compound, the organic electroluminescent device using the nitrogen-containing compound and the photoelectric conversion device using the nitrogen-containing compound, the nitrogen-containing compound has good hole transport characteristics, and can be applied between the anode and the energy conversion layer of the organic electroluminescent device and the photoelectric conversion device to improve the hole transport efficiency between the anode and the energy conversion layer, so as to improve the luminous efficiency of the organic electroluminescent device and the power generation efficiency of the photoelectric conversion device. Because the nitrogen-containing compound also has higher electron tolerance and film-forming property, it can improve the efficiency and the service life of an organic electroluminescent device and a photoelectric conversion device. Moreover, the nitrogen-containing compound has better thermal stability, can keep stable structure at high temperature for a long time, not only ensures the uniform and stable performance of an organic electroluminescent device and a photoelectric conversion device prepared at different stages, but also ensures that the performance of an organic electroluminescent device and a photoelectric conversion device prepared at the later stage of mass production is not reduced.

BRIEF DESCRIPTION OF THE DRAWINGS

The above and other features and advantages of the present disclosure will become more apparent from the detailed description of the exemplary embodiments with reference to the following figures.

Figure 1:
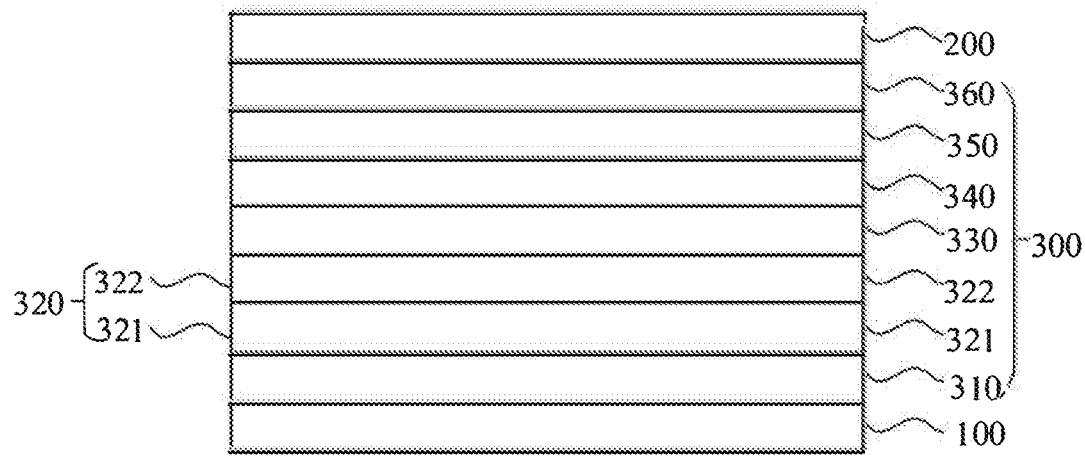
FIG. 1 is a schematic structural view of an organic electroluminescent device according to an embodiment of the present disclosure.

Reference numerals are illustrated as follows:
100, Anode;
200, Cathode;
300, Functional layer;
310, Hole injection layer;
320, Hole transport layer;
321, First hole transport layer;
322, Second hole transport layer;
330, Organic electroluminescent layer;
340, Hole blocking layer;
350, Electron transport layer;
360, Electron injection layer;
370, Photoelectric conversion layer.

DETAILED DESCRIPTION

Exemplary embodiments will now be described more fully with reference to the figures. Exemplary embodiments may, however, be embodied in many different forms and should not be construed as limited to the examples set forth herein; rather, these embodiments are provided so that this disclosure will be full and complete, and will fully convey the concept of exemplary embodiments to those skilled in the art. The described features, structures, or characteristics may be combined in any suitable manner in one or more embodiments. In the following description, numerous specific details are provided to give a full understanding of embodiments of the present disclosure.

In the figures, the thickness of regions and layers may be exaggerated for clarity. The same reference numerals denote the same or similar structures in the figures, and thus detailed descriptions thereof will be omitted.

The described features, structures, or characteristics may be combined in any suitable manner in one or more embodiments. In the following description, numerous specific details are provided to give a full understanding of embodiments of the present disclosure. Those skilled in the art will recognize, however, that the embodiments of the present disclosure can be practiced without one or more of the specific details, or with other methods, components, materials, and so forth. In other instances, well-known structures, materials, or operations are not shown or described in detail to avoid obscuring the primary technical ideas of the present disclosure.

The present disclosure provides a nitrogen-containing compound having a structure represented by Chemical Formula 1:

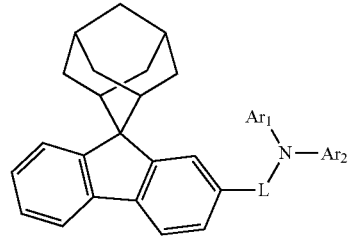

Chemical Formula 1 wherein L is selected from a single bond, a substituted or unsubstituted C6 to C30 arylene group, and a substituted or unsubstituted C1 to C30 heteroarylene group;

$Ar_1$ and $Ar_2$ are each independently selected from a substituted or unsubstituted C1 to C35 alkyl group, a substituted or unsubstituted C2 to C35 alkenyl group, a substituted or unsubstituted C2 to C35 alkynyl group, a substituted or unsubstituted C3 to C35 cycloalkyl group, a substituted or unsubstituted C2 to C35 heterocycloalkyl group, a substituted or unsubstituted C7 to C30 aralkyl group, a substituted or unsubstituted C2 to C30 heteroaralkyl group, a substituted or unsubstituted C6 to C30 aryl group, and a substituted or unsubstituted C1 to C30 heteroaryl group;

the substituents of $Ar_1$, $Ar_2$ and L are each independently selected from deuterium, a cyano group, a nitro group, a halogen, a hydroxyl group, a substituted or unsubstituted C1 to C40 alkyl group, a substituted or unsubstituted C3 to C40 cycloalkyl group, a substituted or unsubstituted C2 to C40 alkenyl group, a substituted or unsubstituted C2 to C40 alkynyl group, a substituted or unsubstituted C2 to C40 heterocycloalkyl group, a substituted or unsubstituted C7 to C40 aralkyl group, a substituted or unsubstituted C2 to C40 heteroaralkyl group, a substituted or unsubstituted C6 to C40 aryl group, a substituted or unsubstituted C1 to C40 heteroaryl group, a substituted or unsubstituted C1 to C40 alkoxy group, a substituted or unsubstituted C6 to C40 alkylamino group, a substituted or unsubstituted C1 to C40 arylamino group, a substituted or unsubstituted C7 to C40 alkylthio group, a substituted or unsubstituted C1 to C24 aralkylamino group, a substituted or unsubstituted C1 to C45 alkylsilyl group, a substituted or unsubstituted C6 to C50 arylsilyl group, a substituted or unsubstituted C6 to C30 aryloxy group, and a substituted or unsubstituted C6 to C30 arylthio group.

In the present disclosure, $Ar_1$ is not 9,9-diphenylfluorene, and $Ar_2$ is not 9,9-diphenylfluorene.

In the present disclosure, the number of carbon atoms of L, $Ar_1$ and $Ar_2$ means all the number of carbon atoms thereon. For Example, if L is a substituted arylene group of 12 carbon atoms, all of the carbon atoms of the arylene group and the substituents thereon are 12.

Alternatively, the unsubstituted C1 to C35 alkyl means a straight chain alkyl having 1 to 35 carbon atoms or a branched alkyl having 1 to 13 carbon atoms, such as methyl, ethyl, propyl, isobutyl, sec-butyl, pentyl, isopentyl, hexyl, tert-butyl and the like. The substituted C1 to C35 alkyl group means that at least one hydrogen atom is substituted with deuterium atom, F, Cl, I, CN, a hydroxyl group, a nitro group, an amino group, etc. In some embodiments, the alkyl is a C1 to C4 alkyl, such as methyl, ethyl, propyl, isobutyl, or tert-butyl.

Alternatively, the unsubstituted C2 to C35 alkenyl means an alkenyl having 2 to 35 carbon atoms, including a C2 to C35 straight-chain alkenyl having a carbon-carbon double bond, or a C1 to C13 branched-chain alkenyl, such as vinyl, propenyl, allyl, isopropenyl, 2-butenyl, etc. The substituted C2 to C35 alkenyl group means that at least one hydrogen atom is substituted with deuterium atom, F, Cl, I, CN, a hydroxyl group, a nitro group, an amino group, etc.

Alternatively, the unsubstituted C2 to C35 alkynyl means an alkynyl having 2 to 35 carbon atoms, including a C2 to C35 straight chain alkynyl having a triple carbon-carbon bond, or a C1 to C10 branched alkynyl having a triple carbon-carbon bond, such as ethynyl, 2-propynyl, etc. The substituted C2 to C35 alkynyl group means that at least one hydrogen atom is substituted with deuterium atom, F, Cl, I, CN, a hydroxyl group, a nitro group, an amino group, etc.

The nitrogen-containing compound disclosed by the present disclosure has good hole transport efficiency, and therefore can be applied as a hole transport material in organic electroluminescent devices and photoelectric conversion devices. For example, the nitrogen-containing compound of the present disclosure may be applied between an anode and an organic electroluminescent layer of an organic electroluminescent device so as to transport holes on the anode to the organic electroluminescent layer. Alternatively, the nitrogen-containing compound of the present disclosure may be applied to any one or more layers of a hole injection layer, a hole transport layer, and an electron blocking layer of an organic electroluminescent device. For another example, the nitrogen-containing compounds of the present disclosure may be applied between an anode and a photoelectric conversion layer of a photoelectric conversion device in order to transport holes on the photoelectric conversion layer to the anode.

In one embodiment of the present disclosure, the substituents of $Ar_1$, $Ar_2$, and L are each independently selected from deuterium, a cyano group, a nitro group, a halogen, a hydroxyl group, a substituted or unsubstituted C1 to C33 alkyl group, a substituted or unsubstituted C3 to C33 cycloalkyl group, a substituted or unsubstituted C2 to C33 alkenyl group, a substituted or unsubstituted C2 to C33 alkynyl group, a substituted or unsubstituted C2 to C33 heterocycloalkyl group, a substituted or unsubstituted C7 to C33 aralkyl group, a substituted or unsubstituted C2 to C33 heteroaralkyl group, a substituted or unsubstituted C6 to C33 aryl group, a substituted or unsubstituted C1 to C33 heteroaryl group, a substituted or unsubstituted C1 to C33 alkoxy group, a substituted or unsubstituted C1 to C33 alkylamino group, a substituted or unsubstituted C6 to C33 arylamino group, a substituted or unsubstituted C1 to C33 alkylthio group, a substituted or unsubstituted C7 to C33 aralkylamino group, a substituted or unsubstituted C1 to C33 heteroarylamino group, a substituted or unsubstituted C1 to C33 alkylsilyl group, a substituted or unsubstituted C6 to C33 arylsilyl group, a substituted or unsubstituted C6 to C33 aryloxy group, and a substituted or unsubstituted C6 to C33 arylthio group.

In one embodiment of the present disclosure, L is selected from a single bond, a substituted or unsubstituted phenylene group, a substituted or unsubstituted naphthylene group, a substituted or unsubstituted biphenylene group, a substituted or unsubstituted terphenylene group, and a substituted or unsubstituted fluorenylene group.

In one embodiment of the present disclosure, the nitrogen-containing compound has a relative molecular mass of not greater than 750, so as to ensure that the nitrogen-containing compound of the present disclosure has good thermal stability and to ensure that the nitrogen-containing compound of the present disclosure maintains stable structure during long-term evaporation.

In one embodiment of the present disclosure, L is selected from a single bond, a substituted or unsubstituted C6 to C12 arylene group. Alternatively, L is selected from a single bond or an unsubstituted C6 to C12 arylene group, so that the preparation difficulty and the preparation cost of the nitrogen-containing compound disclosed herein can be reduced, the cost performance of the nitrogen-containing compound disclosed herein when applied to electronic components on a large scale is improved, the cost of the electronic components is further reduced, and particularly, the cost of organic electroluminescent devices and photoelectric conversion devices is reduced.

In one embodiment of the present disclosure, L is selected from a single bond or the following substituents:

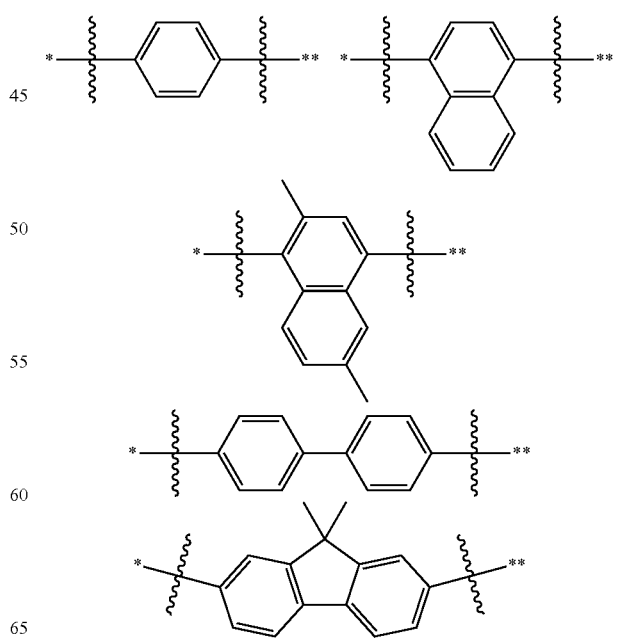

wherein,

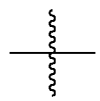

represents a chemical bond;

\* represents a binding site where the above substituent is connected to

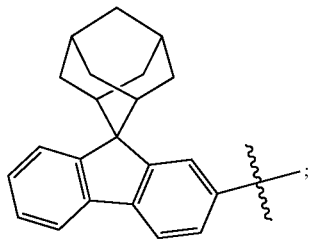 [SMILES: *c1ccc2c(c1)C1(c3ccccc3-2)C2CC3CC(C2)CC1C3]

\*\* represents a binding site where the above substituent is connected to

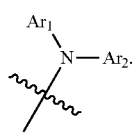

For Example, in the compound

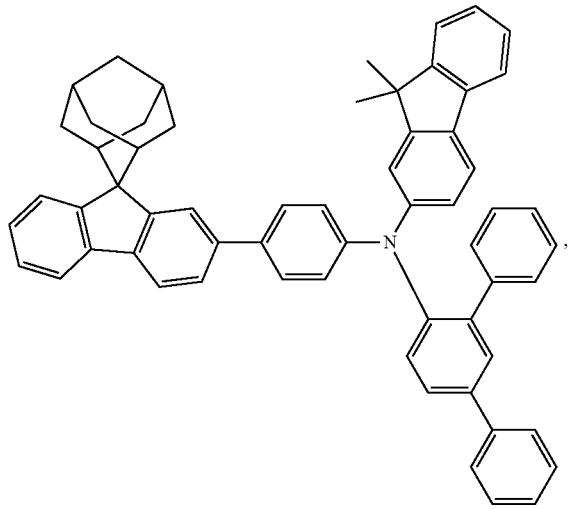 [SMILES: CC1(C)c2ccccc2-c2ccc(N(c3ccc(-c4ccc5c(c4)C4(c6ccccc6-5)C5CC6CC(C5)CC4C6)cc3)c3ccc(-c4ccccc4)cc3-c3ccccc3)cc21]

L is

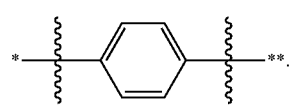

In one embodiment of the present disclosure, $Ar_1$ and $Ar_2$ are each independently selected from a substituted or unsubstituted C6 to C20 aryl group and a substituted or unsubstituted C12 to C20 heteroaryl group.

In one embodiment of the present disclosure, $Ar_1$ and $Ar_2$ are each independently selected from a substituted or unsubstituted C6 to C25 aryl group, and $Ar_1$ is not 9,9-diphenylfluorene and $Ar_2$ is not 9,9-diphenylfluorene.

In one embodiment of the present disclosure, at least one of $Ar_1$ and $Ar_2$ is selected from a substituted aryl group having 6 to 12 ring-forming carbon atoms, and the substituent on the substituted aryl group having 6 to 12 ring-forming carbon atoms is selected from an C6 to C14 aryl group and a C6 to C12 heteroaryl group. For Example, $Ar_1$ is

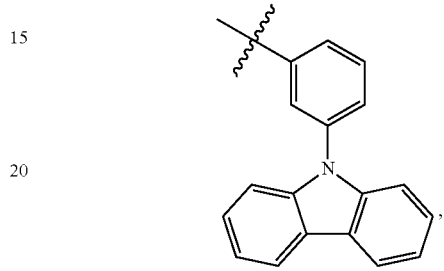

then $Ar_1$ is a substituted aryl group having 6 ring-forming carbon atoms, and the substituent of the substituted aryl group having 6 ring-forming carbon atoms is a C12 heteroaryl group.

In one embodiment of the present disclosure, $Ar_1$ and $Ar_2$ are each independently selected from the following substituents:

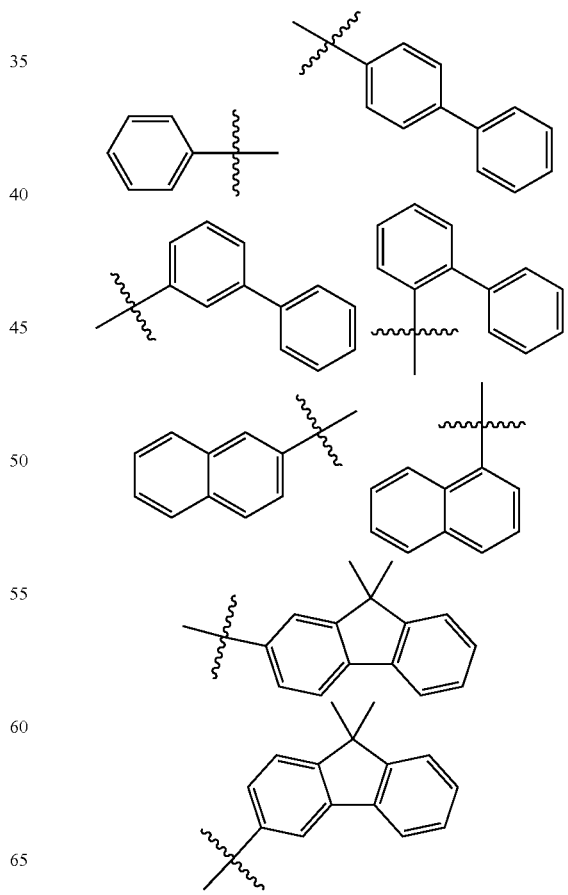

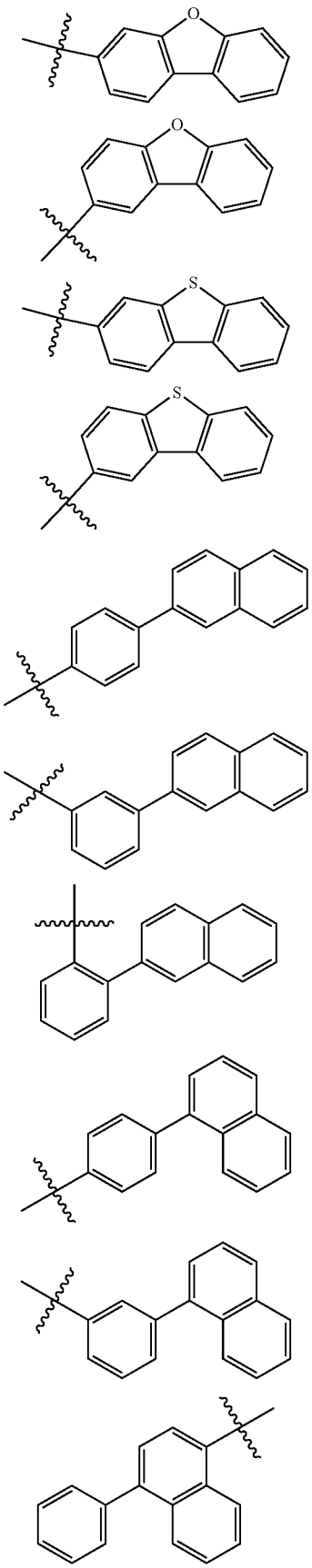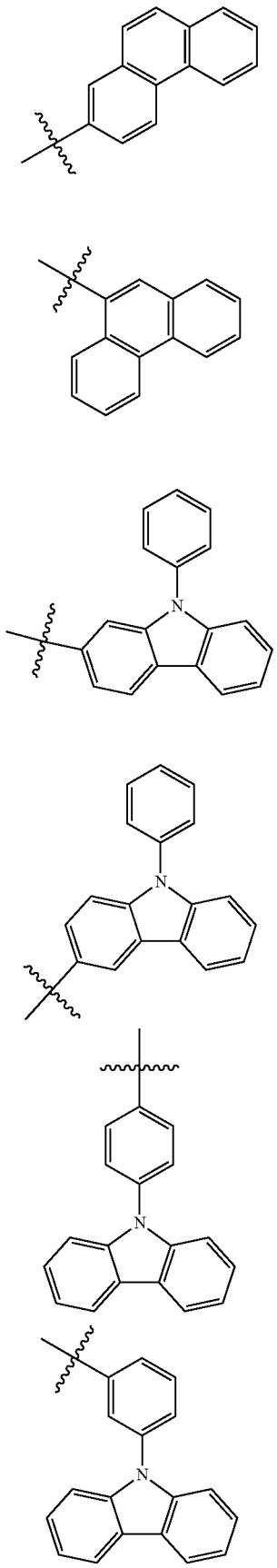

-continued

-continued

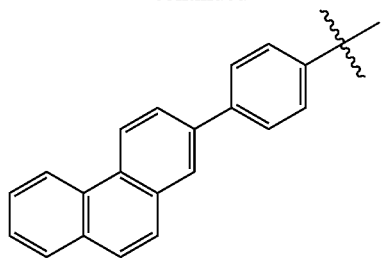

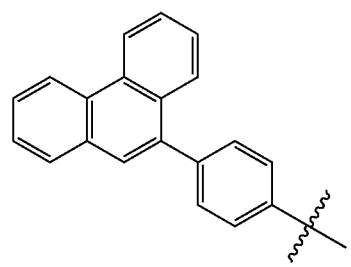

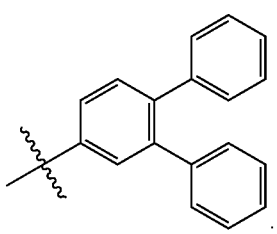

In one embodiment of the present disclosure, $Ar_1$ and $Ar_2$ are each independently selected from the following substituent:

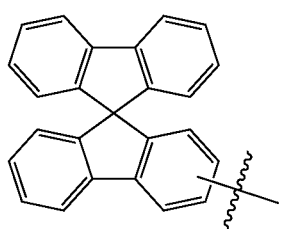

In one embodiment of the present disclosure, $Ar_1$ and $Ar_2$ are each independently selected from the following substituents:

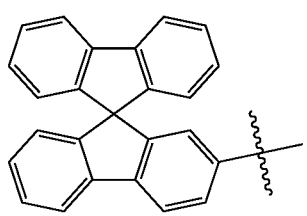

-continued

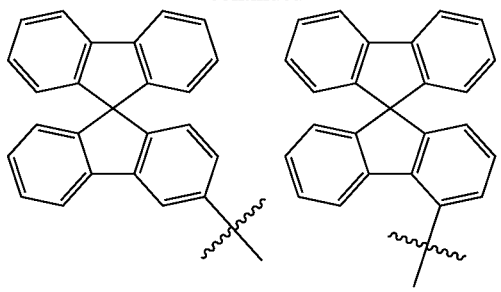

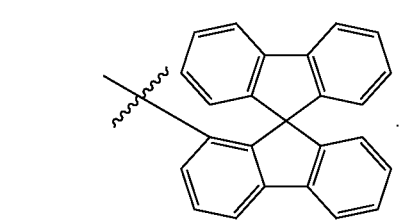

In one embodiment of the present disclosure, the nitrogen-containing compound is selected from the following compounds:

Compound 1

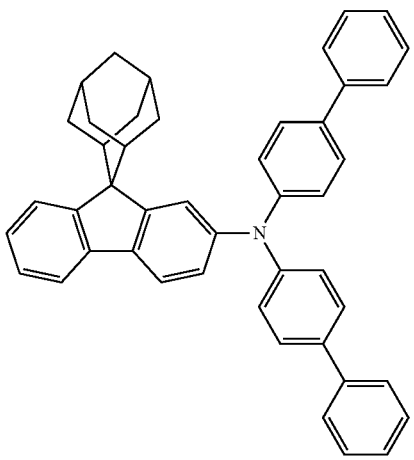

Compound 2

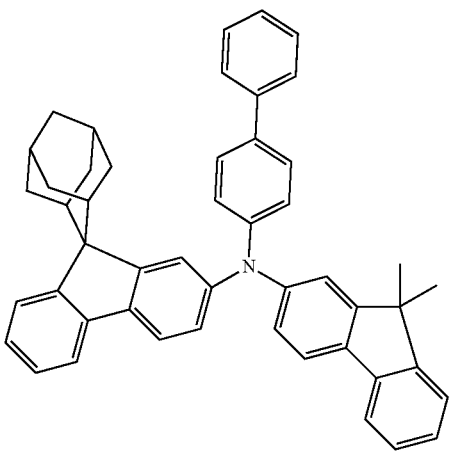

Compound 3
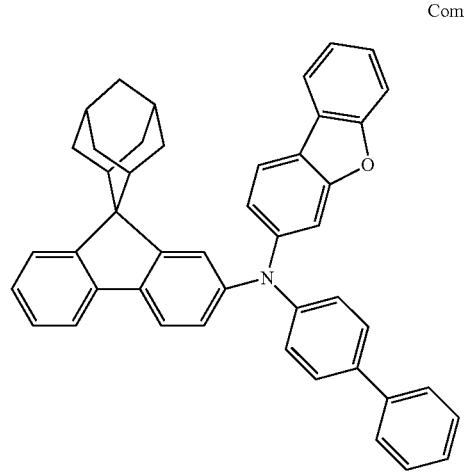
Compound 4
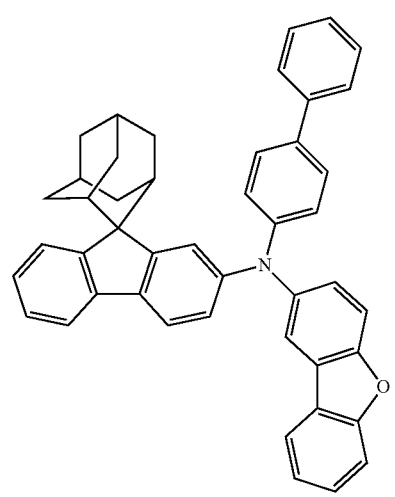
Compound 5
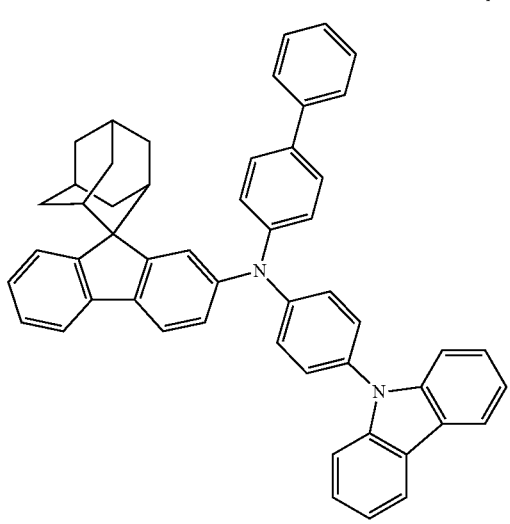
Compound 6
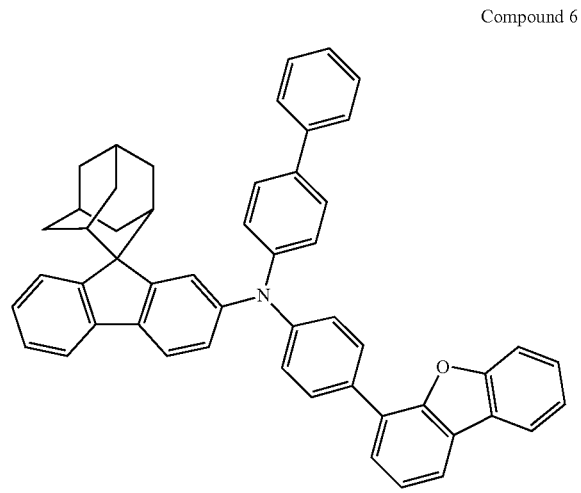
Compound 7
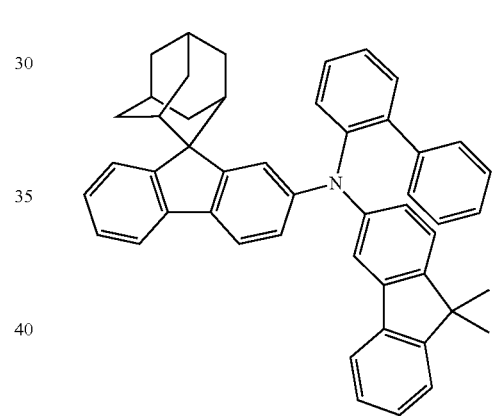
Compound 8
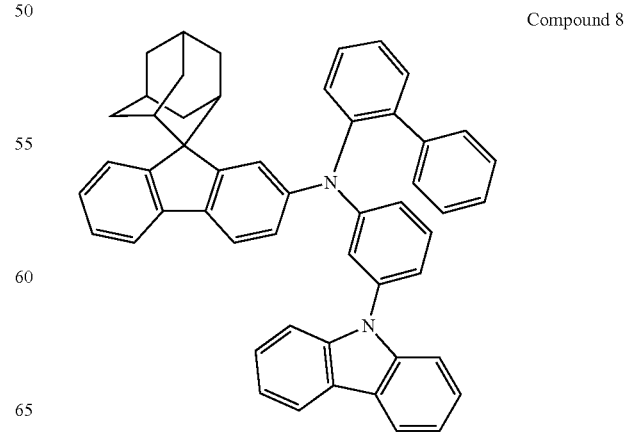

-continued
Compound 9
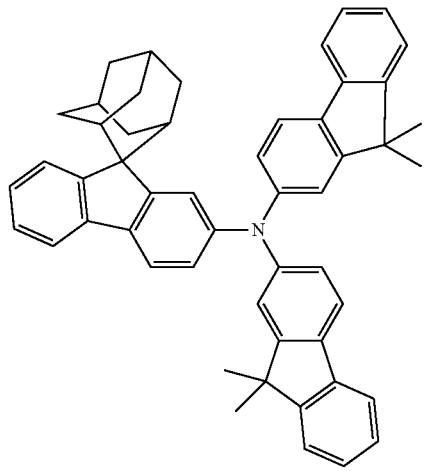
Compound 10
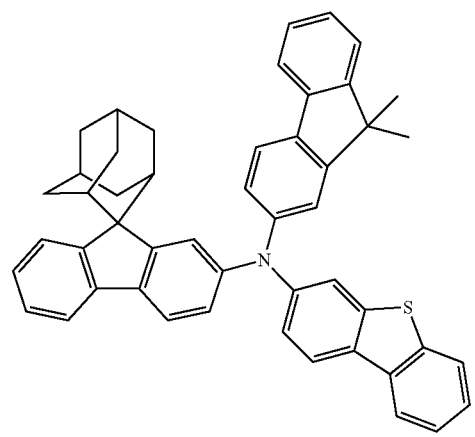
Compound 11
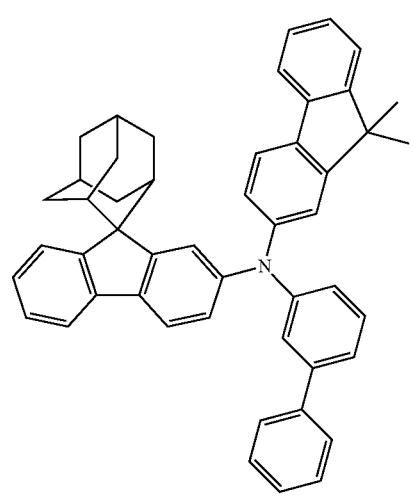
-continued
Compound 12
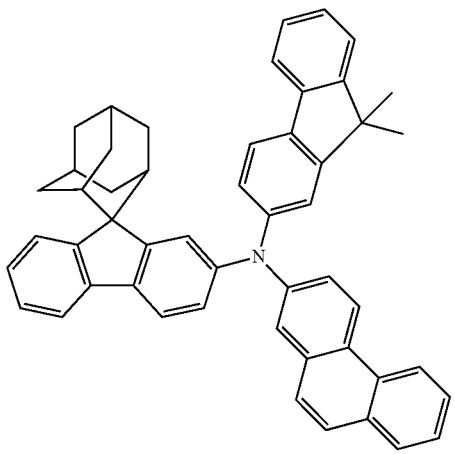
Compound 13
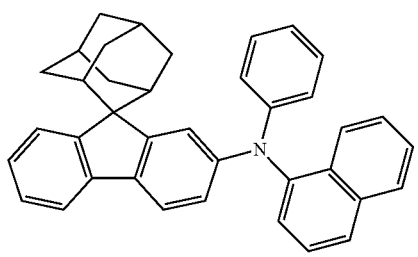
Compound 14
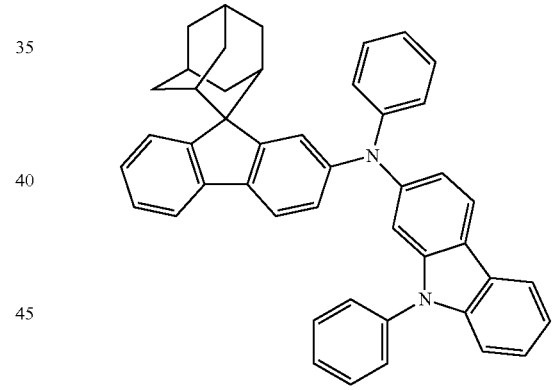
Compound 15
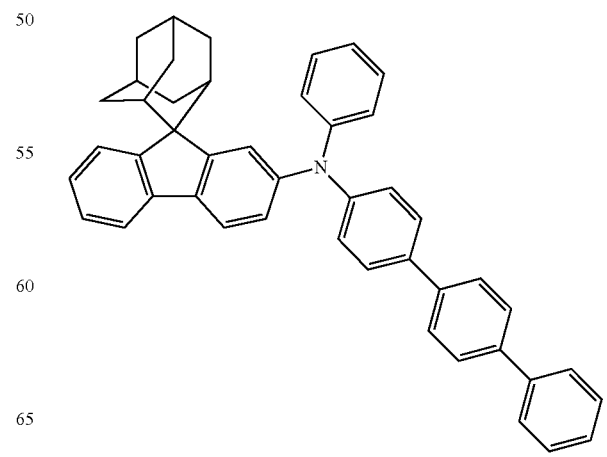

Compound 16
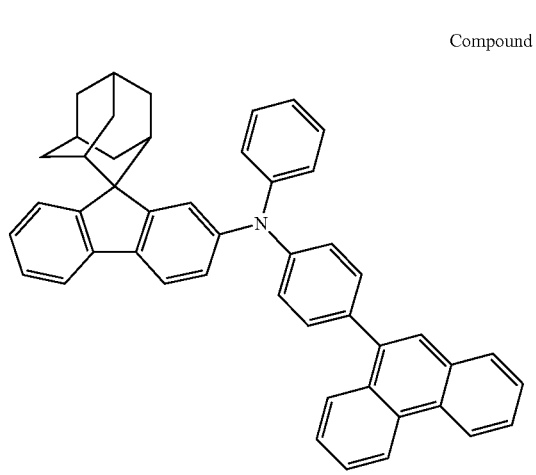
Compound 17
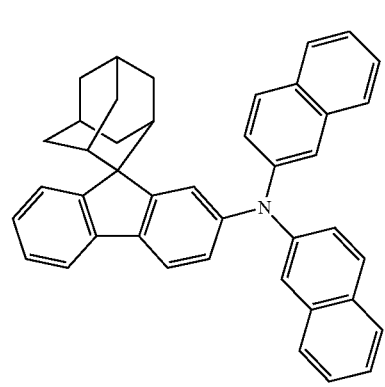
Compound 18
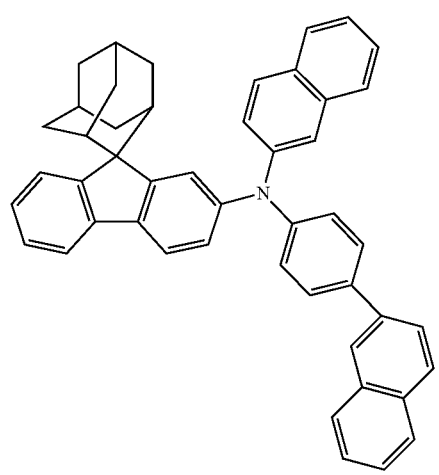
Compound 19
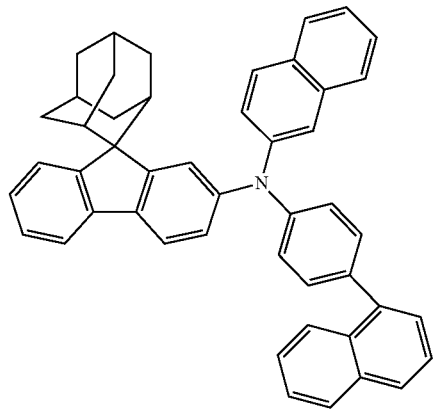
Compound 20
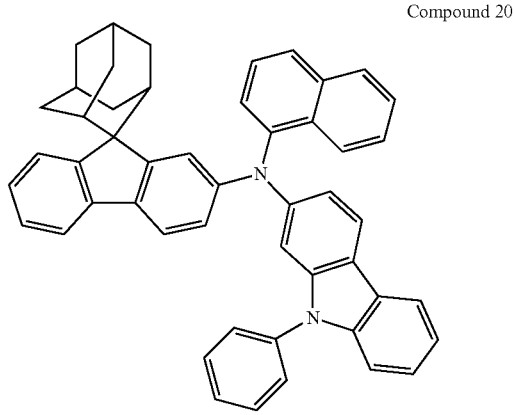
Compound 21
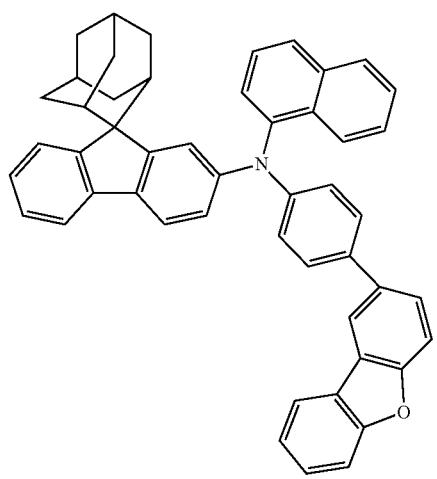

Compound 22
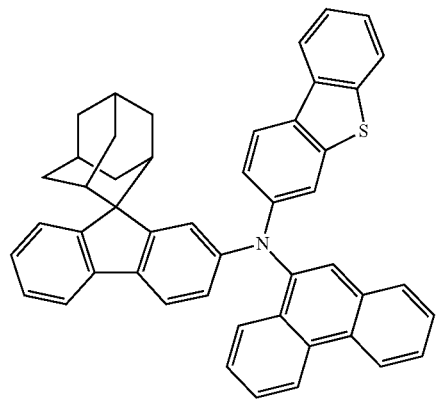
Compound 23
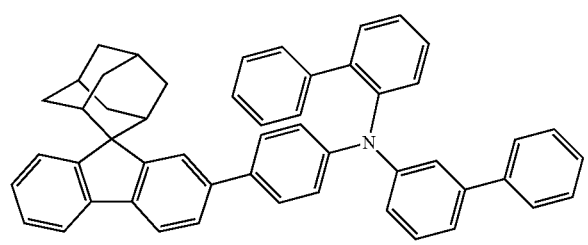
Compound 25
Compound 26
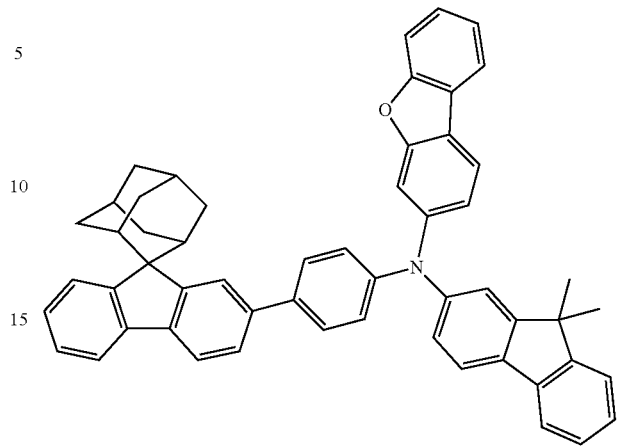
Compound 27
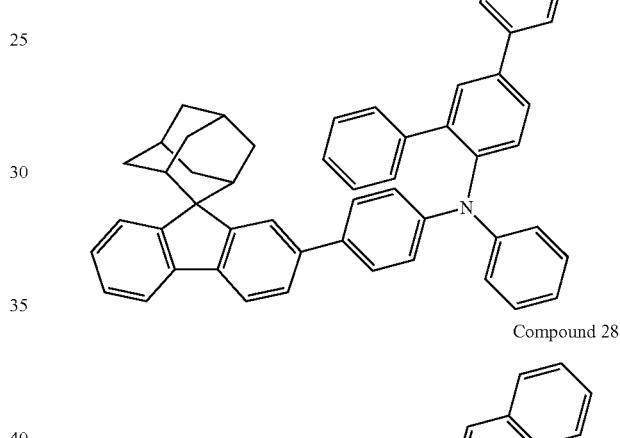
Compound 28
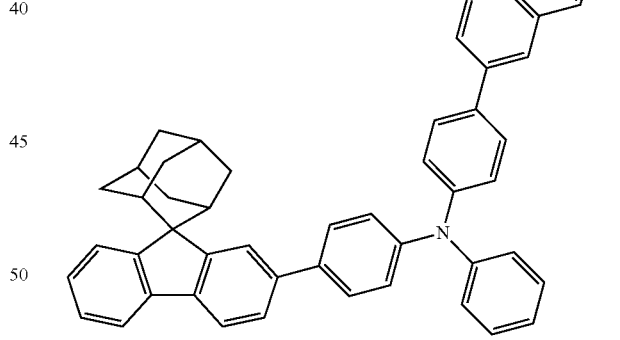
Compound 29
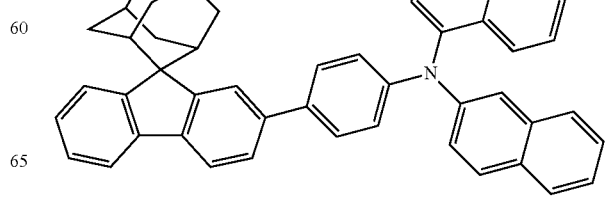

Compound 30
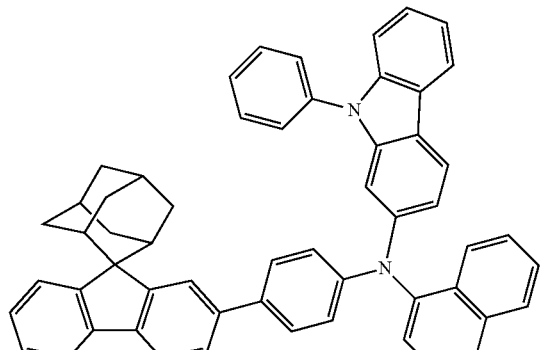
Compound 31
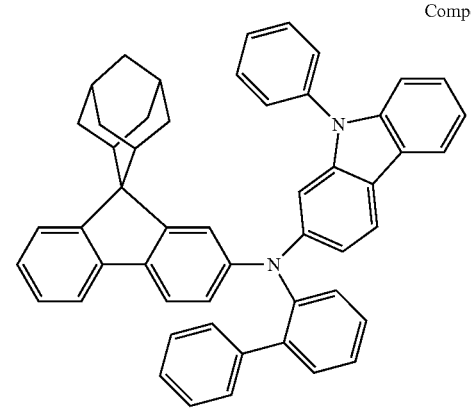
Compound 32
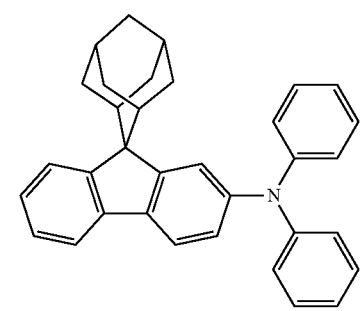
Compound 33
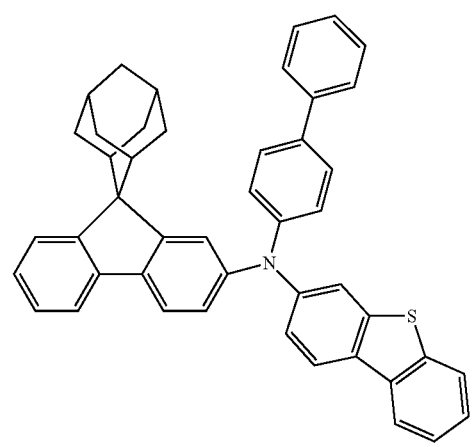
Compound 34
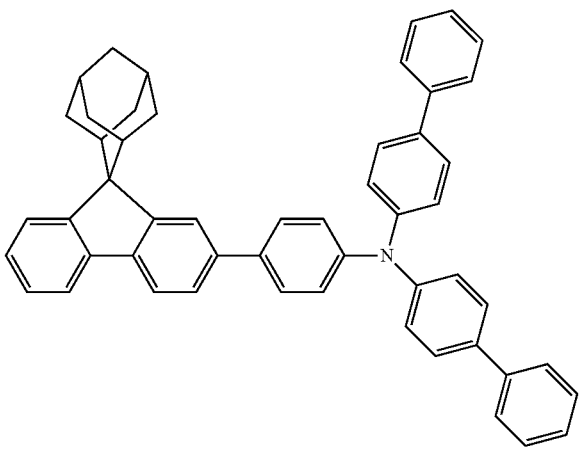
Compound 35
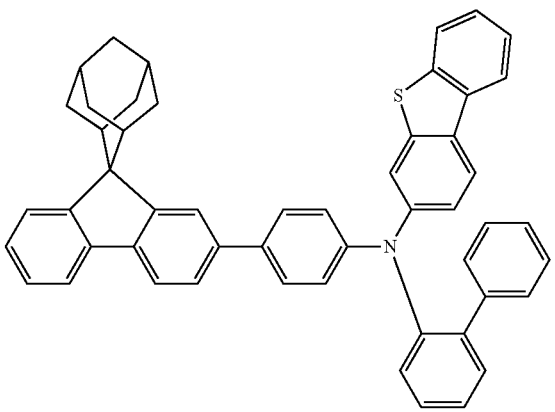
Compound 36
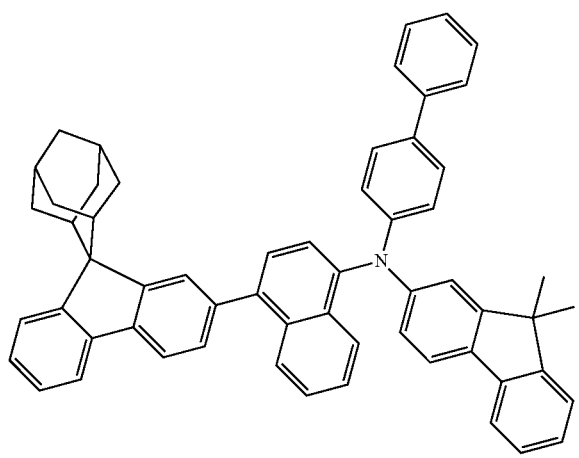

-continued
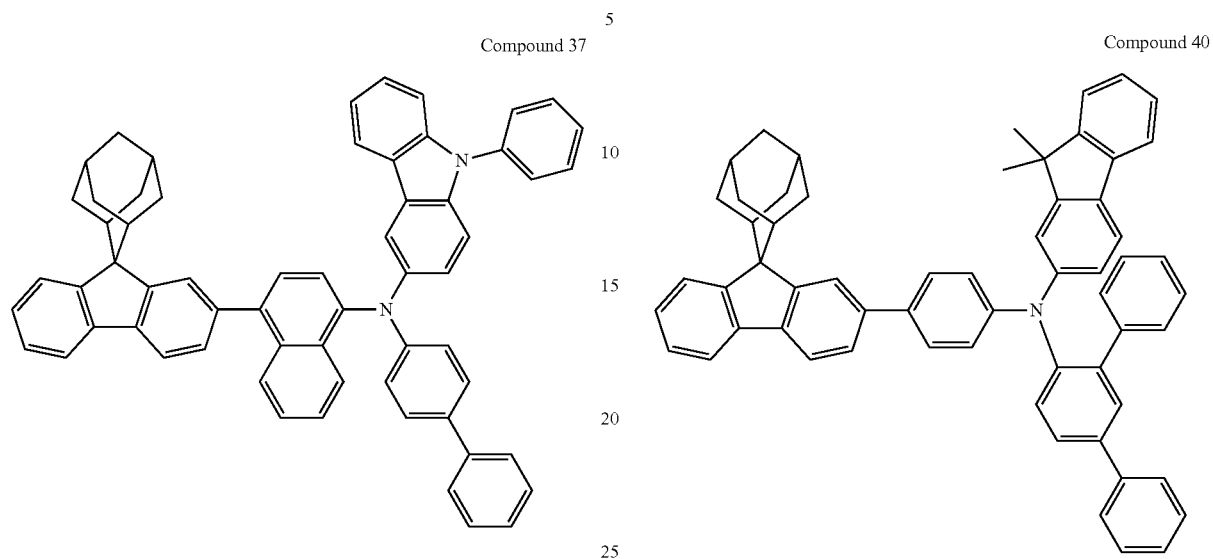
Compound 37
Compound 40
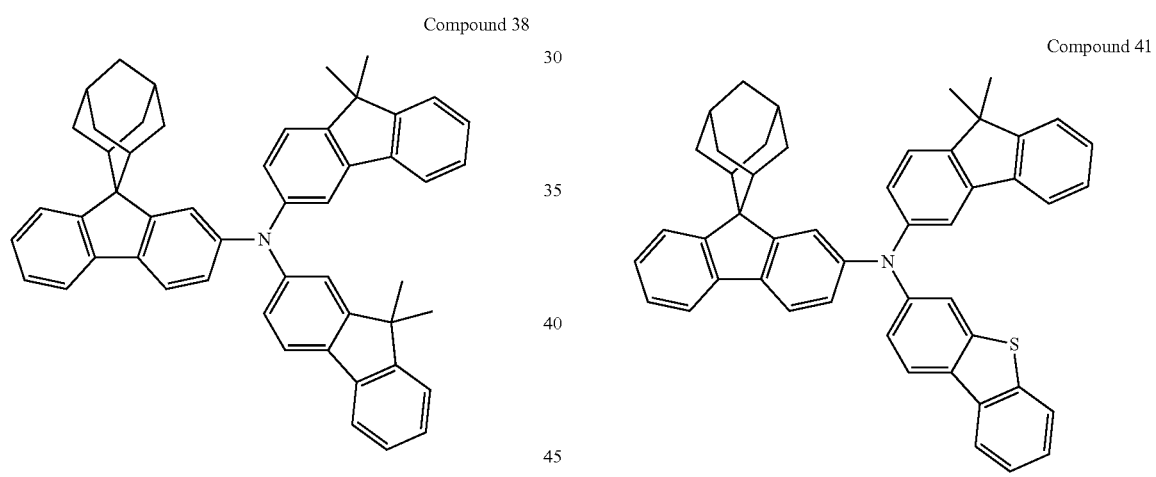
Compound 38
Compound 41
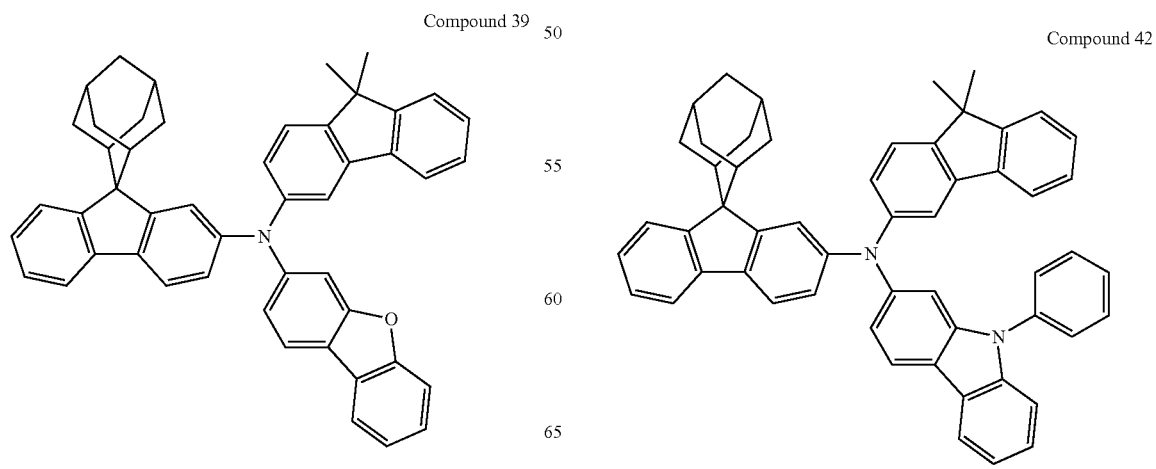
Compound 39
Compound 42

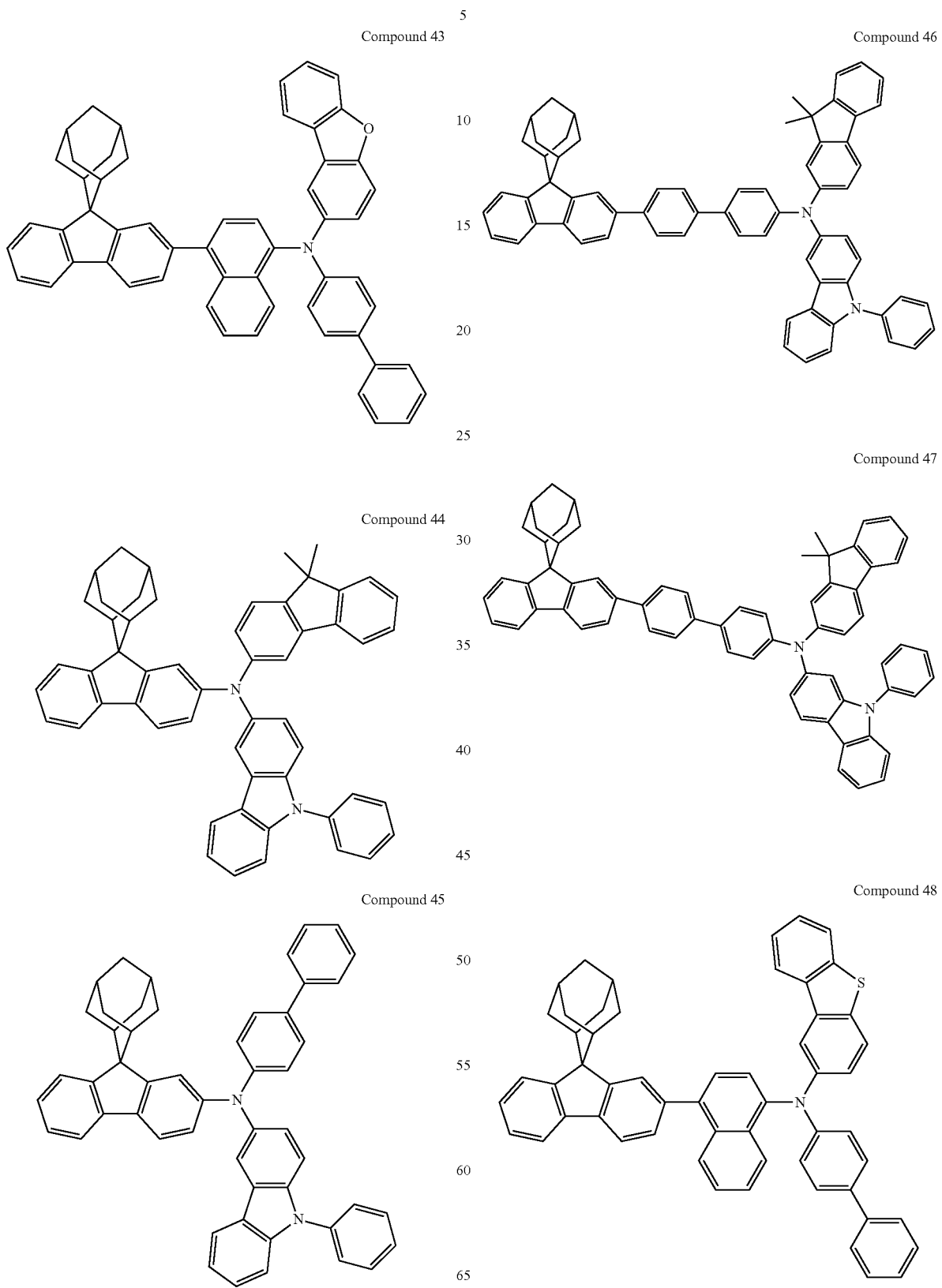

-continued
Compound 49
Compound 50
Compound 51
Compound 52
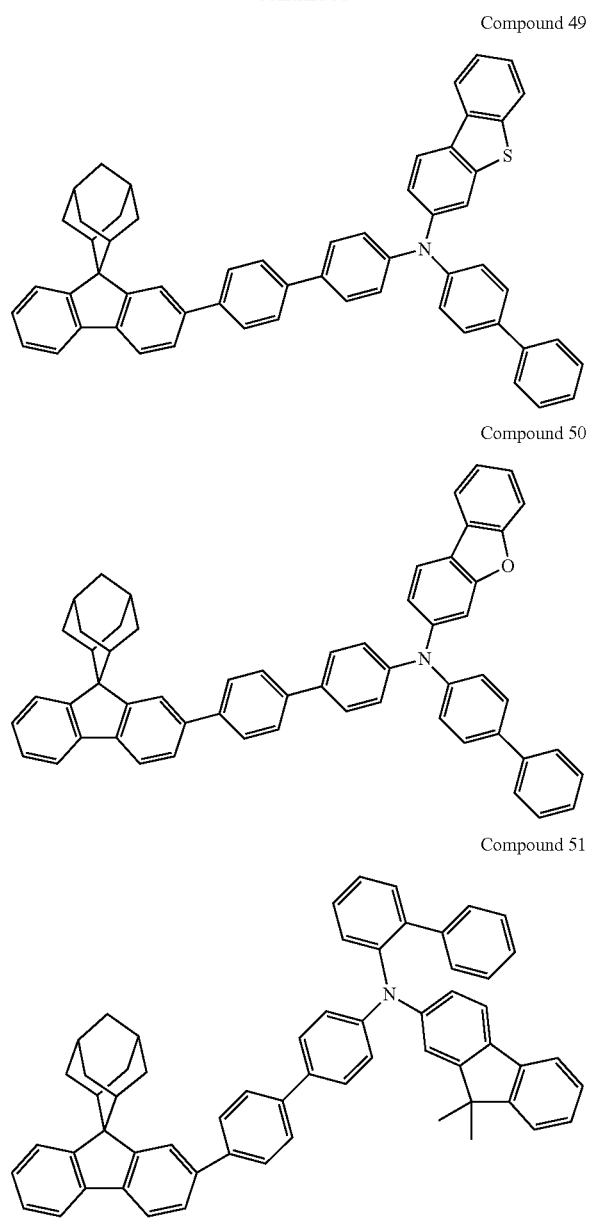
-continued
Compound 53
Compound 54
Compound 55
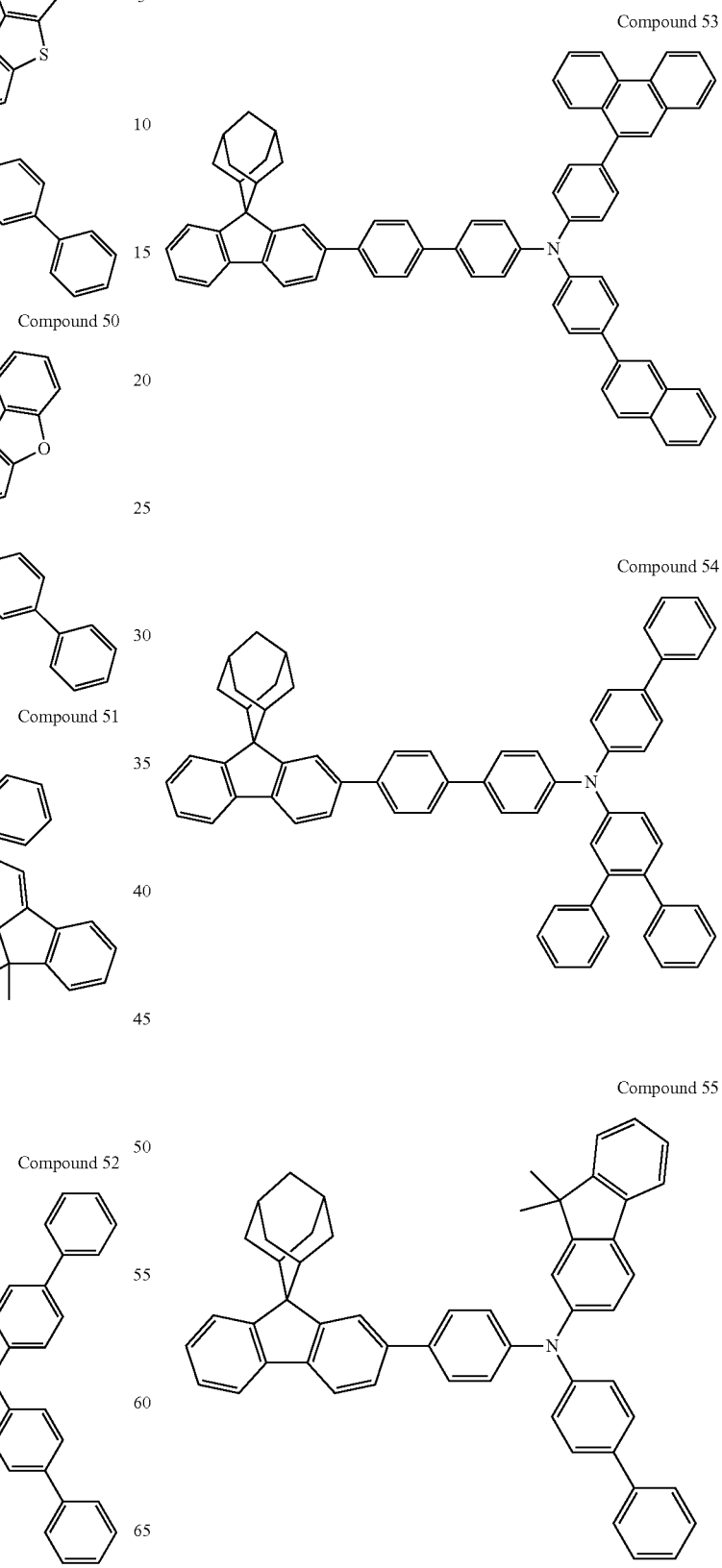

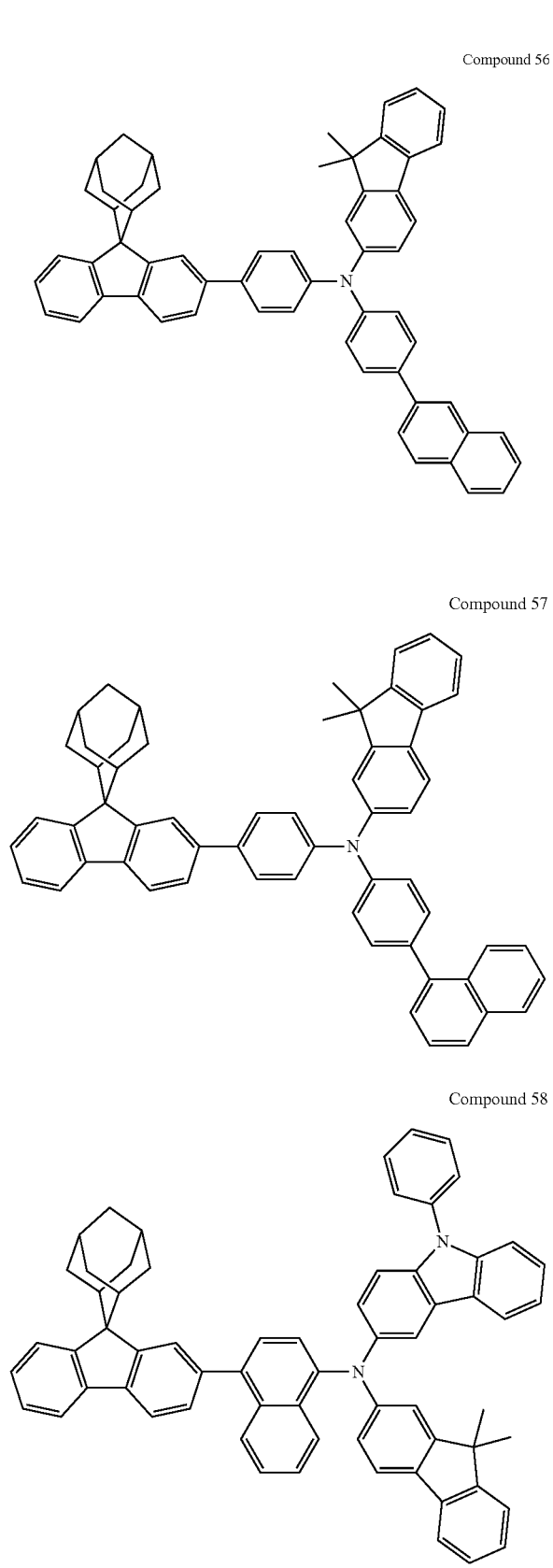
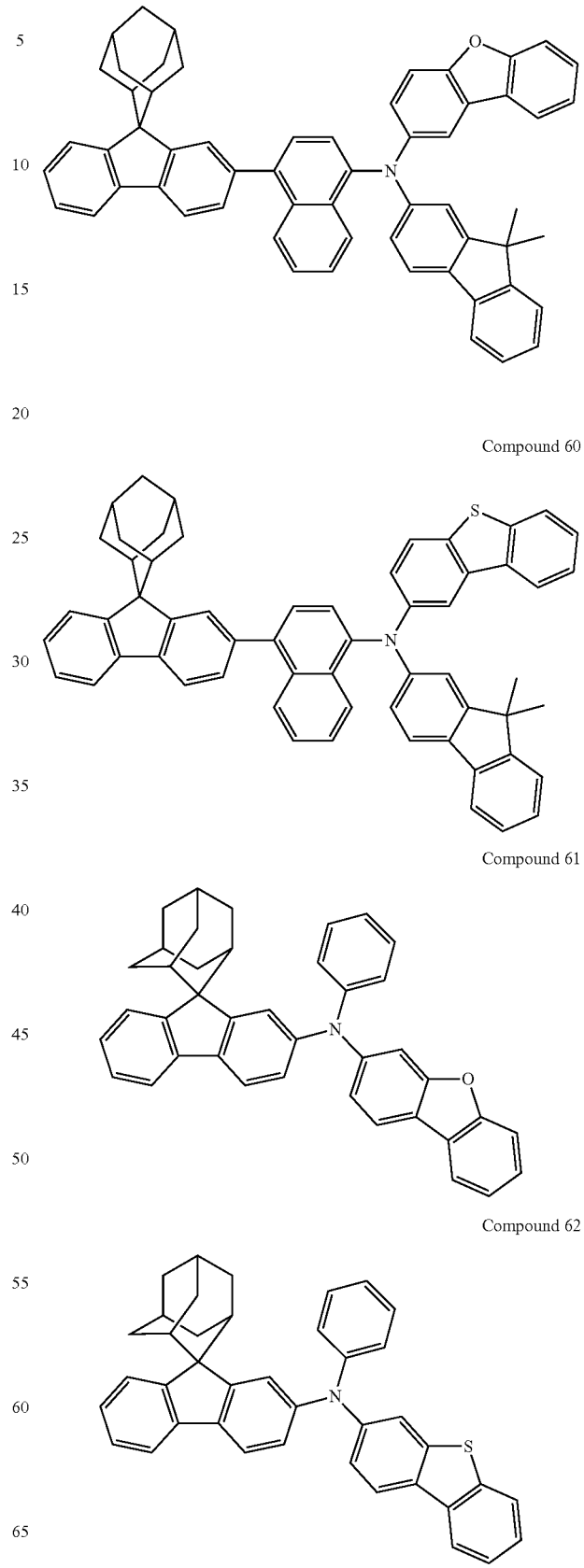

Compound 63
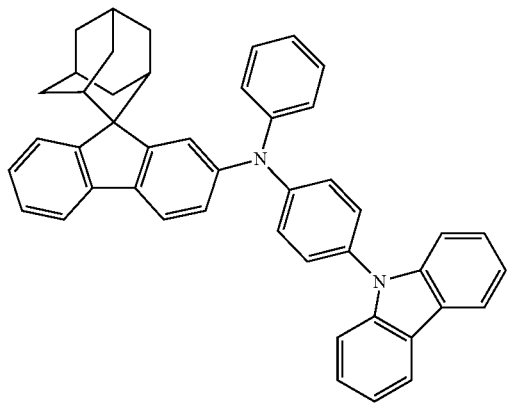
Compound 64
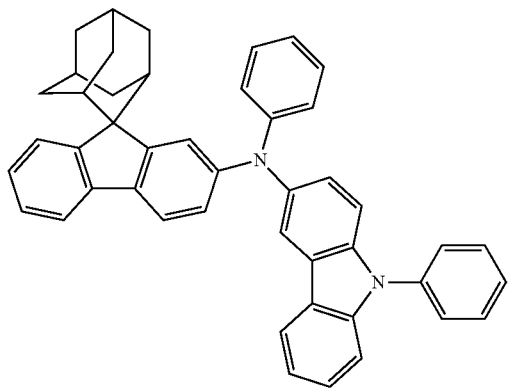
Compound 65
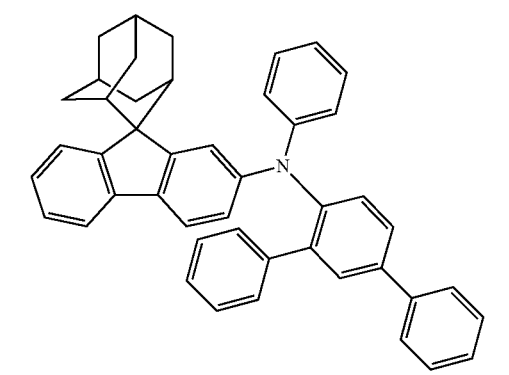
Compound 66
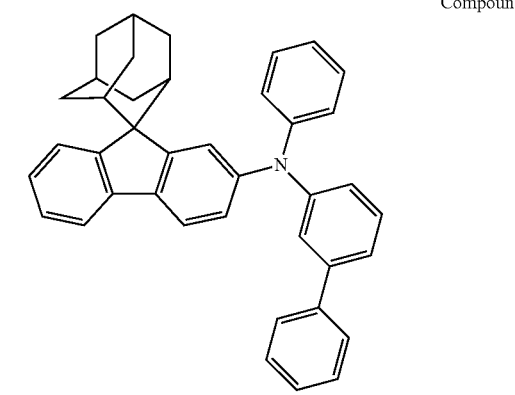
Compound 67
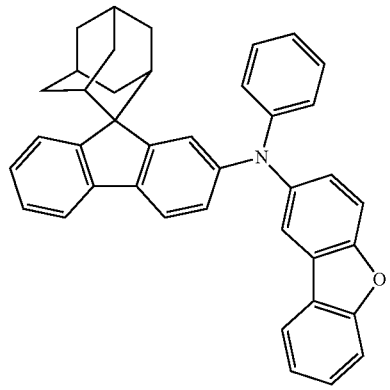
Compound 68
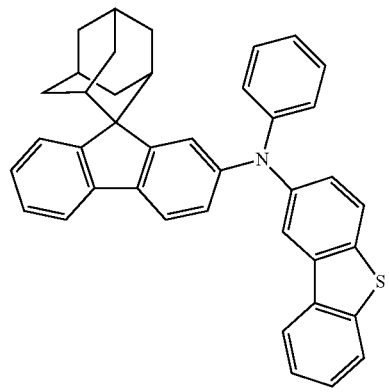
Compound 69
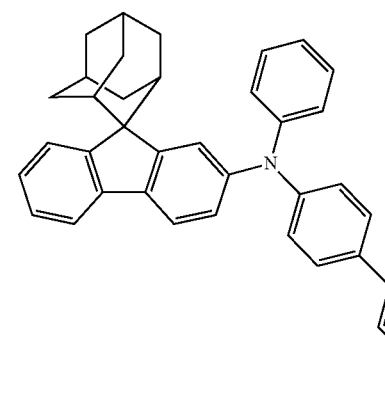
Compound 70
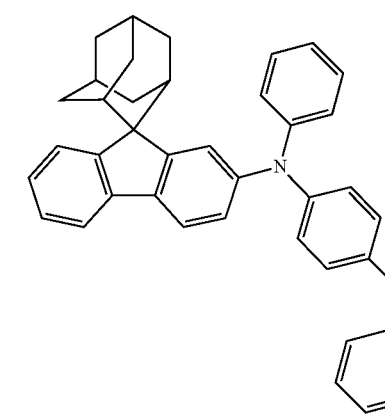

Compound 71
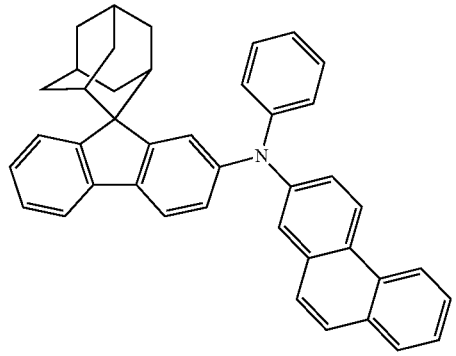
Compound 72
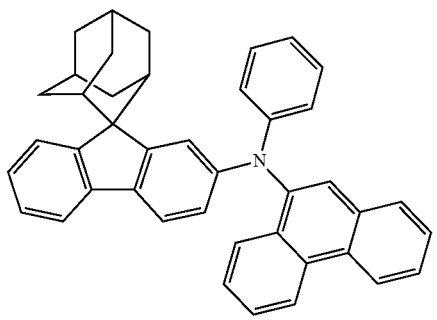
Compound 73
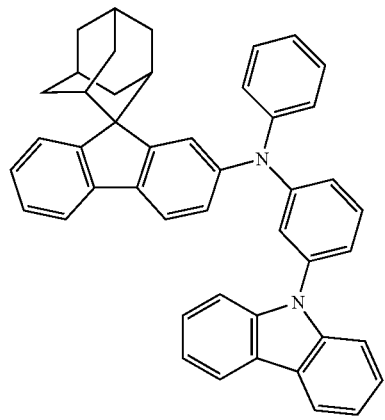
Compound 74
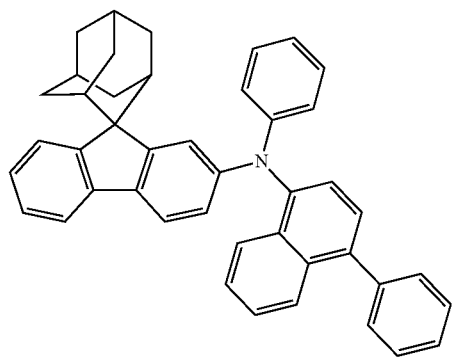
Compound 75
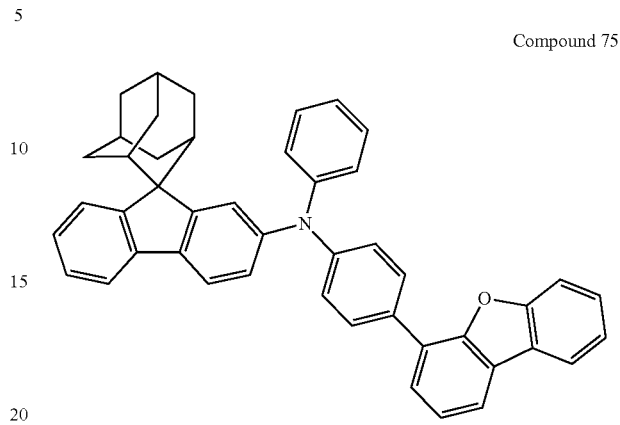
Compound 76
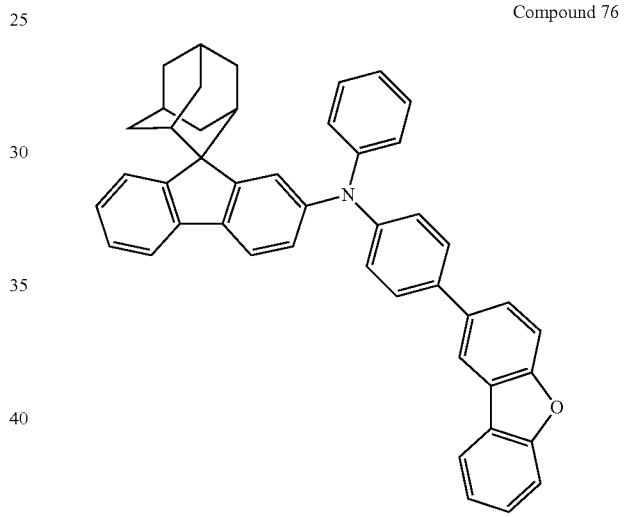
Compound 77
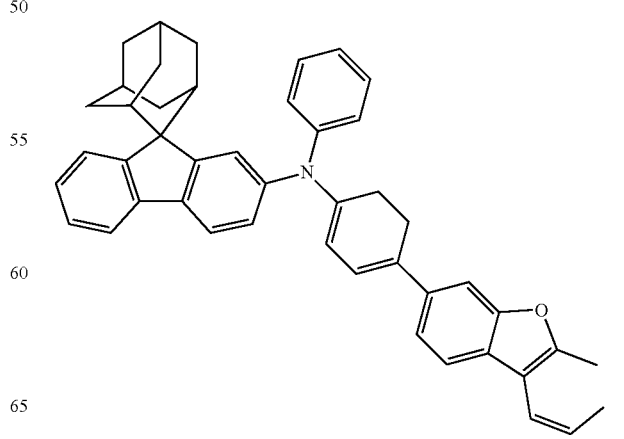

Compound 78
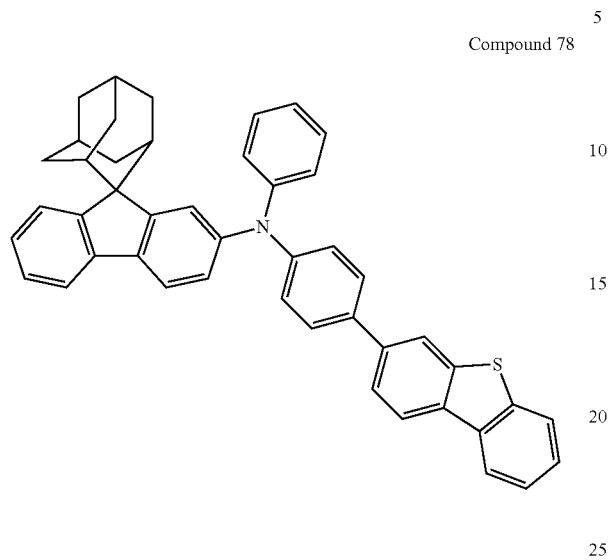
Compound 79
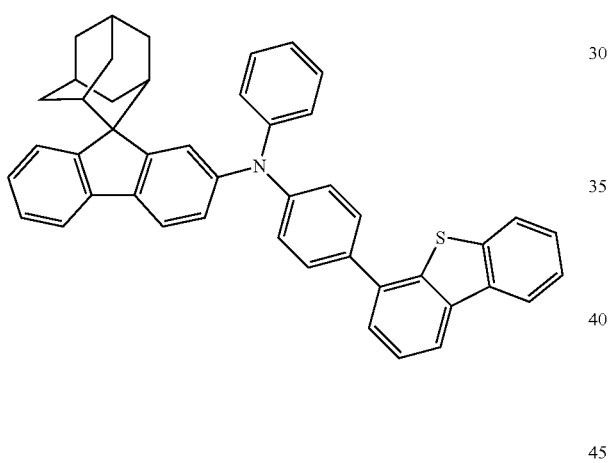
Compound 80
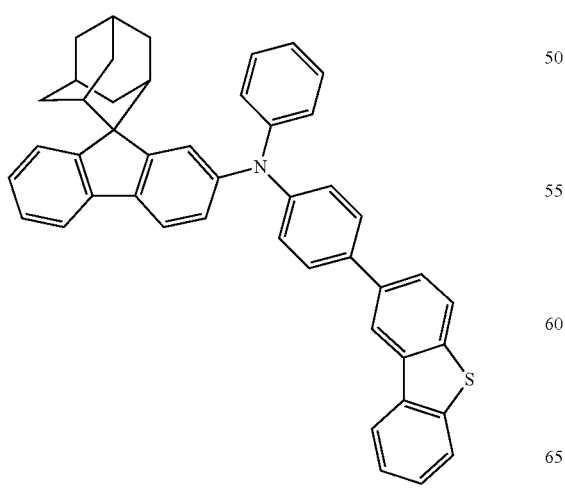
Compound 81
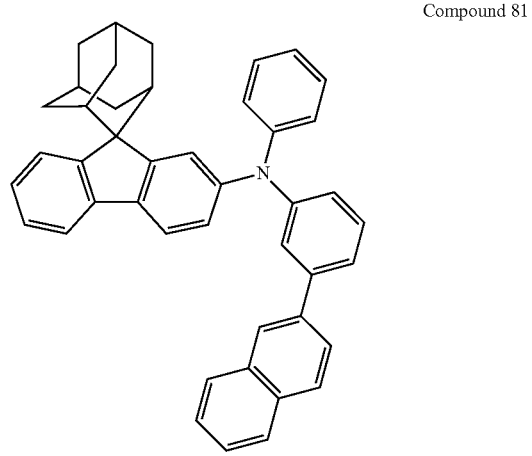
Compound 82
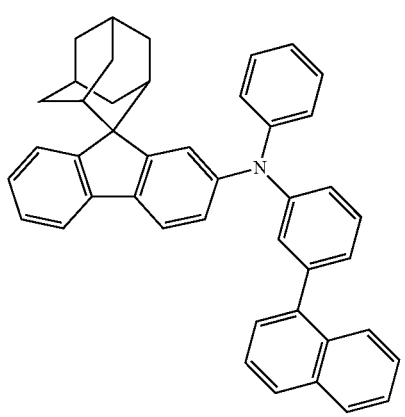
Compound 83
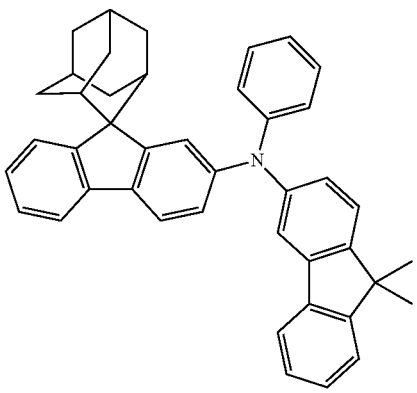

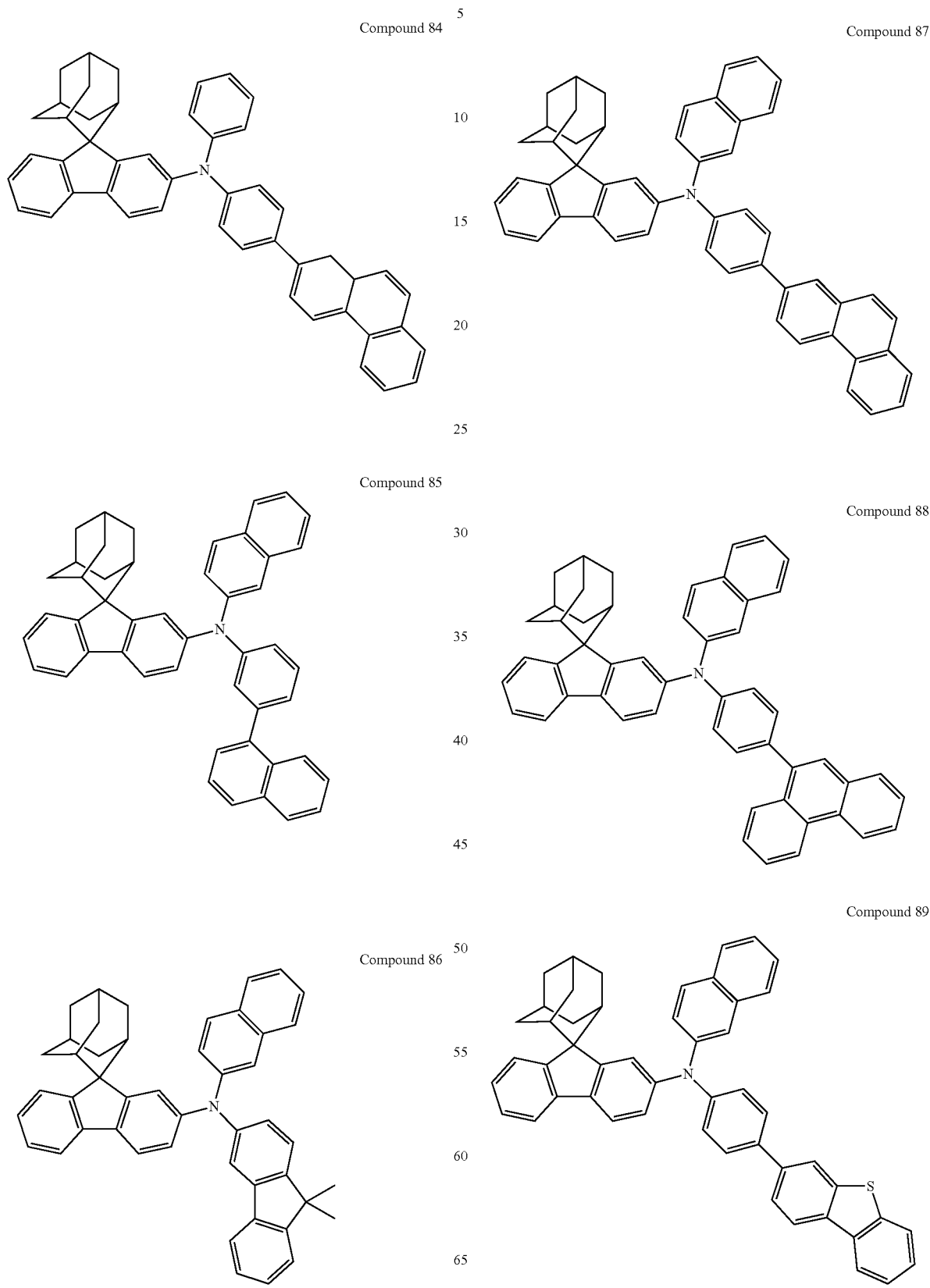

Compound 90
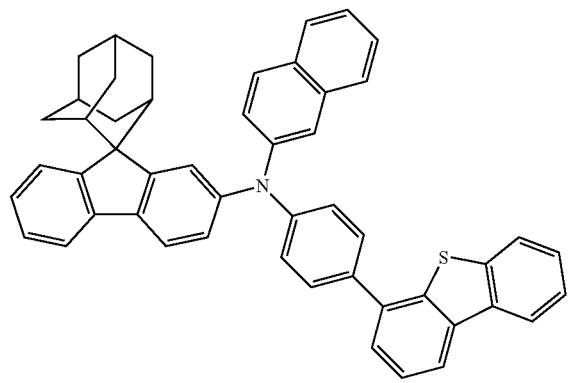
Compound 91
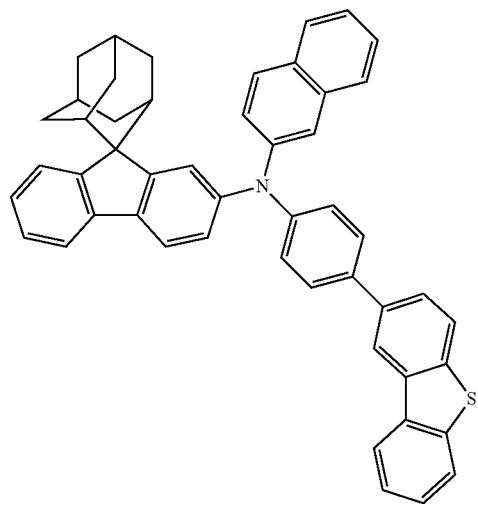
Compound 92
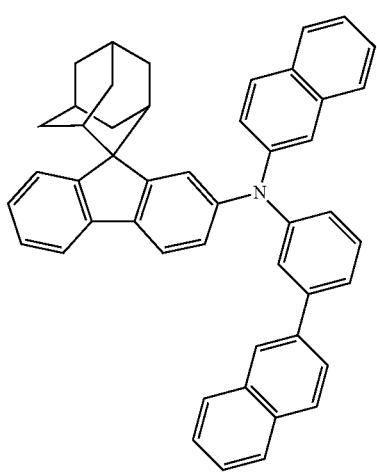
Compound 93
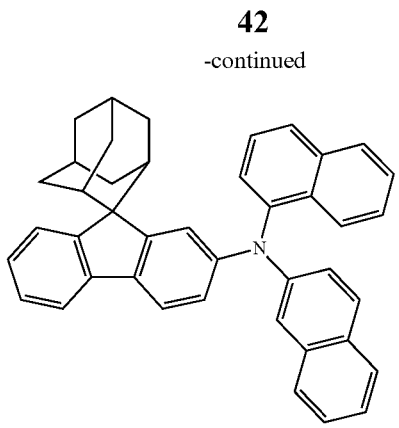
Compound 94
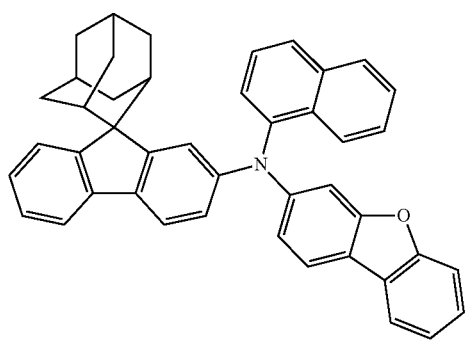
Compound 95
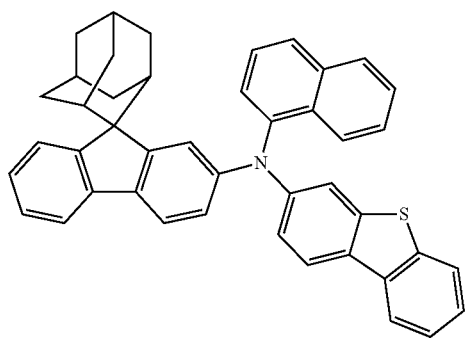
Compound 96
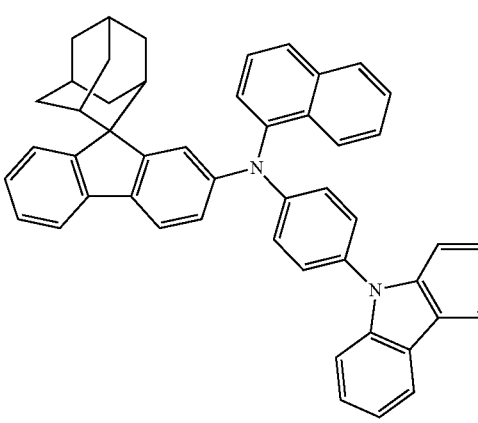

Compound 97
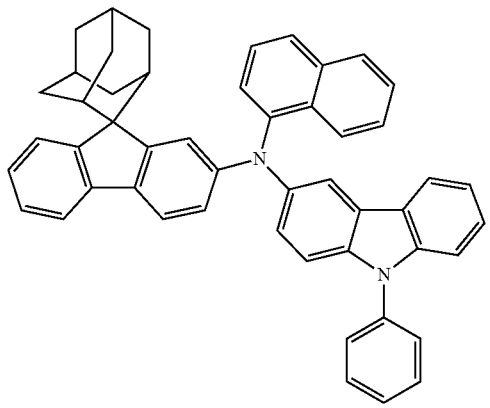
Compound 98
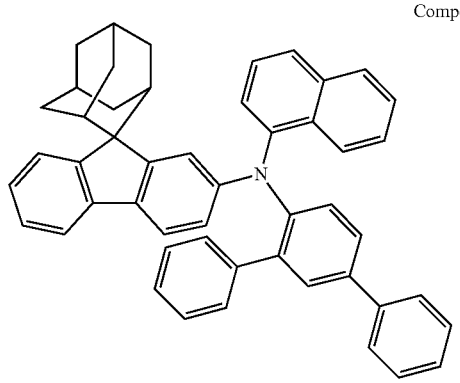
Compound 99
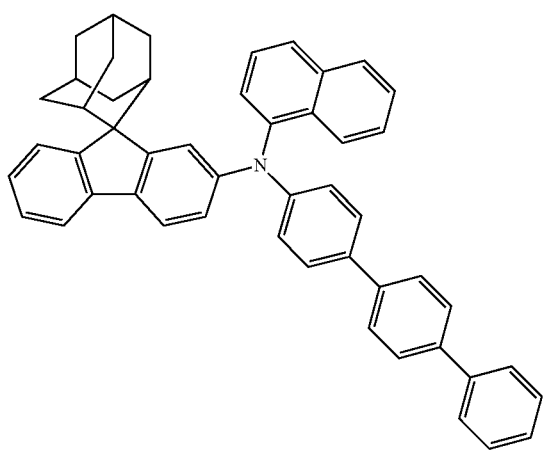
Compound 100
Compound 101
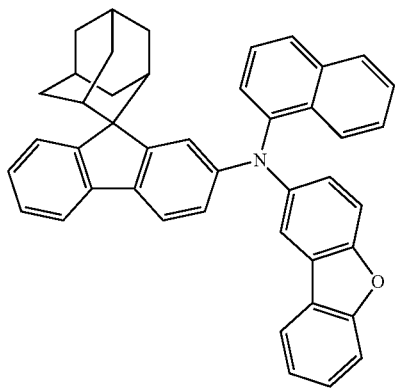
Compound 102
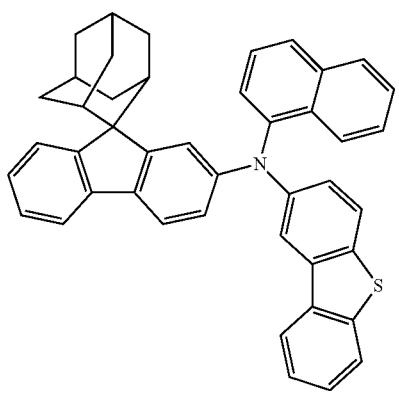
Compound 103
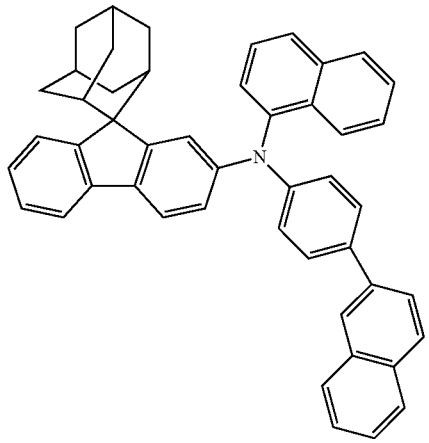
Compound 104
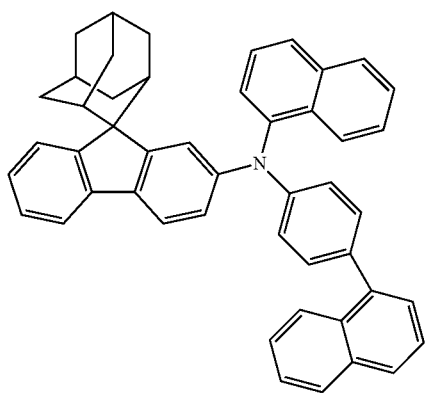

Compound 105
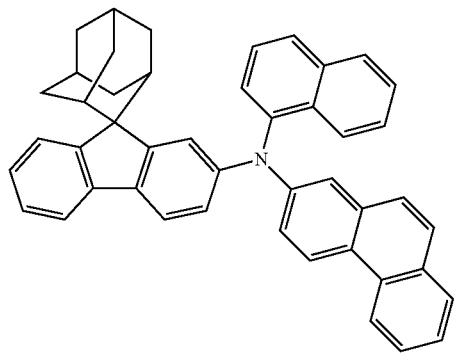
Compound 106
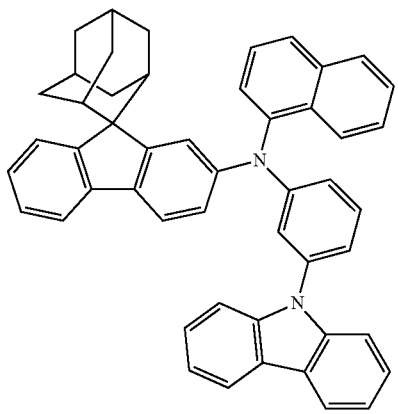
Compound 107
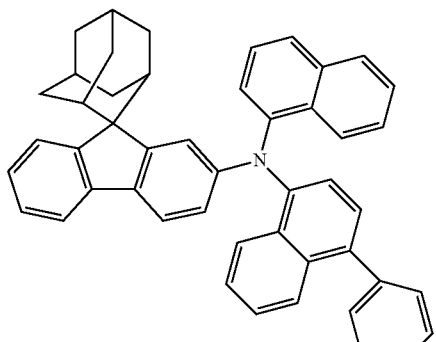
Compound 108
Compound 109
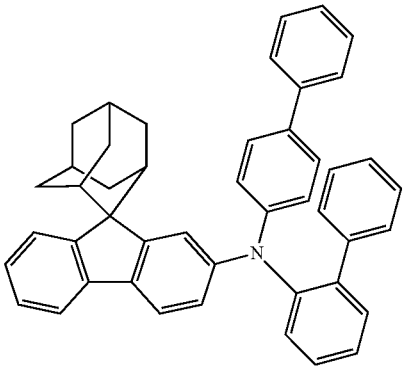
Compound 110
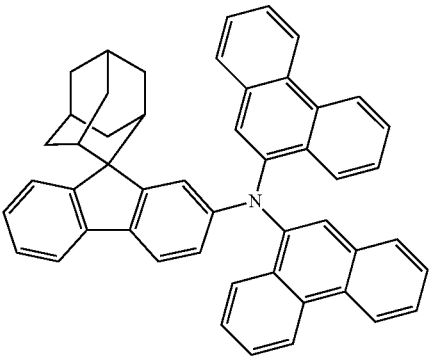
Compound 111
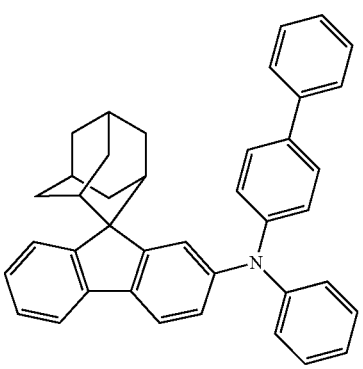
Compound 112
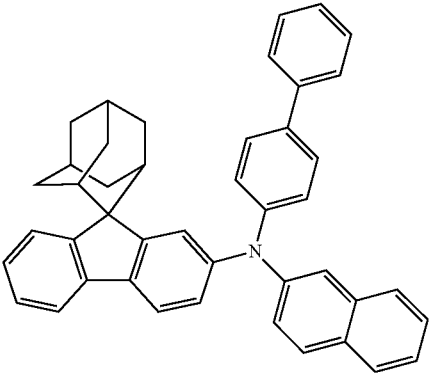

Compound 114
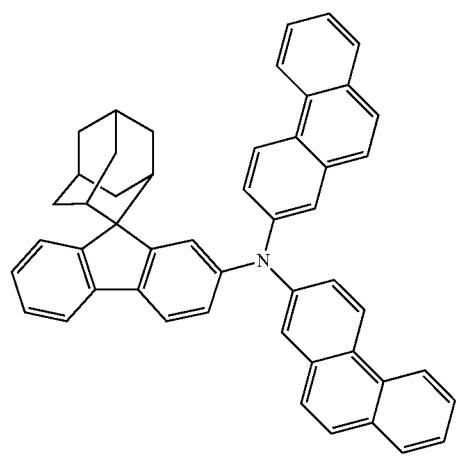
Compound 115
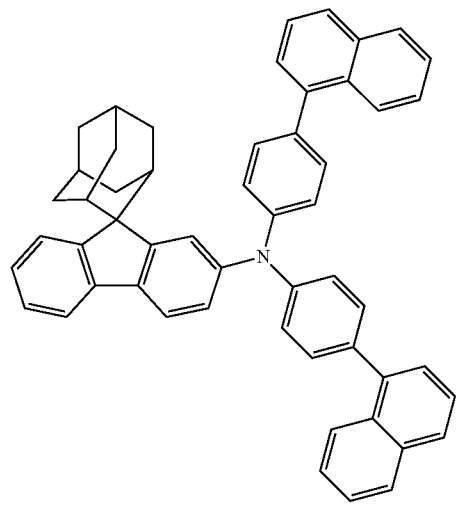
Compound 116
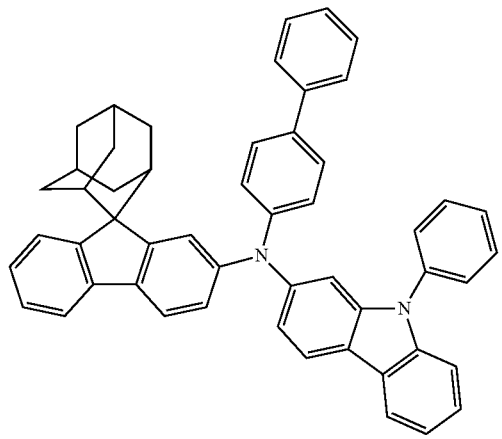
Compound 117
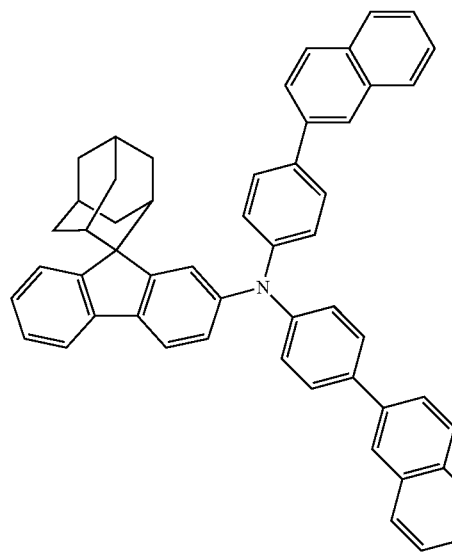
Compound 118
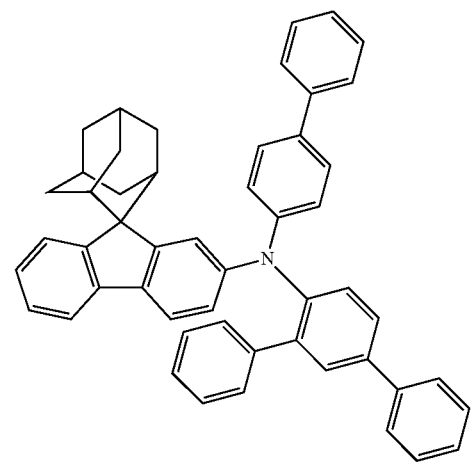
Compound 119
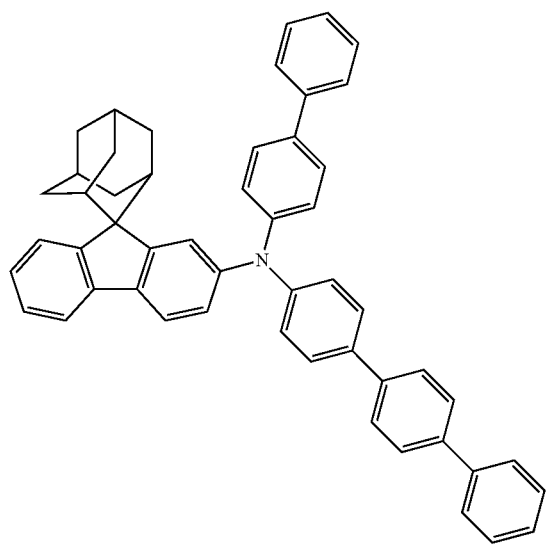

Compound 120
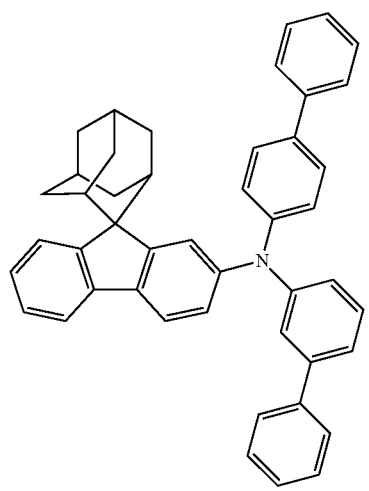
Compound 121
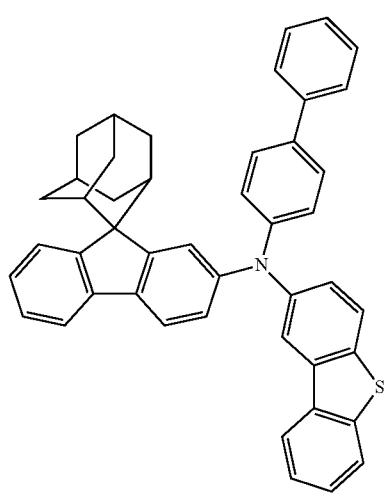
Compound 122
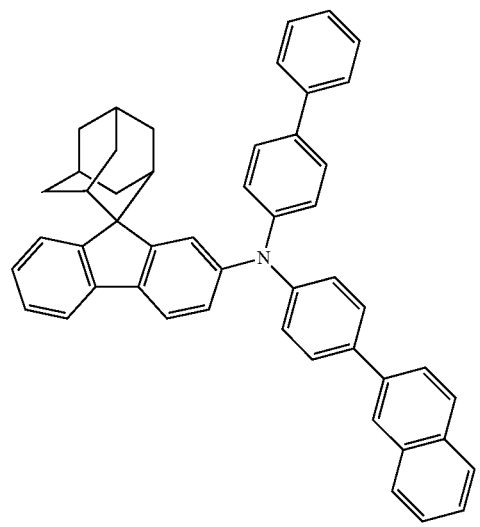
Compound 123
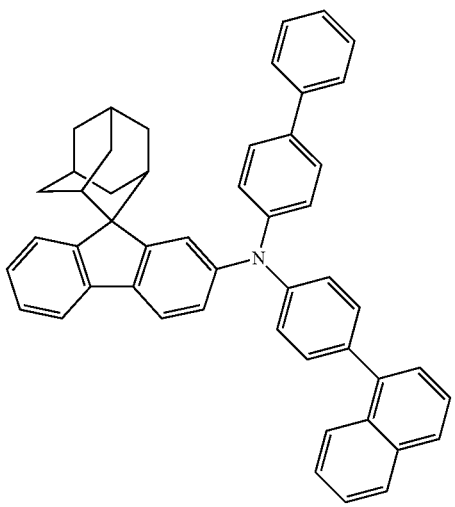
Compound 124
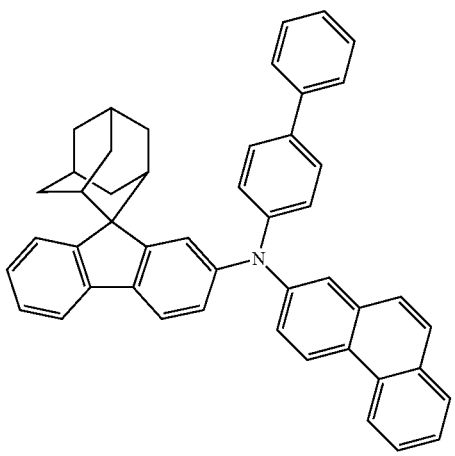
Compound 125
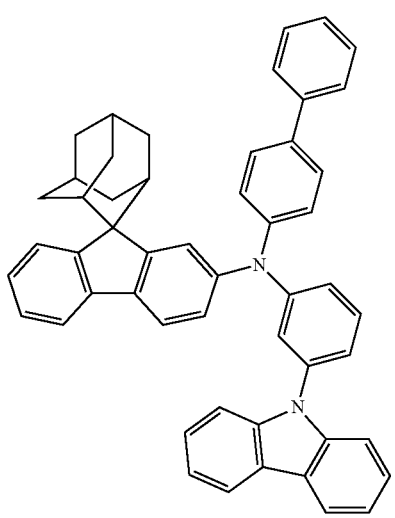

-continued
Compound 126
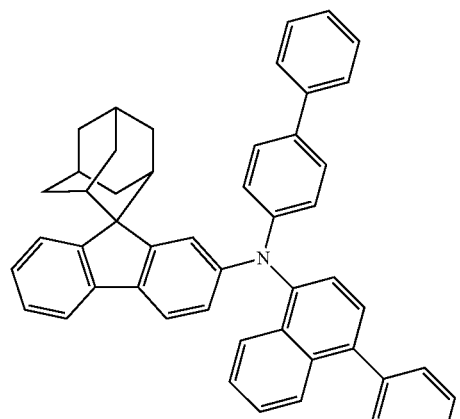
Compound 127
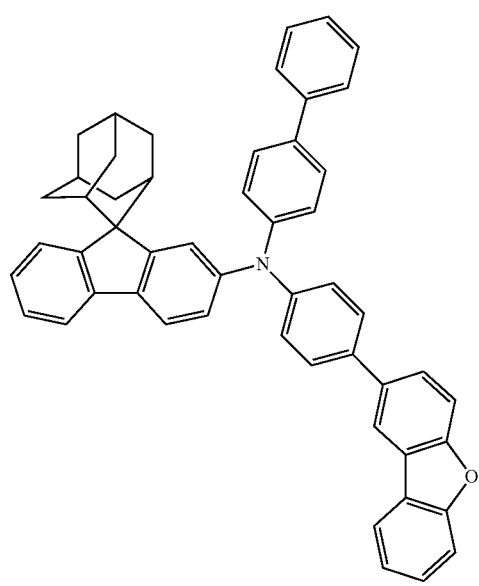
Compound 128
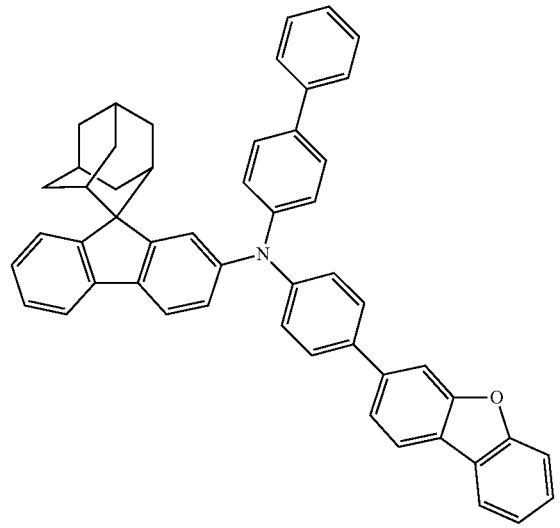
Compound 129
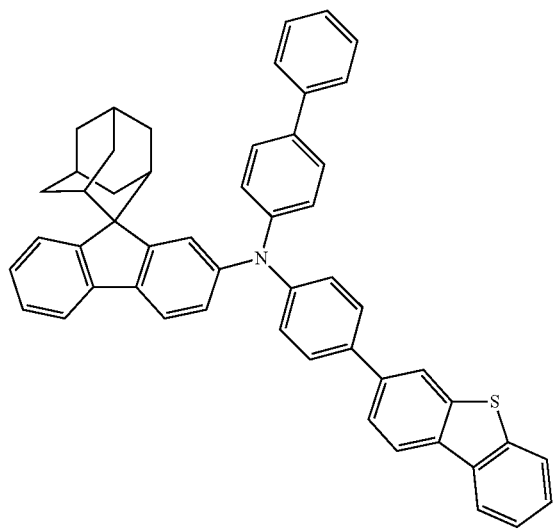
Compound 130
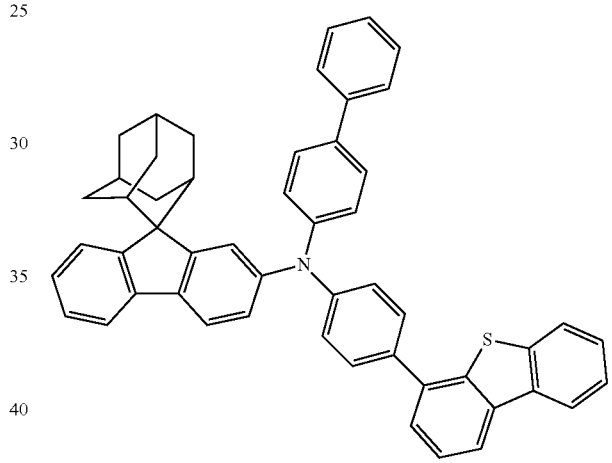
Compound 131
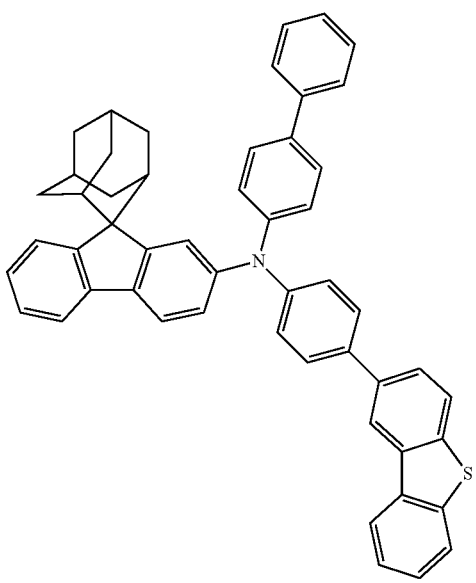

Compound 132
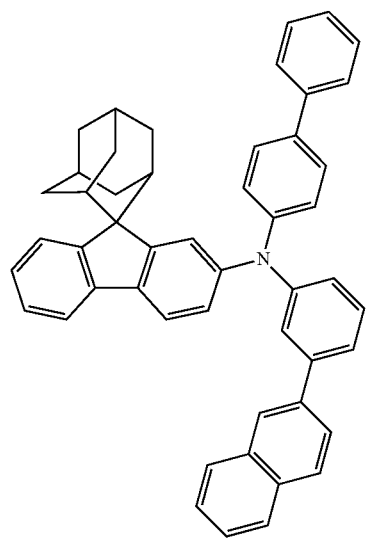
Compound 135
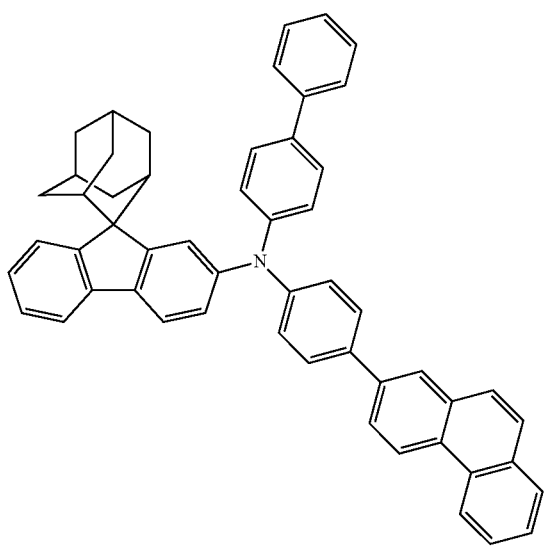
Compound 133
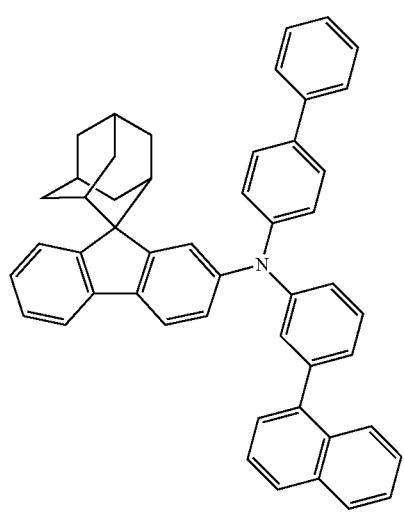
Compound 136
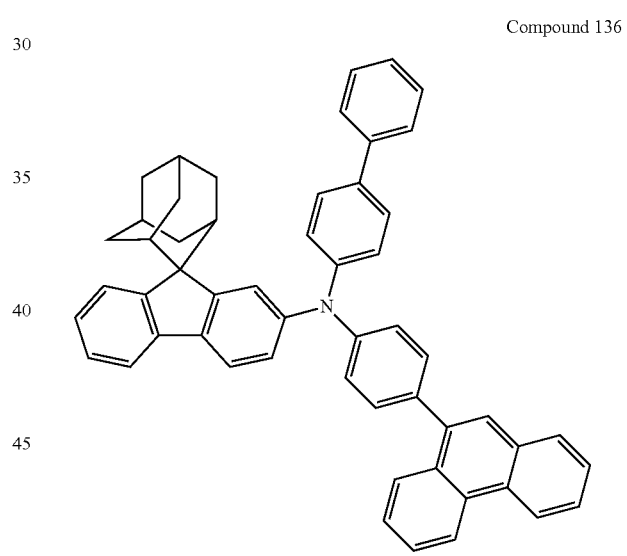
Compound 134
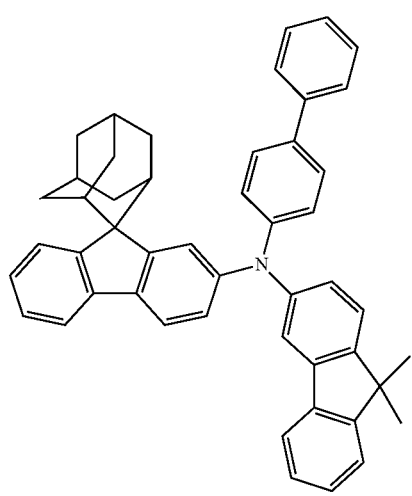
Compound 137
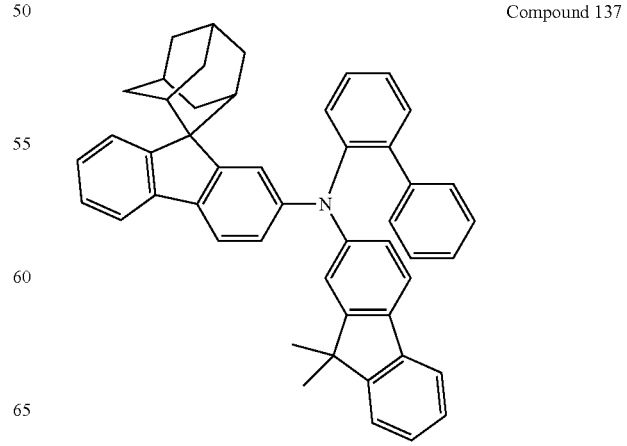

Compound 138
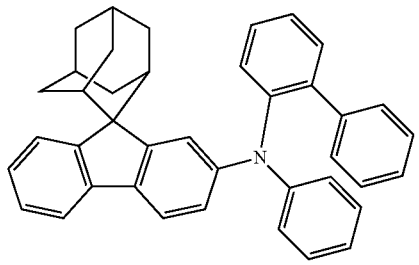
Compound 139
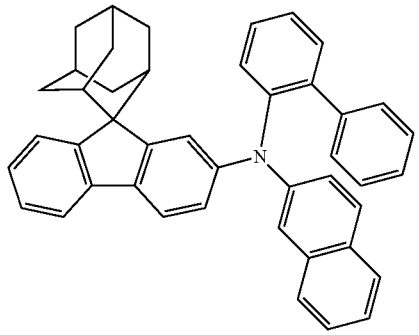
Compound 140
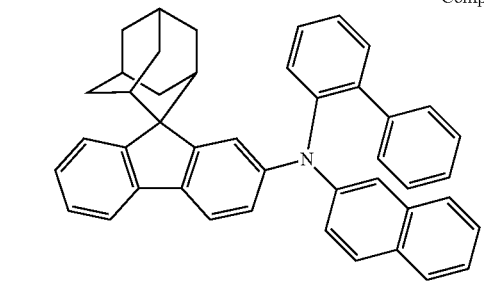
Compound 141
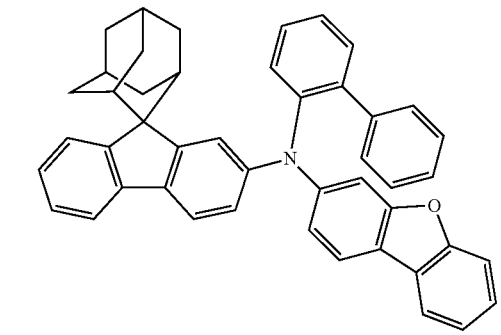
Compound 142
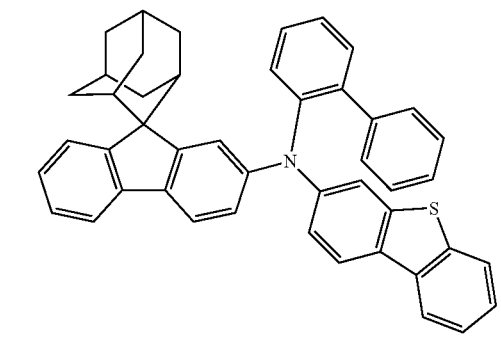
Compound 143
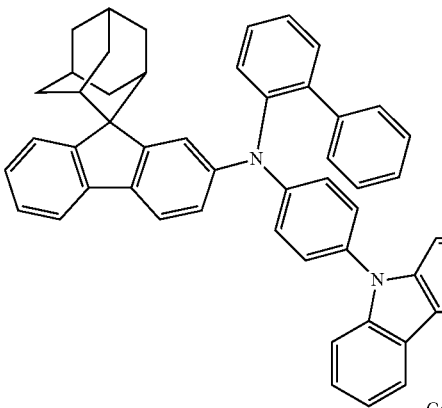
Compound 144
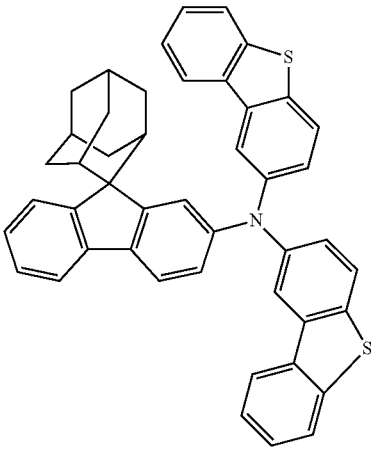
Compound 145
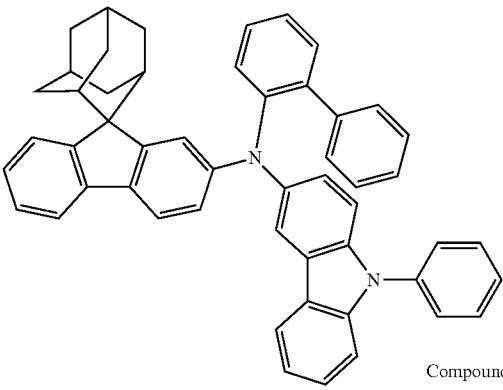
Compound 146
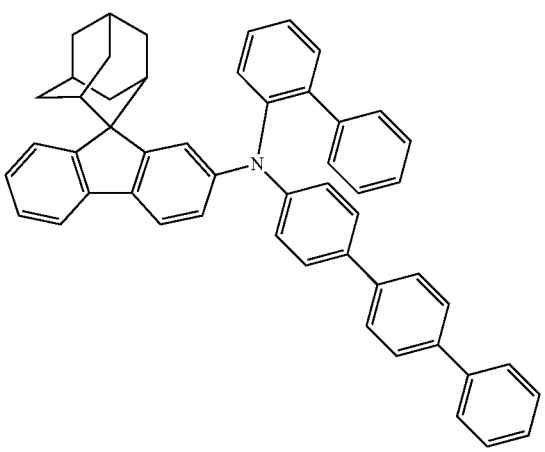

Compound 147
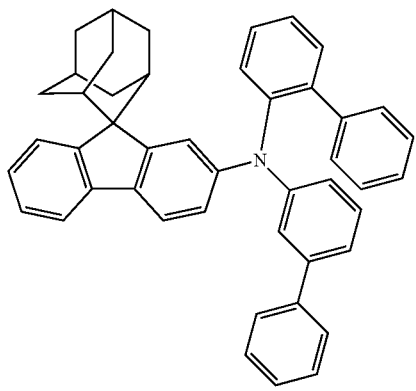
Compound 148
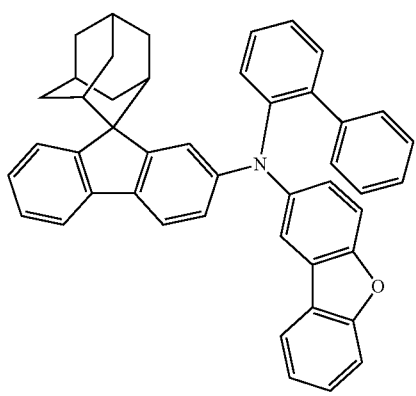
Compound 149
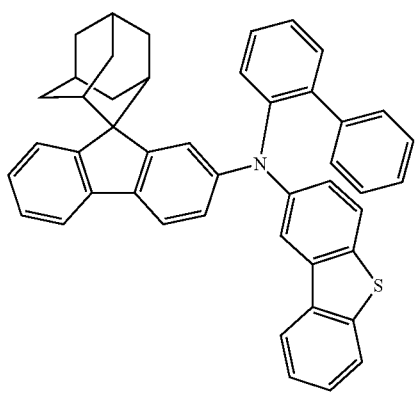
Compound 150
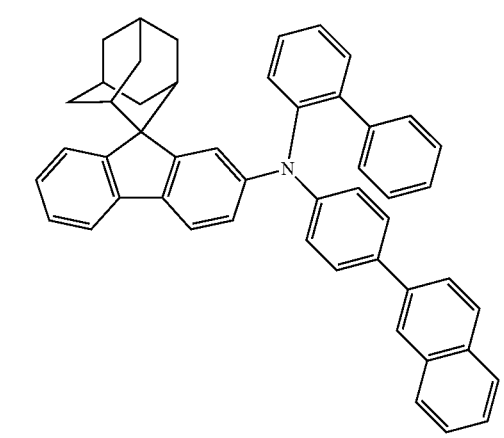
Compound 151
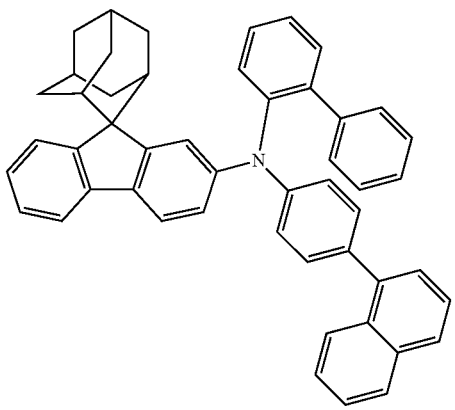
Compound 152
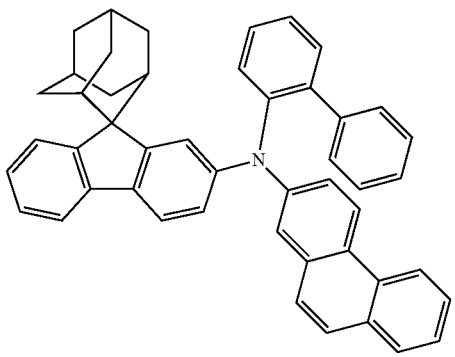
Compound 153
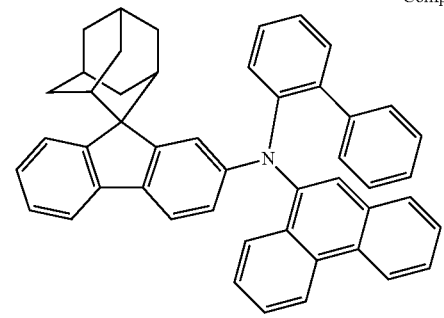
Compound 154
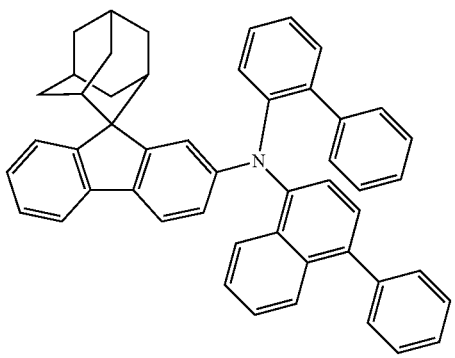

Compound 155
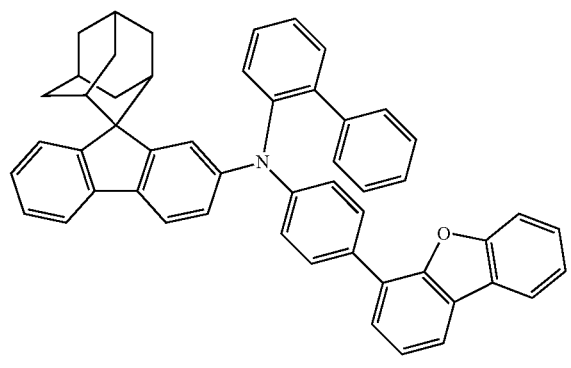
Compound 158
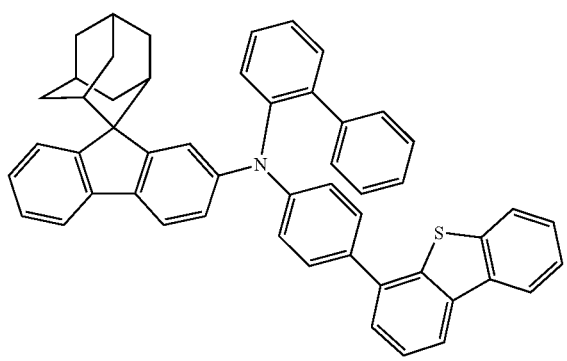
Compound 156
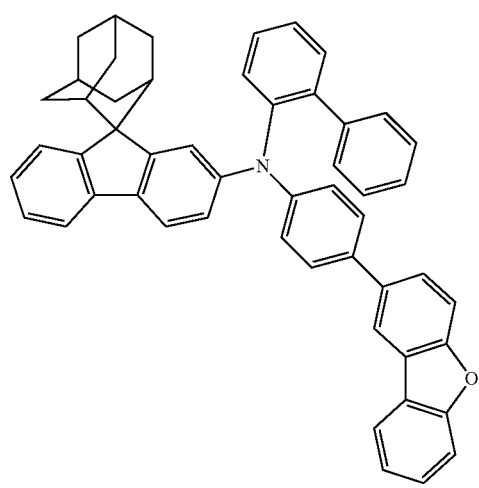
Compound 159
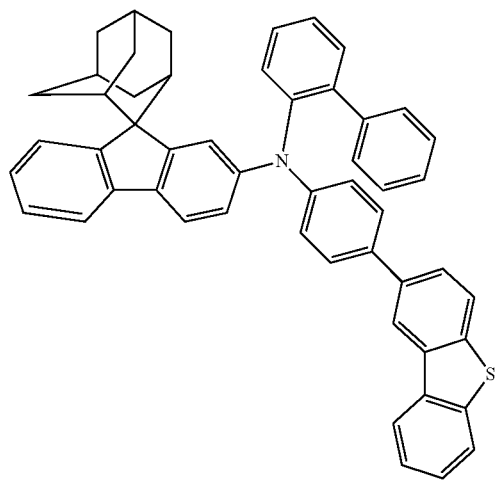
Compound 157
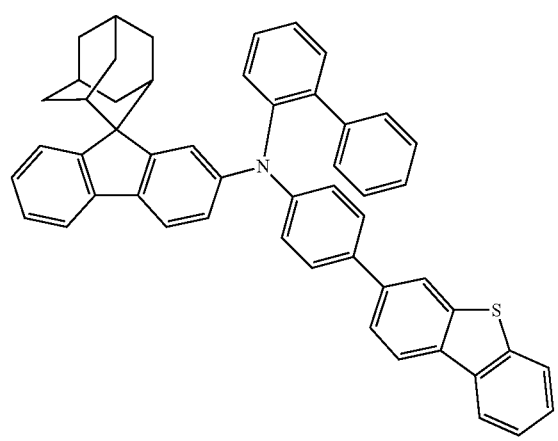
Compound 160
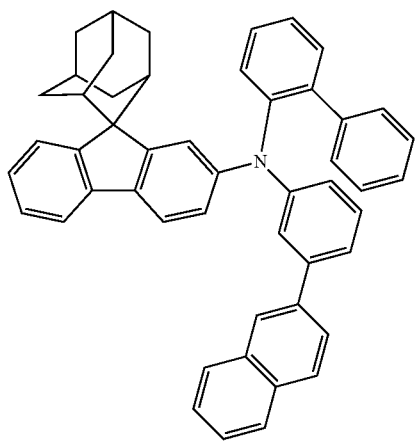

Compound 161
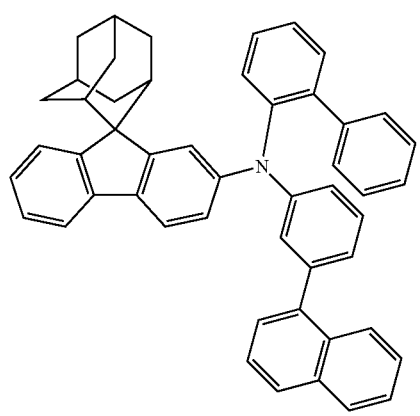
Compound 162
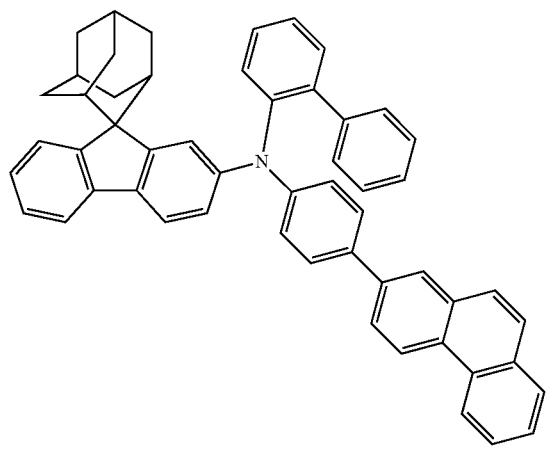
Compound 163
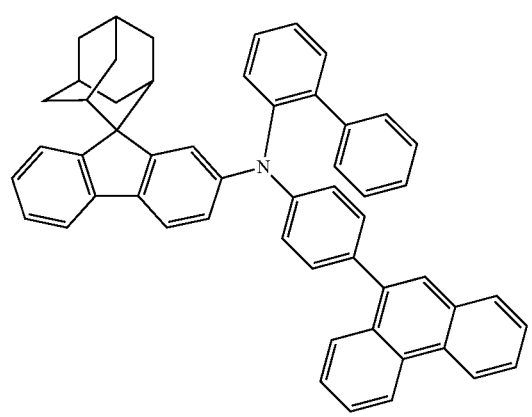
Compound 164
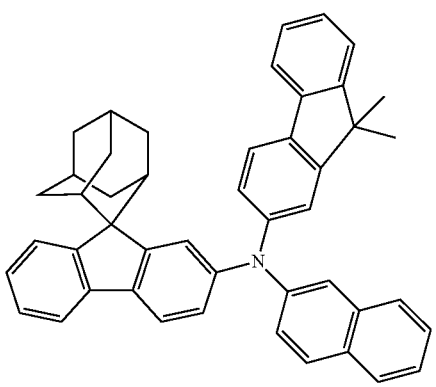
Compound 165
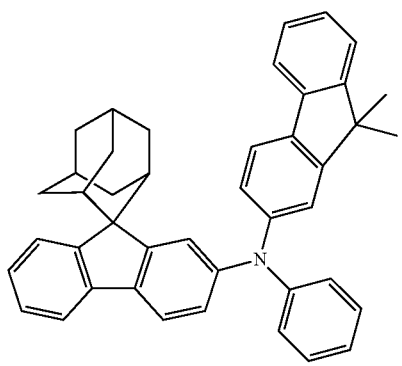
Compound 166
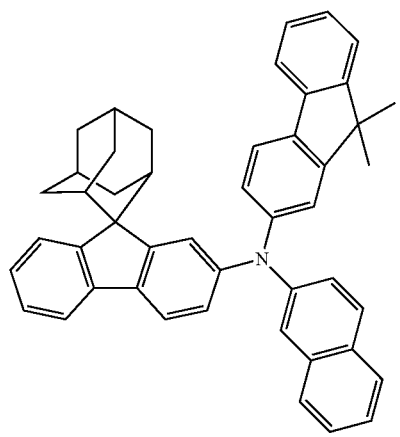

Compound 167
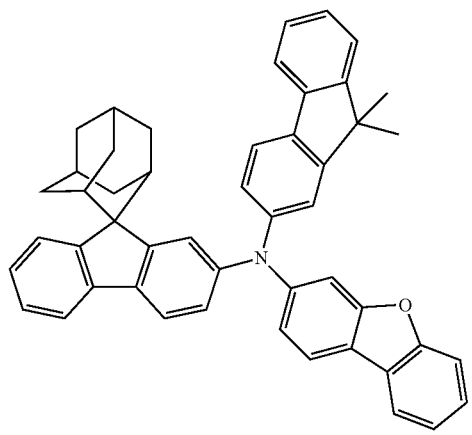
Compound 168
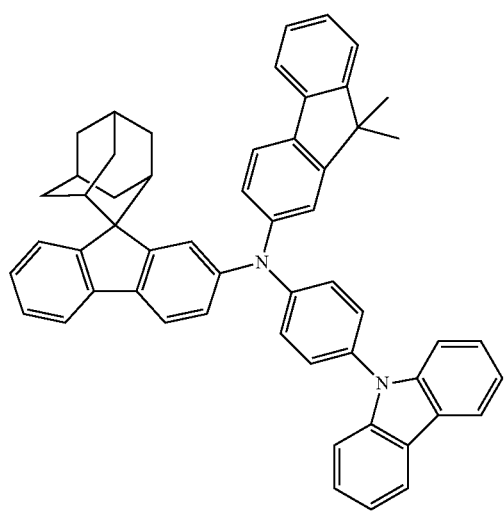
Compound 169
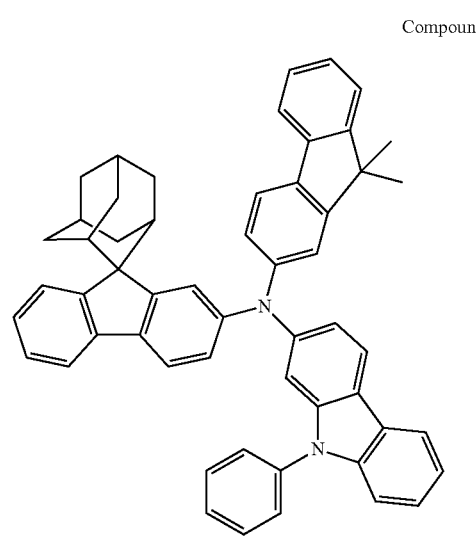
Compound 170
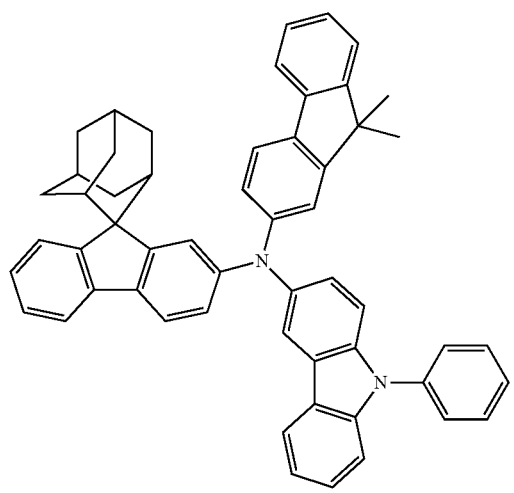
Compound 171
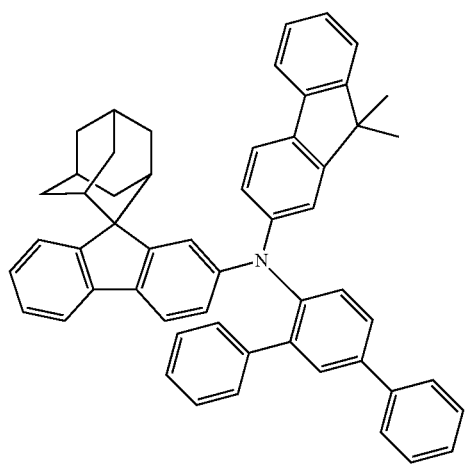
Compound 172
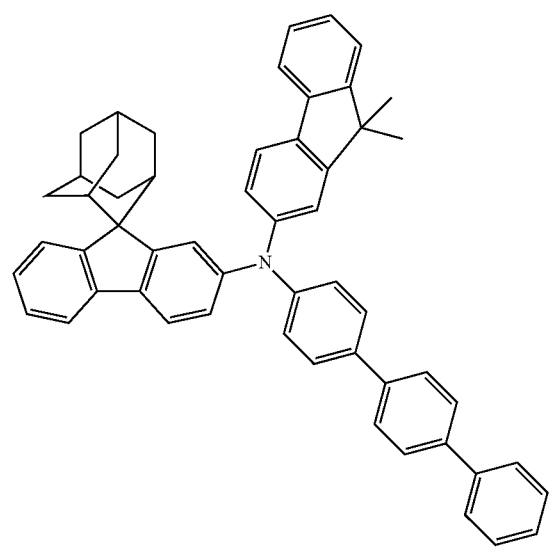

Compound 173
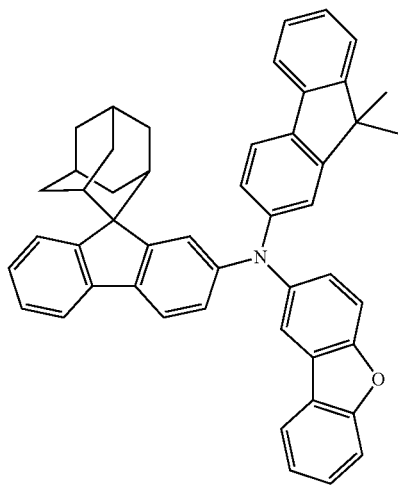
Compound 174
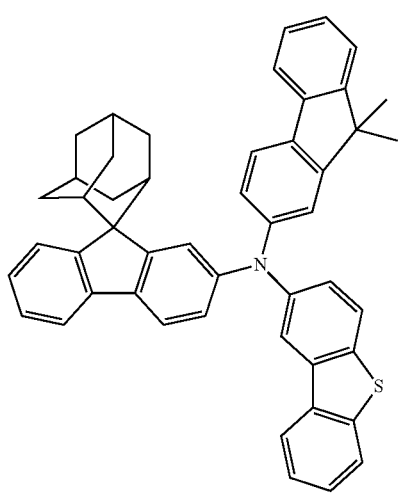
Compound 175
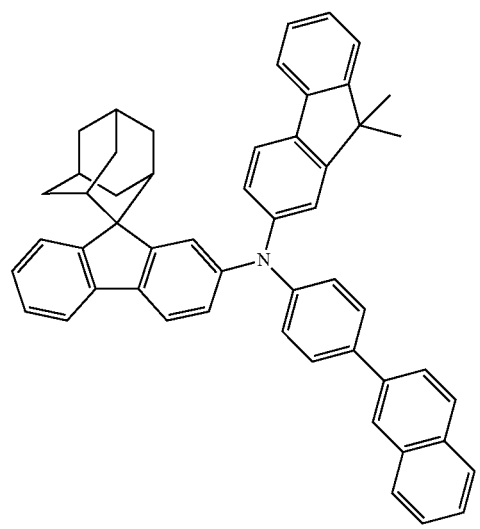
Compound 176
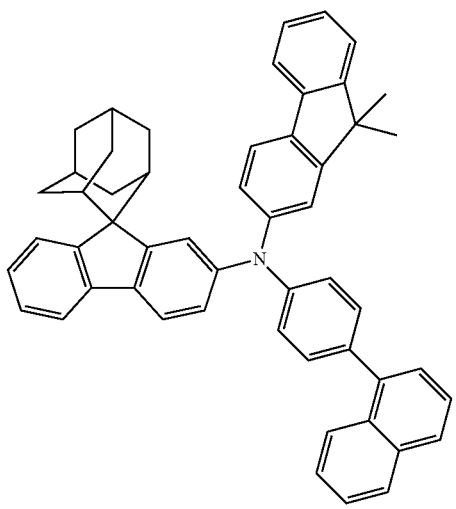
Compound 177
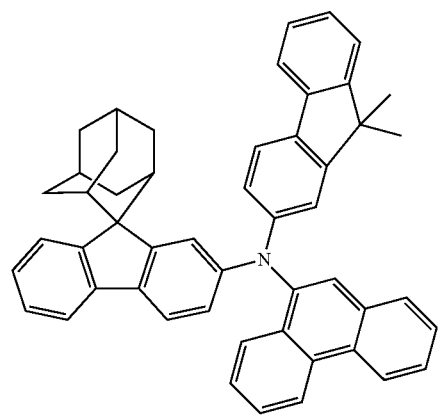
Compound 178
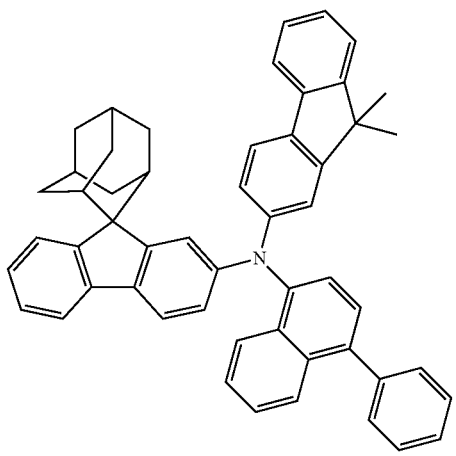

Compound 179
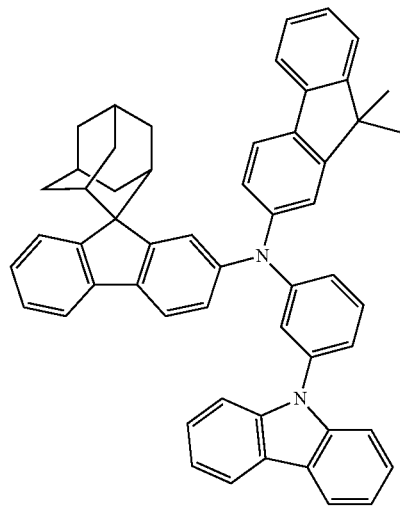
Compound 180
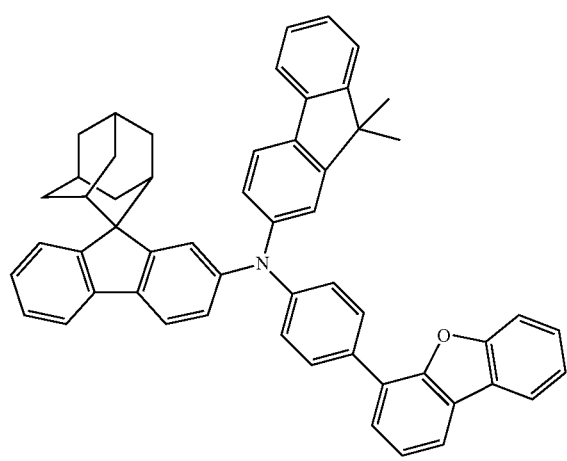
Compound 181
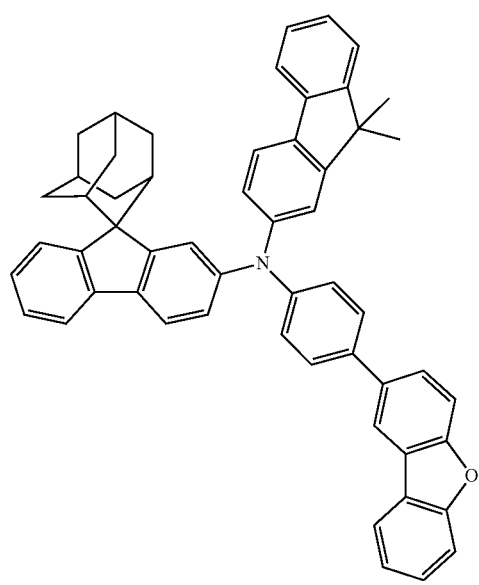
Compound 182
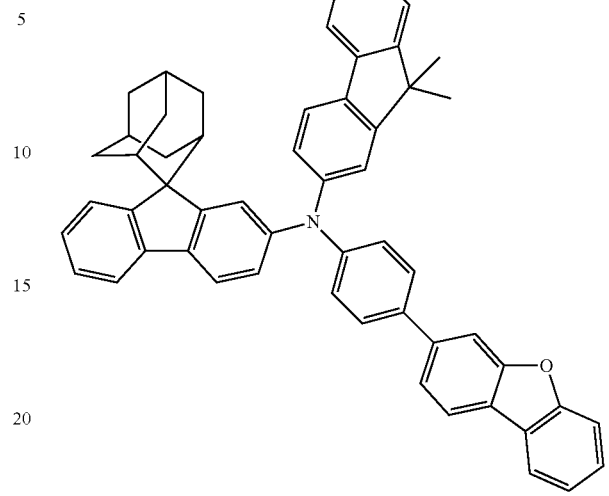
Compound 183
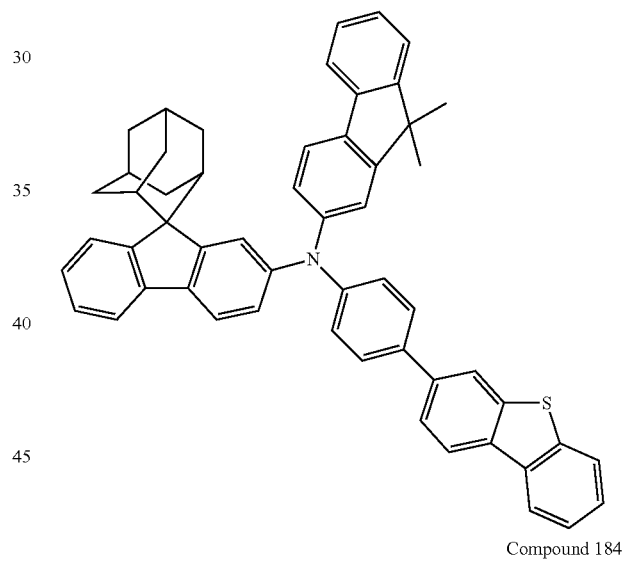
Compound 184
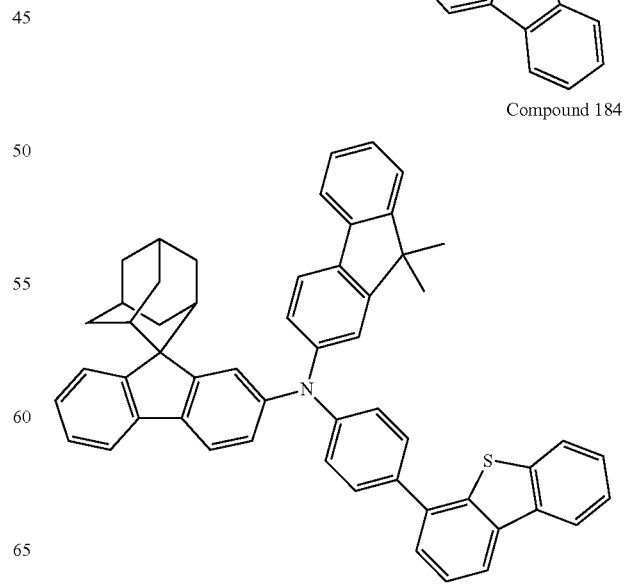

Compound 185
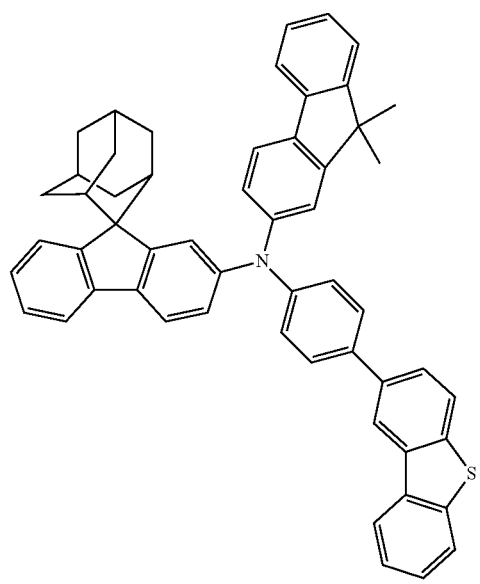
Compound 186
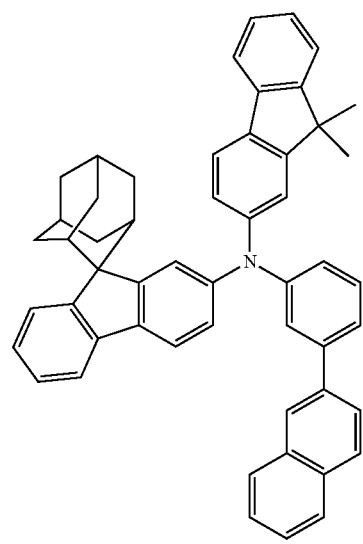
Compound 187
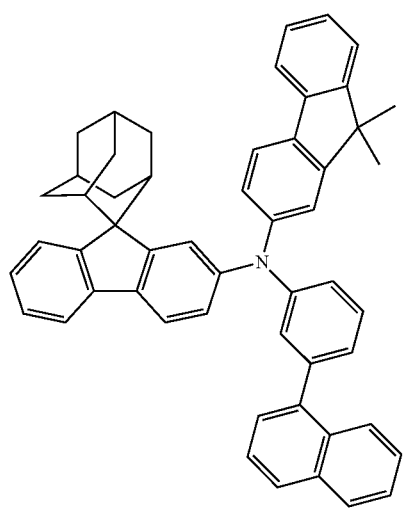
Compound 188
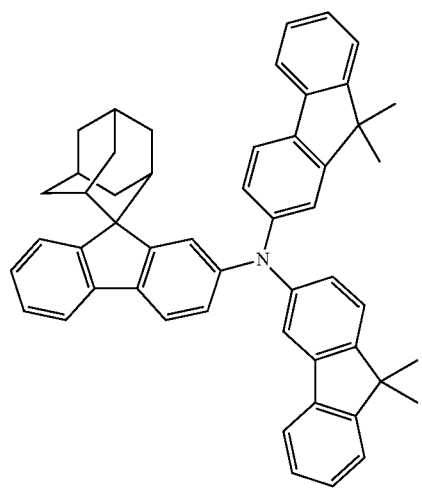
Compound 190
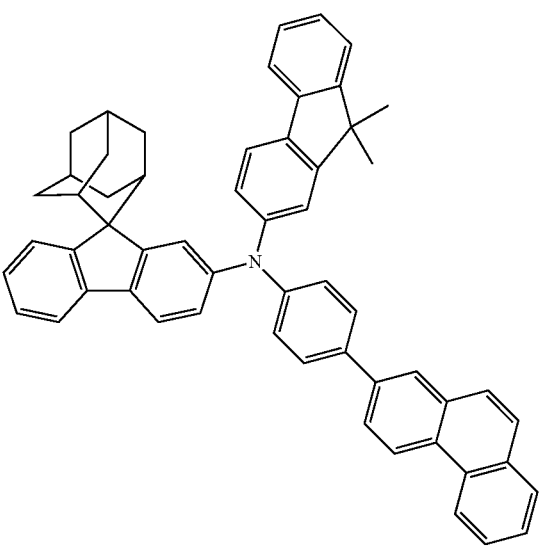
Compound 191
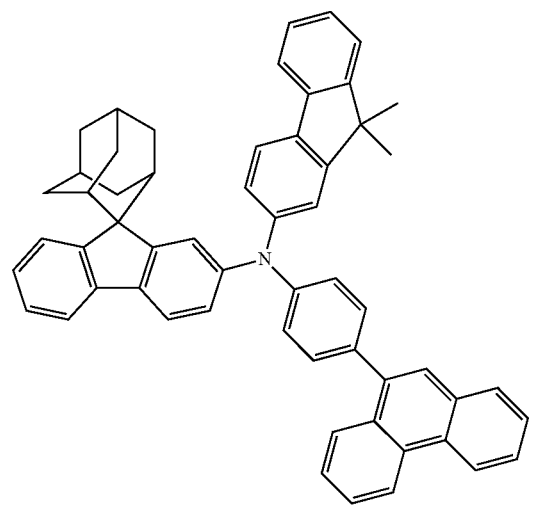

Compound 193
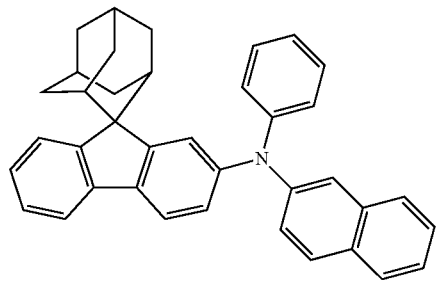
Compound 195
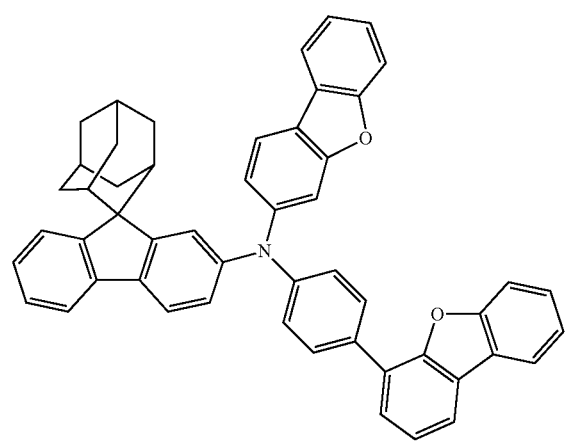
Compound 196
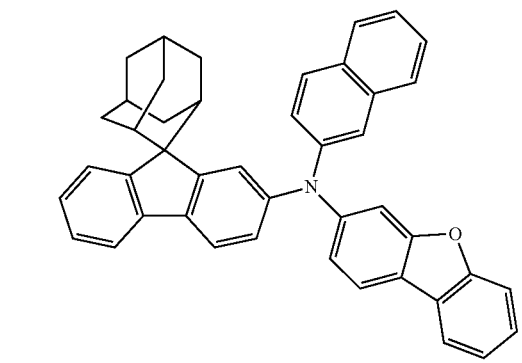
Compound 197
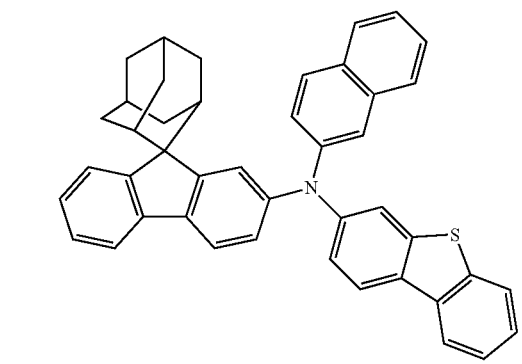
Compound 198
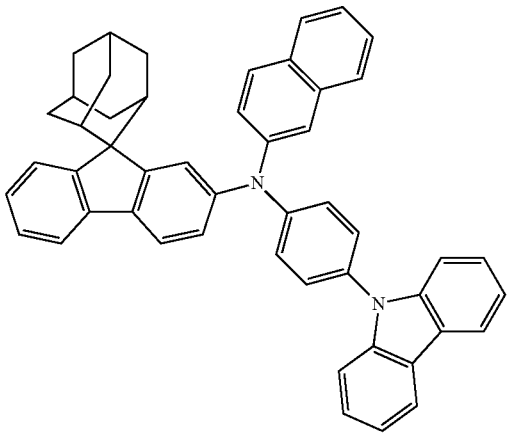
Compound 199
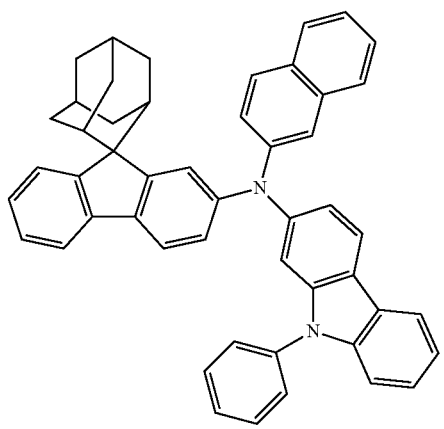
Compound 200
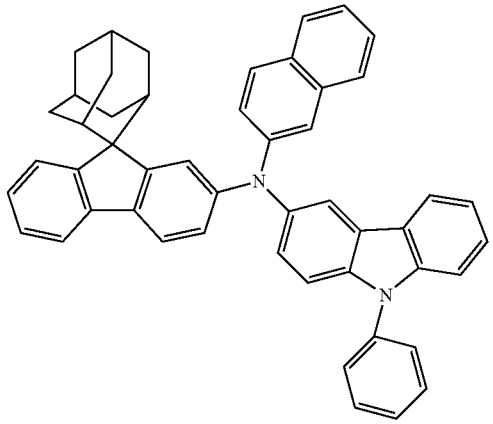

-continued
Compound 201
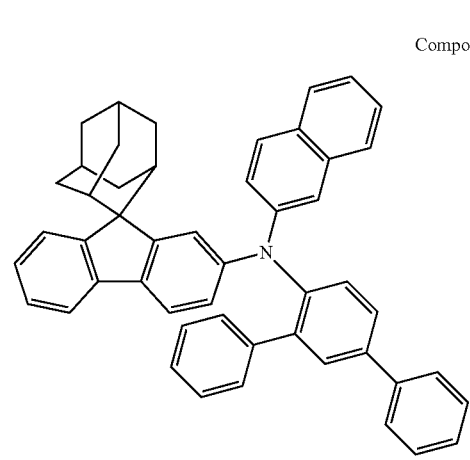
Compound 204
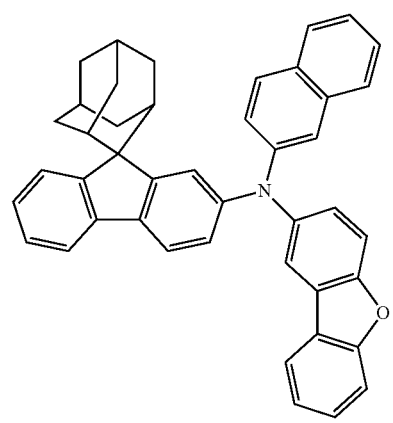
Compound 202
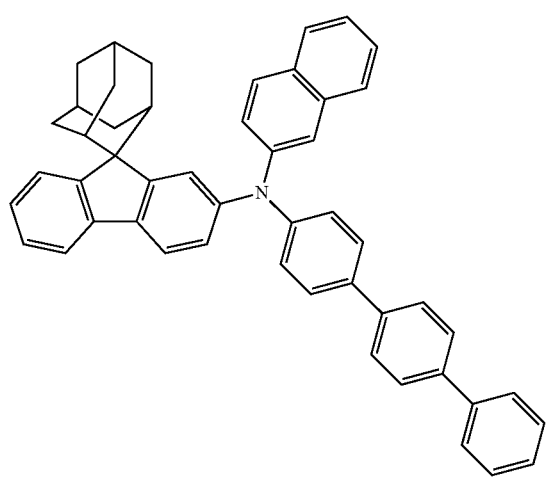
Compound 205
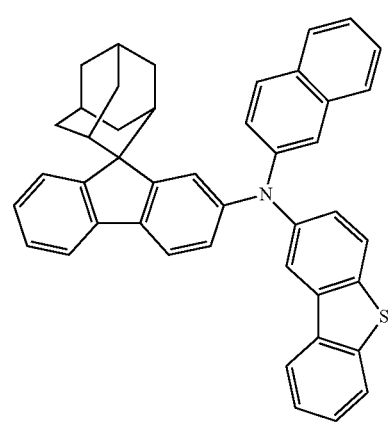
Compound 203
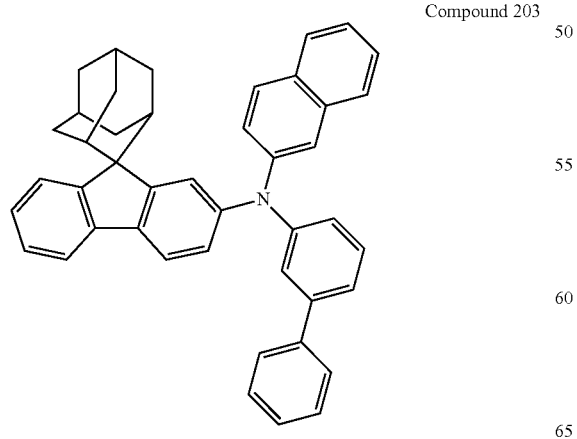
Compound 206
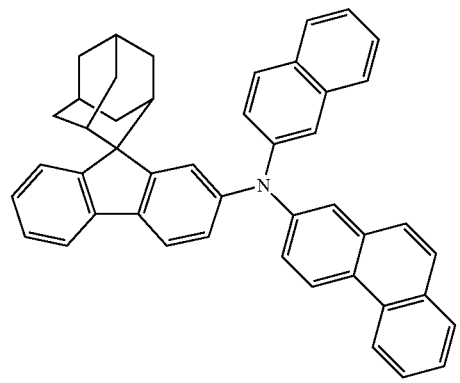

-continued
Compound 207
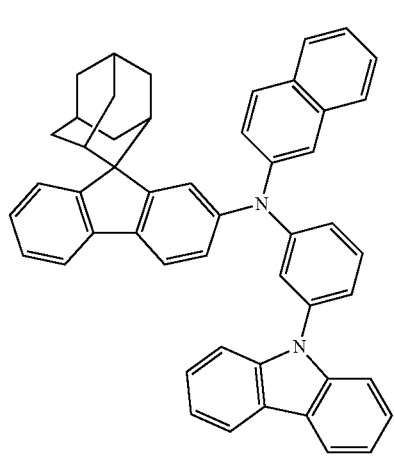
Compound 208
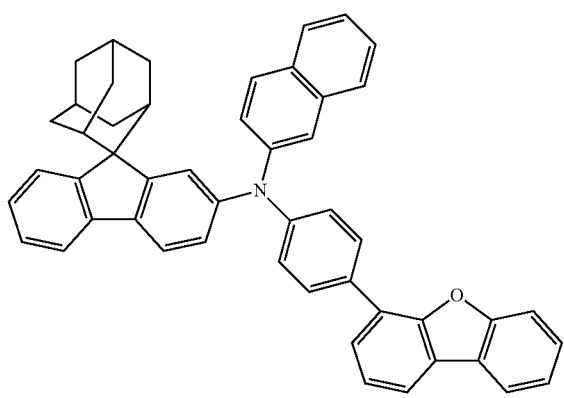
Compound 209
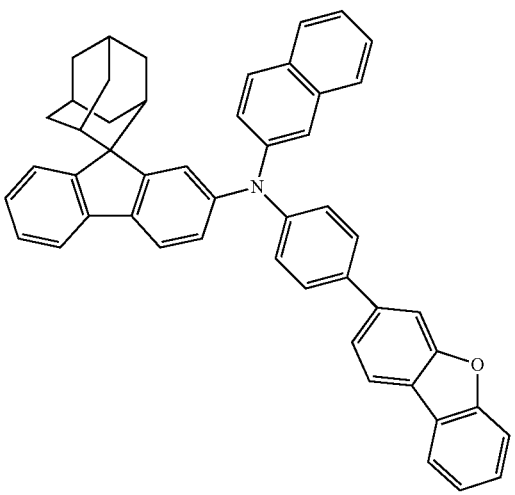
-continued
Compound 210
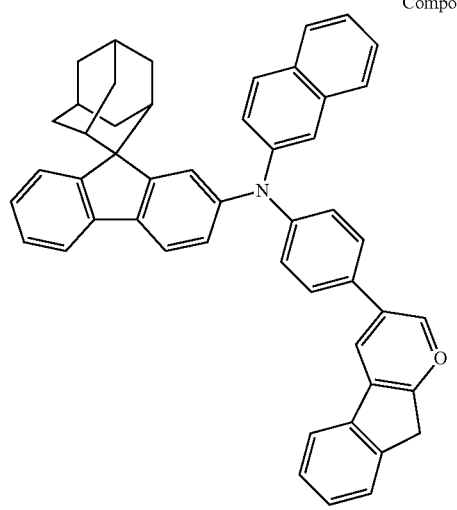
Compound 211
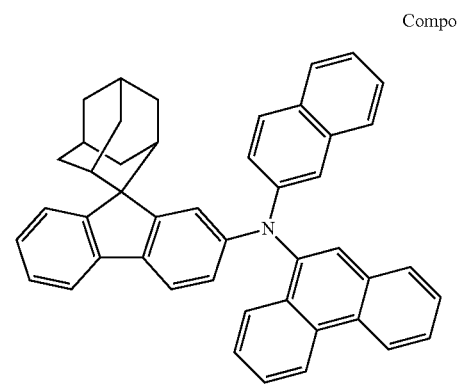
Compound 212
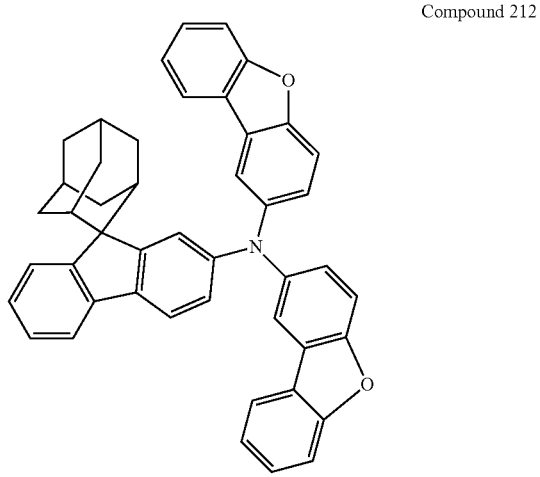

Compound 213
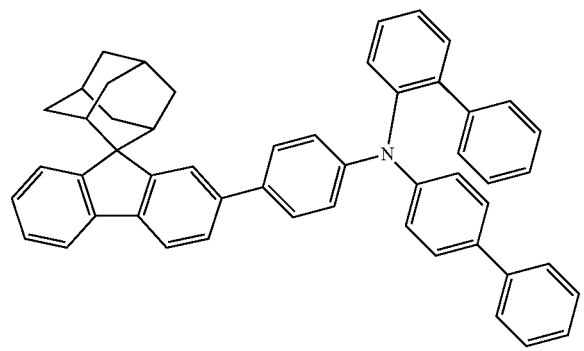
Compound 214
Compound 215
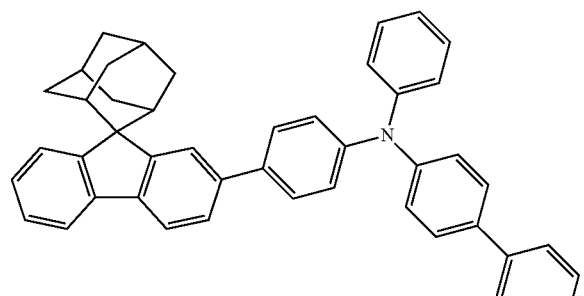
Compound 216
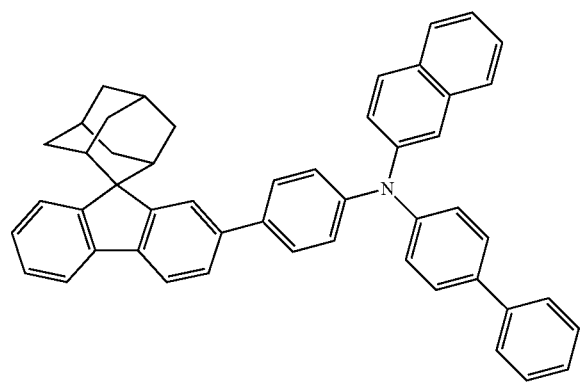
Compound 217
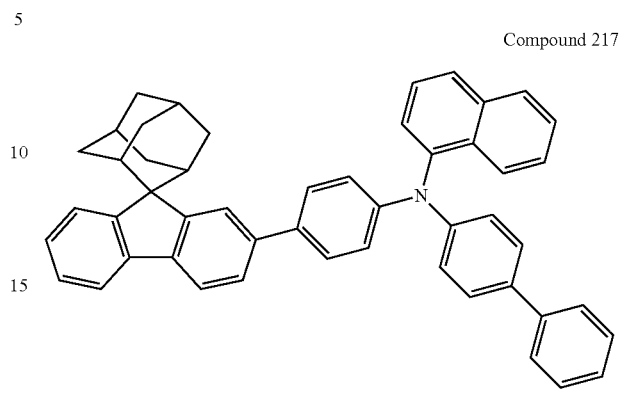
Compound 218
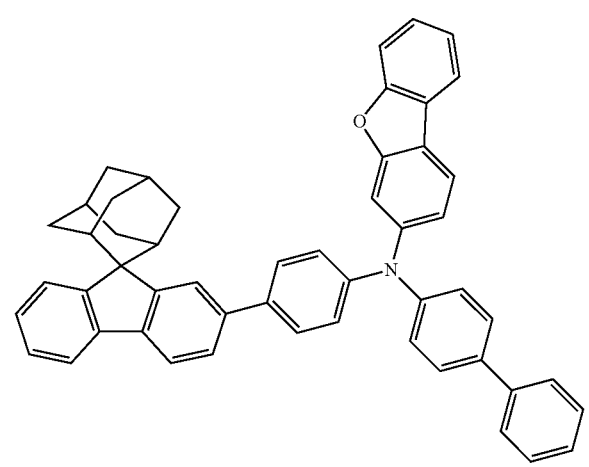
Compound 219
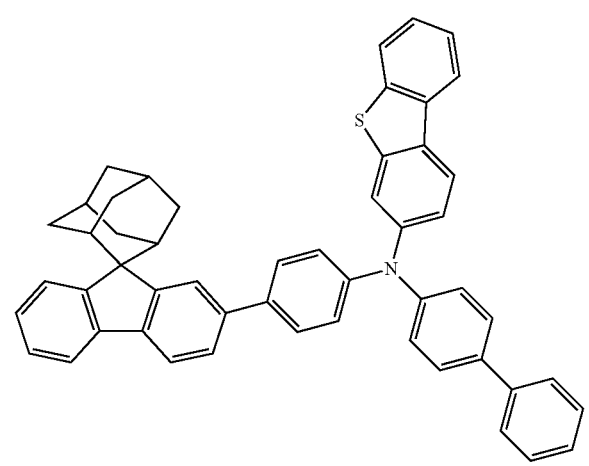

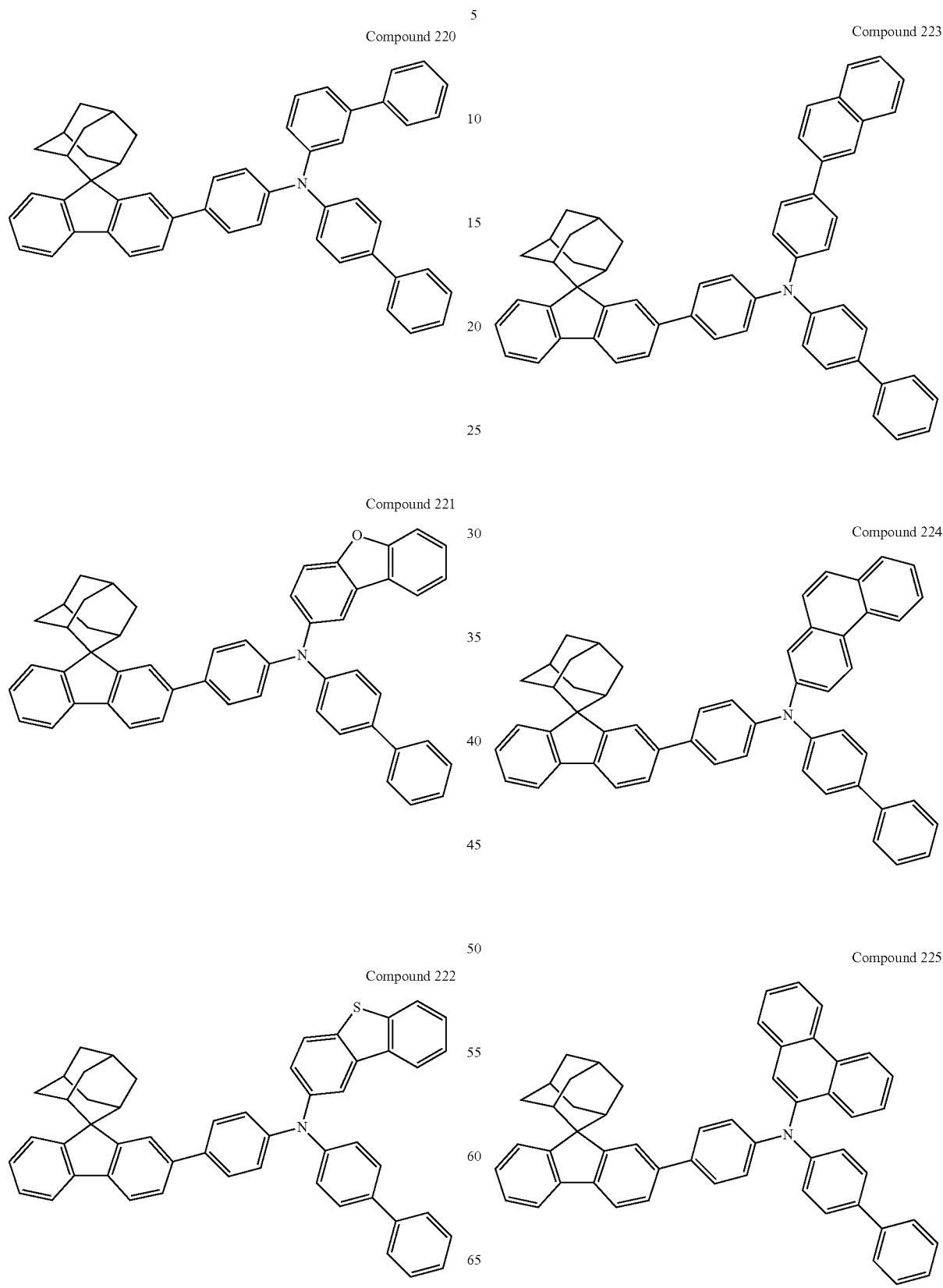

Compound 226
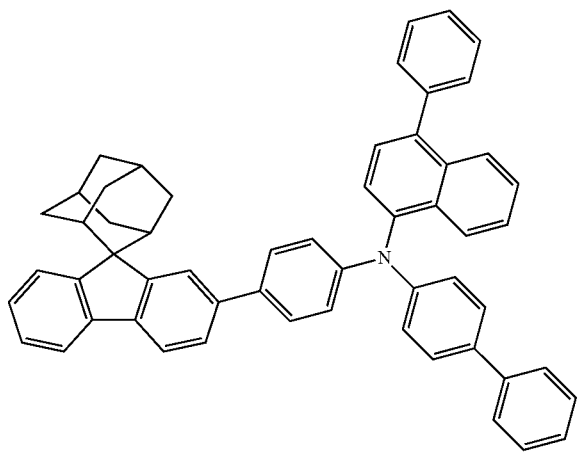
Compound 227
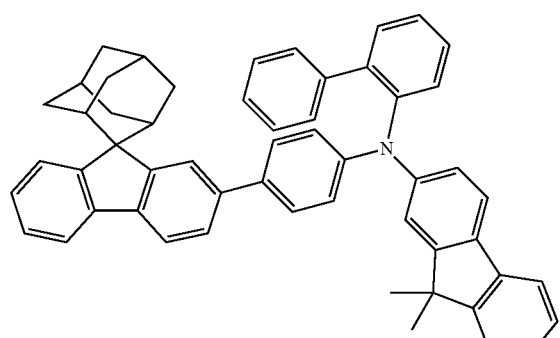
Compound 228
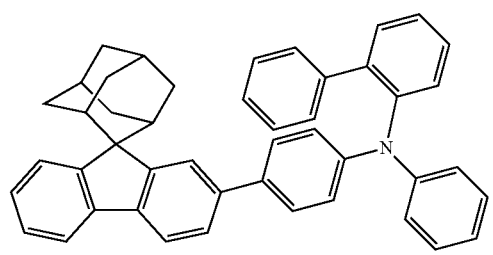
Compound 229
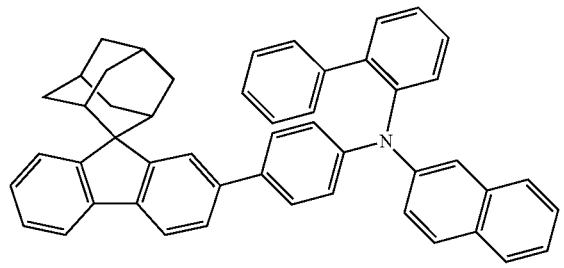
Compound 230
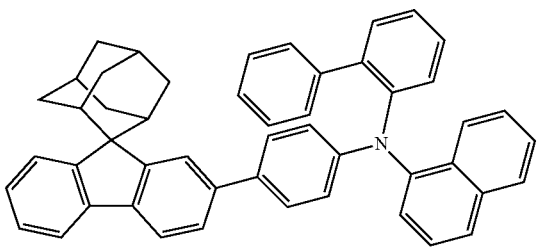
Compound 231
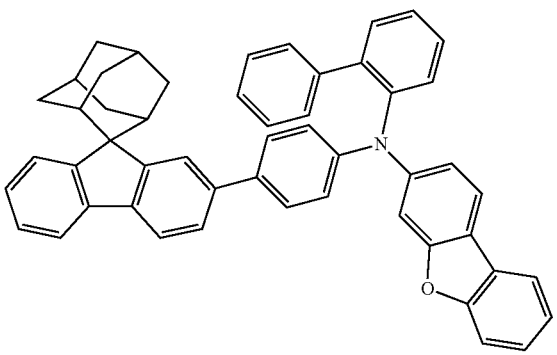
Compound 232
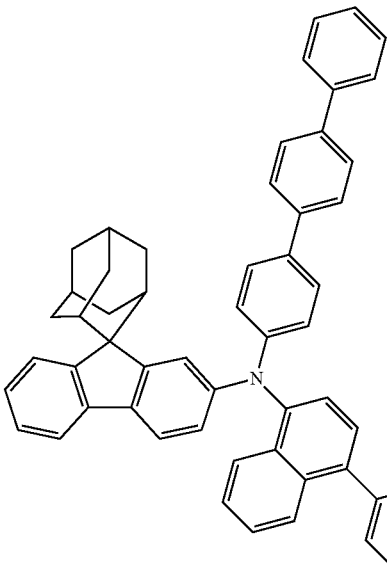
Compound 233
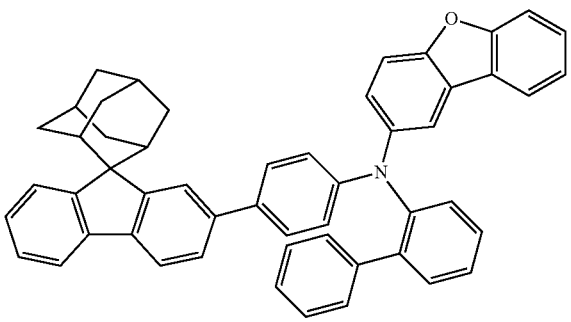

Compound 234
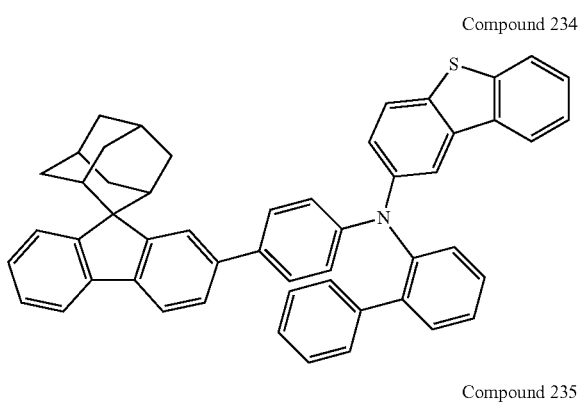
Compound 235
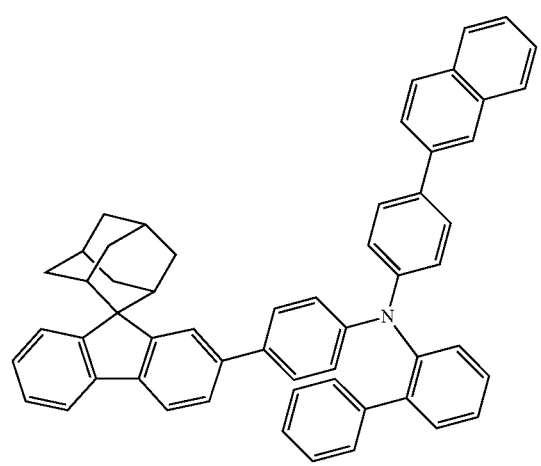
Compound 236
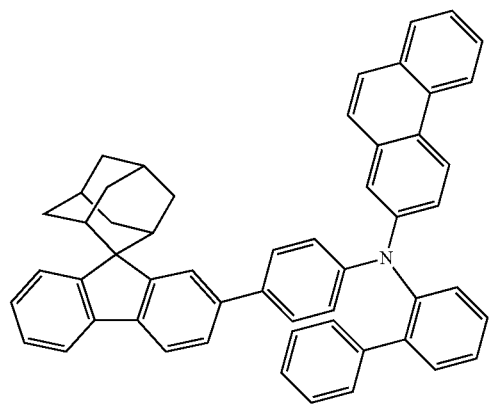
Compound 237
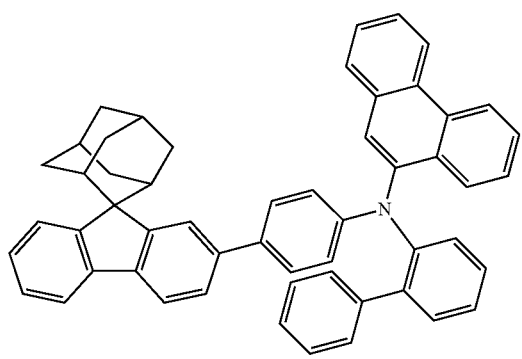
Compound 238
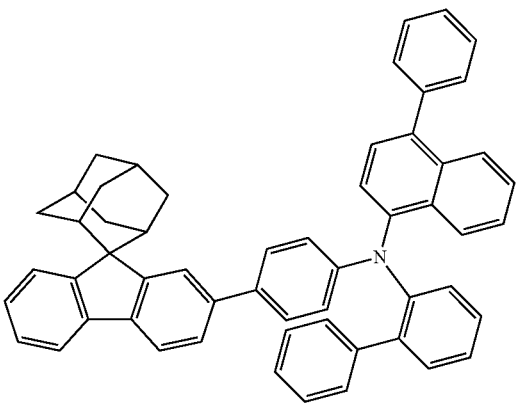
Compound 239
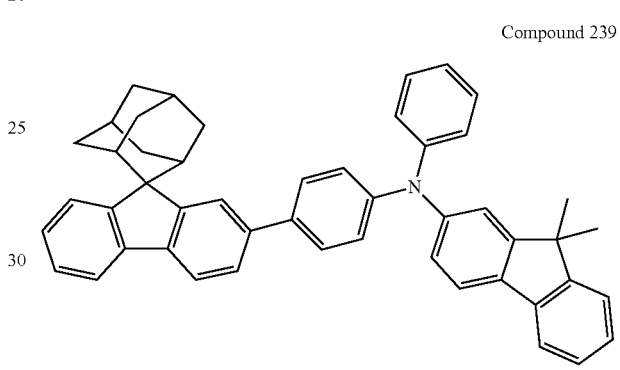
Compound 240
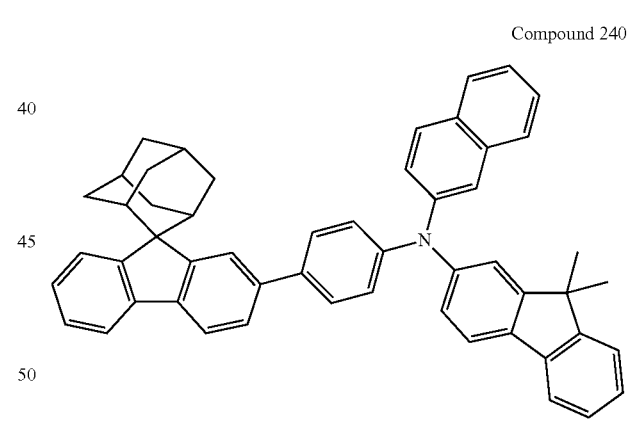
Compound 241
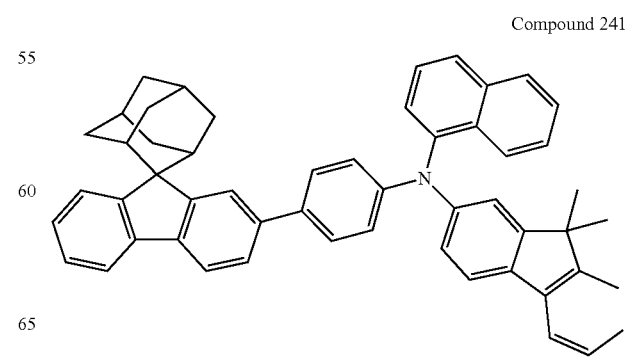

Compound 242
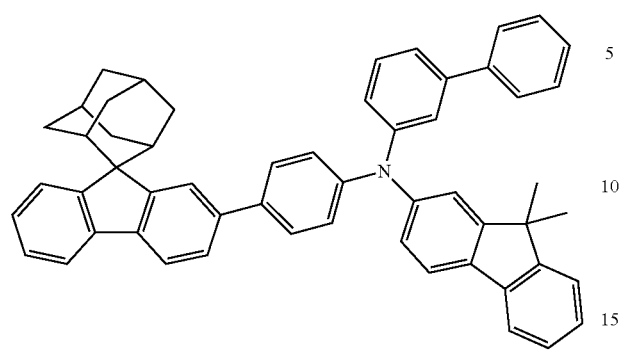
Compound 243
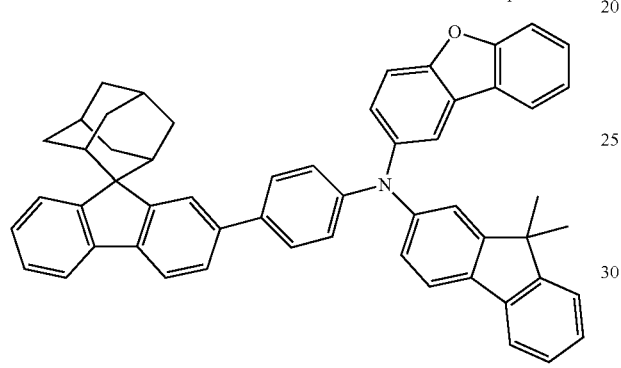
Compound 244
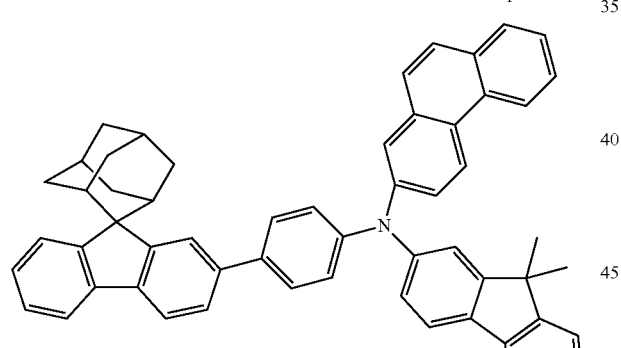
Compound 245
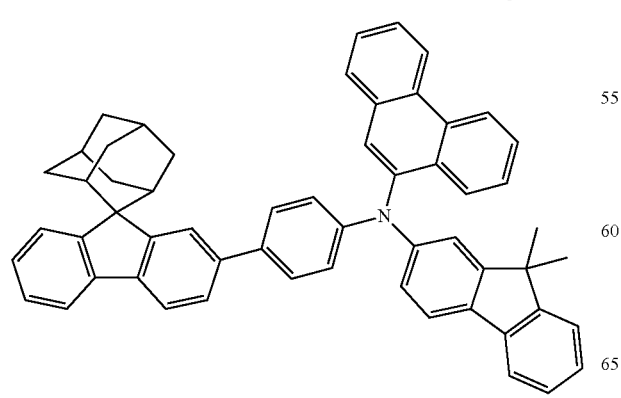
Compound 246
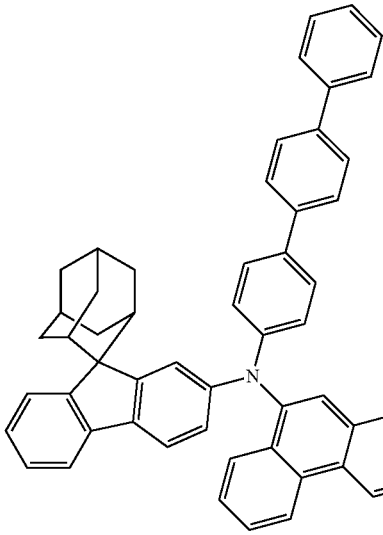
Compound 247
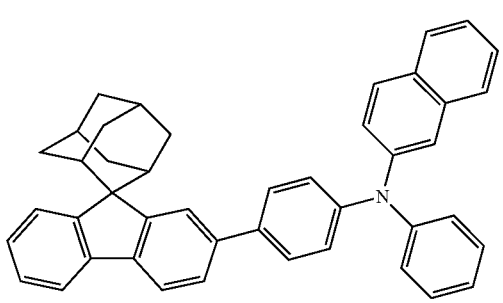
Compound 248
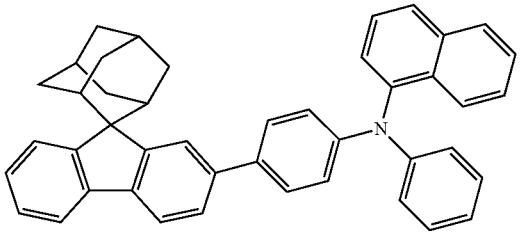
Compound 249
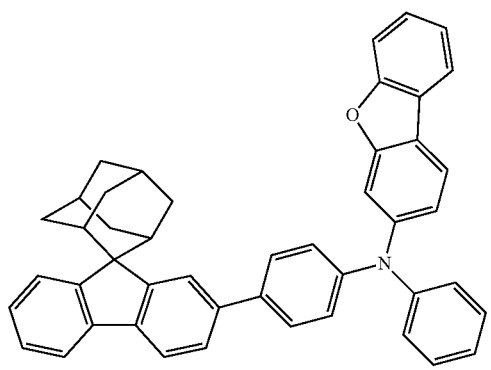

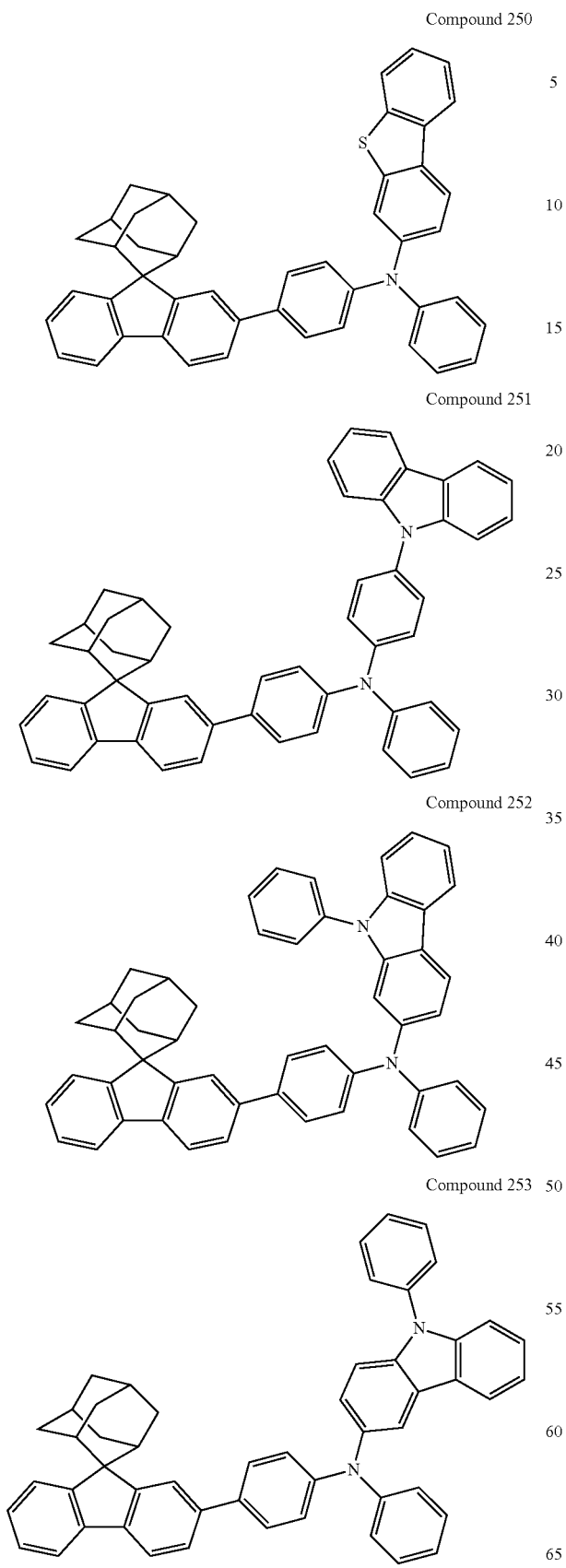
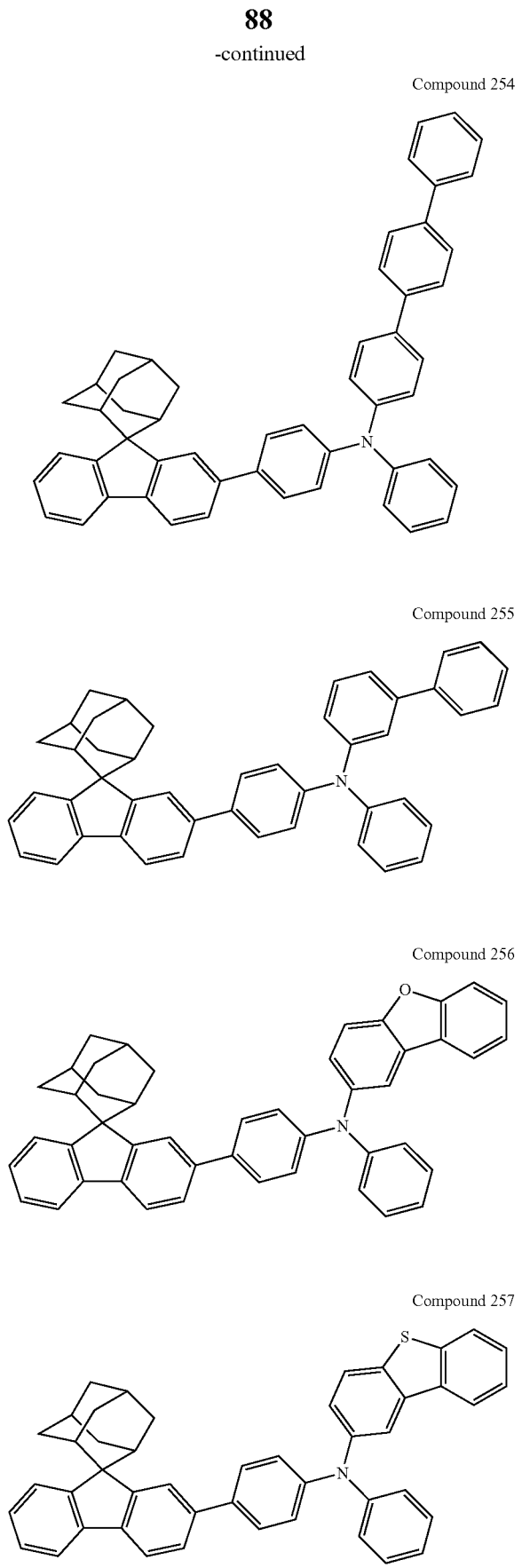

Compound 258
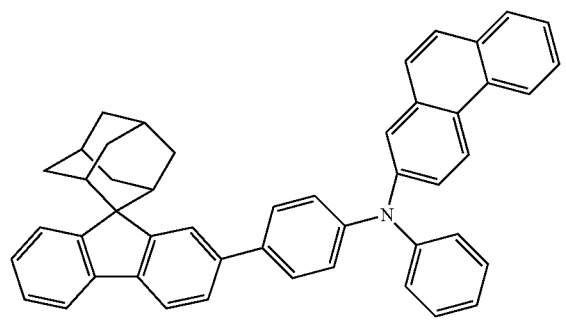
Compound 259
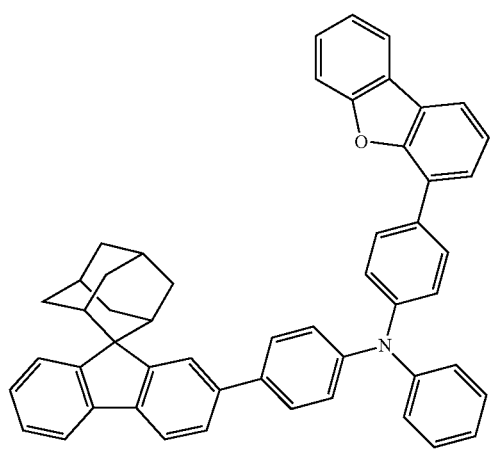
Compound 260
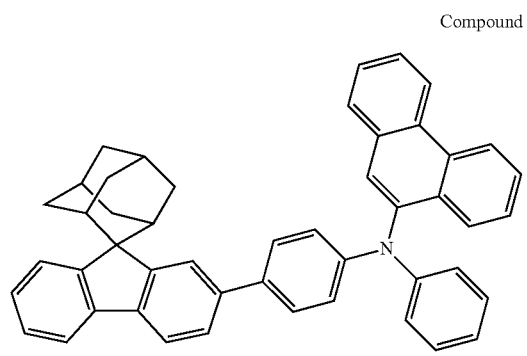
Compound 261
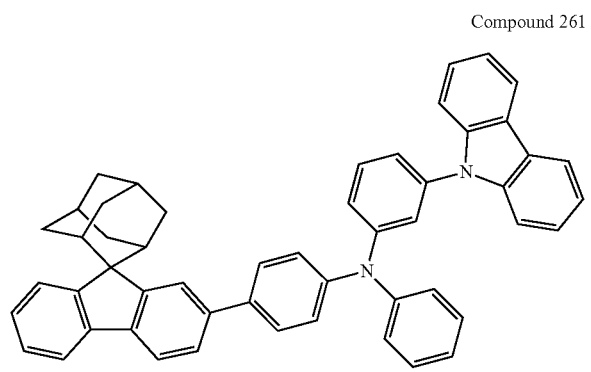
Compound 262
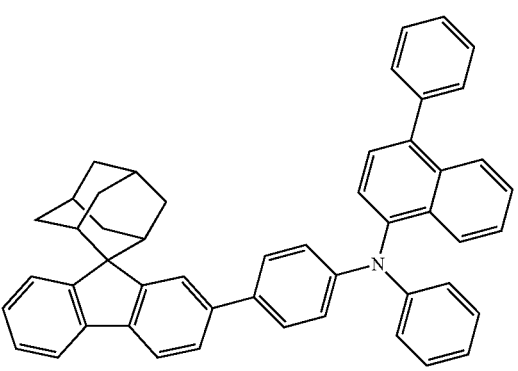
Compound 263
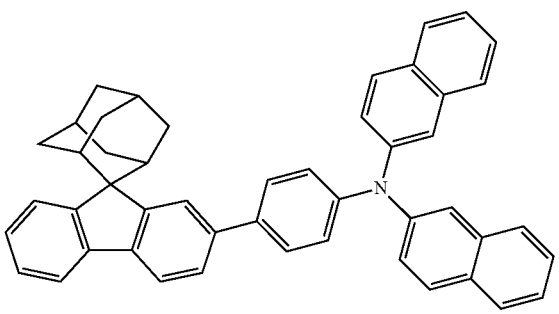
Compound 264
Compound 265
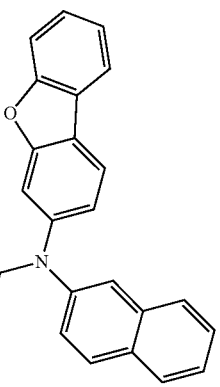

Compound 266
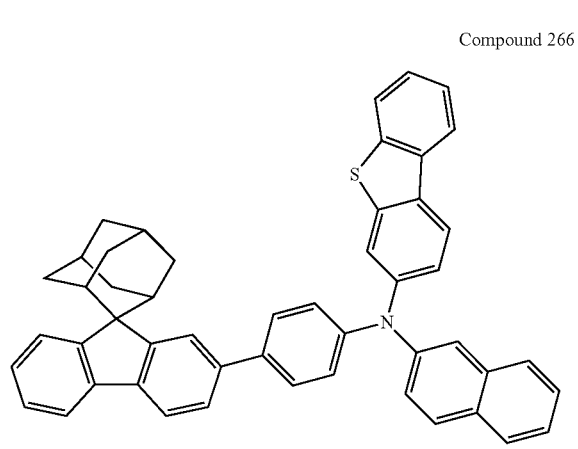
Compound 269
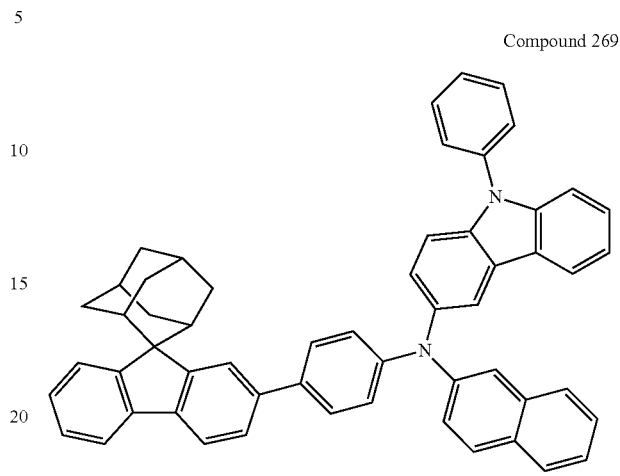
Compound 267
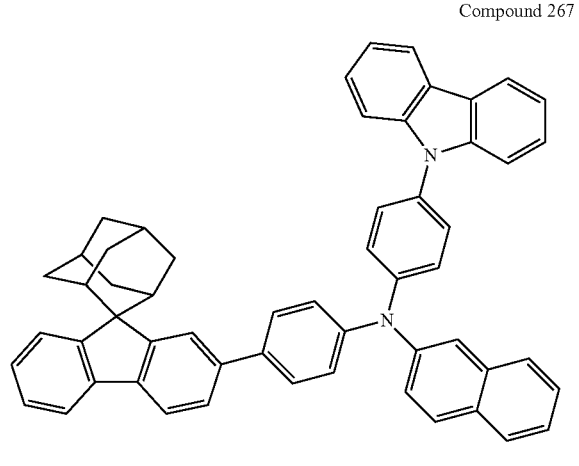
Compound 270
Compound 268
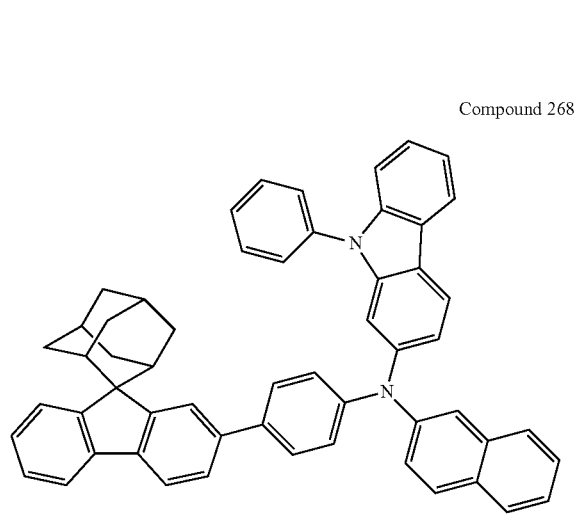
Compound 271
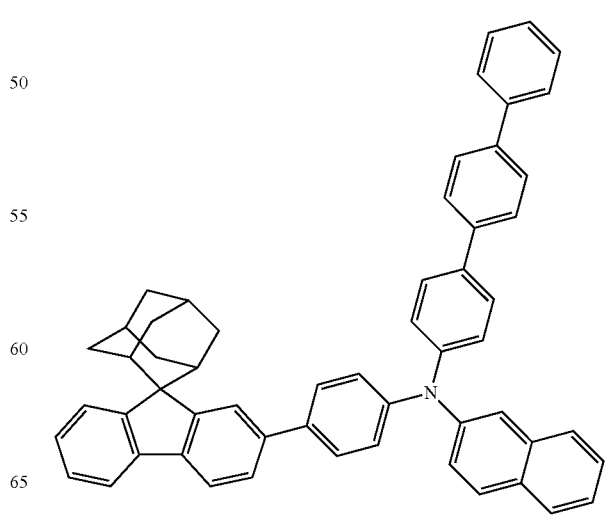

Compound 272
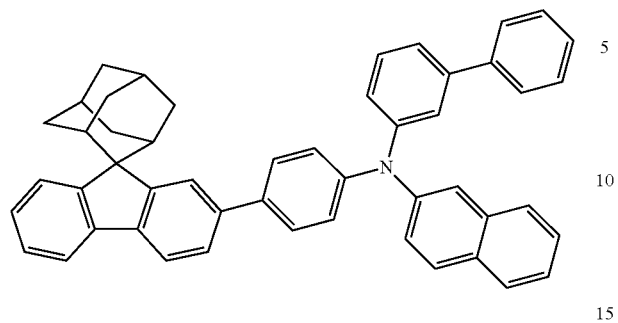
Compound 276
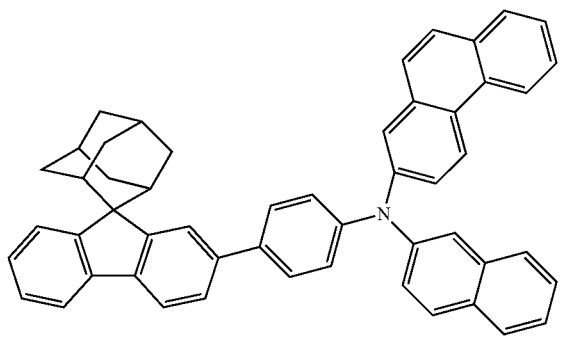
Compound 273
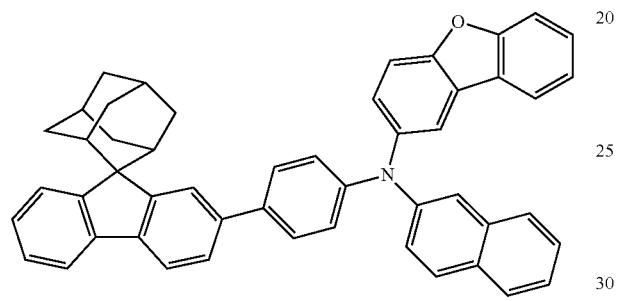
Compound 277
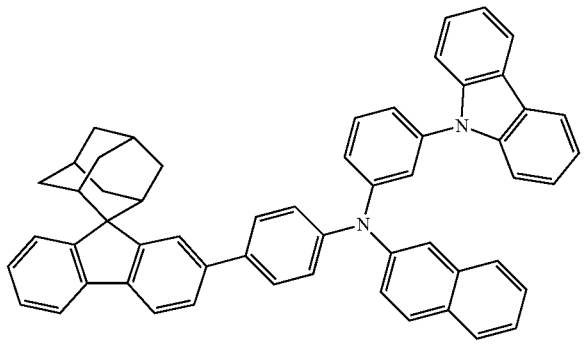
Compound 274
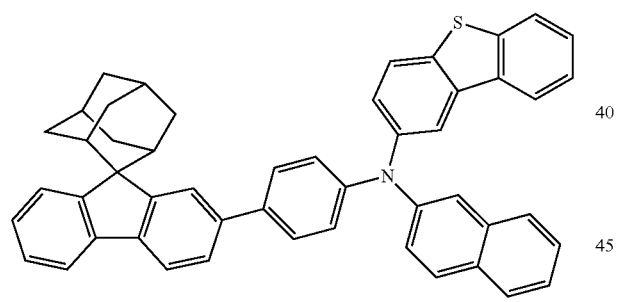
Compound 278
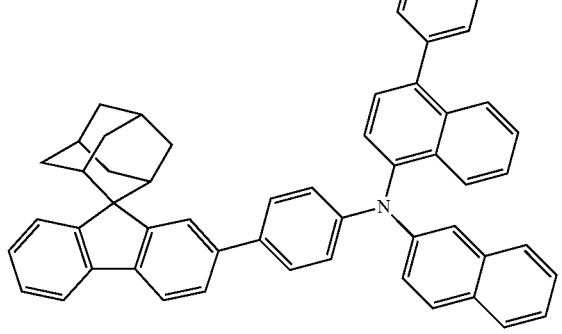
Compound 275
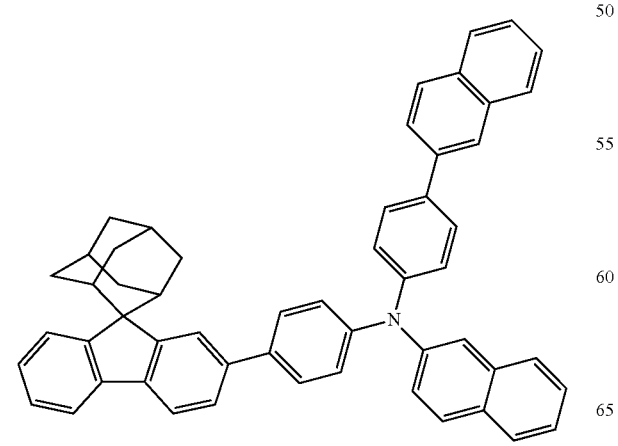
Compound 279
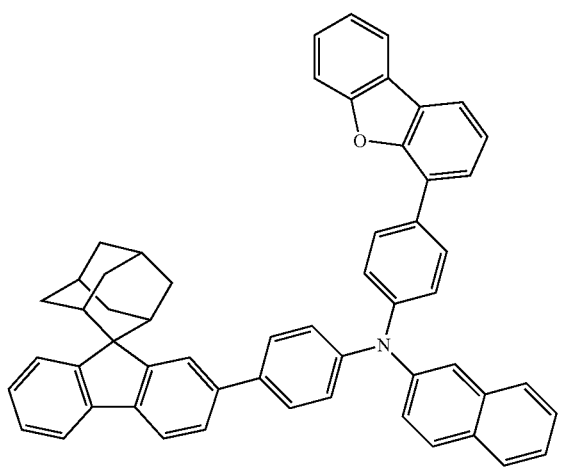

Compound 281
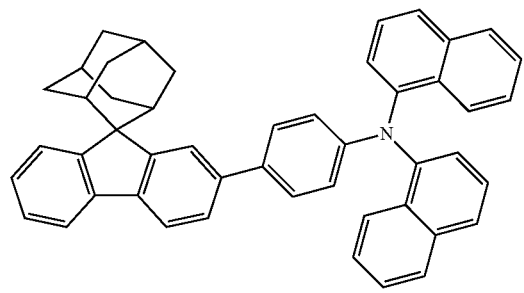
Compound 282
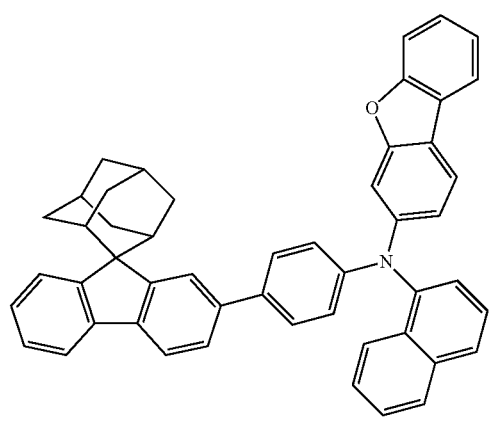
Compound 283
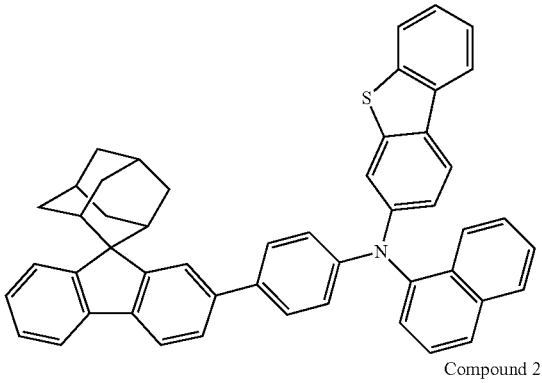
Compound 284
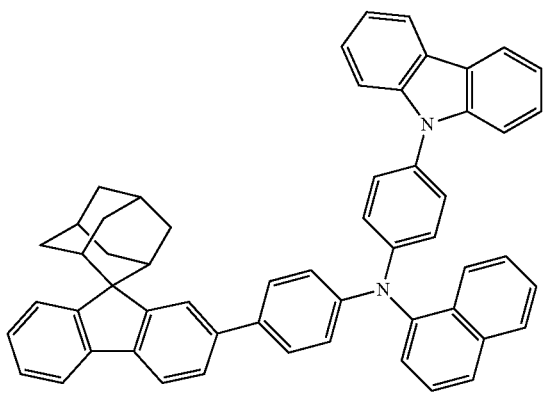
Compound 285
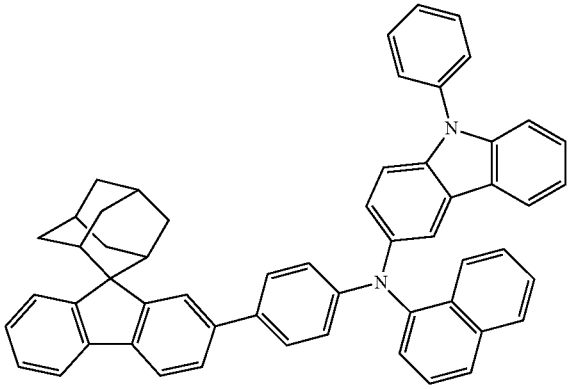
Compound 286
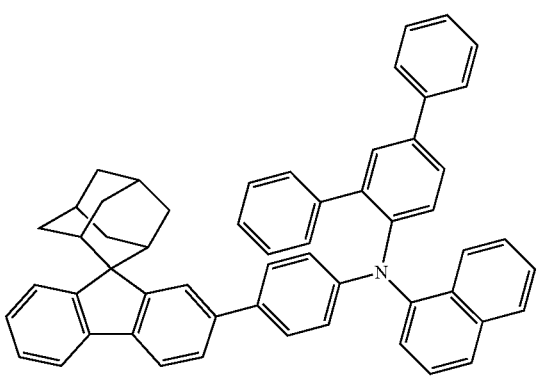
Compound 287
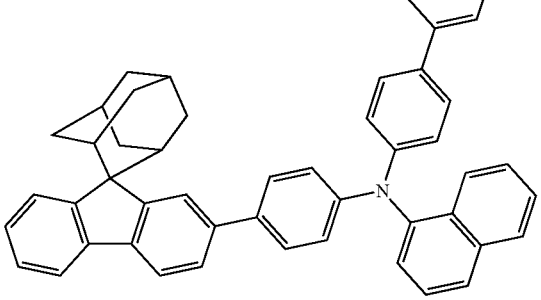

Compound 288
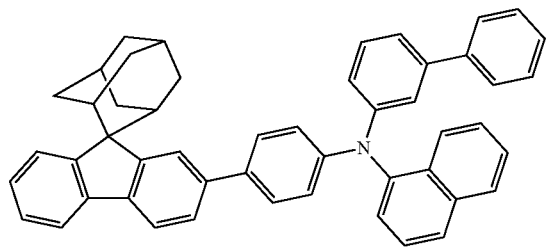
Compound 289
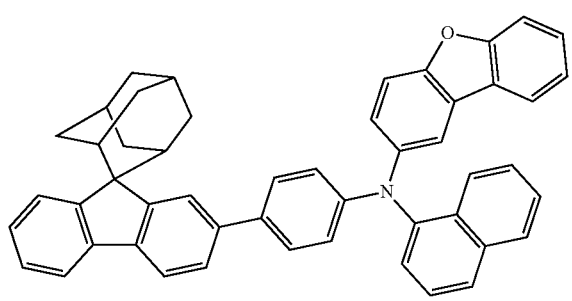
Compound 290
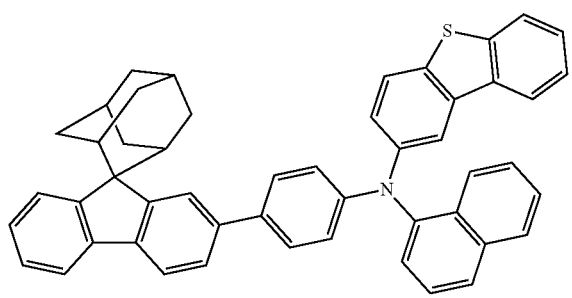
Compound 291
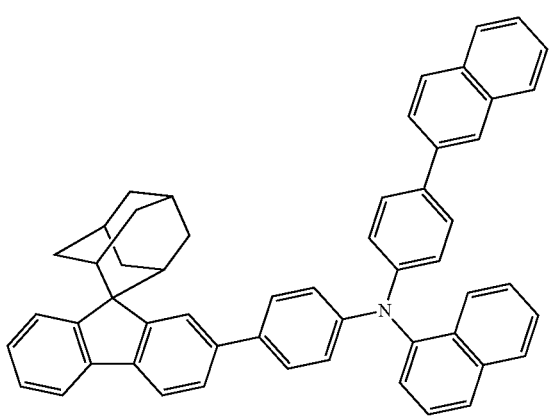
Compound 292
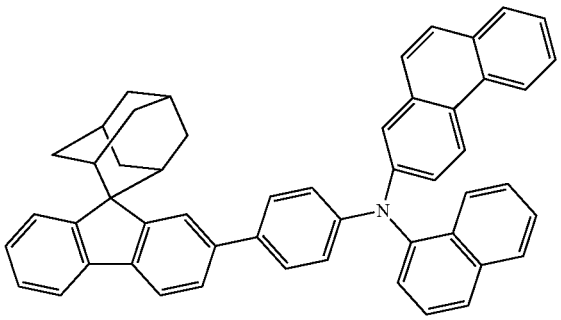
Compound 293
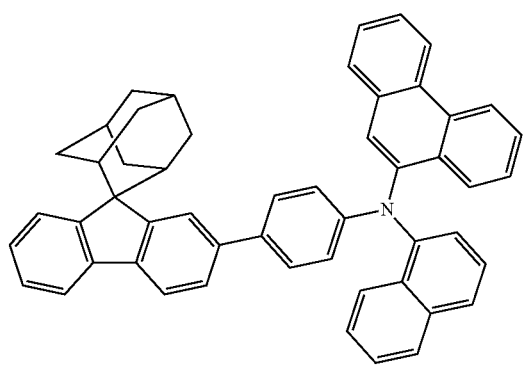
Compound 294
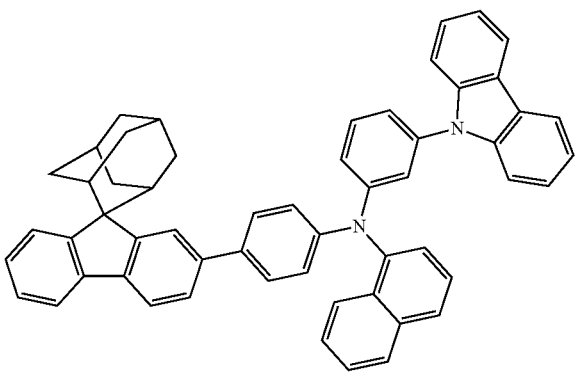
Compound 295
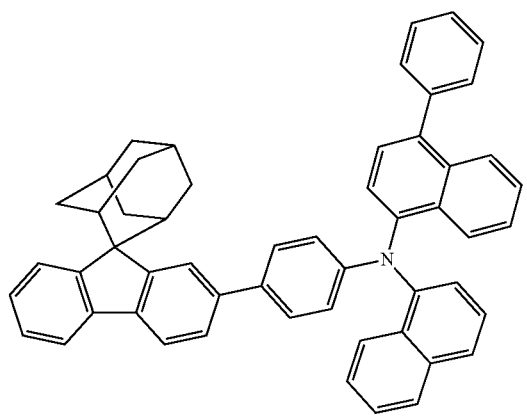

Compound 296
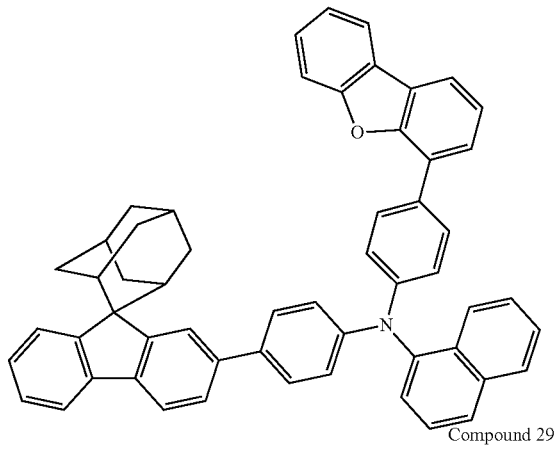
Compound 298
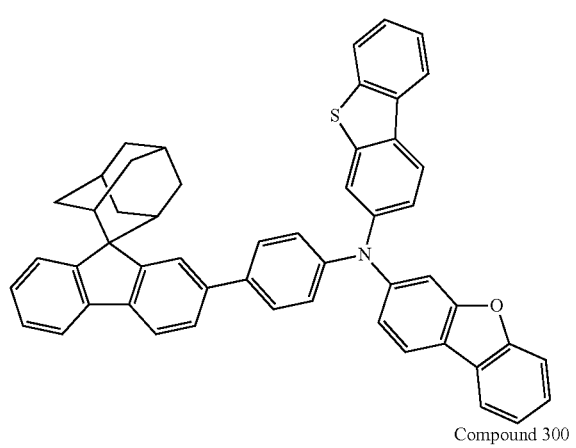
Compound 299
Compound 300
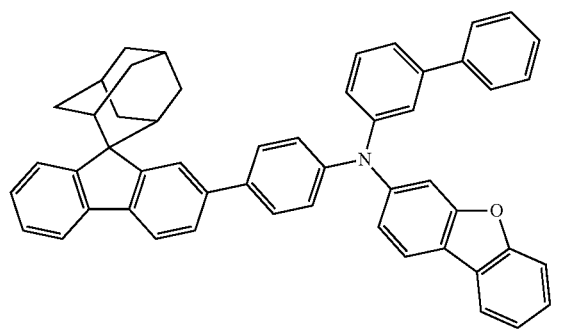
Compound 301
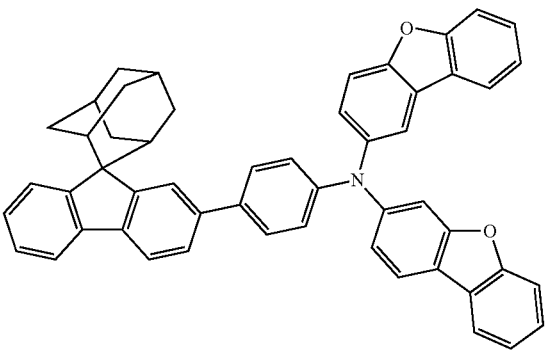
Compound 302
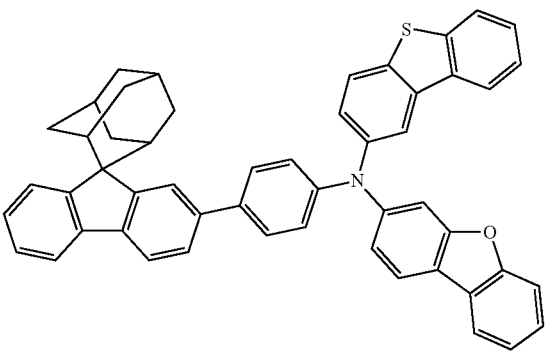
Compound 303
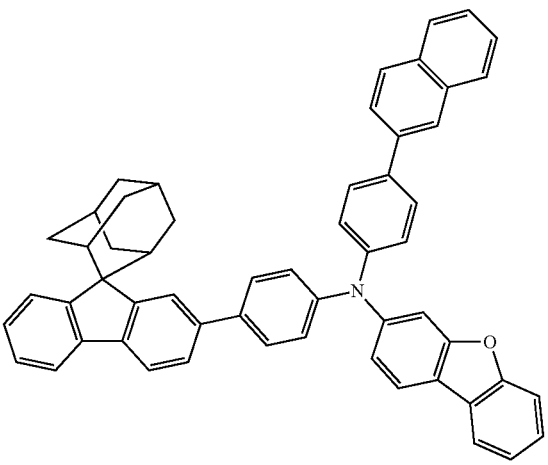
Compound 304
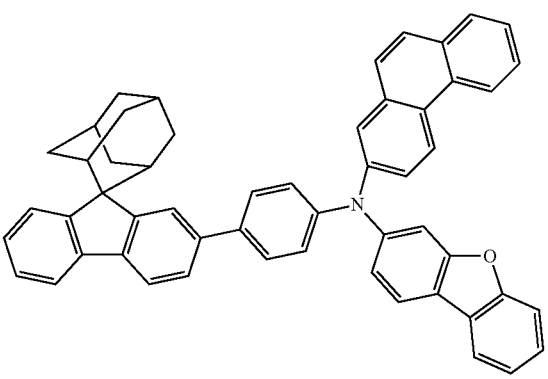

Compound 305
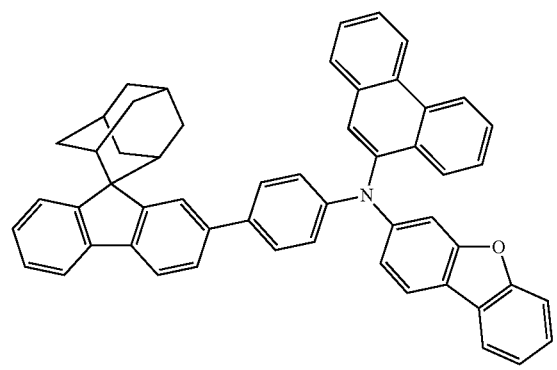
Compound 310
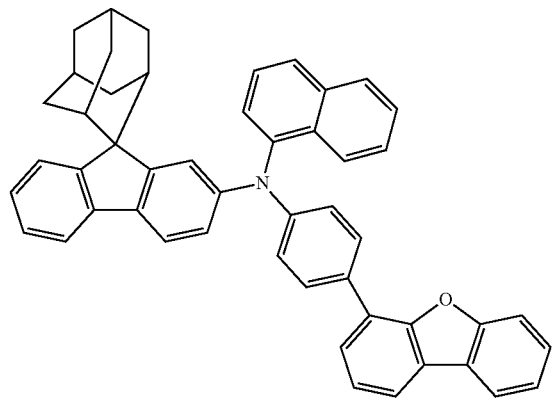
Compound 306
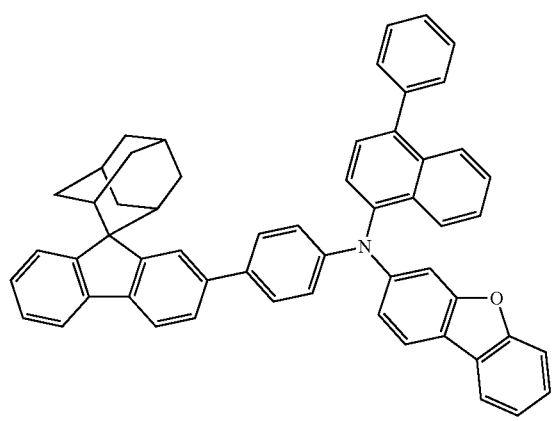
Compound 311
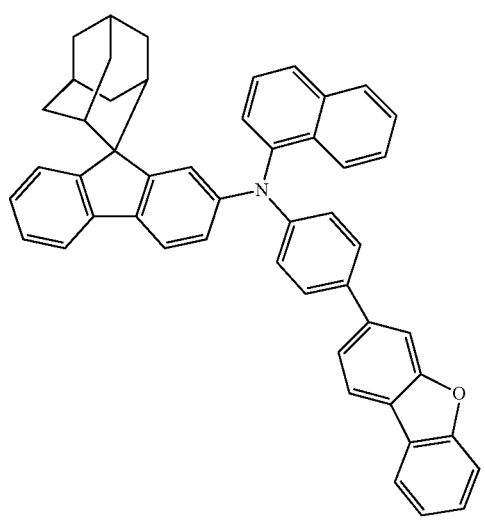
Compound 309
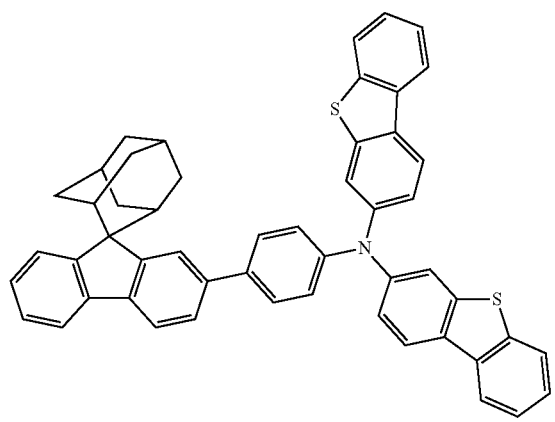
Compound 312
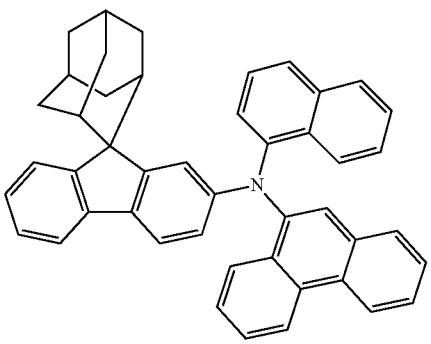

Compound 313
Compound 314
Compound 315
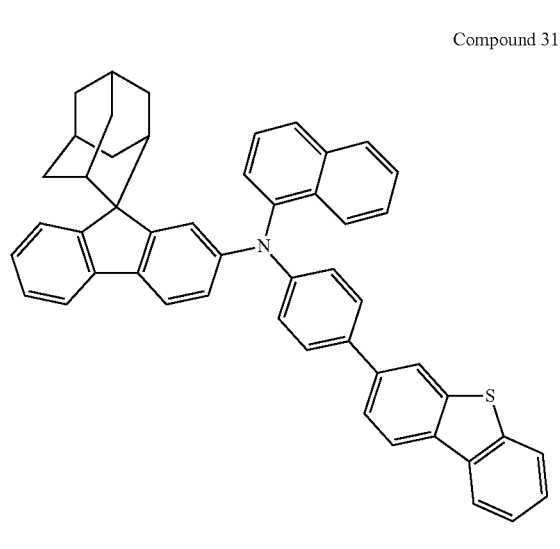
Compound 316
Compound 317
Compound 318
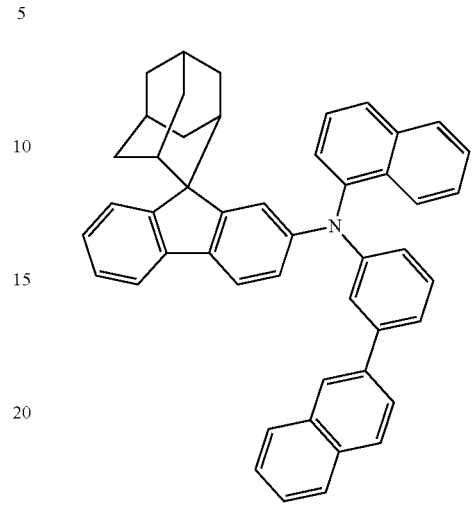
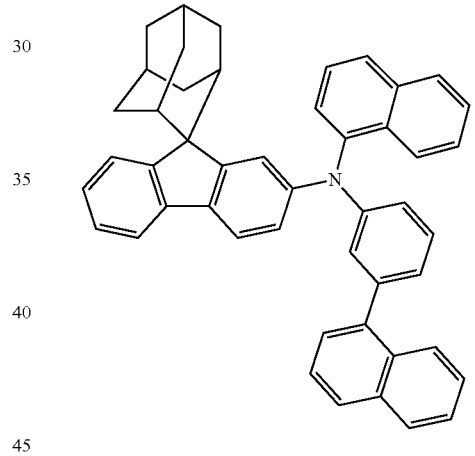
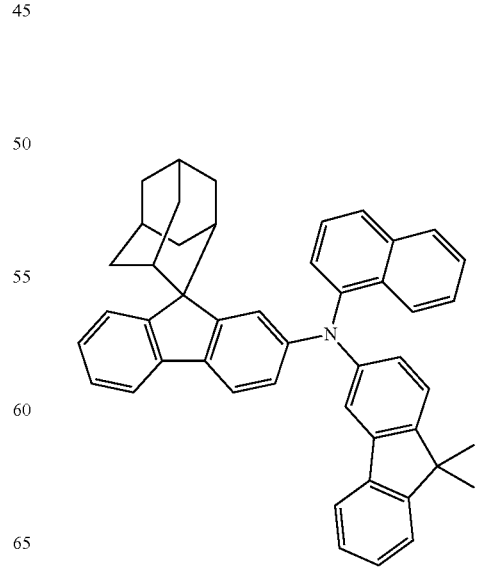

Compound 319
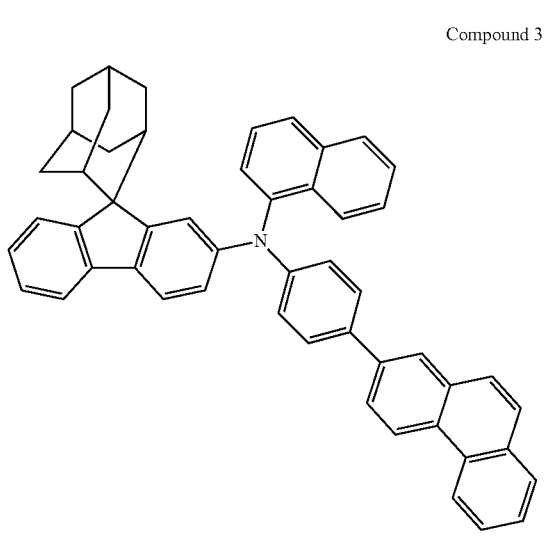
Compound 320
Compound 321
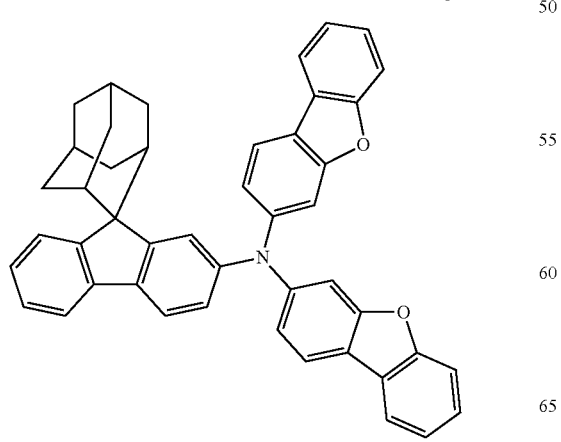
Compound 322
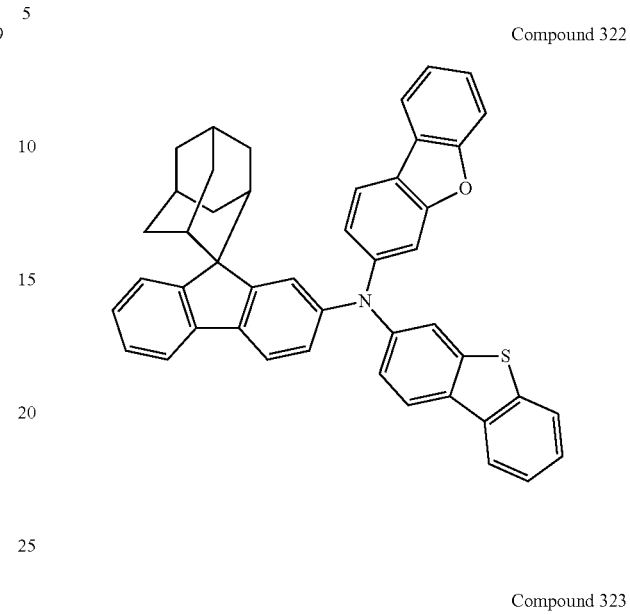
Compound 323
Compound 324
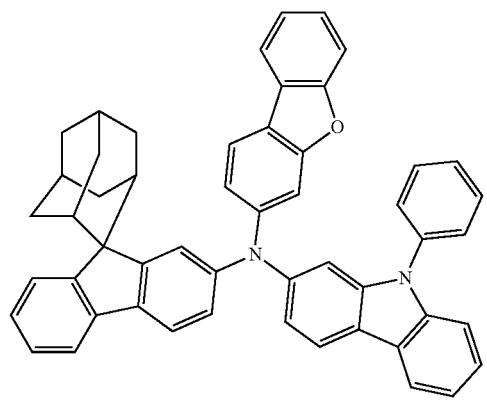

Compound 325
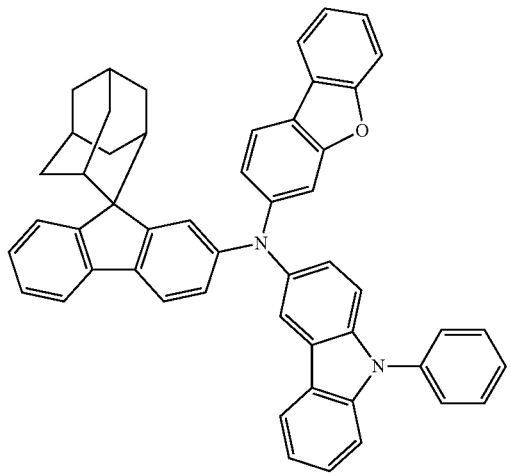
Compound 326
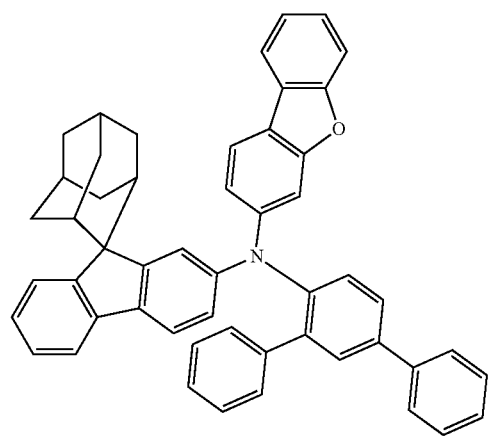
Compound 327
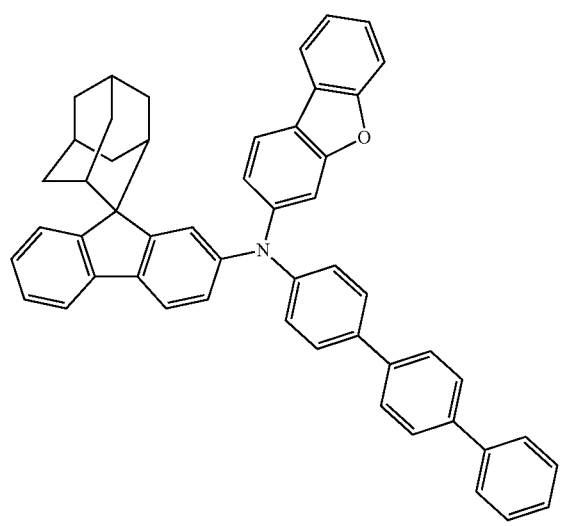
Compound 328
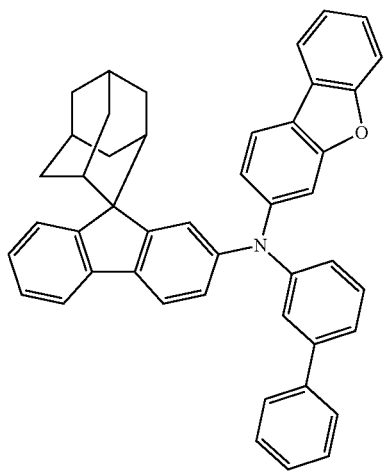
Compound 329
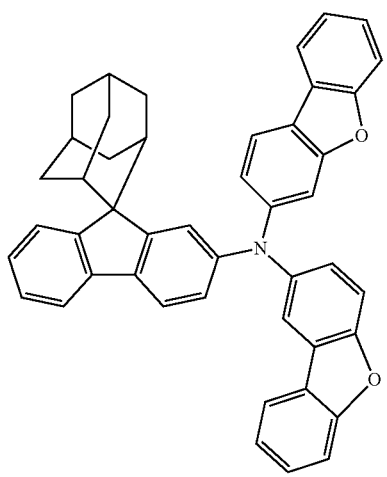
Compound 330
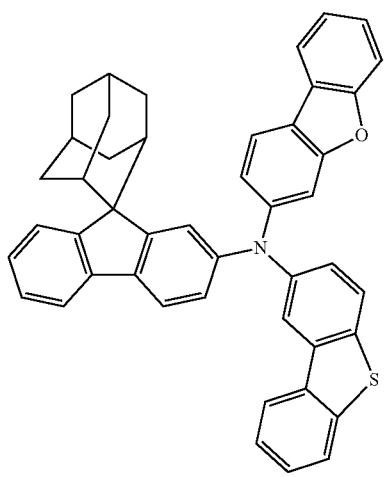

Compound 331
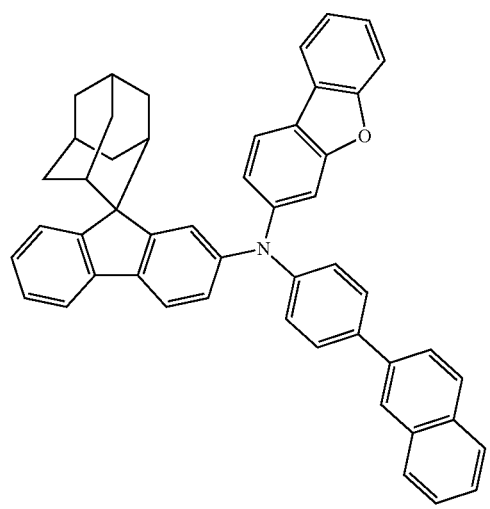
Compound 332
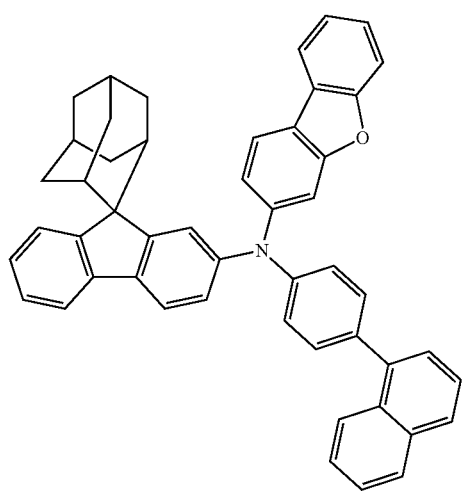
Compound 333
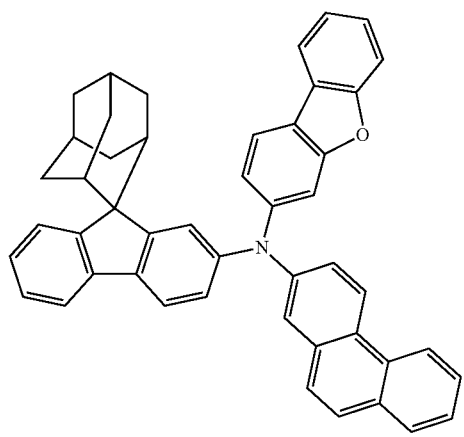
Compound 334
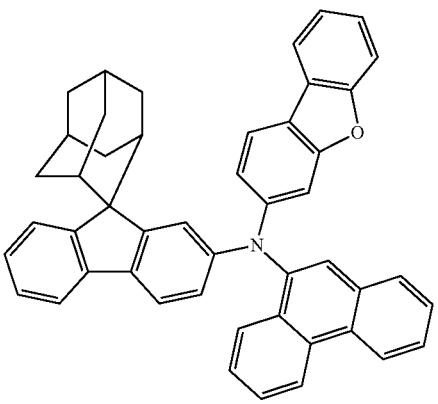
Compound 335
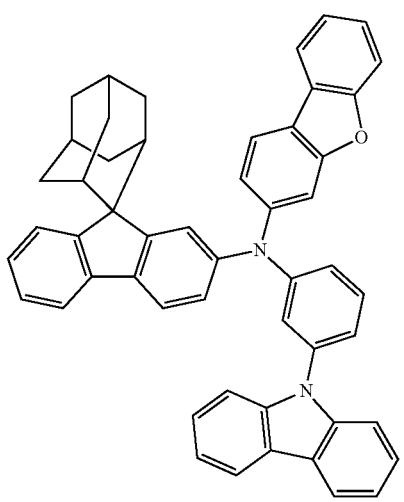
Compound 336
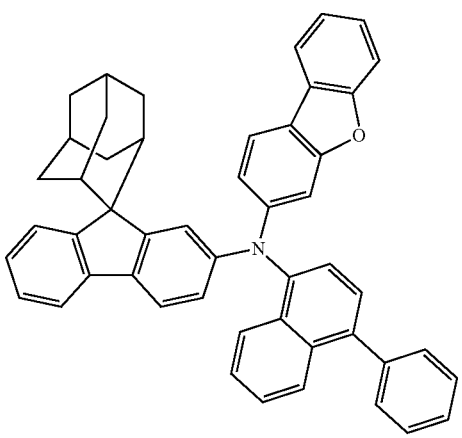

Compound 337
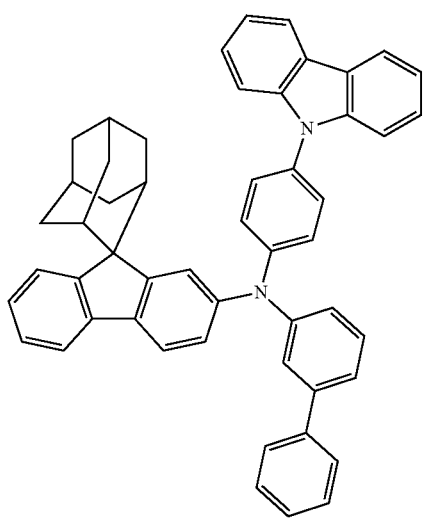
Compound 338
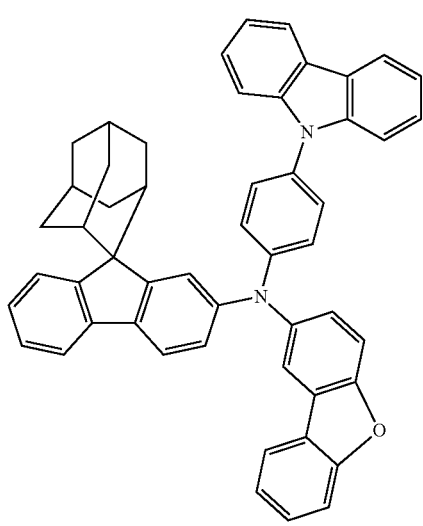
Compound 339
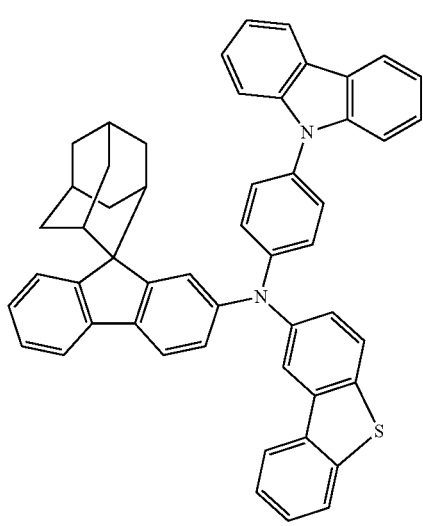
Compound 340
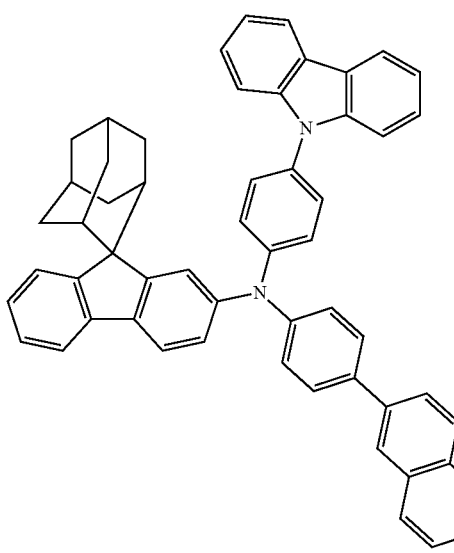
Compound 341
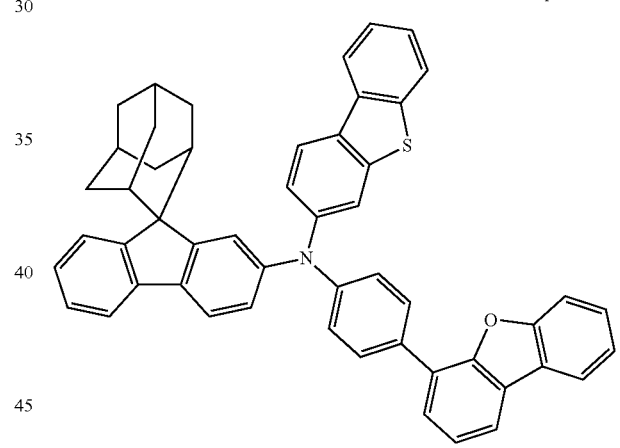
Compound 342
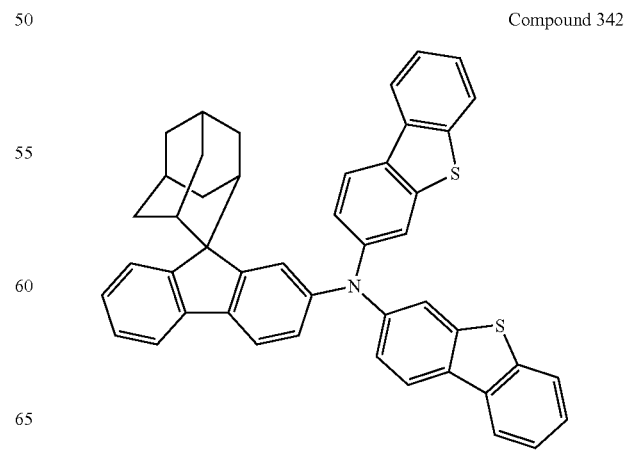

Compound 343
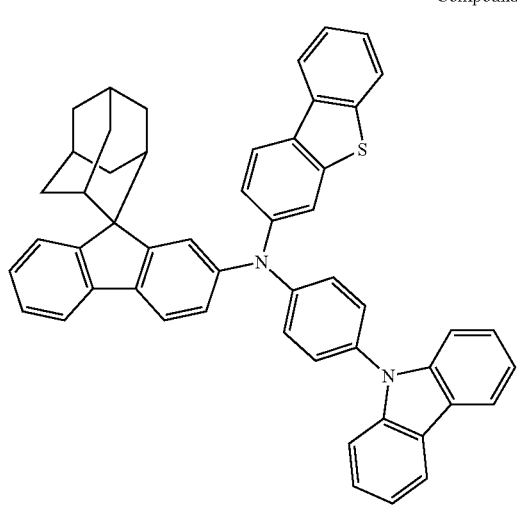
Compound 344
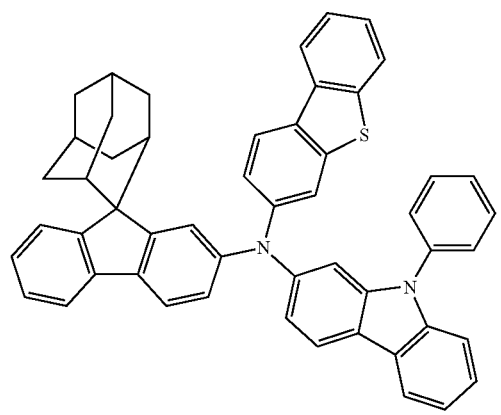
Compound 345
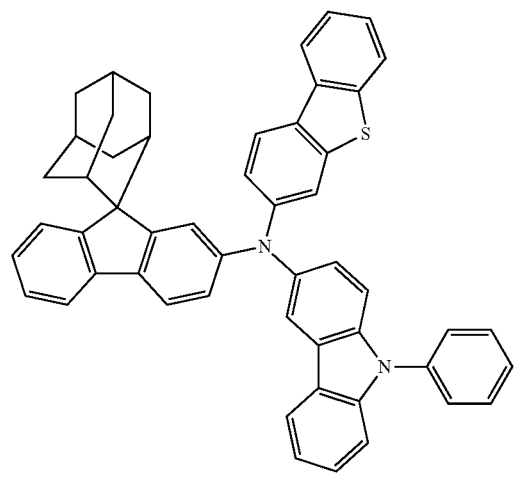
Compound 346
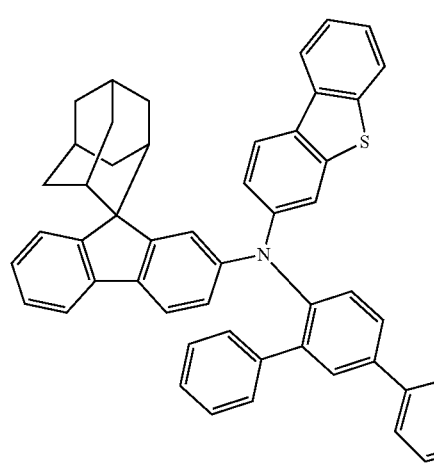
Compound 347
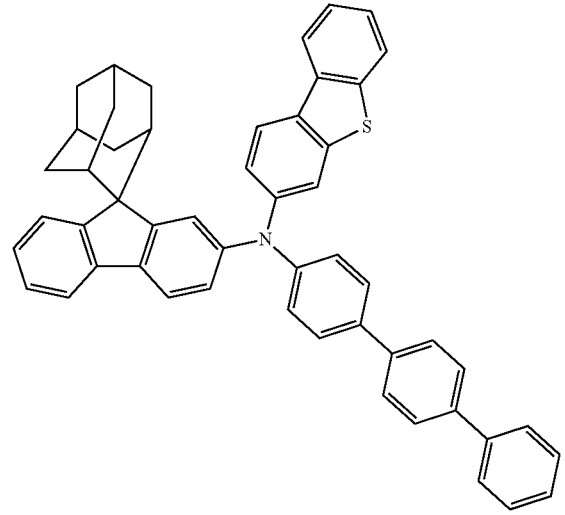
Compound 348
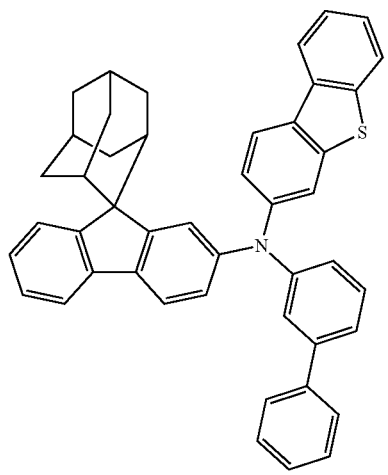

Compound 349
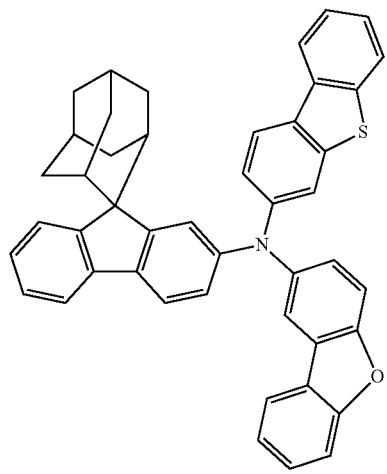
Compound 350
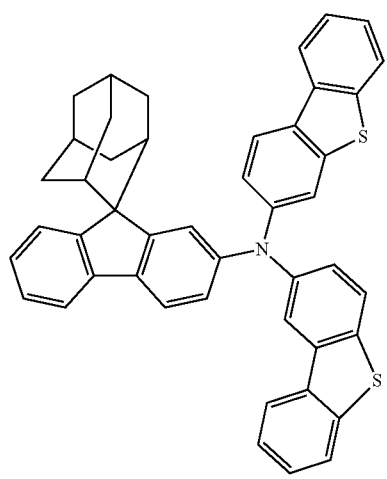
Compound 351
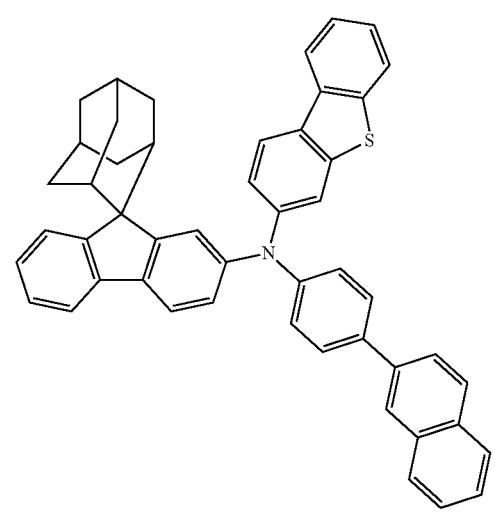
Compound 352
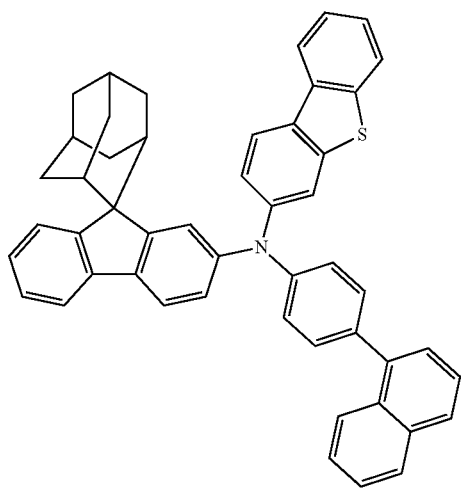
Compound 353
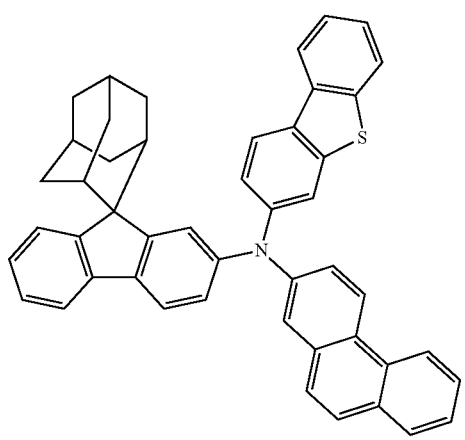
Compound 354
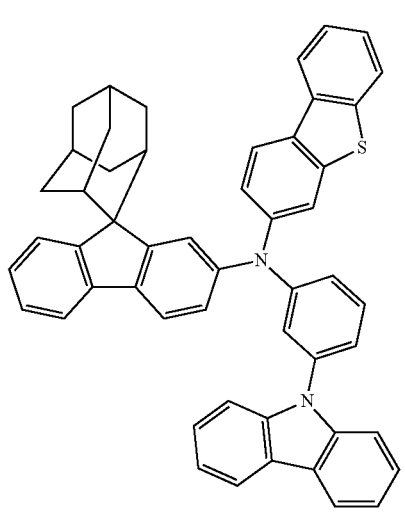

Compound 355
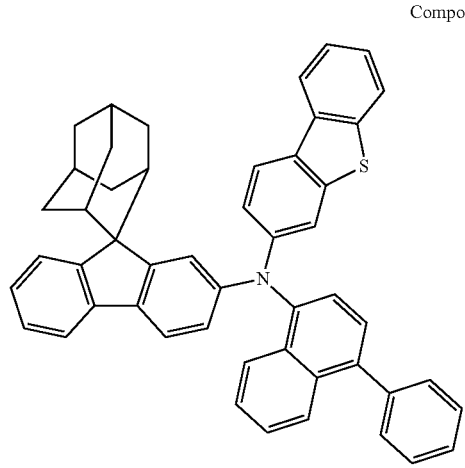
Compound 358
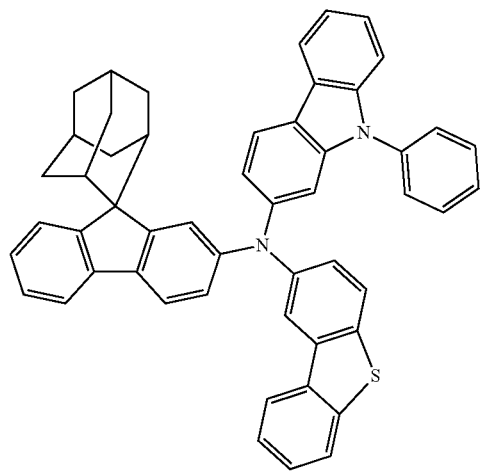
Compound 356
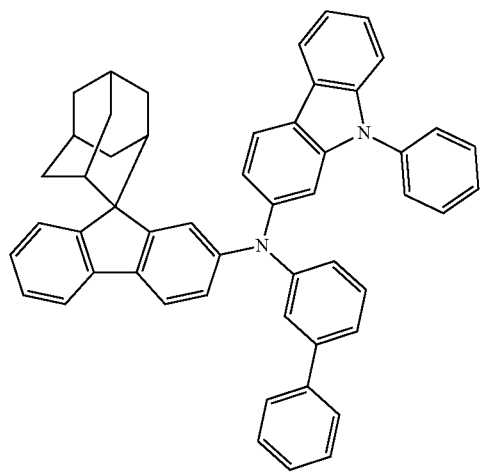
Compound 359
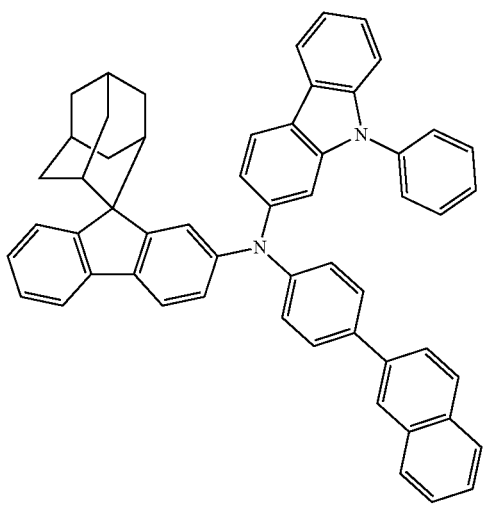
Compound 357
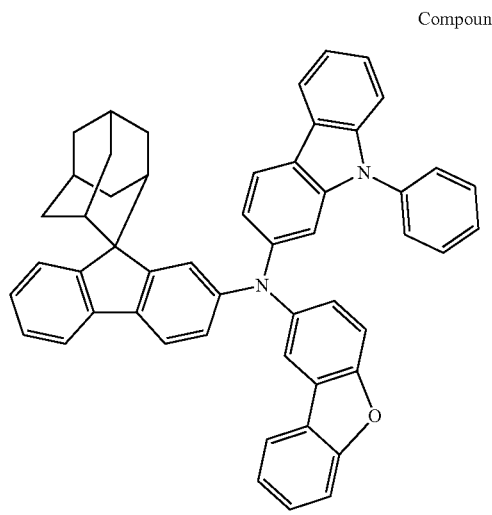
Compound 360
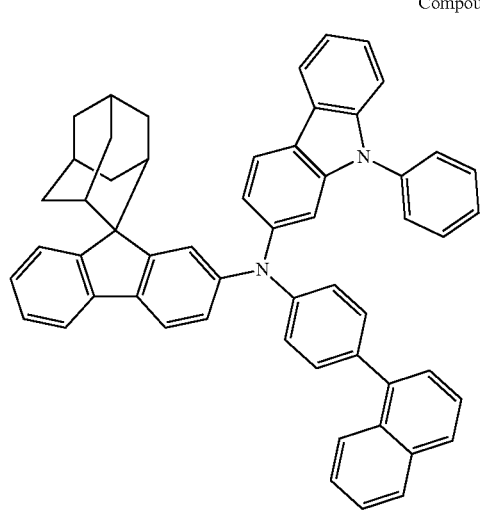

Compound 361
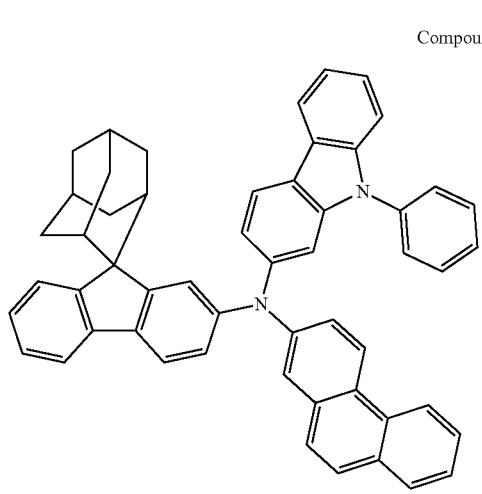
Compound 362
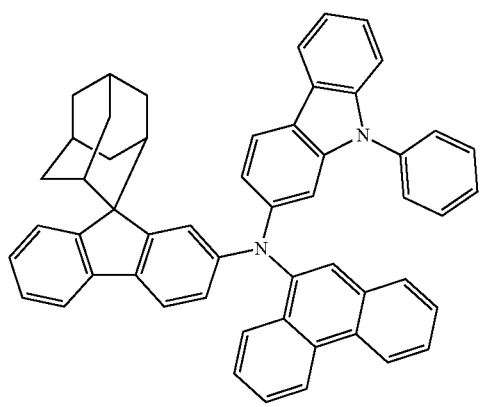
Compound 363
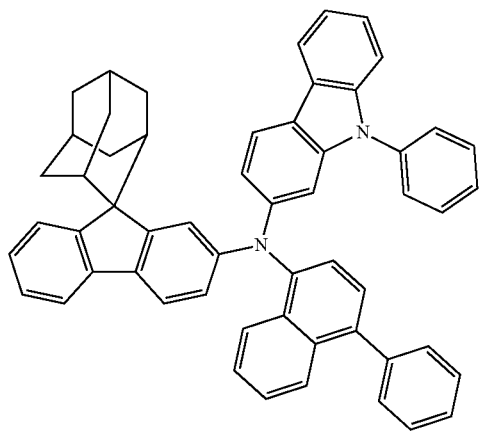
Compound 364
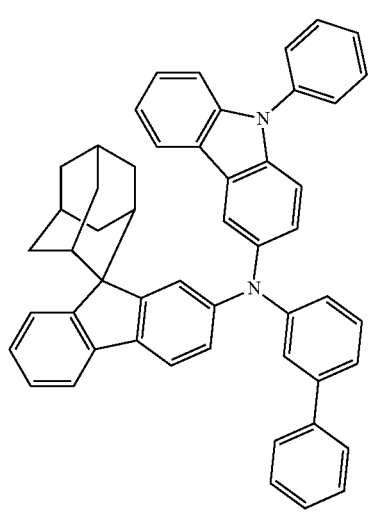
Compound 365
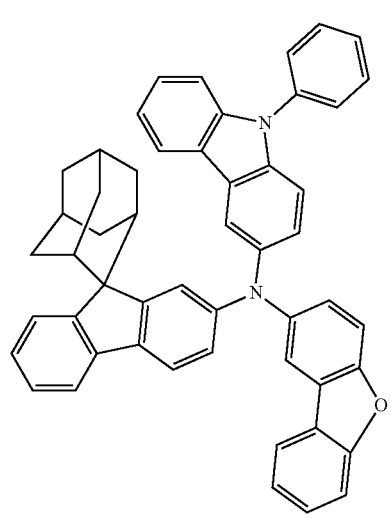
Compound 366
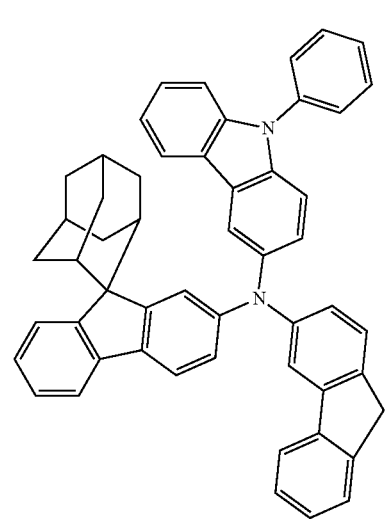

Compound 367
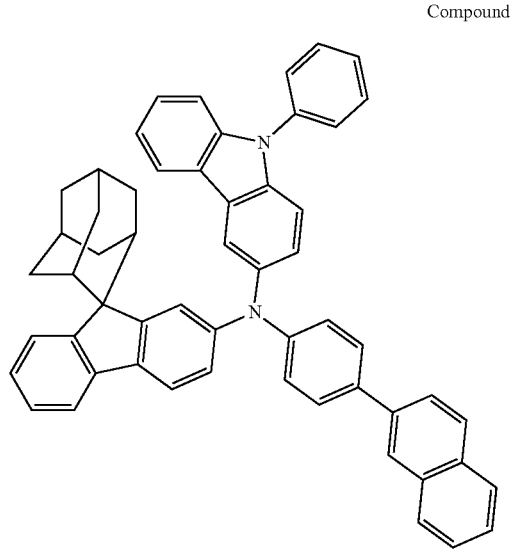
Compound 368
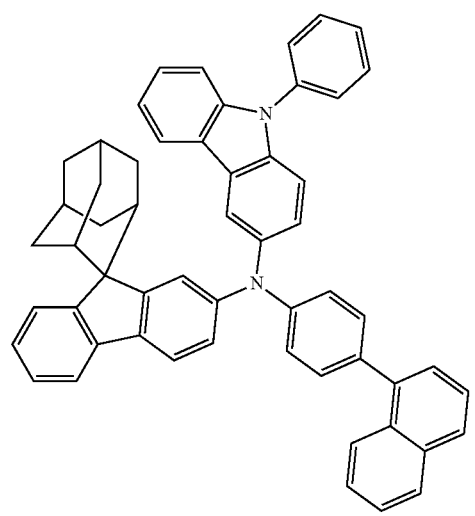
Compound 369
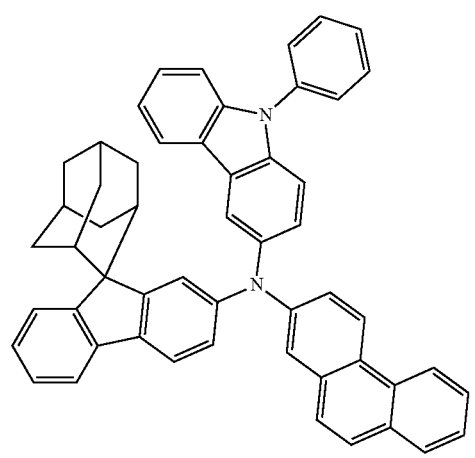
Compound 370
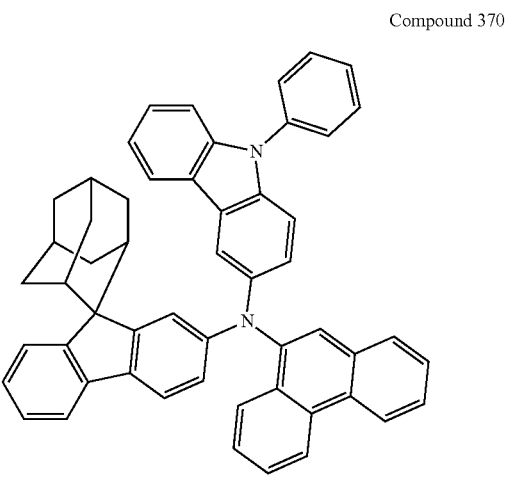
Compound 371
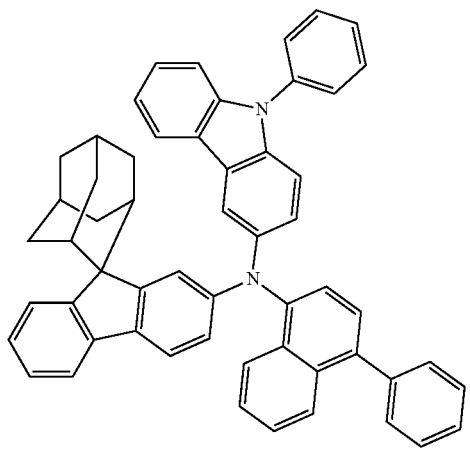
Compound 372
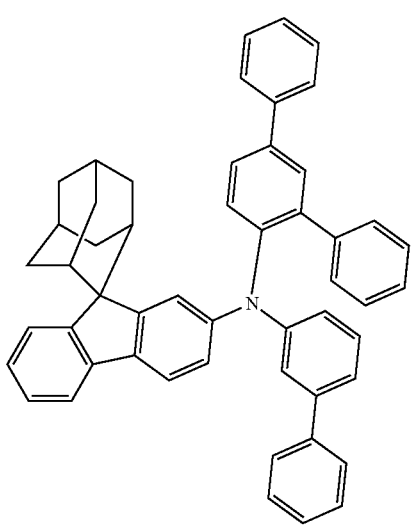

Compound 373
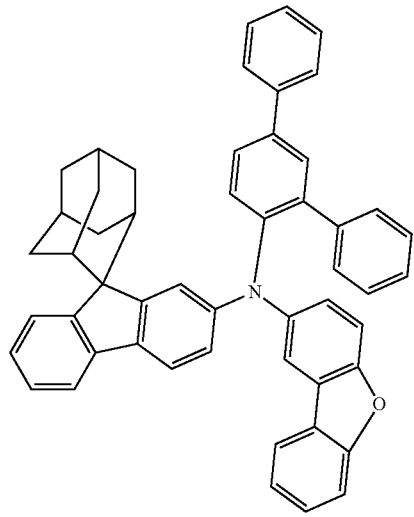
Compound 374
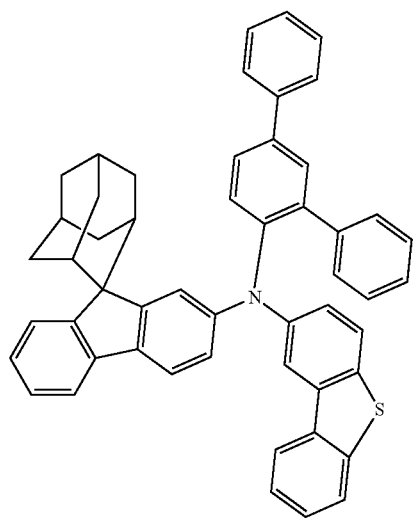
Compound 375
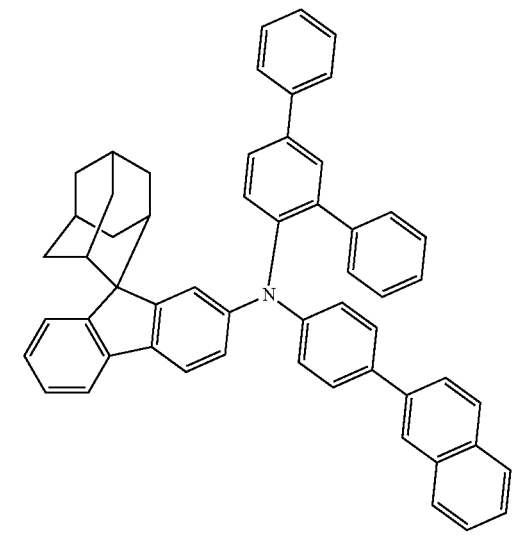
Compound 376
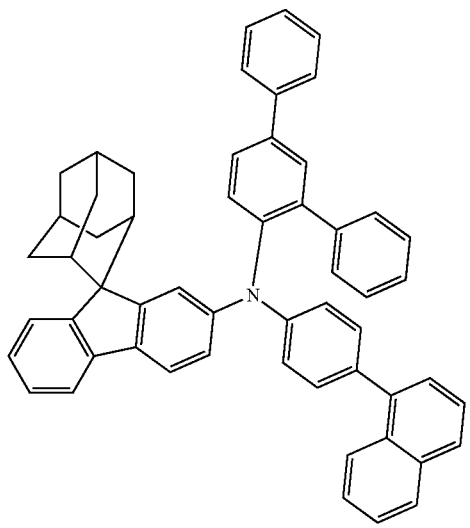
Compound 377
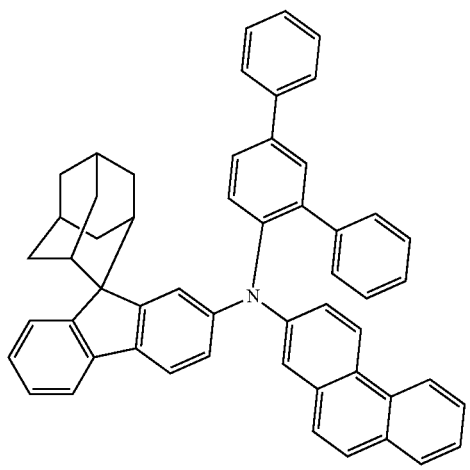
Compound 378
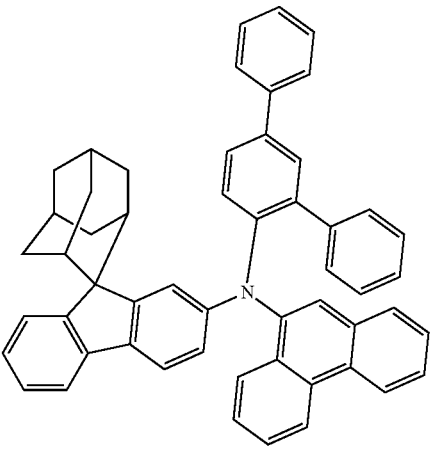

Compound 379
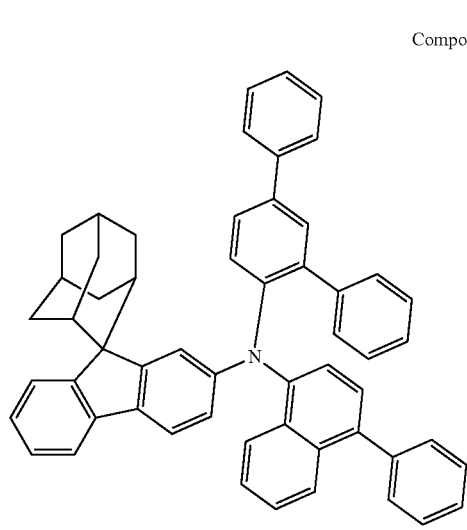
Compound 381
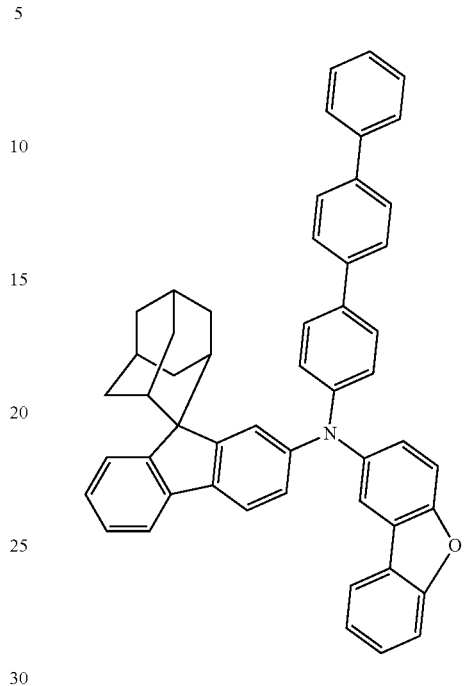
Compound 380
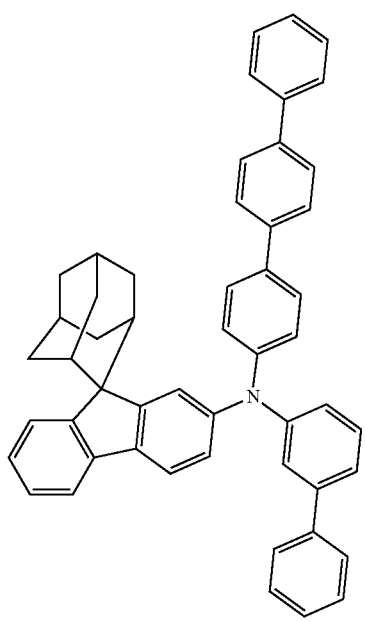
Compound 382
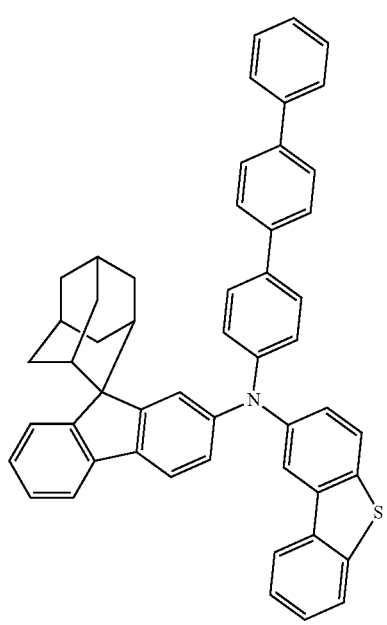

Compound 383
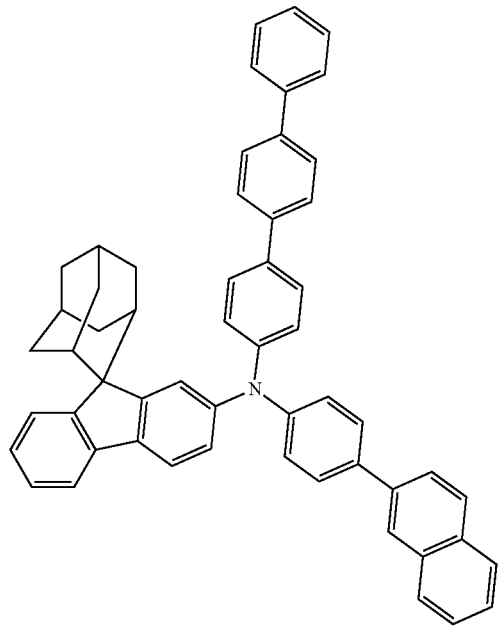
Compound 384
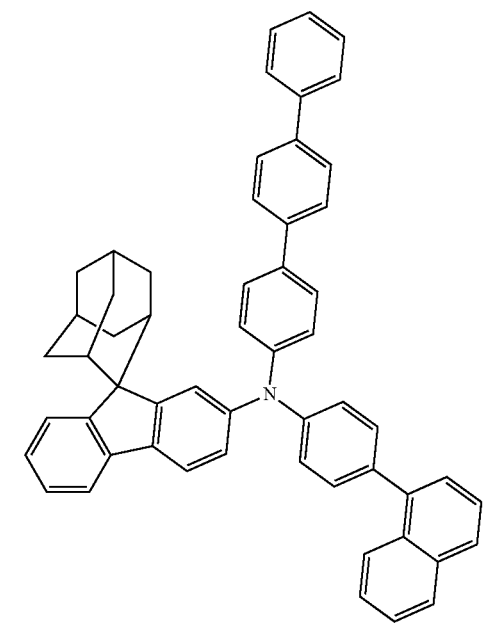
Compound 385
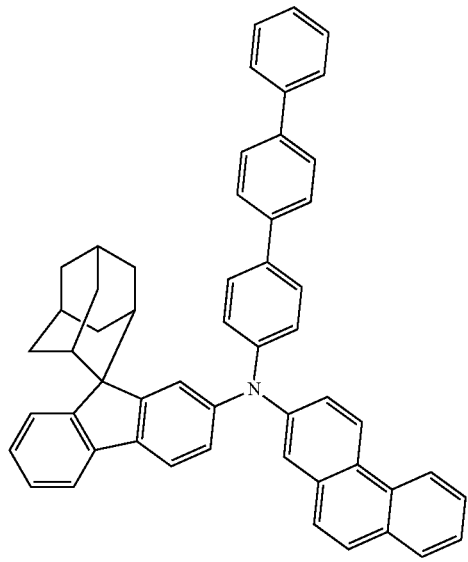
Compound 386
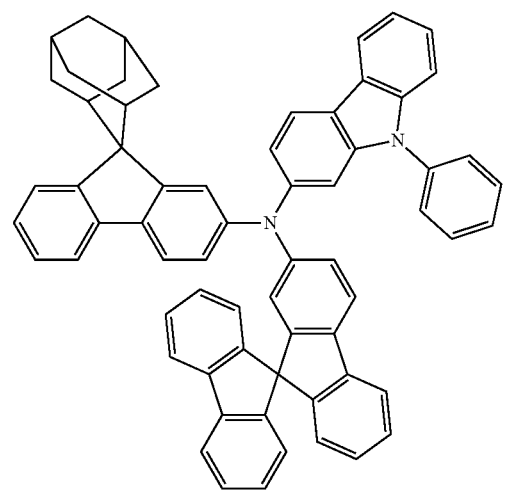
Compound 387
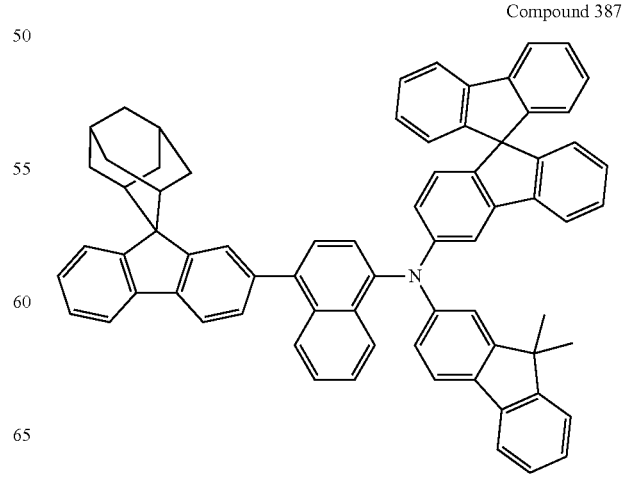

Compound 388

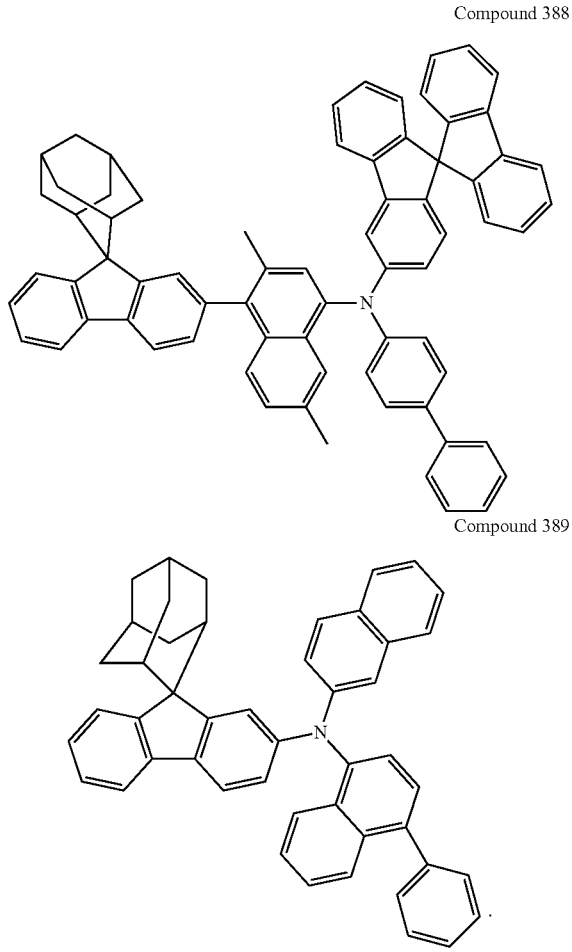

Compound 389

The nitrogen-containing compound of the present disclosure introduces an adamantane-2-yl structure at the 9-position of fluorene, the adamantyl can improve the electron density of a conjugated system of a fluorene ring and the whole nitrogen-containing compound through a hyperconjugation effect, so that the hole conduction efficiency of the nitrogen-containing compound is improved, and further the carrier conduction efficiency and the service life of an organic electroluminescent device and a photoelectric conversion device are improved. The adamantane-2-yl group is introduced at the 9-position of fluorene rather than at the end, and into the side chains of the amines of the nitrogen-containing compounds of the present disclosure rather than at the end. Due to the large steric hindrance effect of the adamantane-2-yl, the angle and the conjugation degree between each branched chain of amine can be adjusted, and further the HOMO value of the nitrogen-containing compound can be adjusted, so that the HOMO value of the nitrogen-containing compound can be more matched with an adjacent film layer, the driving voltage of an organic electroluminescent device can be further reduced, or the open-circuit voltage of a photoelectric conversion device can be improved.

Moreover, in the nitrogen-containing compound of the present disclosure, compared with the modification of the fluorene group with an aryl group, the modification of the fluorene group with an alkyl structure having a large volume can avoid the excessive π-π stacking effect, and can reduces the symmetry of the nitrogen-containing compounds of the present disclosure, which in turn can improve the film-forming properties of the nitrogen-containing compounds. Moreover, the adamantane-2-yl group can ensure that the nitrogen-containing compound of the present disclosure has an appropriate molecular weight, further ensure that the nitrogen-containing compound of the present disclosure has an appropriate glass transition temperature, and improve the physical and thermal stability during the preparation of an organic electroluminescent device and a photoelectric conversion device.

The present disclosure also provides an organic electroluminescent device. As shown in FIG. 1, the organic electroluminescent device includes an anode 100 and a cathode 200 disposed opposite to each other, and a functional layer 300 disposed between the anode 100 and the cathode 200. The functional layer 300 includes the nitrogen-containing compound provided by the present disclosure.

In one embodiment of the present disclosure, the nitrogen-containing compound provided by the present disclosure may be used to form at least one organic film layer in the functional layer 300, so as to improve the performance of the organic electroluminescent device, in particular, to improve the service life of the organic electroluminescent device, to improve the luminous efficiency of the organic electroluminescent device, to reduce the driving voltage of the organic electroluminescent device, or to improve the uniformity and stability of the organic electroluminescent device in mass production.

In one embodiment of the present disclosure, the functional layer 300 includes a hole transport layer 320, and the hole transport layer 320 includes the nitrogen-containing compound provided by the present disclosure. The hole transport layer 320 may be composed of the nitrogen-containing compound provided by the present disclosure, and also may be composed of the nitrogen-containing compound provided by the present disclosure and other materials.

Alternatively, the hole transport layer 320 includes a first hole transport layer 321 and a second hole transport layer 322, and the first hole transport layer 321 is disposed on the surface of the second hole transport layer 322 close to the anode 100. The first hole transport layer 321 or the second hole transport layer 322 includes the nitrogen-containing compound provided by the present disclosure. That is, one of the first hole transporting layer 321 and the second hole transporting layer 322 may contain the nitrogen-containing compound provided by the present disclosure, or both the first hole transporting layer 321 and the second hole transporting layer 322 may contain the nitrogen-containing compound provided by the present disclosure. It is to be understood that the first hole transport layer 321 or the second hole transport layer 322 may or may not contain other materials.

Further alternatively, the first hole transport layer 321 or the second hole transport layer 322 is composed of the nitrogen-containing compound provided by the present disclosure.

In one embodiment of the present disclosure, the functional layer 300 includes a hole injection layer 310, and the hole injection layer 310 may include the nitrogen-containing compound provided by the present disclosure. The hole injection layer 310 may be composed of the nitrogen-containing compound provided by the present disclosure, or may be composed of the nitrogen-containing compound provided by the present disclosure and other materials.

Alternatively, the hole injection layer 310 is composed of the nitrogen-containing compound provided by the present disclosure.

In one embodiment of the present disclosure, the anode 100 includes an anode material, which is preferably a material having a large work function that facilitates hole injection into the functional layer. Specific Examples of the anode material include: metals such as nickel, platinum, vanadium, chromium, copper, zinc and gold or alloys thereof; metal oxides such as zinc oxide, indium oxide, indium tin oxide (ITO), and indium zinc oxide (IZO); combinations of metals and oxides, such as ZnO:Al or $SnO_2$:Sb; or conductive polymers such as poly(3-methylthiophene), poly[3,4-(ethylene-1,2-dioxy)thiophene](PEDT), polypyrrole, and polyaniline, but not limited thereto. Preferably, a transparent electrode including indium tin oxide (ITO) is included as an anode.

In one embodiment of the present disclosure, the cathode 200 includes a cathode material that is a material having a small work function that facilitates electron injection into the functional layer. Specific Examples of the cathode material include: metals such as magnesium, calcium, sodium, potassium, titanium, indium, yttrium, lithium, gadolinium, aluminum, silver, tin, and lead or alloys thereof; or multi-layer materials such as LiF/Al, Liq/Al, $LiO_2$/Al, LiF/Ca, LiF/Al and $BaF_2$/Ca, but not limited thereto. Preferably, a metal electrode including aluminum is included as a cathode.

In one embodiment of the present disclosure, as shown in FIG. 1, the organic electroluminescent device may include an anode 100, a hole injection layer 310, a hole transport layer 320, an organic electroluminescent layer 330, a hole blocking layer 340, an electron transport layer 350, an electron injection layer 360, and a cathode 200, which are sequentially stacked. Wherein at least one of the hole injection layer 310 and the hole transport layer 320 includes the nitrogen-containing compound of the present disclosure.

Figure 2:
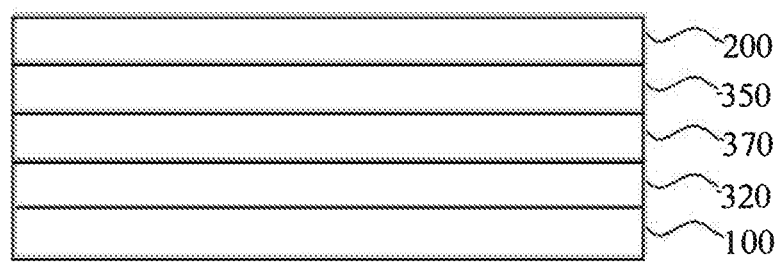
FIG. 2 is a schematic structural view of a photoelectric conversion device according to an embodiment of the present disclosure.

The present disclosure also provides a photoelectric conversion device, which may include an anode 100 and a cathode 200 disposed opposite to each other, and a functional layer 300 disposed between the anode 100 and the cathode 200, as shown in FIG. 2. The functional layer 300 includes the nitrogen-containing compound provided by the present disclosure.

In one embodiment of the present disclosure, the nitrogen-containing compound provided by the present disclosure may be used to form at least one organic thin layer in the functional layer 300 to improve the performance of the photoelectric conversion device, in particular, to improve the service life of the photoelectric conversion device, to improve the open circuit voltage of the photoelectric conversion device, or to improve the uniformity and stability of the photoelectric conversion device in mass production.

In one embodiment of the present disclosure, the functional layer 300 includes a hole transport layer 320, and the hole transport layer 320 includes the nitrogen-containing compound of the present disclosure. The hole transport layer 320 may be composed of the nitrogen-containing compound provided by the present disclosure, or may be composed of the nitrogen-containing compound provided by the present disclosure and other materials.

Alternatively, the hole transport layer 320 may further include an inorganic doping material to improve the hole transport property of the hole transport layer 320.

In one embodiment of the present disclosure, as shown in FIG. 2, the photoelectric conversion device may include an anode 100, a hole transport layer 320, a photoelectric conversion layer 370, an electron transport layer 350, and a cathode 200, which are sequentially stacked.

Alternatively, the photoelectric conversion device may be a solar cell, and particularly may be an organic thin film solar cell.

Synthesis of Compounds

Synthesis of Compounds 1 to 23 by the Following Synthetic Route

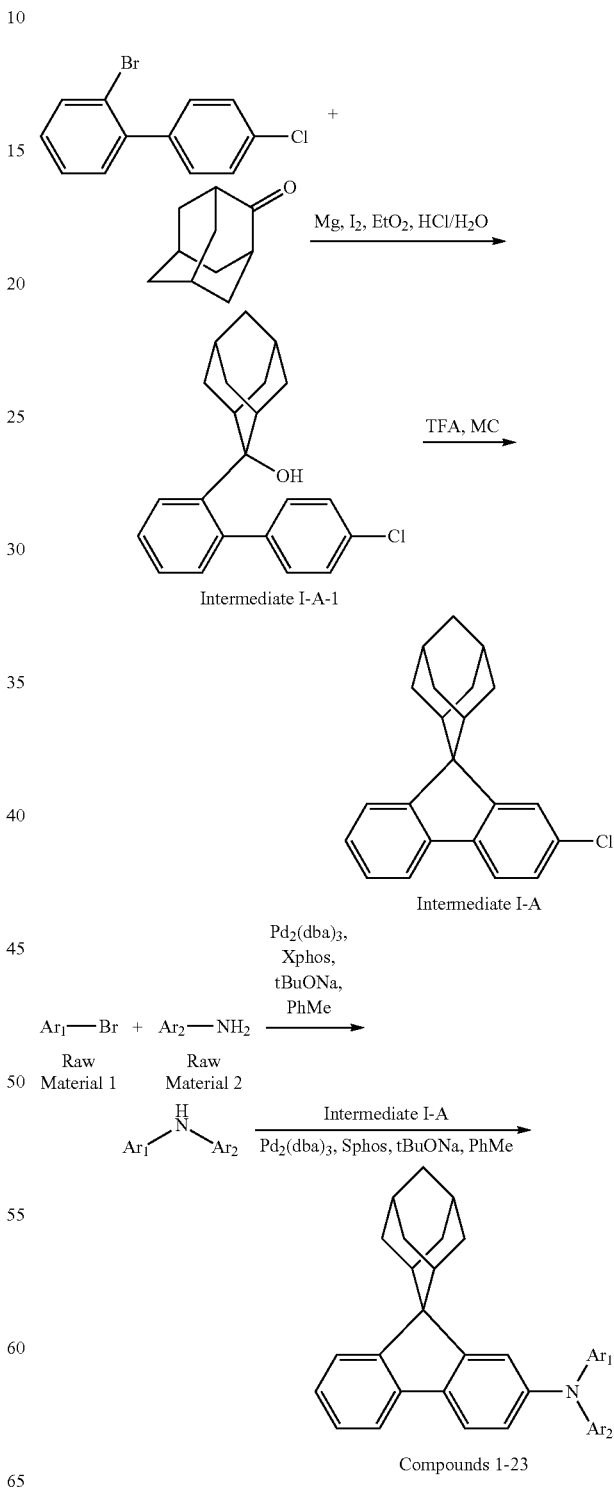

Synthesis of Compound 1

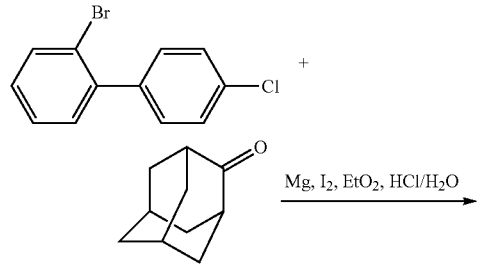

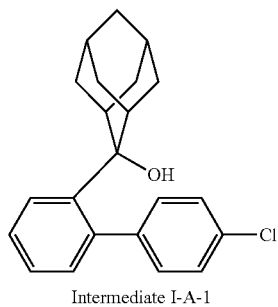

Intermediate I-A-1

Magnesium strips (13.54 g, 564 mmol) and diethyl ether (100 mL) were placed in a dry round bottom flask under the protection of nitrogen, and iodine (100 mg) was added. Then, the solution of 2'-bromo-4-chlorobiphenyl (50.00 g, 187.0 mmol) dissolved in diethyl ether (200 mL) was slowly dripped into the flask, the temperature was raised to 35° C. after dropping, and the stirring was carried out for 3 hours. The reaction solution was cooled to 0° C., the solution of adamantanone (22.45 g, 149 mmol) dissolved in diethyl ether (200 mL) was slowly dropped, the temperature was raised to 35° C. after dropping, and stirring was carried out for 6 hours. The reaction solution was cooled to room temperature, 5% hydrochloric acid was added into the reaction solution until the pH value was less than 7, and the stirring was carried out for 1 hour. Diethyl ether (200 mL) was added into the reaction solution for extraction, the combined organic phases were dried by using anhydrous magnesium sulfate, the mixture was filtered, and the solvent was removed under reduced pressure. The crude product was purified by silica column chromatography using ethyl acetate/n-heptane (1:2) as mobile phase to obtain Intermediate I-A-1 (43 g, 68% yield) as a white solid.

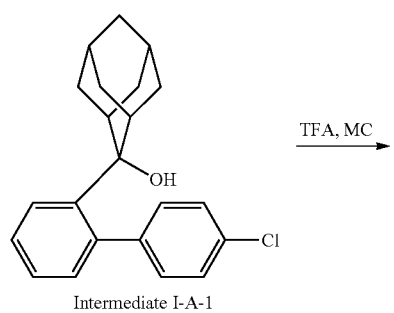

Intermediate I-A-1

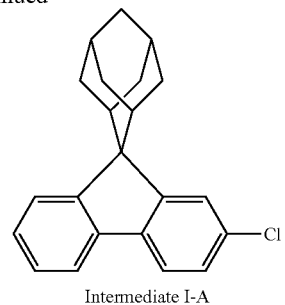

Intermediate I-A

Intermediate I-A-1 (43 g, 126.9 mmol), trifluoroacetic acid (36.93 g, 380.6 mmol) and dichloromethane (300 mL) were added into a round-bottom flask, and the stirring was carried out under the protection of nitrogen for 2 hours. Then, an aqueous solution of sodium hydroxide was added into the reaction solution until the pH value to 8, followed by liquid separation, the organic phase was dried with anhydrous magnesium sulfate, the mixture was filtered, and the solvent was removed under reduced pressure. The crude product was purified by silica column chromatography using dichloromethane/n-heptane (1:2) to obtain Intermediate I-A (39.2 g, 96.3% yield) as a white solid.

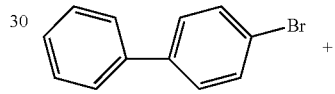

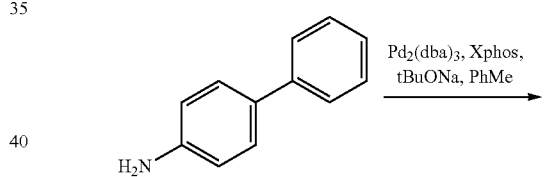

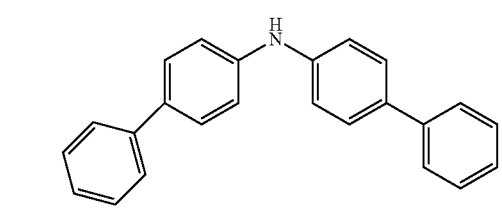

Intermediate II-A 4-bromobiphenyl (5.0 g, 21.0 mmol), 4-aminobiphenyl (3.63 g, 21.45 mmol), tris (dibenzylideneacetone) dipalladium (0.20 g, 0.21 mmol), 2-dicyclohexylphosphino-2',4',6'-triisopropylbiphenyl (0.20 g, 0.42 mmol) and sodium tert-butoxide (3.09 g, 32.18 mmol) were added into toluene (80 mL), the reaction solution was heated to 108° C. under the protection of nitrogen and stirred for 2 h. Then, the reaction solution was cooled to room temperature, the reaction solution was washed with water, magnesium sulfate was added for drying, the mixture was filtered, and the solvent was removed under reduced pressure. The crude product was purified by recrystallization using a dichloromethane/ethyl acetate system to obtain Intermediate II-A (5.61 g, 81.5% yield) as a pale-yellow solid.

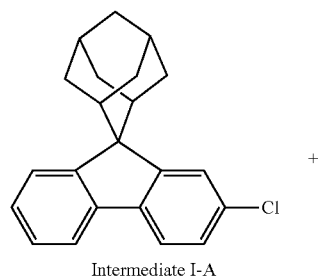

Intermediate I-A

+

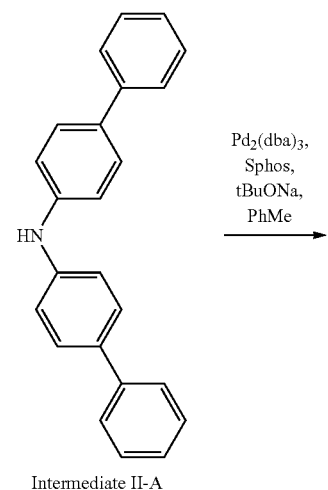

Intermediate II-A

Pd$_2$(dba)$_3$,
Sphos,
tBuONa,
PhMe
→

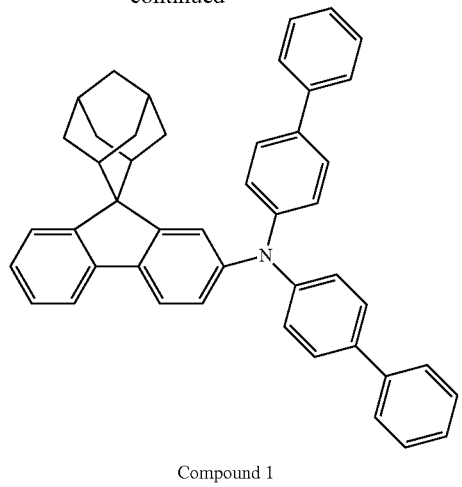

Compound 1

Intermediate I-A (5.6 g, 17.46 mmol), Intermediate II-A (5.61 g, 17.46 mmol), tris(dibenzylideneacetone)dipalladium (0.16 g, 0.17 mmol), 2-dicyclohexylphosphino-2',6'-dimethoxybiphenyl (0.14 g, 0.35 mmol) and sodium tert-butoxide (2.52 g, 26.18 mmol) were added into toluene (40 mL), the reaction solution was heated to 108° C. under the protection of nitrogen, and stirred for 3 h. Then, the reaction solution was cooled to room temperature, the reaction solution was washed with water, magnesium sulfate was added for drying, the mixture was filtered, and the solvent was removed from the filtrate under reduced pressure. The crude product was purified by recrystallization using a toluene system to obtain Compound 1 (4.35 g, 41% yield) as a white solid. Mass spectrum: m/z=606.3 (M+H)$^+$. $^1$H NMR (400 MHz, CD$_2$Cl$_2$): 8.09 (d, 1H), 7.91 (s, 1H), 7.74-7.71 (m, 2H), 7.61 (d, 4H), 7.55 (d, 4H), 7.43 (t, 4H), 7.37-7.30 (m, 3H), 7.25-7.24 (m, 5H), 7.18 (dd, 1H), 2.91 (d, 2H), 2.61 (d, 2H), 2.16 (s, 1H), 1.90 (s, 3H), 1.77 (d, 2H), 1.69 (d, 2H), 1.60 (s, 2H) ppm.

Referring to the Synthesis of Compound 1, Compounds 2 to 23 were prepared with Raw Material 2 instead of 4-bromobiphenyl and Raw Material 1 instead of 4-aminobiphenyl. Wherein, the Compound Number, Compound Structures, Raw Materials, Synthesis Yields, and Characterization Data of Compounds 2 to 23 are shown in Table 1.

TABLE 1

Compound Structure, Preparation and Characterization Data

| Compound number | Raw Material 1 | Raw Material 2 | Compound Structure | Yield (%) | Mass (m/z) (M + H)$^+$ |
|---|---|---|---|---|---|
| 2 | ![H$_2$N-biphenyl] | ![Br-dimethylfluorene] | ![compound 2 structure] | 67 | 646.3 |

TABLE 1-continued
Compound Structure, Preparation and Characterization Data
| Compound number | Raw Material 1 | Raw Material 2 | Compound Structure | Yield (%) | Mass (m/z) (M + H)+ |
|---|---|---|---|---|---|
| 3 | | 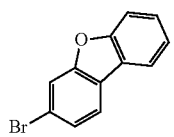 [SMILES: Brc1ccc2c(c1)oc1ccccc12] | 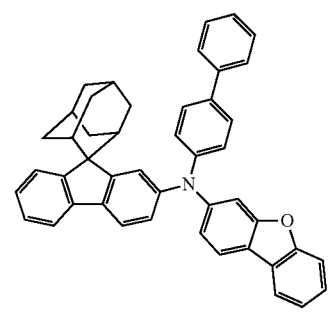 [SMILES: c1ccc(-c2ccc(N(c3ccc4c(c3)C3(c5ccccc5-4)C4CC5CC(C4)CC3C5)c3ccc4c(c3)oc3ccccc34)cc2)cc1] | 69 | 620.3 |
| 4 | |  | 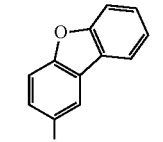 | 72 | 620.3 |
| 5 | | 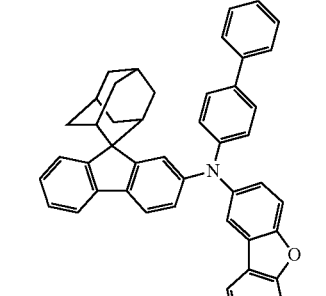 | 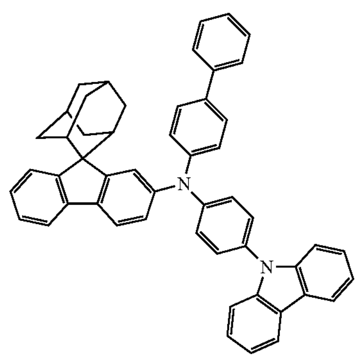 | 67 | 695.3 |
| 6 | | 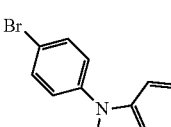 | 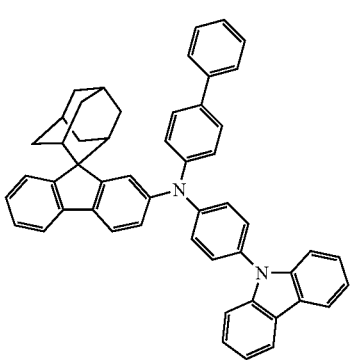 [SMILES: c1ccc(-c2ccc(N(c3ccc(-n4c5ccccc5c5ccccc54)cc3)c3ccc4c(c3)C3(c5ccccc5-4)C4CC5CC(C4)CC3C5)cc2)cc1] | 54 | 696.3 |

TABLE 1-continued
Compound Structure, Preparation and Characterization Data
| Compound number | Raw Material 1 | Raw Material 2 | Compound Structure | Yield (%) | Mass (m/z) (M + H)+ |
|---|---|---|---|---|---|
| 7 | 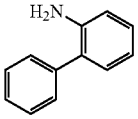 [SMILES: Nc1ccccc1-c1ccccc1] | 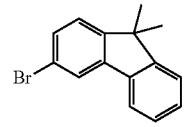 | 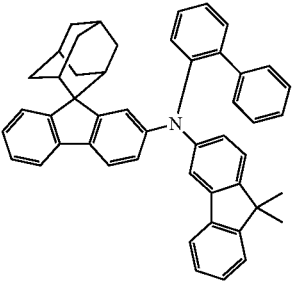 [SMILES: CC1(C)c2ccccc2-c2cc(N(c3ccc4c(c3)C3(c5ccccc5-4)C4CC5CC(C4)CC3C5)c3ccccc3-c3ccccc3)ccc21] | 55 | 646.3 |
| 8 | | 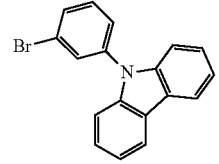 [SMILES: Brc1cccc(-n2c3ccccc3c3ccccc32)c1] | 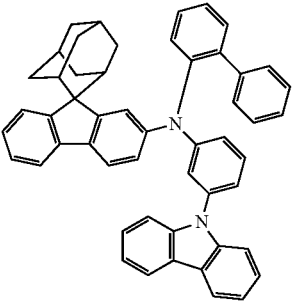 [SMILES: c1ccc(-c2ccccc2N(c2cccc(-n3c4ccccc4c4ccccc43)c2)c2ccc3c(c2)C2(c4ccccc4-3)C3CC4CC(C3)CC2C4)cc1] | 59 | 695.3 |
| 9 | 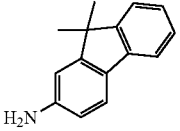 | 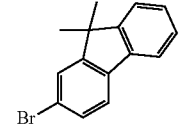 | 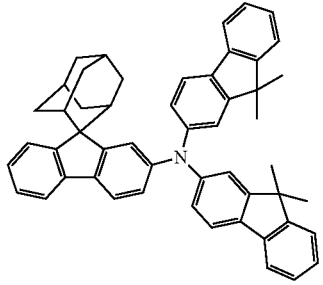 [SMILES: CC1(C)c2ccccc2-c2ccc(N(c3ccc4c(c3)C(C)(C)c3ccccc3-4)c3ccc4c(c3)C3(c5ccccc5-4)C4CC5CC(C4)CC3C5)cc21] | 61 | 686.4 |
| 10 | | 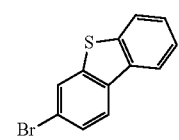 | 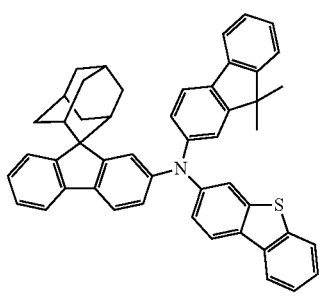 [SMILES: CC1(C)c2ccccc2-c2ccc(N(c3ccc4c(c3)C3(c5ccccc5-4)C4CC5CC(C4)CC3C5)c3ccc4c(c3)sc3ccccc34)cc21] | 62 | 676.3 |

TABLE 1-continued
Compound Structure, Preparation and Characterization Data
| Compound number | Raw Material 1 | Raw Material 2 | Compound Structure | Yield (%) | Mass (m/z) (M + H)+ |
|---|---|---|---|---|---|
| 11 | | 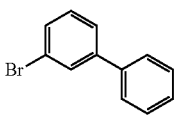 | 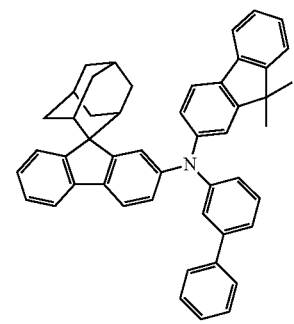 [SMILES: CC1(C)c2ccccc2-c2ccc(N(c3cccc(-c4ccccc4)c3)c3ccc4c(c3)C3(c5ccccc5-4)C4CC5CC(C4)CC3C5)cc21] | 47 | 646.3 |
| 12 | | 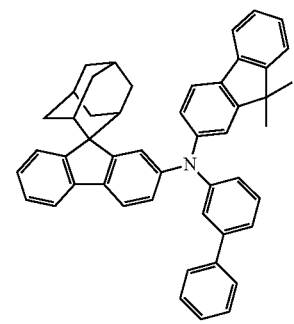 [SMILES: CC1(C)c2ccccc2-c2ccc(N(c3cccc(-c4ccccc4)c3)c3ccc4c(c3)C3(c5ccccc5-4)C4CC5CC(C4)CC3C5)cc21] | 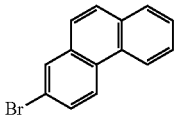 | 49 | 670.3 |
| 13 | 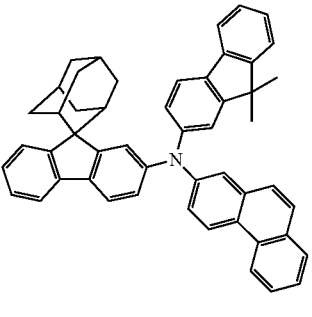 [SMILES: CC1(C)c2ccccc2-c2ccc(N(c3ccc4c(c3)C3(c5ccccc5-4)C4CC5CC(C4)CC3C5)c3ccc4c(ccc5ccccc54)c3)cc21] | 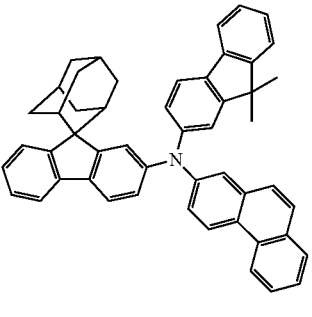 [SMILES: CC1(C)c2ccccc2-c2ccc(N(c3ccc4c(c3)C3(c5ccccc5-4)C4CC5CC(C4)CC3C5)c3ccc4c(ccc5ccccc54)c3)cc21] | 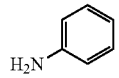 | 53 | 504.3 |
| 14 | | 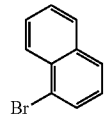 | 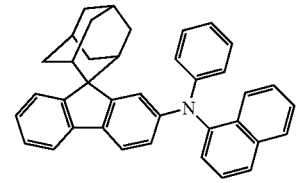 [SMILES: c1ccc(N(c2ccc3c(c2)C2(c4ccccc4-3)C3CC4CC(C3)CC2C4)c2cccc3ccccc23)cc1] | 55 | 619.3 |
| 15 | | 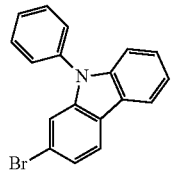 [SMILES: Brc1ccc2c3ccccc3n(-c3ccccc3)c2c1] | 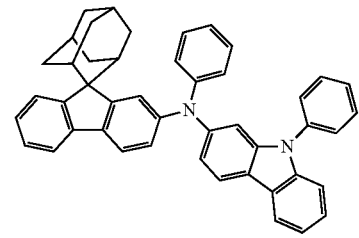 [SMILES: c1ccc(N(c2ccc3c(c2)C2(c4ccccc4-3)C3CC4CC(C3)CC2C4)c2ccc3c4ccccc4n(-c4ccccc4)c3c2)cc1] | 67 | 606.3 |

TABLE 1-continued
Compound Structure, Preparation and Characterization Data
| Compound number | Raw Material 1 | Raw Material 2 | Compound Structure | Yield (%) | Mass (m/z) (M + H)+ |
|---|---|---|---|---|---|
| 16 | | 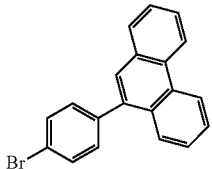 [SMILES: Brc1ccc(-c2cc3ccccc3c3ccccc23)cc1] | 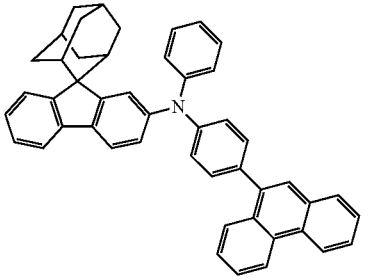 [SMILES: c1ccc(N(c2ccc(-c3cc4ccccc4c4ccccc34)cc2)c2ccc3c(c2)C2(c4ccccc4-3)C3CC4CC(C3)CC2C4)cc1] | 69 | 630.3 |
| 17 | 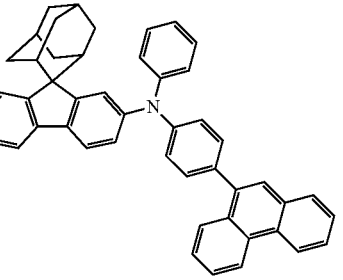 | 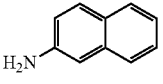 | 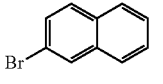 | 70 | 554.3 |
| 18 | | 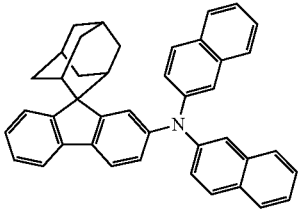 [SMILES: c1ccc2c(c1)-c1ccc(N(c3ccc4ccccc4c3)c3ccc4ccccc4c3)cc1C21C2CC3CC(C2)CC1C3] | 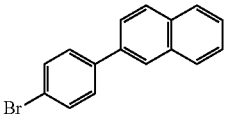 | 50 | 630.3 |
| 19 | | 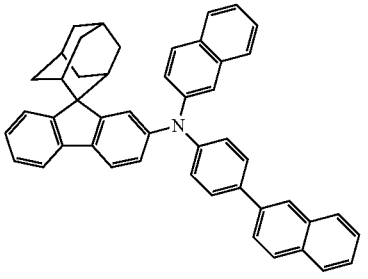 [SMILES: c1ccc2c(c1)-c1ccc(N(c3ccc(-c4ccc5ccccc5c4)cc3)c3ccc4ccccc4c3)cc1C21C2CC3CC(C2)CC1C3] | 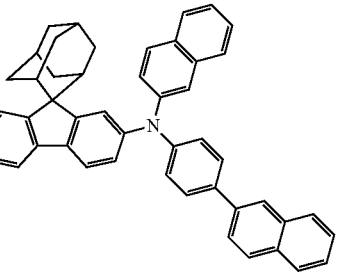 | 43 | 630.3 |
| 20 | 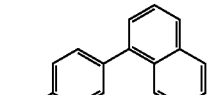 | 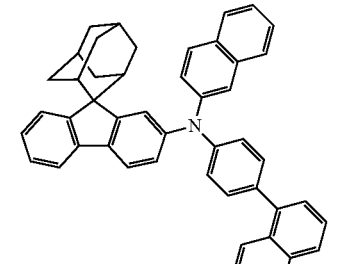 | 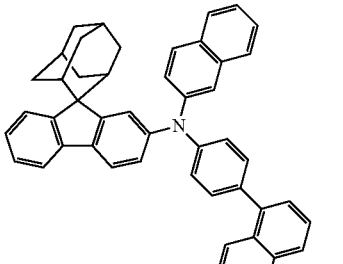 | 49 | 669.3 |

TABLE 1-continued

Compound Structure, Preparation and Characterization Data

| Compound number | Raw Material 1 | Raw Material 2 | Compound Structure | Yield (%) | Mass (m/z) (M + H)+ |
|---|---|---|---|---|---|
| 21 | | | 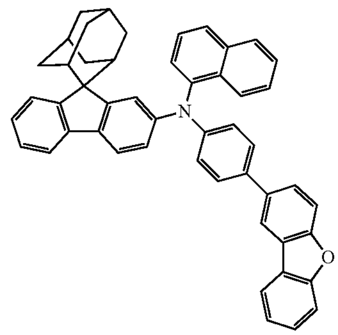 [SMILES: c1ccc2c(c1)-c1ccc(N(c3ccc(-c4ccc5oc6ccccc6c5c4)cc3)c3cccc4ccccc34)cc1C21C2CC3CC(C2)CC1C3] | 48 | 670.3 |
| 22 | | | 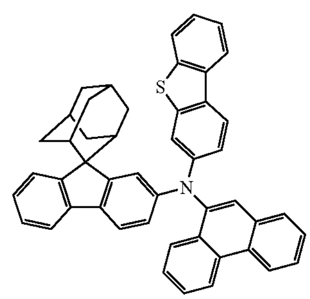 [SMILES: c1ccc2c(c1)-c1ccc(N(c3ccc4c(c3)sc3ccccc34)c3cc4ccccc4c4ccccc34)cc1C21C2CC3CC(C2)CC1C3] | 54 | 660.3 |
| 23 | | | 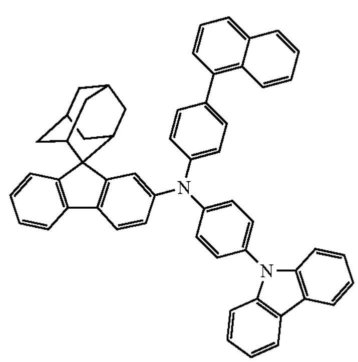 [SMILES: c1ccc2c(c1)-c1ccc(N(c3ccc(-c4cccc5ccccc45)cc3)c3ccc(-n4c5ccccc5c5ccccc54)cc3)cc1C21C2CC3CC(C2)CC1C3] | 58 | 745.4 |

Compound 3 was identified by ¹H-NMR.

¹H-NMR (400 MHz, CD$_2$Cl$_2$): 8.09 (d, 1H), 7.94 (s, 1H), 7.90 (d, 1H), 7.84 (d, 1H), 7.73 (t, 2H), 7.61 (d, 2H), 7.56 (d, 2H), 7.51 (d, 1H), 7.45-7.31 (m, 7H), 7.27-7.24 (m, 3H), 7.20 (dd, 2H), 2.91 (d, 2H), 2.60 (d, 2H), 2.15 (s, 1H), 1.88 (s, 3H), 1.76 (d, 2H), 1.67 (d, 2H), 1.60 (s, 2H) ppm.

Compound 7 was identified by ¹H-NMR.

¹H-NMR (400 MHz, CD$_2$Cl$_2$): 8.03 (d, 2H), 7.64 (d, 1H), 7.58-7.57 (m, 2H), 7.51 (d, 1H), 7.47 (d, 1H), 7.42-7.39 (m, 2H), 7.36 (t, 2H), 7.33-7.26 (m, 3H), 7.22-7.18 (m, 4H), 7.06 (t, 2H), 7.01-6.99 (m, 2H), 6.89 (dd, 2H), 2.86 (d, 2H), 2.43 (d, 2H), 2.11 (s, 1H), 1.84 (s, 2H), 1.78 (s, 1H), 1.71 (d, 2H), 1.58 (d, 2H), 1.47 (s, 2H), 1.30 (s, 6H) ppm.

Synthesis of Compounds 24 to 30 by the Following Synthetic Route

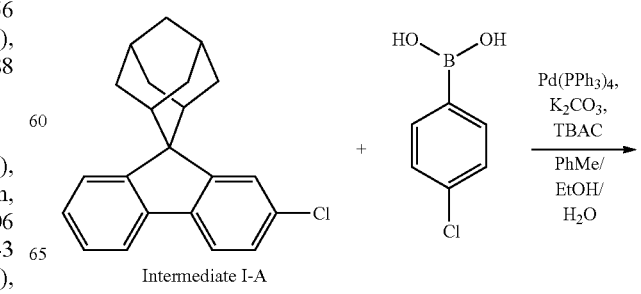

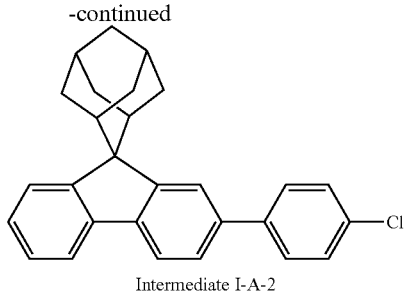

Intermediate I-A-2

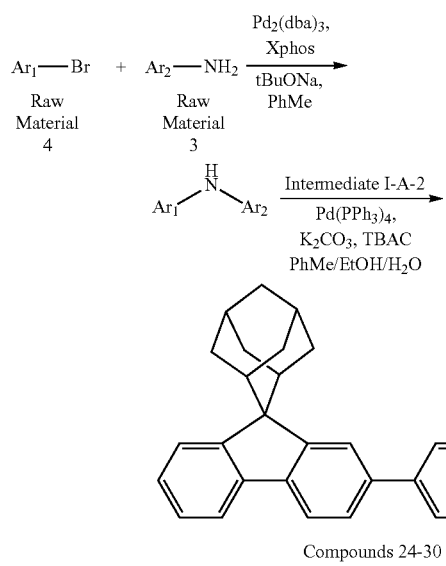

Compounds 24-30

Synthesis of Compound 24

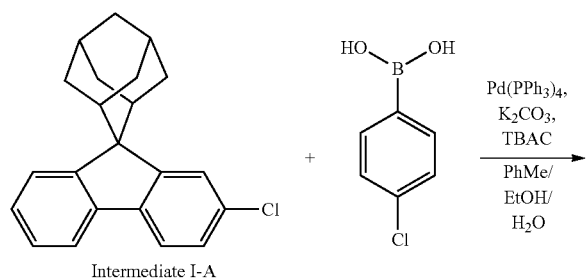

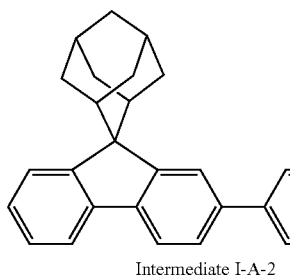

Intermediate I-A-2

Intermediate I-A (20 g, 62.34 mmol), p-chlorobenzoic acid (9.75 g, 62.34 mmol), tetrakis(triphenylphosphine)palladium (0.72 g, 0.62 mmol), potassium carbonate (17.2 g, 124.6 mmol), tetrabutylammonium chloride (0.34 g, 1.25 mmol), toluene (160 mL), ethanol (40 mL) and deionized water (40 mL) were added into a round bottom flask, the reaction solution was heated to 78° C. under the protection of nitrogen, and stirred for 8 hours. The reaction solution was cooled to room temperature, toluene (100 mL) was added for extraction, the combined organic phases were dried by using anhydrous magnesium sulfate, the mixture was filtered, and the solvent was removed under reduced pressure. The crude product was purified by silica column chromatography using n-heptane as mobile phase, followed by recrystallization using a dichloromethane/ethyl acetate system to obtain Intermediate I-A-2 (18.6 g, 75%) as a white solid.

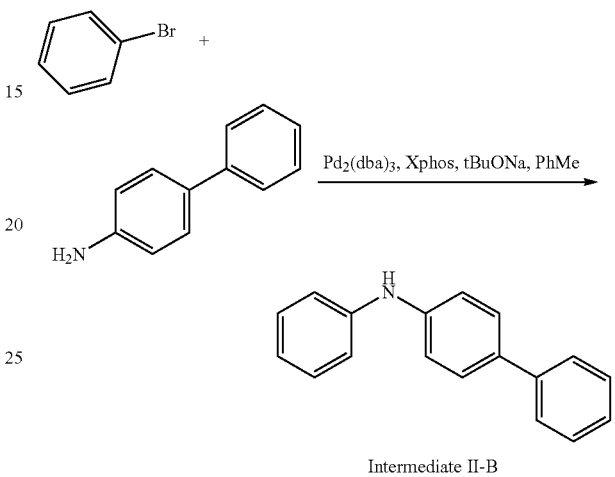

Intermediate II-B

Bromobenzene (10.0 g, 38.0 mmol), 4-aminobiphenyl (7.07 g, 41.8 mmol), tris(dibenzylideneacetone)dipalladium (0.35 g, 0.38 mmol), 2-dicyclohexylphosphino-2',4',6'-triisopropylbiphenyl (0.36 g, 0.76 mmol) and sodium tert-butoxide (5.48 g, 57.0 mmol) were added into toluene (80 mL), the reaction solution heated to 108° C. under the protection of nitrogen and stirred for 2 h. Then, the reaction solution was cooled to room temperature, magnesium sulfate was added for drying after washing with water, the mixture was filtered, and the solvent was removed from the filtrate under reduced pressure. The crude product was purified by recrystallization using a dichloromethane/ethyl acetate system to obtain Intermediate II-B (11.5 g, 86%) as a pale-yellow solid.

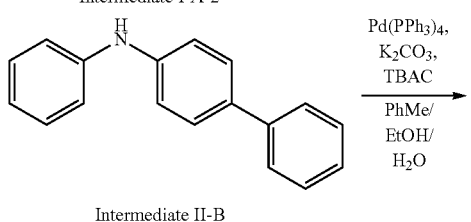

Intermediate II-B

-continued

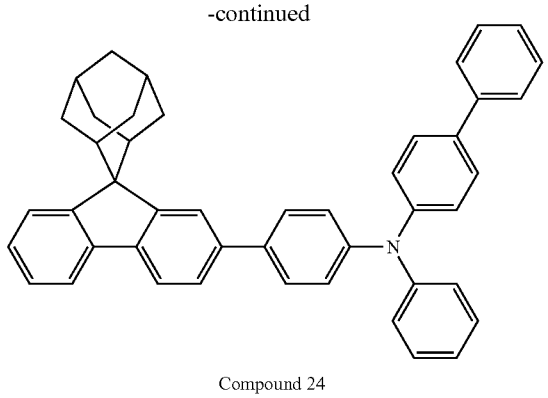

Compound 24

Intermediate I-A-2 (3.50 g, 10.9 mmol), Intermediate II-B (3.51 g, 10.9 mmol), tris(dibenzylideneacetone)dipalladium (0.20 g, 0.22 mmol), 2-dicyclohexyl phosphorus-2',6'-dimethoxy biphenyl (0.18 g, 0.44 mmol) and sodium tert-butoxide (1.58 g, 16.4 mmol) were added into toluene (30 mL), the reaction solution was heated to 110° C. under the protection of nitrogen, and stirred for 8 h. Then, the reaction solution was cooled to room temperature, magnesium sulfate was added for drying after washing with water, the mixture was filtered, and the solvent was removed from the filtrate under reduced pressure. The crude product was purified by recrystallization using a toluene system to obtain Compound 24 (4.35 g, 65.81%) as a white solid. Mass spectrum: m/z=606.3 (M+H)$^+$.

Referring to the synthesis of Compound 24, Compounds 25 to 30 were prepared with Raw Material 3 instead of 4-aminobiphenyl and Raw Material 4 instead of bromobenzene. Wherein, the Compound Number, Compound Structures, Raw Materials, Synthesis Yields, and Characterization Data of Compounds 25 to 30 are shown in Table 2.

TABLE 2

Compound Structure, Preparation and Characterization Data

| Compound Number | Raw Material 3 | Raw Material 4 | Compound Structure | Yield (%) | Mass (m/z) (M + H)$^+$ |
|---|---|---|---|---|---|
| 25 | | | 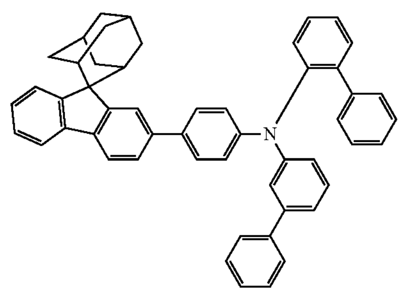 [SMILES: c1ccc(-c2cccc(N(c3ccc(-c4ccc5c(c4)C4(c6ccccc6-5)C5CC6CC(C5)CC4C6)cc3)c3ccccc3-c3ccccc3)c2)cc1] | 61 | 682.3 |
| 26 | | | 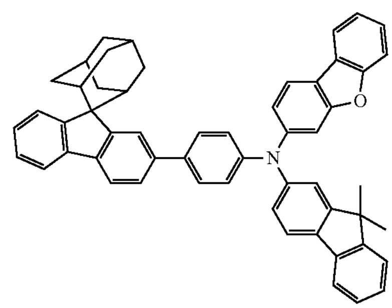 [SMILES: CC1(C)c2ccccc2-c2ccc(N(c3ccc(-c4ccc5c(c4)C4(c6ccccc6-5)C5CC6CC(C5)CC4C6)cc3)c3ccc4c(c3)oc3ccccc34)cc21] | 54 | 736.4 |
| 27 | | | 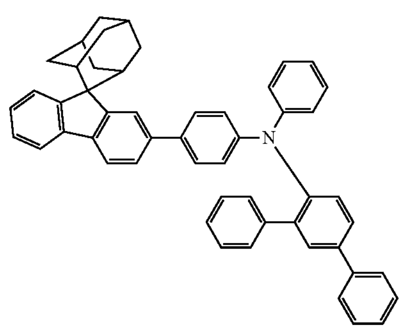 [SMILES: c1ccc(-c2ccc(N(c3ccccc3)c3ccc(-c4ccc5c(c4)C4(c6ccccc6-5)C5CC6CC(C5)CC4C6)cc3)c(-c3ccccc3)c2)cc1] | 59 | 682.3 |

TABLE 2-continued

Compound Structure, Preparation and Characterization Data

| Compound Number | Raw Material 3 | Raw Material 4 | Compound Structure | Yield (%) | Mass (m/z) (M + H)+ |
|---|---|---|---|---|---|
| 28 | | | 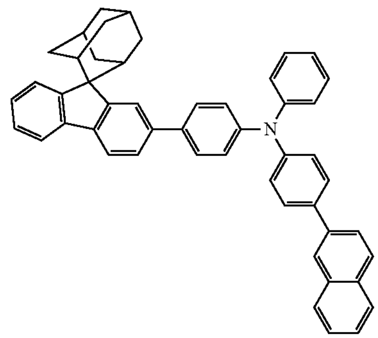 [SMILES: c1ccc(N(c2ccc(-c3ccc4c(c3)C3(c5ccccc5-4)C4CC5CC(C4)CC3C5)cc2)c2ccc(-c3ccc4ccccc4c3)cc2)cc1] | 63 | 656.3 |
| 29 | | | 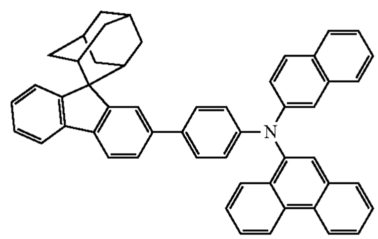 [SMILES: c1ccc2c(c1)-c1ccc(-c3ccc(N(c4ccc5ccccc5c4)c4cc5ccccc5c5ccccc45)cc3)cc1C21C2CC3CC(C2)CC1C3] | 66 | 680.3 |
| 30 | | | 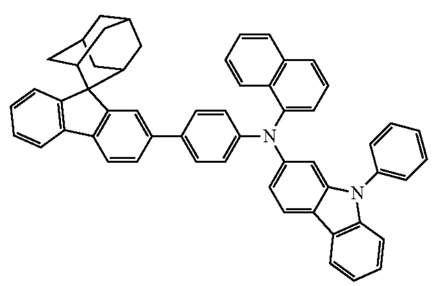 [SMILES: c1ccc(-n2c3ccccc3c3ccc(N(c4ccc(-c5ccc6c(c5)C5(c7ccccc7-6)C6CC7CC(C6)CC5C7)cc4)c4cccc5ccccc45)cc32)cc1] | 41 | 745.4 |

Synthesis of Compound 31

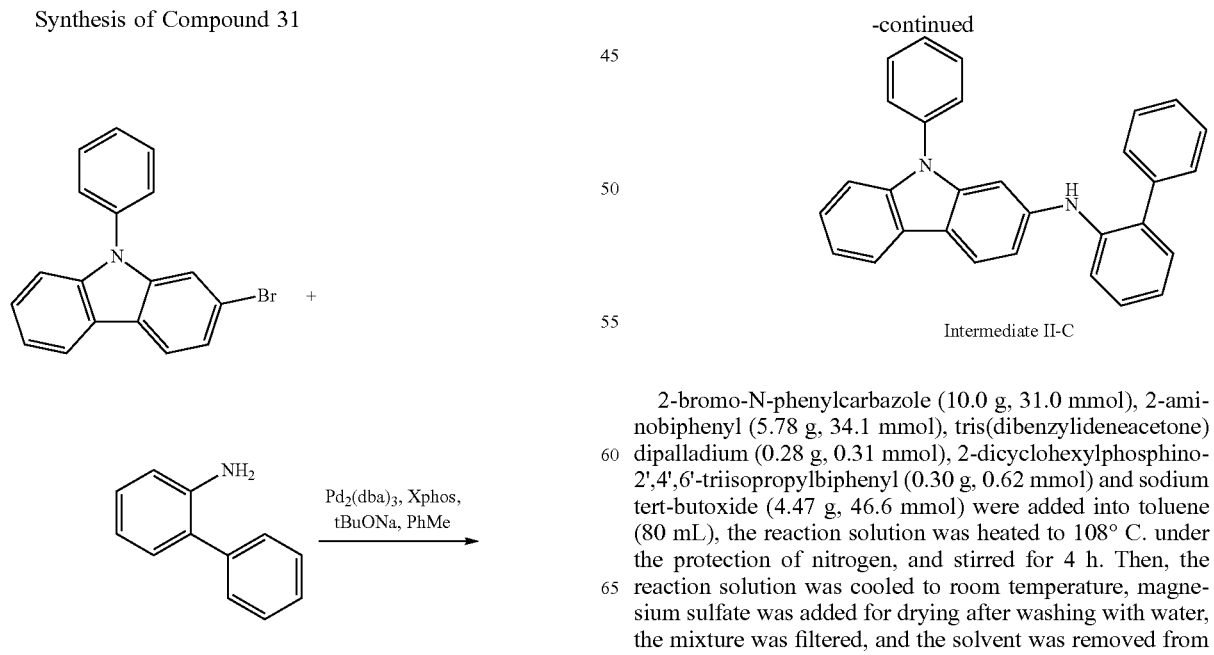

Intermediate II-C 2-bromo-N-phenylcarbazole (10.0 g, 31.0 mmol), 2-aminobiphenyl (5.78 g, 34.1 mmol), tris(dibenzylideneacetone)dipalladium (0.28 g, 0.31 mmol), 2-dicyclohexylphosphino-2',4',6'-triisopropylbiphenyl (0.30 g, 0.62 mmol) and sodium tert-butoxide (4.47 g, 46.6 mmol) were added into toluene (80 mL), the reaction solution was heated to 108° C. under the protection of nitrogen, and stirred for 4 h. Then, the reaction solution was cooled to room temperature, magnesium sulfate was added for drying after washing with water, the mixture was filtered, and the solvent was removed from the filtrate under reduced pressure. The crude product was purified by recrystallization using a dichloromethane/n-heptane system to obtain Intermediate II-C (8.65 g, 67.81% yield) as an orange solid.

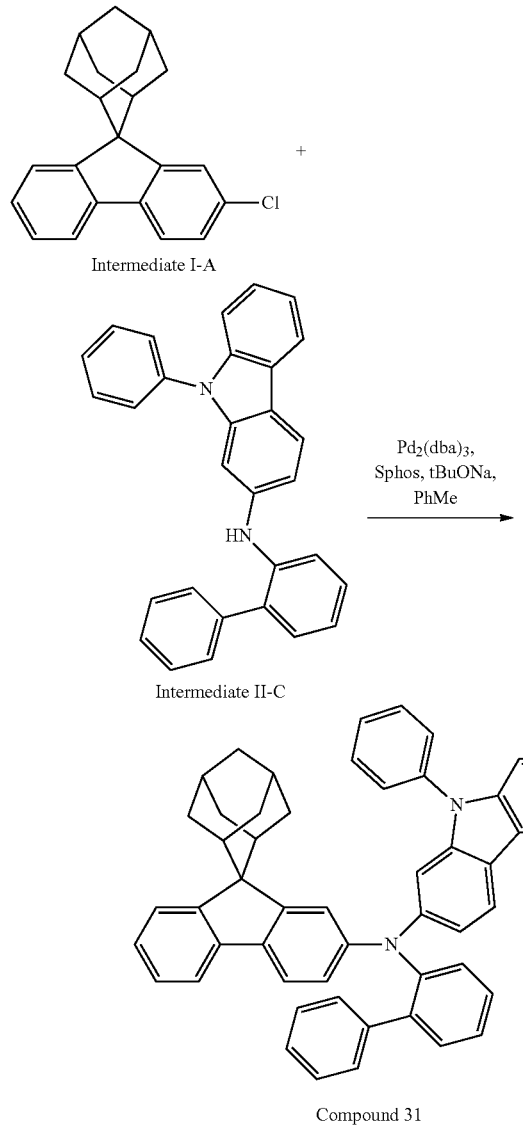

Intermediate I-A (3.5 g, 10.9 mmol), Intermediate II-C (4.48 g, 10.9 mmol), tris(dibenzylideneacetone)dipalladium (0.20 g, 0.22 mmol), 2-dicyclohexylphosphino-2',6'-dimethoxy biphenyl (0.18 g, 0.44 mmol) and the sodium tert-butoxide (1.57 g, 16.3 mmol) were added into toluene (30 mL), the reaction solution was heated to 108° C. under the protection of nitrogen, and stirred for 10 h. The reaction solution was cooled to room temperature, magnesium sulfate was added for drying after washing with water, the mixture was filtered, the filtrate was purified with silica column chromatography using dichloromethane/n-heptane (1/5) as mobile phase, and the solvent was removed from the column solution under reduced pressure. The crude product was purified by recrystallization using a dichloroethane system to obtain Compound 31 (5.42 g, 71.5% yield) as a white solid. Mass spectrum: m/z=695.3 (M+H)$^+$.

Synthesis of Compound 32

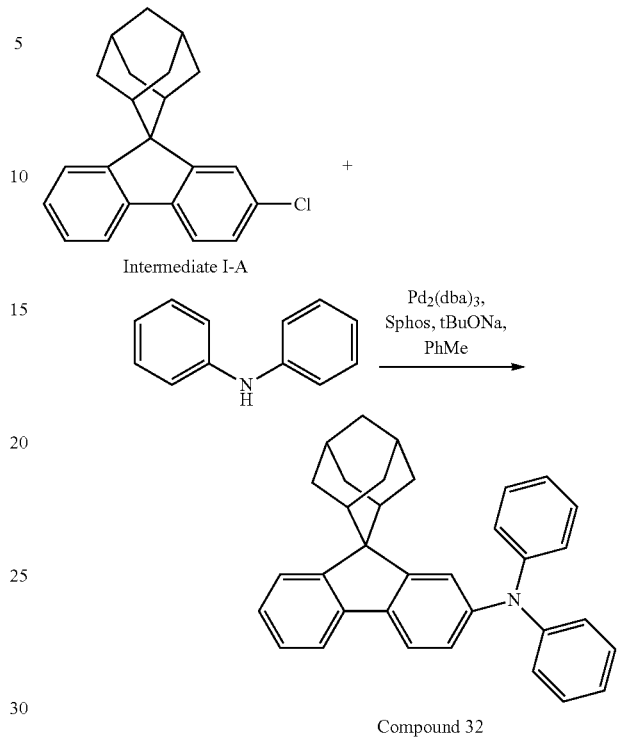

Intermediate I-A (3.5 g, 10.9 mmol), diphenylamine (1.85 g, 10.9 mmol), tris(dibenzylideneacetone)dipalladium (0.20 g, 0.22 mmol), 2-dicyclohexylphosphino-2',6'-dimethoxybiphenyl (0.18 g, 0.44 mmol) and sodium tert-butoxide (1.57 g, 16.4 mmol) were added into toluene (30 mL), the reaction solution was heated to 108° C. under the protection of nitrogen, and stirred for 2 h. Then, the reaction solution was cooled to room temperature, magnesium sulfate was added for drying after washing with water, the mixture was filtered, the filtrate was passed through a short silica column, and the solvent was removed under reduced pressure. The crude product was purified by recrystallization using a dichloromethane/ethyl acetate system to obtain Compound 32 (3.06 g, 61.94% yield) as a white solid. Mass spectrum: m/z=454.2 (M+H)$^+$.

Synthesis of Compound 33

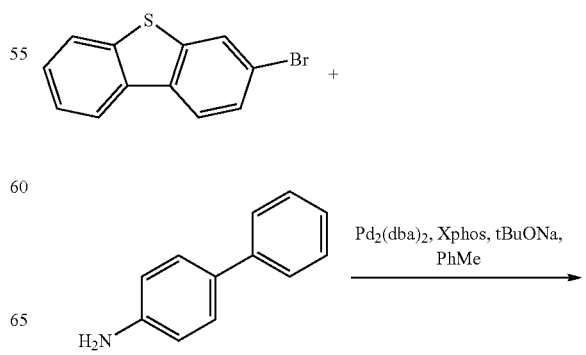

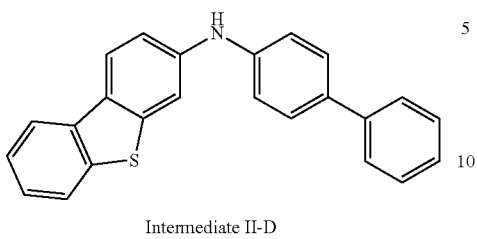

Intermediate II-D 3-bromodibenzothiophene (10.0 g, 38.0 mmol), 4-amino-biphenyl (7.07 g, 41.8 mmol), tris(dibenzylideneacetone)dipalladium (0.35 g, 0.38 mmol), 2-dicyclohexylphosphino-2',4',6'-triisopropylbiphenyl (0.36 g, 0.76 mmol), and sodium tert-butoxide (5.48 g, 57.0 mmol) were added into toluene (80 mL), the reaction solution was heated to 108° C. under the protection of nitrogen, and stirred for 5 h. Then, the reaction solution was cooled to room temperature, magnesium sulfate was added for drying after washing with water, the mixture was filtered, and the solvent was removed under reduced pressure. The crude product was purified by recrystallization using a dichloromethane/ethyl acetate system to obtain Intermediate II-D (11.5 g, 86% yield) as a pale-yellow solid.

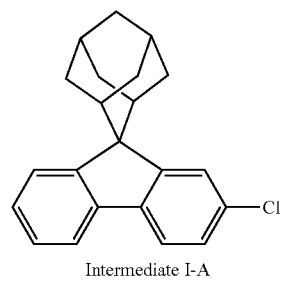

Intermediate I-A

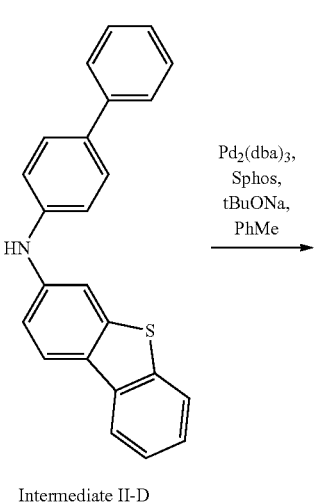

Intermediate II-D

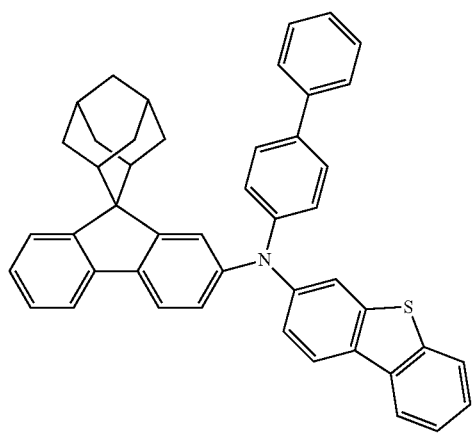

Compound 33

Intermediate I-A (3.5 g, 10.9 mmol), Intermediate II-D (3.83 g, 10.9 mmol), the tris(dibenzylideneacetone)dipalladium (0.20 g, 0.22 mmol), 2-dicyclohexylphosphino-2',6'-dimethoxy biphenyl (0.18 g, 0.44 mmol) and sodium tert-butoxide (1.58 g, 16.4 mmol) were added into toluene (30 mL), the reaction solution was heated to 108° C. under the protection of nitrogen, and stirred for 6 h. The reaction solution was cooled to room temperature, magnesium sulfate was added for drying after washing with water, the mixture was filtered, the filtrate was purified with silica column chromatography using dichloromethane/n-heptane (1/3) as mobile phase, and the solvent was removed from the column solution under reduced pressure. The crude product was purified by recrystallization using toluene to obtain Compound 33 (3.35 g, 47.5% yield) as a white solid. Mass spectrum: m/z=636.3 (M+H)$^+$.

Synthesis of Compound 34

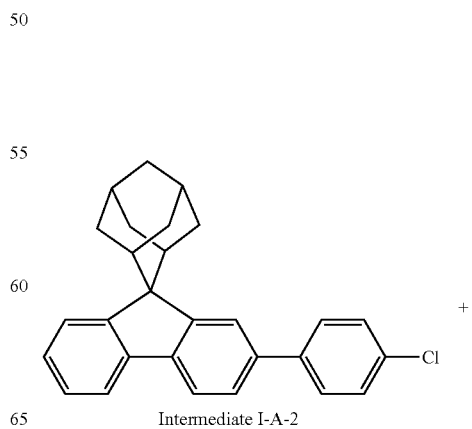

Intermediate I-A-2

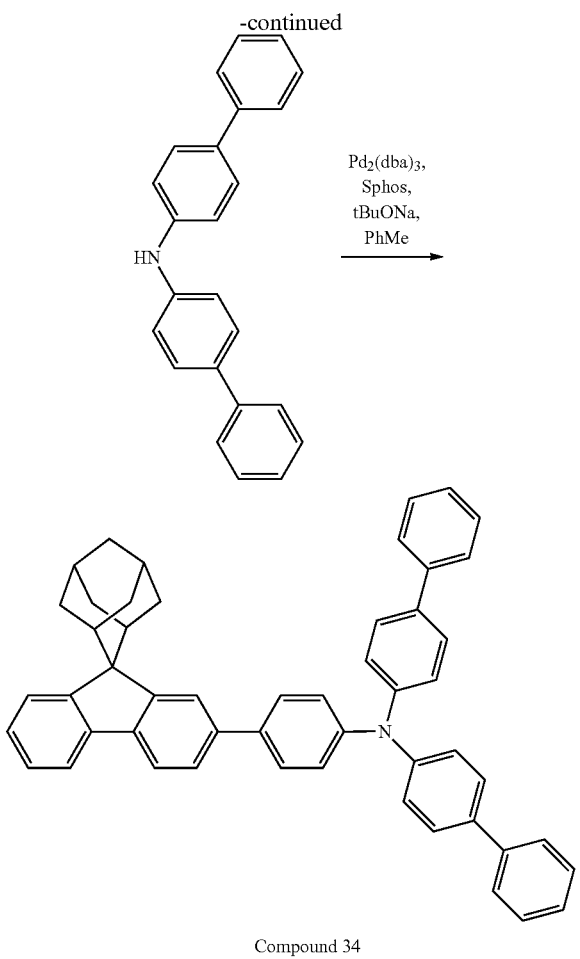

Compound 34

Intermediate I-A-2 (3 g, 7.6 mmol), bis-(4-biphenylyl)amine (2.43 g, 7.6 mmol), tris(dibenzylideneacetone)dipalladium (0.14 g, 0.15 mmol), 2-dicyclohexylphosphino-2',6'-dimethoxybiphenyl (0.12 g, 0.30 mmol) and sodium tert-butoxide (1.09 g, 11.33 mmol) were added into toluene (25 mL), the reaction solution was heated to 108° C. under the protection of nitrogen and stirred for 2 h. The reaction solution cooled to room temperature, magnesium sulfate was added for drying after washing with water, the mixture was filtered, the filtrate was passed through a short silica column, and the solvent was removed under reduced pressure. The crude product was purified by recrystallization using a toluene system to obtain Compound 34 (2.68 g, 52% yield) as a white solid. Mass spectrum: m/z=682.3 (M+H)⁺.

Synthesis of Compound 35

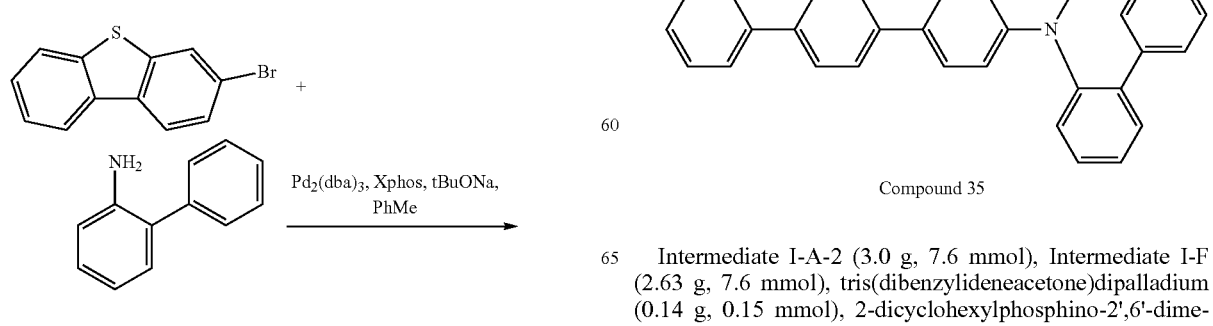

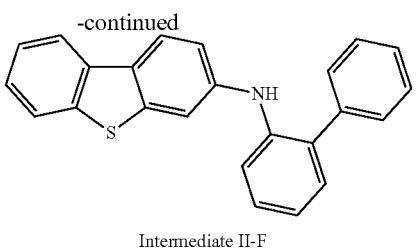

Intermediate II-F 3-bromodibenzothiophene (10.0 g, 38.0 mmol), 2-aminobiphenyl (7.07 g, 41.8 mmol), tris(dibenzylideneacetone)dipalladium (0.35 g, 0.38 mmol), 2-dicyclohexylphosphino-2',4',6'-triisopropylbiphenyl (0.36 g, 0.76 mmol), and sodium tert-butoxide (5.48 g, 57.0 mmol) were added into toluene (80 mL), the reaction solution heated to 108° C. under the protection of nitrogen, and stirred for 1.5 h. The reaction solution was cooled to room temperature, magnesium sulfate was added for drying after washing with water, the mixture was filtered, the filtrate was passed through a short silica column, and the solvent was removed under reduced pressure. The crude product was purified by recrystallization using a dichloromethane/ethyl acetate system to obtain Intermediate II-F (11.5 g, 86% yield) as a white solid.

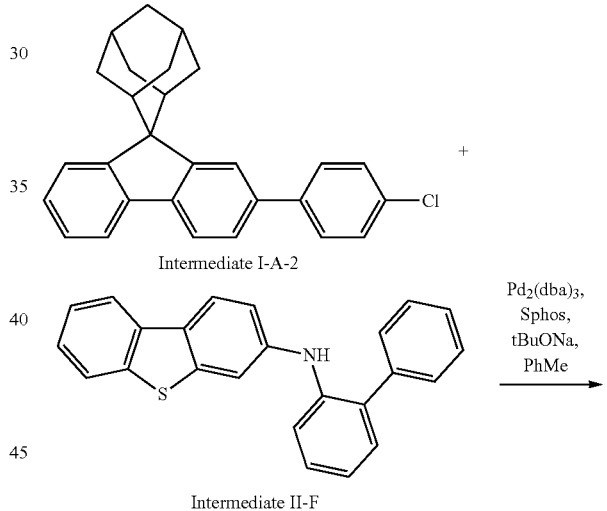

Compound 35

Intermediate I-A-2 (3.0 g, 7.6 mmol), Intermediate I-F (2.63 g, 7.6 mmol), tris(dibenzylideneacetone)dipalladium (0.14 g, 0.15 mmol), 2-dicyclohexylphosphino-2',6'-dimethoxybiphenyl (0.12 g, 0.30 mmol) and sodium tert-butoxide (1.09 g, 11.33 mmol) were added into toluene (25 mL), the reaction solution was heated to 108° C. under the protection of nitrogen and stirred for 3 h. The reaction solution was cooled to room temperature, magnesium sulfate was added for drying after washing with water, the mixture was filtered, the filtrate was passed through a short silica column, and the solvent was removed under reduced pressure. The crude product was purified by recrystallization using a toluene system to obtain Compound 35 (2.17 g, 42% yield) as a white solid. Mass spectrum: m/z=712.3 (M+H)$^+$.

Synthesis of Compound 36

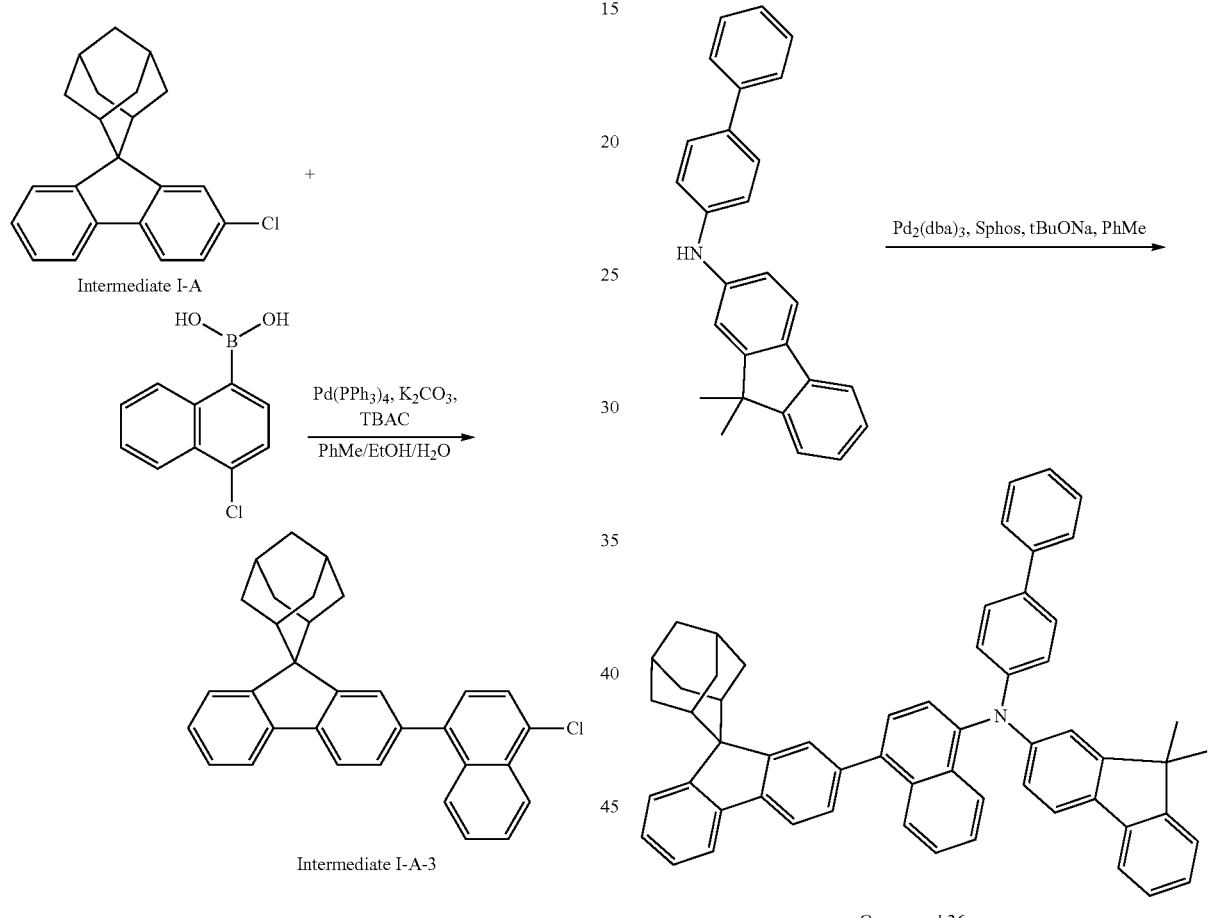

Intermediate I-A (3.0 g, 9.45 mmol), 4-chloro-1-naphthalene boronic acid (1.3 g, 6.30 mmol), tetrakis(triphenylphosphine)palladium (0.15 g, 0.13 mmol), potassium carbonate (1.74 g, 12.6 mmol), tetrabutylammonium chloride (0.09 g, 0.31 mmol), toluene (25 mL), ethanol (6 mL) and deionized water (6 mL) were added into a round bottom flask, the reaction solution was heated to 78° C. under the protection of nitrogen, and stirred for 16 hours. The reaction solution was cooled to room temperature, toluene (30 mL) was added for extraction, the combined organic phases were dried by using anhydrous magnesium sulfate, the mixture was filtered, and the solvent was removed under reduced pressure. The crude product was purified by silica column chromatography using n-heptane as mobile phase, followed by recrystallization using a dichloromethane/ethyl acetate system to obtain Intermediate I-A-3 (1.89 g, yield 67%) as a white solid.

Intermediate I-A-3 (1.89 g, 2.91 mmol), Intermediate II-G (1.05 g, 2.91 mmol), tris(dibenzylideneacetone)dipalladium (0.05 g, 0.06 mmol), 2-dicyclohexylphosphino-2',6'-dimethoxy biphenyl (0.05 g, 0.12 mmol) and sodium tert-butoxide (0.42 g, 4.36 mmol) were add into toluene (20 mL), the reaction solution was heated to 108° C. under the protection of nitrogen and stirred for 2 h. The reaction solution was cooled to room temperature, magnesium sulfate was added for drying after washing with water, the mixture was filtered, the filtrate was passed through a short silica column, and the solvent was removed under reduced pressure. The crude product was purified by recrystallization using a dichloromethane/ethyl acetate system to obtain Compound 36 (2.05 g, 91%) as a white solid. Mass spectrum: m/z=772.4 (M+H)$^+$.

Thermal Stability of the Compounds

When the compound is used for mass production of devices, it needs to be heated for a long time under the evaporation condition. If the compound has a poor thermal stability of a molecular structure under a heated condition, the purity of the compound will decrease under the heated condition for a long time, resulting in large differences in the performance of the devices prepared in the early, middle and late stage of mass production.

The stability of the molecular structure of the nitrogen-containing compounds of the present disclosure under the heated condition for a long time during the mass production evaporation is evaluated by the following method:

Under a high vacuum environment (<10-6 Pa), and the heat resistance test (heat treatment) was performed for 200 hours for each of Compounds 1 to 30 at a temperature corresponding to the deposition rate of 5 Å per second. The stability of the nitrogen-containing compounds of the present disclosure under mass production condition was evaluated by the decreased value in purity before and after the heat resistance test, and the following two relative compounds were used as controls:

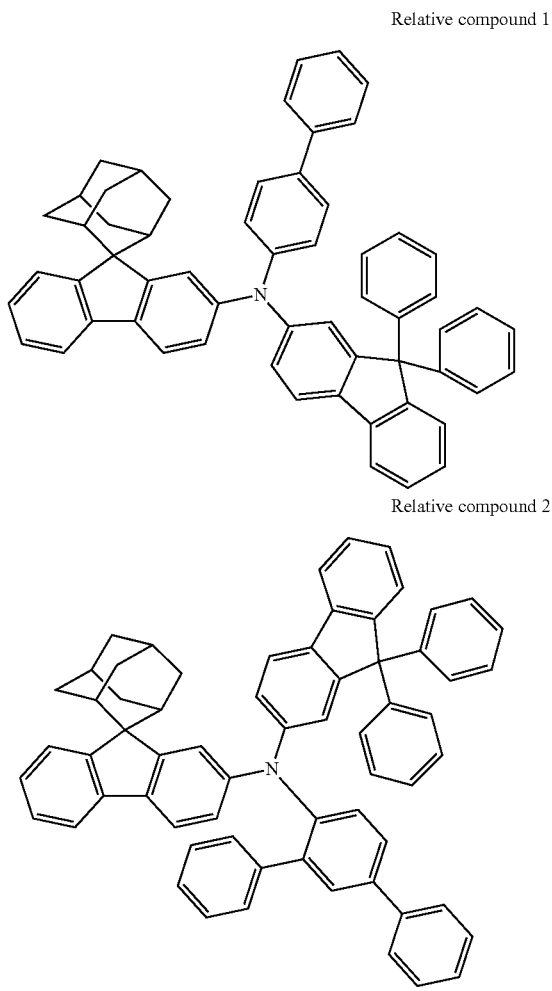

Relative compound 1

Relative compound 2

The temperature in the heat resistance test and decreased values in purity of the nitrogen-containing compound are shown in Table 3:

TABLE 3

Temperature in the Test and Decreased Values in Purity of Nitrogen-containing Compounds

| Compound | Molecular Weight | Evaporation Temperature corresponding to 5 Å/s | Decreased Values in Purity (HPLC, %) |
| --- | --- | --- | --- |
| Compound 1 | 605.8 | 264 | 0.05 |
| Compound 2 | 645.9 | 277 | 0.02 |
| Compound 3 | 619.8 | 278 | 0.08 |
| Compound 4 | 619.8 | 274 | 0.01 |
| Compound 5 | 694.9 | 305 | 0.48 |
| Compound 6 | 695.9 | 307 | 0.51 |
| Compound 7 | 645.9 | 266 | 0.14 |
| Compound 8 | 694.9 | 288 | 0.25 |
| Compound 9 | 686.0 | 292 | 0.24 |
| Compound 10 | 675.9 | 301 | 0.30 |
| Compound 11 | 645.9 | 275 | 0.10 |
| Compound 12 | 669.9 | 289 | 0.09 |
| Compound 13 | 503.7 | 221 | 0.00 |
| Compound 14 | 618.8 | 268 | 0.01 |
| Compound 15 | 605.8 | 263 | 0.02 |
| Compound 16 | 629.8 | 269 | 0.02 |
| Compound 17 | 553.7 | 248 | 0.12 |
| Compound 18 | 629.8 | 276 | 0.17 |
| Compound 19 | 629.8 | 265 | 0.15 |
| Compound 20 | 668.9 | 273 | 0.01 |
| Compound 21 | 669.9 | 291 | 0.17 |
| Compound 22 | 659.9 | 291 | 0.16 |
| Compound 23 | 745.0 | 319 | 0.65 |
| Compound 24 | 605.8 | 263 | 0.03 |
| Compound 25 | 681.9 | 282 | 0.23 |
| Compound 26 | 736.0 | 318 | 0.68 |
| Compound 27 | 681.9 | 284 | 0.22 |
| Compound 28 | 655.9 | 285 | 0.21 |
| Compound 29 | 679.9 | 286 | 0.20 |
| Compound 30 | 745.0 | 316 | 0.59 |
| Relative Compound 1 | 770.0 | 331 | 1.24 |
| Relative Compound 2 | 846.1 | 352 | 3.63 |

As can be seen from Table 3, the nitrogen-containing compounds of the present disclosure all had a decreased value in purity of less than 0.7%, most of which were less than 0.3%. The relative compounds containing diphenylfluorene substituents had decreased values in purity exceeding 1%. Therefore, the thermal stability of the nitrogen-containing compounds of the present disclosure is far superior to that of Comparative Compounds 1 and 2.

It may be due to the fact that the decomposition rate of the fluorene-triarylamine-containing structure is greatly accelerated at temperatures above 320° C. According to the data in Table 3, it can be deduced that the evaporation temperature of the nitrogen-containing compound is in positive correlation with the molecular weight, and the molecular weight corresponding to the evaporation temperature of 320° C. is about 750. Therefore, when the nitrogen-containing compound is introduced with a diphenylfluorene substituent with large molecular weight, the nitrogen-containing compound is easy to have a molecular weight of more than 750, so that the purity of the compound decreases more at the same evaporation speed.

When the decreased value in purity of the compound exceeds 1%, the efficiency and the service life of a device are obviously reduced. Therefore, such thermolabile compounds can cause large differences in the performance of devices prepared in the early, middle and late stage of the actual mass production. In the present disclosure, the molecular weights of Compounds 1 to 30 are all small, so that the evaporation temperatures are relatively low, and the heat resistance tests prove that the decreased values in purity are all less than 0.7%, so that the nitrogen-containing compounds of the present disclosure have excellent mass production thermal stability.

Preparation and Evaluation of Organic Electroluminescent Devices

Example 1

A blue organic electroluminescent device was prepared by the following method:

An ITO substrate (manufactured by Corning) with a thickness of 1500 Å was cut into a size of 40 mm (length)× 40 mm (width)×0.7 mm (thickness), and prepared into an experimental substrate having a cathode, an anode and an insulating layer pattern using a photolithography process. The surface was treated with ultraviolet ozone and $O_2:N_2$ plasma to increase the work function of the anode (experimental substrate) and to remove scum.

m-MTDATA was vacuum-evaporated on the experimental substrate (anode) to form a hole injection layer (HIL) with a thickness of 100 Å, and Compound 1 was vacuum-evaporated on the hole injection layer to form a first hole transport layer with a thickness of 1000 Å.

TCTA was vacuum-evaporated on the first hole transport layer to form a second hole transport layer with a thickness of 100 Å.

A light emitting layer (EML) with a thickness of 200 Å was formed by using α,β-ADN as a host material and BD-1 as a dopant in a film thickness ratio of 100:3.

DBimiBphen and LiQ were mixed in a weight ratio of 1:1 and evaporated to form an electron transport layer (ETL) with a thickness of 300 Å, and LiQ was evaporated on the electron transport layer to form an electron injection layer (EIL) with a thickness of 10 Å. Then magnesium (Mg) and silver (Ag) were mixed at an evaporation rate of 1:9, and vacuum-evaporated on the electron injection layer to form a cathode with a thickness of 120 Å.

CP-1 with a thickness of 650 Å was evaporated on the cathode to fabricate an organic light emitting device.

Wherein, when the electroluminescent device was fabricated, the structures of the used materials were as follows:

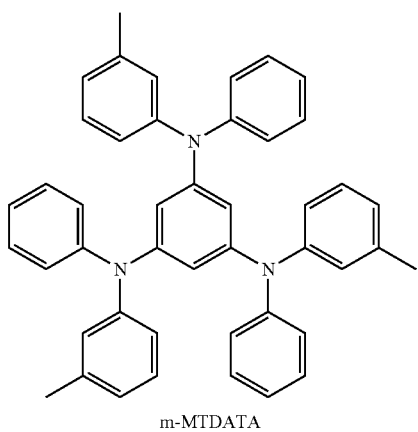

m-MTDATA

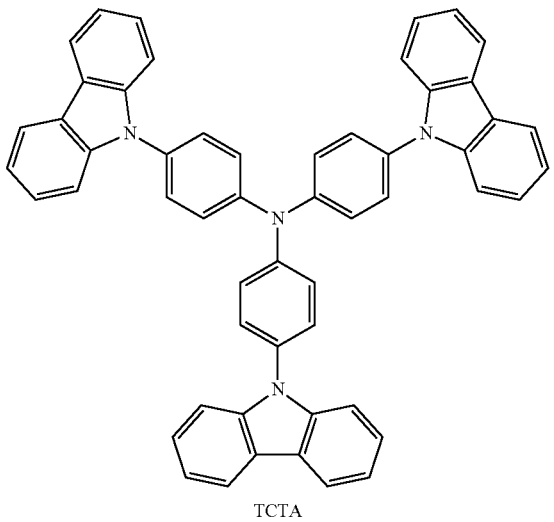

TCTA

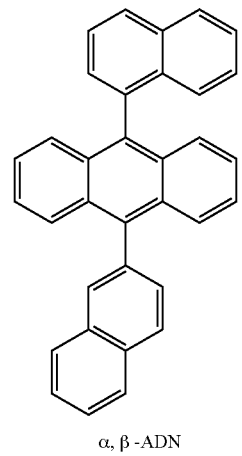

α, β -ADN

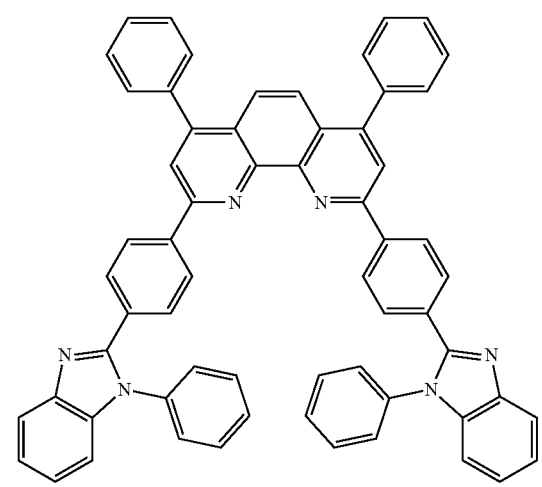

DBimiBphen

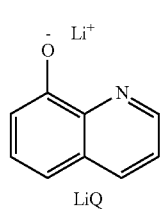

LiQ

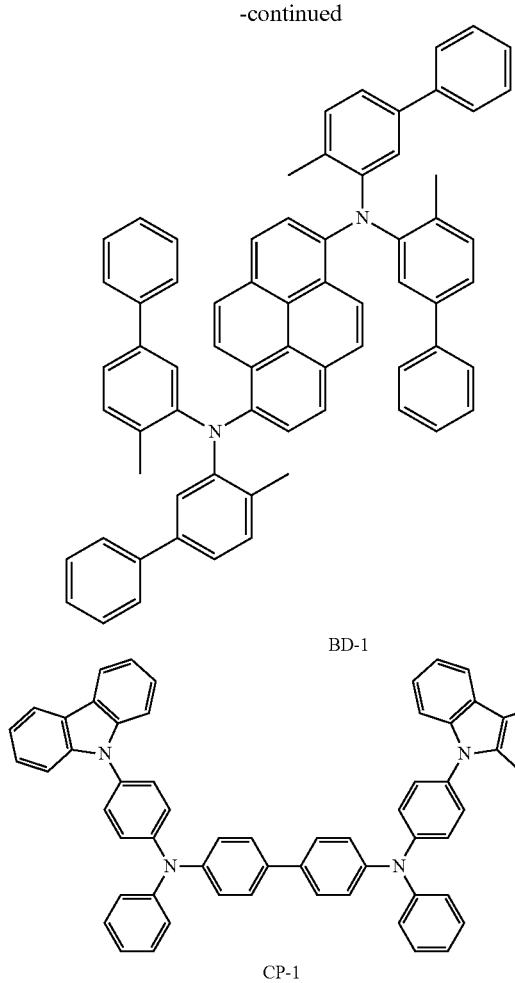

BD-1

CP-1

Examples 2 to 7

Corresponding blue organic electroluminescent devices were fabricated in the same manner as in Example 1, using the first hole transport layer materials listed in Table 4 instead of Compound 1 in Example 1.

That is, in Example 2, a blue organic electroluminescent device was fabricated using Compound 2 instead of Compound 1.

In Example 3, a blue organic electroluminescent device was fabricated using Compound 4 instead of Compound 1.

In Example 4, a blue organic electroluminescent device was fabricated using Compound 6 instead of Compound 1.

In Example 5, a blue organic electroluminescent device was fabricated using Compound 7 instead of Compound 1.

In Example 6, a blue organic electroluminescent device was fabricated using Compound 9 instead of Compound 1.

In Example 7, a blue organic electroluminescent device was fabricated using Compound 10 instead of Compound 1.

Examples 8 to 13

Corresponding blue organic electroluminescent devices were fabricated in the same manner as in Example 1, using the first hole transport layer materials listed in Table 4 instead of Compound 1 in Example 1 and the second hole transport layer materials listed in Table 2 instead of TCTA in Example 1.

That is, in Example 8, a blue organic electroluminescent device was fabricated using NPB instead of Compound 1 and Compound 8 instead of TCTA.

In Example 9, a blue organic electroluminescent device was fabricated using NPB instead of Compound 1 and Compound 24 instead of TCTA.

In Example 10, a blue organic electroluminescent device was fabricated using NPB instead of Compound 1 and Compound 25 instead of TCTA.

In Example 11, a blue organic electroluminescent device was fabricated using NPB instead of Compound 1 and Compound 27 instead of TCTA.

In Example 12, a blue organic electroluminescent device was fabricated using NPB instead of Compound 1 and Compound 28 instead of TCTA.

In Example 13, a blue organic electroluminescent device was fabricated using NPB instead of Compound 1 and Compound 29 instead of TCTA.

Wherein, the structure of NPB was as follows:

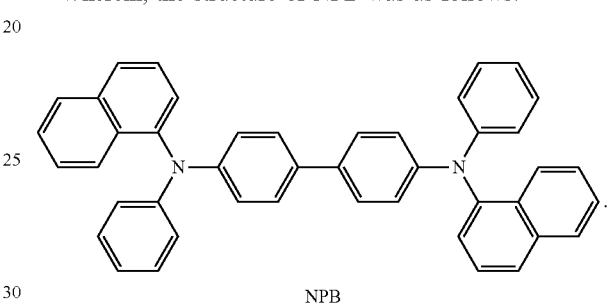

NPB

Comparative Example 1

A blue organic electroluminescent device was fabricated in the same manner as in Example 1, using NPB instead of Compound 1 in Example 1.

Comparative Example 2

A blue organic electroluminescent device was fabricated in the same manner as in Example 1, using Compound C instead of Compound 1 in Example 1.

Wherein, the structure of Compound C was as follows:

Compound C

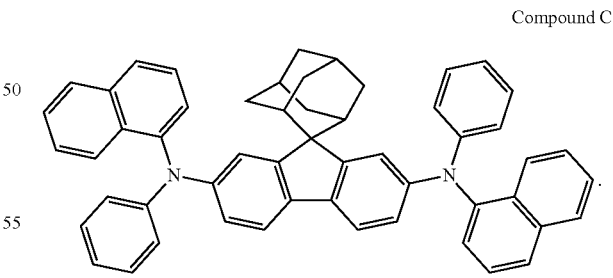

Comparative Example 3

A blue organic electroluminescent device was fabricated in the same manner as in Example 1, using NPB instead of Compound 1 in Example 1 and Compound D instead of TCTA in Example 1.

Wherein, the structure of the Compound D was as follows:

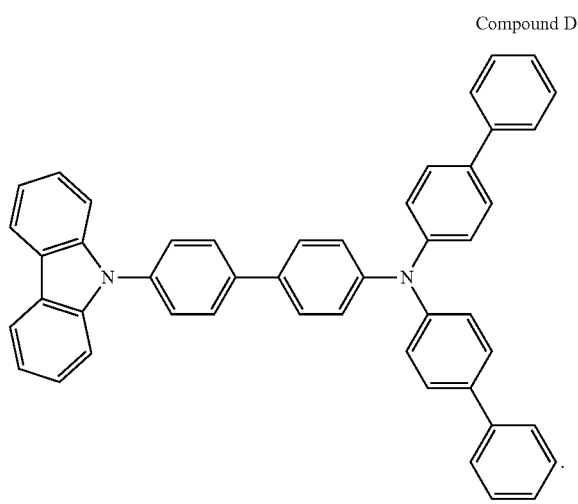 [SMILES: c1ccc(-c2ccc(N(c3ccc(-c4ccccc4)cc3)c3ccc(-c4ccc(-n5c6ccccc6c6ccccc65)cc4)cc3)cc2)cc1]

Compound D

The blue organic electroluminescent devices fabricated in Examples 1 to 13 and Comparative Examples 1 to 3 were measured. The IVL performances of the devices were measured at 10 mA/cm², and the T95 life was measured at a constant current density of 20 mA/cm². The measured results were shown in Table 4.

at least 69.5%. This is a very significant improvement, particularly for blue devices.

As can be seen from Table 4, in the case of little differences in color coordinates CIEy, the blue organic electroluminescent devices fabricated in Examples 8 to 13 have lower driving voltage, higher current efficiency and external quantum efficiency, and longer service life compared with Comparative Examples 1 and 3. Compared with Comparative Examples 1 and 3, the driving voltage of the blue organic electroluminescent devices fabricated in Examples 8 to 13 is reduced by a maximum of 6.4%, the current efficiency is improved by at least 21.1%, the external quantum efficiency is improved by at least 25%, and the T95 life is prolonged by at least 69%. This is a very significant improvement for blue devices.

Wherein, the external quantum efficiency (EQE %) can be calculated according to the following formula: EQE %=umber of Photons Emitted out of Organic Electroluminescent Device/Number of Injected Electrons. Of course, the calculation can also be performed as follows: EQE %=Light Extraction Rate* Internal Quantum Efficiency (light extraction rate less than 1). For the blue organic electroluminescent device, the organic light emitting layer uses a fluorescent material, the fluorescent material can only emit light by using singlet excitons, and the limit value of the internal quantum efficiency is 25%. When the blue organic electrolu-

TABLE 4

Performance Measured Results of Blue Organic Electroluminescent Device

|  | First Hole Transport Layer Material | Second Hole Transport Layer Material | Driving Voltage (V) | Current Efficiency (Cd/A) | Color Coordinate CIEy | External Quantum Efficiency EQE(%) | T95 Lift at 20 mA/cm²(h) |
|---|---|---|---|---|---|---|---|
| Example 1 | Compound 1 | TCTA | 4.17 | 6.1 | 0.047 | 12.6 | 195 |
| Example 2 | Compound 2 | TCTA | 4.18 | 6.2 | 0.048 | 12.8 | 197 |
| Example 3 | Compound 4 | TCTA | 4.21 | 6.1 | 0.048 | 12.6 | 218 |
| Example 4 | Compound 6 | TCTA | 4.18 | 6.3 | 0.046 | 12.9 | 215 |
| Example 5 | Compound 7 | TCTA | 4.23 | 6.3 | 0.047 | 12.9 | 220 |
| Example 6 | Compound 9 | TCTA | 4.21 | 6.2 | 0.046 | 12.8 | 205 |
| Example 7 | Compound 10 | TCTA | 4.17 | 6.1 | 0.048 | 12.5 | 200 |
| Example 8 | NPB | Compound 8 | 4.32 | 6.4 | 0.047 | 13.2 | 207 |
| Example 9 | NPB | Compound 24 | 4.29 | 6.5 | 0.047 | 13.5 | 198 |
| Example 10 | NPB | Compound 25 | 4.32 | 6.4 | 0.047 | 13.3 | 196 |
| Example 11 | NPB | Compound 27 | 4.29 | 6.3 | 0.048 | 13.0 | 191 |
| Example 12 | NPB | Compound 28 | 4.26 | 6.4 | 0.047 | 13.2 | 200 |
| Example 13 | NPB | Compound 29 | 4.24 | 6.5 | 0.046 | 13.3 | 203 |
| Comparative Example 1 | NPB | TCTA | 4.43 | 4.9 | 0.047 | 9.8 | 102 |
| Comparative Example 2 | Compound C | TCTA | 4.61 | 5.3 | 0.047 | 10.7 | 115 |
| Comparative Example 3 | NPB | Compound D | 4.53 | 5.2 | 0.047 | 10.4 | 113 |

As can be seen from Table 4, in the case of little differences in color coordinates CIEy, the blue organic electroluminescent devices fabricated in Examples 1 to 7 have lower driving voltage, higher external quantum efficiency and longer service life compared with Comparative Examples 1 and 2. Compared with Comparative Examples 1 and 2, the driving voltage of the blue organic electroluminescent devices fabricated in Examples 1 to 7 is reduced by a maximum of 9.5%, the external quantum efficiency is improved by at least 16.8%, and the T95 life is prolonged by minescent device emits light externally, light loss is caused by coupling in the organic electroluminescent device, and therefore the limit value of the external quantum efficiency of the blue organic electroluminescent device is 25%. On the premise that the theoretical limit value is 25%, compared with Comparative Examples 1 and 2, the external quantum efficiency of the blue organic electroluminescent devices fabricated in Examples 1 to 7 is at least improved to 12.9% from 10.7%, and the lifting amplitude of the blue organic electroluminescent devices is up to 17.6% relative to the theoretical limit value, so that the lifting is very remarkable. On the premise that the theoretical limit value is 25%, compared with Comparative Examples 1 and 3, the external quantum efficiency of the blue organic electroluminescent devices fabricated in Examples 8 to 13 is at least improved to 13.5% from 10.4%, and the lifting amplitude is up to 15.9% relative to the theoretical limit value, so that the lifting is very remarkable.

Therefore, when the nitrogen-containing compound of the present disclosure is used for fabricating an organic electroluminescent device, the driving voltage of the electroluminescent device can be effectively reduced, the external quantum efficiency can be improved, and the service life of the organic electroluminescent device can be prolonged.

Example 14

A red organic electroluminescent device was fabricated by the following method:

An ITO substrate (manufactured by Corning) with a thickness of 1500 Å was cut into a size of 40 mm (length)× 40 mm (width)×0.7 mm (thickness), and prepared into an experimental substrate having a cathode, an anode and an insulating layer pattern using a photolithography process. The surface was treated with ultraviolet ozone and $O_2:N_2$ plasma to increase the work function of the anode (experimental substrate) and to remove scum.

m-MTDATA was vacuum-evaporated on the experimental substrate (anode) to form a hole injection layer (HIL) with a thickness of 100 Å, and Compound 11 was vacuum-evaporated on the hole injection layer to form a first hole transport layer with a thickness of 1000 Å.

TPD was vacuum-evaporated on the first hole transport layer to form a second hole transport layer with a thickness of 850 Å.

A light emitting layer (EML) with a thickness of 350 Å was formed by using CBP as a host material and Ir(piq)$_2$(acac) as a dipant material in a film thickness ratio of 100:3.

DBimiBphen and LiQ were mixed in a weight ratio of 1:1 and evaporated to form an electron transport layer (ETL) with a thickness of 300 Å, and LiQ was evaporated on the electron transport layer to form an electron injection layer (EIL) with a thickness of 10 Å. Then magnesium (Mg) and silver (Ag) were mixed at an evaporation rate of 1:9, and vacuum-evaporated on the electron injection layer to form a cathode with a thickness of 105 Å.

CP-1 was evaporated on the cathode to form an organic capping layer (CPL) with a thickness of 650 Å.

Wherein, the structures of TPD, CBP, Ir(piq)$_2$(acac) were as follows:

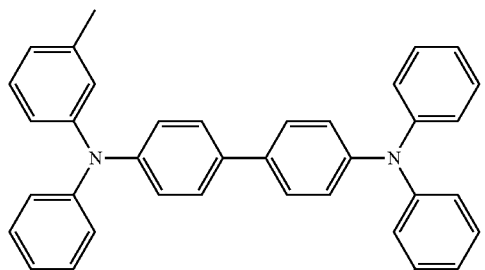

TPD

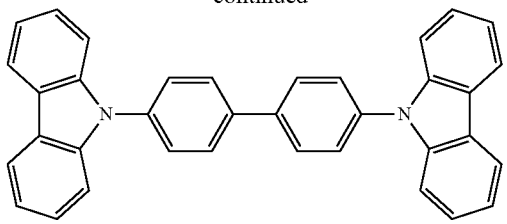

CBP

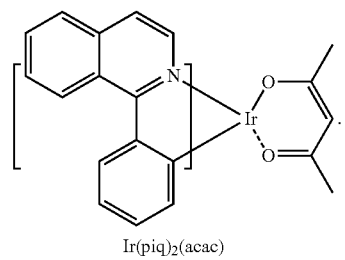

Ir(piq)$_2$(acac)

Examples 15 to 20

Corresponding red organic electroluminescent devices were fabricated in the same manner as in Example 14, using the first hole transport layer materials listed in Table 5 instead of Compound 11 in Example 14.

That is, in Example 15, a red organic electroluminescent device was fabricated using Compound 12 instead of Compound 11.

In Example 16, a red organic electroluminescent device was fabricated using Compound 13 instead of Compound 11.

In Example 17, a red organic electroluminescent device was fabricated using Compound 14 instead of Compound 11.

In Example 18, a red organic electroluminescent device was fabricated using Compound 18 instead of Compound 11.

In Example 19, a red organic electroluminescent device was fabricated using Compound 19 instead of Compound 11.

In Example 20, a red organic electroluminescent device was fabricated using Compound 20 instead of Compound 11.

Examples 21 to 30

Corresponding red organic electroluminescent devices were fabricated in the same manner as in Example 14, using the first hole transport layer material listed in Table 5 instead of Compound 11 in Example 14, and using the second hole transport layer material listed in Table 5 instead of TPD in Example 14.

That is, in Example 21, a red organic electroluminescent device was fabricated using NPB instead of Compound 11 and Compound 3 instead of TPD.

In Example 22, a red organic electroluminescent device was fabricated using NPB instead of Compound 11 and Compound 5 instead of TPD.

In Example 23, a red organic electroluminescent device was fabricated using NPB instead of Compound 11 and Compound 15 instead of TPD.

In Example 24, a red organic electroluminescent device was fabricated using NPB instead of Compound 11 and Compound 16 instead of TPD.

In Example 25, a red organic electroluminescent device was fabricated using NPB instead of Compound 11 and Compound 17 instead of TPD.

In Example 26, a red organic electroluminescent device was fabricated using NPB instead of Compound 11 and Compound 21 instead of TPD.

In Example 27, a red organic electroluminescent device was fabricated using NPB instead of Compound 11 and Compound 22 instead of TPD.

In Example 28, a red organic electroluminescent device was fabricated using NPB instead of Compound 11 and Compound 23 instead of TPD.

In Example 29, a red organic electroluminescent device was fabricated using NPB instead of Compound 11 and using Compound 26 instead of TPD.

In Example 30, a red organic electroluminescent device was fabricated using NPB instead of Compound 11 and using Compound 30 instead of TPD.

Comparative Example 4

A red organic electroluminescent device was fabricated in the same manner as in Example 14, using NPB instead of Compound 11 in Example 14.

Comparative Example 5

A red organic electroluminescent device was fabricated in the same manner as in Example 14, using NPB instead of Compound 11 in Example 14 and using Compound E instead of TPD in Example 14.

Wherein, the structural formula of Compound E was as follows:

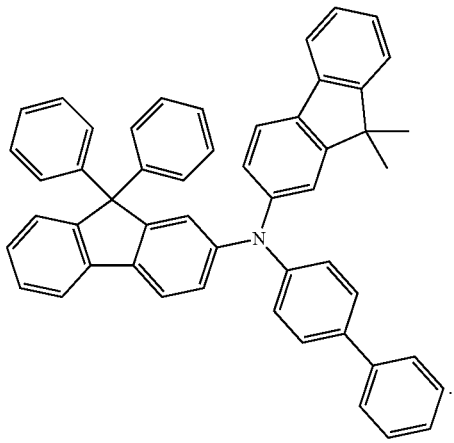

compound E

Comparative Example 6

A red organic electroluminescent device was fabricated in the same manner as in Example 14, using NPB instead of compound 11 in Example 14 and using compound F instead of TPD in Example 14.

Wherein, the structural formula of the compound F was as follows:

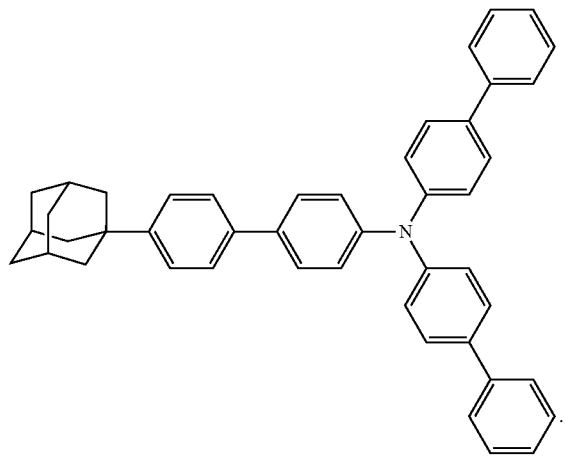

Compound F

The red organic electroluminescent devices fabricated as above were measured. The IVL performances of the devices were measured at 10 mA/cm$^2$, and the T95 life was measured at a constant current density of 20 mA/cm$^2$. The measured results were shown in Table 5.

TABLE 5

Performance Measured Results of Red Organic Electroluminescent Device

| | First Hole Transport Layer Material | Second Hole Transport Layer Material | Driving Voltage (V) | Current Efficiency (Cd/A) | Color Coordinate CIEy | External Quantum Efficiency EQE(%) | T95 Service life at 20 mA/cm$^2$(h) |
|---|---|---|---|---|---|---|---|
| Example14 | Compound 11 | TPD | 3.91 | 34.7 | 0.674 | 24.6 | 494 |
| Example15 | Compound 12 | TPD | 3.92 | 34.4 | 0.672 | 24.4 | 482 |
| Example16 | Compound 13 | TPD | 3.94 | 34.2 | 0.673 | 24.1 | 475 |
| Example17 | Compound 14 | TPD | 3.90 | 34.8 | 0.675 | 24.8 | 483 |
| Example18 | Compound 18 | TPD | 3.91 | 34.6 | 0.674 | 24.6 | 476 |
| Example19 | Compound 19 | TPD | 3.93 | 34.4 | 0.672 | 24.3 | 475 |

TABLE 5-continued

Performance Measured Results of Red Organic Electroluminescent Device

| | First Hole Transport Layer Material | Second Hole Transport Layer Material | Driving Voltage (V) | Current Efficiency (Cd/A) | Color Coordinate CIEy | External Quantum Efficiency EQE(%) | T95Service life at 20 mA/cm$^2$(h) |
|---|---|---|---|---|---|---|---|
| Example20 | Compound 20 | TPD | 3.92 | 34.6 | 0.673 | 24.3 | 473 |
| Example21 | NPB | Compound 3 | 3.88 | 33.6 | 0.674 | 23.5 | 455 |
| Example22 | NPB | Compound 5 | 3.89 | 33.9 | 0.675 | 23.7 | 456 |
| Example23 | NPB | Compound 15 | 3.87 | 33.8 | 0.677 | 23.6 | 466 |
| Example24 | NPB | Compound 16 | 3.88 | 33.5 | 0.678 | 23.6 | 460 |
| Example25 | NPB | Compound 17 | 3.89 | 33.7 | 0.676 | 23.8 | 455 |
| Example26 | NPB | Compound 21 | 3.87 | 33.6 | 0.674 | 23.8 | 469 |
| Example27 | NPB | Compound 22 | 3.86 | 33.7 | 0.678 | 23.9 | 468 |
| Example28 | NPB | Compound 23 | 3.89 | 33.8 | 0.677 | 23.7 | 465 |
| Example29 | NPB | Compound 26 | 3.89 | 33.5 | 0.675 | 23.5 | 455 |
| Example30 | NPB | Compound 30 | 3.87 | 33.6 | 0.673 | 23.5 | 459 |
| Comparative Example 4 | NPB | TPD | 4.20 | 27.0 | 0.674 | 19.1 | 260 |
| Comparative Example 5 | NPB | Compound E | 4.12 | 28.3 | 0.677 | 20.0 | 290 |
| Comparative Example 6 | NPB | Compound F | 4.08 | 28.8 | 0.676 | 20.3 | 295 |

As can be seen from Table 5, in the case of little differences in color coordinates CIEy, the red organic electroluminescent devices fabricated in Examples 14 to 20 have lower driving voltage, higher external quantum efficiency and longer service life compared with Comparative Example 4. Compared with Comparative Example 4, the driving voltage of the red organic electroluminescent device fabricated in Examples 14 to 20 is reduced by at least 4.4%, the current efficiency is improved by at least 20.8%, the external quantum efficiency is improved by at least 20.5%, and the T95 life is prolonged by at least 163%.

As can be seen from Table 5, in the case of little differences in color coordinates CIEy, the red organic electroluminescent devices fabricated in Examples 21 to 30 have lower driving voltage, higher current efficiency and external quantum efficiency, and longer service life than those of Comparative Examples 5 and 6. Compared with Comparative Examples 5 and 6, the driving voltage of the red organic electroluminescent devices fabricated in Examples 21 to 30 is reduced by at least 4.6%, the current efficiency is improved by at least 16.3%, the external quantum efficiency is improved by at least 15.7%, and the T95 life is prolonged by at least 154%.

Therefore, when the nitrogen-containing compound of the present disclosure is used for fabricating an organic electroluminescent device, the driving voltage of the electroluminescent device can be effectively reduced, the external quantum efficiency can be improved, and the service life of the organic electroluminescent device can be prolonged.

As can be seen from Tables 4 and 5, when the compound of the present disclosure is used as a hole transport layer material, the voltage of the organic electroluminescent device can be reduced, and the efficiency and service life of the organic electroluminescent device can be improved.

Example 31

Blue organic electroluminescent device fabricated by the following method

An ITO substrate (manufactured by Corning) with a thickness of 1500 Å was cut into a size of 40 mm (length)× 40 mm (width)×0.7 mm (thickness), and prepared into an experimental substrate having a cathode, an anode and an insulating layer pattern using a photolithography process. The surface was treated with ultraviolet ozone and $O_2$:$N_2$ plasma to increase the work function of the anode (experimental substrate) and to remove scum.

m-MTDATA was vacuum-evaporated on the experimental substrate (anode) to form a hole injection layer (HIL) with a thickness of 100 Å, and Compound 2 was vacuum-evaporated on the hole injection layer to form a first hole transport layer with a thickness of 800 Å.

TCTA was vacuum-evaporated on the first hole transport layer to form a second hole transport layer with a thickness of 300 Å.

A light emitting layer (EML) with a thickness of 220 Å was formed by using α,β-ADN as a host material and 4,4'-(3,8-diphenylpyrene-1,6-diylbis(N,N-diphenylaniline)) as a dopant material in a film thickness ratio of 100:3 to form.

DBimiBphen and LiQ were mixed in a weight ratio of 1:1 and evaporated to form an electron transport layer (ETL) with a thickness of 300 Å, and LiQ was evaporated on the electron transport layer to form an electron injection layer (EIL) with a thickness of 10 Å. Then magnesium (Mg) and silver (Ag) were mixed at an evaporation rate of 1:9, and vacuum-evaporated on the electron injection layer to form a cathode with a thickness of 120 Å.

N-(4-(9H-carbazol-9-yl)phenyl)-4'-(9H-carbazol-9-yl)-N-phenyl-[1,1'-biphenyl]-4-amine with a thickness of 650 Å was evaporated on the cathode.

Examples 32 to 37

Corresponding blue organic electroluminescent devices were fabricated in the same manner as in Example 31, using the compounds listed in Table 6 instead of Compound 2 in Example 31.

That is, in Example 32, a blue organic electroluminescent device was fabricated using Compound 31 instead of Compound 2. In Example 33, a blue organic electroluminescent device was fabricated using Compound 3 instead of Compound 2. In Example 34, a blue organic electroluminescent device was fabricated using Compound 32 instead of Compound 2. In Example 35, a blue organic electroluminescent device was fabricated using Compound 33 instead of Compound 2.

Comparative Examples 7 to 9

Blue organic electroluminescent devices were fabricated in the same manner as in Example 31, using NPB, NPD and TPD, respectively, instead of Compound 2 in Example 31.

Wherein, the structures of NPD and TPD were as follows:

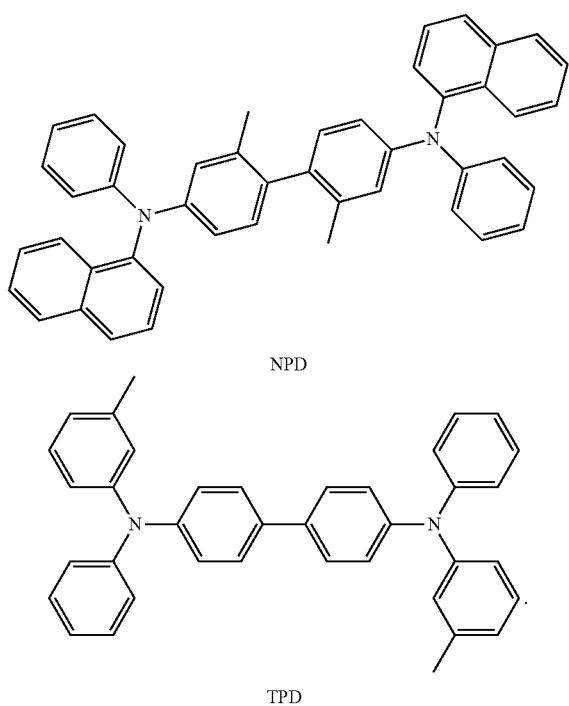

NPD

TPD

The blue organic electroluminescent devices fabricated in Examples 31 to 35 and Comparative Examples 7 to 9 were measured. The IVL performances of the devices were measured at 10 mA/cm$^2$, and the T95 life was measured at a constant current density of 20 mA/cm$^2$.

The measured results were shown in Table 6.

TABLE 6

Performance Measured Results of Blue Organic Electroluminescent Device

| Example | Compound | Driving Vogtive (V) | Luminous Efficacy (Cd/A) | External Quantum Efficiency EQE(%) | T95 life at 20 mA/cm$^2$(h) | Color Coordinate CIEy |
|---|---|---|---|---|---|---|
| Example31 | Compound 2 | 4.13 | 6.3 | 13.2 | 195 | 0.047 |
| Example32 | Compound 31 | 4.19 | 6.2 | 12.9 | 189 | 0.046 |
| Example33 | Compound 3 | 4.12 | 6.2 | 13.0 | 200 | 0.047 |
| Example34 | Compound 32 | 4.10 | 6.4 | 13.4 | 196 | 0.048 |
| Example35 | Compound 1 | 4.20 | 6.3 | 13.2 | 205 | 0.045 |
| Comparative Example 7 | NPB | 4.430 | 4.9 | 9.8 | 102 | 0.047 |
| Comparative Example 8 | NPD | 4.520 | 5.2 | 10.3 | 110 | 0.048 |
| Comparative Example 9 | TPD | 4.42 | 5.3 | 9.5 | 113 | 0.046 |

As can be seen from Table 6, in the case of little differences in color coordinates CIEy, the blue organic electroluminescent devices fabricated in Examples 31 to 35 have lower driving voltage, higher luminous efficiency, higher external quantum efficiency, and longer service life than those of Comparative Examples 7 to 9. Compared with Comparative Examples 7 to 9, the driving voltage of the blue organic electroluminescent devices fabricated in Examples 31 to 35 is reduced by at least 5%, the luminous efficiency is improved by at least 17%, the external quantum efficiency is improved by at least 25.2%, and the T95 life is prolonged by at least 67%.

Therefore, when the nitrogen-containing compound of the present disclosure is used for fabricating an organic electroluminescent device, the driving voltage of the electroluminescent device can be effectively reduced, the luminous efficiency can be improved, the external quantum efficiency can be improved, and the service life of the organic electroluminescent device can be prolonged.

Example 36

Red organic electroluminescent device fabricated by the following method

An ITO substrate (manufactured by Corning) with a thickness of 1500 Å was cut into a size of 40 mm (length)× 40 mm (width)×0.7 mm (thickness), and prepared into an experimental substrate having a cathode, an anode and an insulating layer pattern using a photolithography process. The surface was treated with ultraviolet ozone and $O_2$:$N_2$ plasma to increase the work function of the anode (experimental substrate) and to remove scum.

m-MTDATA was vacuum-evaporated on the experimental substrate (anode) to form a hole injection layer (HIL) with a thickness of 100 Å, and NPB was evaporated on the hole injection layer to form a first hole transport layer with a thickness of 800 Å.

Compound 33 was vacuum-evaporated on the first hole transport layer to form a second hole transport layer with a thickness of 850 Å.

A light emitting layer (EML) with a thickness of 350 Å was formed by using CBP as a host material and Ir(piq)$_2$(acac) as a dopant material in a film thickness ratio of 35:5 to form.

DBimiBphen and LiQ were mixed in a weight ratio of 1:1 and evaporated to form an electron transport layer (ETL) with a thickness of 300 Å, and LiQ was evaporated on the electron transport layer to form an electron injection layer (EIL) with a thickness of 10 Å. Then magnesium (Mg) and silver (Ag) were mixed at an evaporation rate of 1:9, and vacuum-evaporated on the electron injection layer to form a cathode with a thickness of 105 Å.

N-(4-(9H-carbazol-9-yl)phenyl)-4'-(9H-carbazol-9-yl)-N-phenyl-[1,1'-biphenyl]-4-amine was evaporated on the cathode to formed an organic capping layer (CPL) with a thickness of 650 Å.

Examples 37 to 39

Corresponding red organic electroluminescent devices were fabricated in the same manner as in Example 36, using the compounds listed in Table 7 instead of Compound 33 in Example 36.

That is, in Example 37, a red organic electroluminescent device was fabricated using Compound 34 instead of Compound 33.

In Example 38, a red organic electroluminescent device was fabricated using Compound 35 instead of Compound 33.

In Example 39, a red organic electroluminescent device was fabricated using Compound 36 instead of Compound 33.

Comparative Example 10

A red organic electroluminescent device was fabricated in the same manner as in Example 36, using NPB instead of Compound 33 in Example 36.

Comparative Example 11

A red organic electroluminescent device was fabricated in the same manner as in Example 36, using TPD instead of Compound 33 in Example 36.

Comparative Example 12

A red organic electroluminescent device was fabricated in the same manner as in Example 36, except that the second hole transport layer was not formed.

The red organic electroluminescent devices fabricated as above were measured. The IVL performances of the devices were measured at 10 mA/cm2, and the T95 life was measured at a constant current density of 20 mA/cm2. The measured results were shown in Table 7.

TABLE 7

Performance Measured Results of Red Organic Electroluminescent Device

| Example | Compound | Driving Voltage (V) | Luminous Efficacy (Cd/A) | External Quantum Efficiency EQE(%) | T95 life at 20 mA/$cm^2$(h) | CIEx |
|---|---|---|---|---|---|---|
| Example 36 | Compound 33 | 3.89 | 34.32 | 23.64 | 472 | 0.677 |
| Example 37 | Compound 34 | 3.95 | 34.34 | 23.52 | 462 | 0.676 |
| Example 38 | Compound 35 | 3.98 | 34.15 | 23.69 | 486 | 0.675 |
| Comparative Example 10 | NPD | 4.02 | 27.15 | 20.30 | 290 | 0.676 |
| Comparative Example 11 | TPD | 4.13 | 27.22 | 19.40 | 285 | 0.677 |
| Comparative Example 12 | — | 4.03 | 28.30 | 19.57 | 245 | 0.678 |

As can be seen from Table 7, in the case of little differences in color coordinates CIEy, the red organic electroluminescent devices fabricated in Examples 36 to 39 have lower driving voltage, higher luminous efficiency, higher external quantum efficiency, and longer service life than those of Comparative Examples 10 to 12. Compared with Comparative Examples 10 to 12, the luminous efficiency of the red organic electroluminescent devices fabricated in Examples 36 to 39 is improved by at least 20.7%, the external quantum efficiency is improved by at least 15.9%, and the T95 life is prolonged by at least 59%. Therefore, when the nitrogen-containing compound of the present disclosure is used for fabricating an organic electroluminescent device, the driving voltage of the electroluminescent device can be effectively reduced, the luminous efficiency can be improved, the external quantum efficiency can be improved, and the service life of the organic electroluminescent device can be prolonged.

The nitrogen-containing compound of the present disclosure introduces an adamantane-2-yl structure at the 9-position of fluorene, the adamantyl can improve the electron density of a fluorene ring and a conjugated system of the whole nitrogen-containing compound through a hyperconjugation effect, so that the hole conduction efficiency of the nitrogen-containing compound is improved, and further the carrier conduction efficiency and the service life of an organic electroluminescent device and a photoelectric conversion device are improved. The adamantan-2-yl group is introduced at the 9-position of fluorene rather than at the end, and into the side chains of the amines of the nitrogen-containing compounds of the present disclosure rather than at the end. Due to the large steric hindrance effect of the adamantane-2-yl, the angle and the conjugation degree between each branched chain of amine can be adjusted, and further the HOMO value of the nitrogen-containing compound can be adjusted, so that the HOMO value of the nitrogen-containing compound can be more matched with an adjacent film layer, the driving voltage of an organic electroluminescent device can be further reduced, or the open-circuit voltage of a photoelectric conversion device can be improved.

Moreover, the nitrogen-containing compound of the present disclosure is a modification of the fluorenyl with the bulky alkyl structure, so that compared with a modification with aryl, an excessively strong π-π stacking effect can be avoided, the symmetry of the nitrogen-containing compound of the present disclosure can be reduced, and the film-forming property of the nitrogen-containing compound can be further improved. Moreover, the adamantane-2-yl group can ensure that the nitrogen-containing compound of the present disclosure has an appropriate molecular weight, further ensure that the nitrogen-containing compound of the present disclosure has an appropriate glass transition temperature, and improve the physical and thermal stability during the preparation of an organic electroluminescent device and a photoelectric conversion device.

What is claimed is:

1. A nitrogen-containing compound, having a structure represented by Chemical Formula 1:

Chemical Formula 1

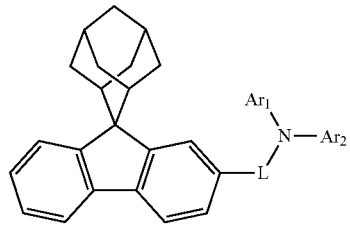

wherein L is selected from a single bond, or a substituted or an unsubstituted C6 to C12 arylene group;
wherein $Ar_1$ and $Ar_2$ are each independently selected from a substituted or an unsubstituted C6 to C20 aryl group or from a substituted or an unsubstituted C12 to C20 heteroaryl group;
the substituents of $Ar_1$, $Ar_2$ and L are each independently selected from an aryl group, a heteroaryl group, or a methyl group;
the substituted C6 to C12 arylene group means that the total number of carbon atoms of the arylene group and the substituents thereon combined are from 6 to 12;
the substituted C6 to C20 aryl group means that the total number of carbon atoms of the aryl group and the substituents thereon combined are from 6 to 20;
the substituted C12 to C20 heteroaryl group means that the total number of carbon atoms of the heteroaryl group and the substituents thereon combined are from 12 to 20.

2. The nitrogen-containing compound according to claim 1, wherein L is selected from a single bond, a substituted or an unsubstituted phenylene group, a substituted or an unsubstituted naphthylene group, or a substituted or an unsubstituted biphenylene group.

3. The nitrogen-containing compound according to claim 1, wherein the nitrogen-containing compound has a relative molecular mass of not greater than 750.

4. The nitrogen-containing compound according to claim 1, wherein L is selected from a single bond or the following substituents:

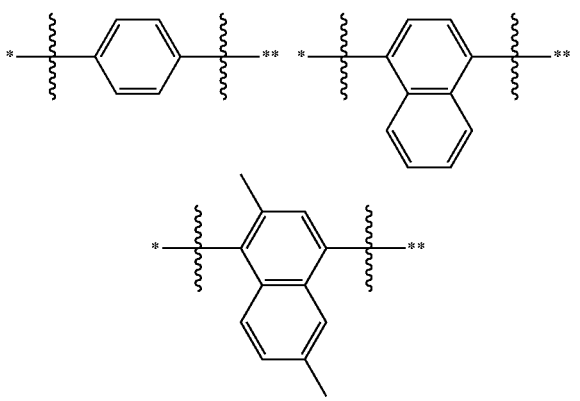

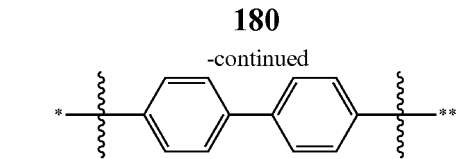

wherein,

represents a chemical bond;
* represents a binding site where the above substituent is connected to

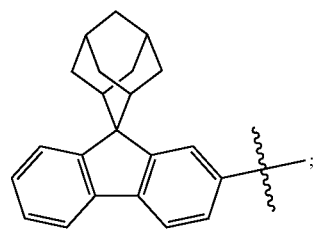 [SMILES: *c1ccc2c(c1)C1(c3ccccc3-2)C2CC3CC(C2)CC1C3]

** represents a binding site where the above substituent is connected to

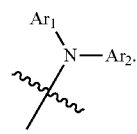

5. The nitrogen-containing compound according to claim 1, wherein at least one of $Ar_1$ And $Ar_2$ is selected from a substituted aryl group having 6 to 12 ring-forming carbon atoms, and the substituent on the substituted aryl group having 6 to 12 ring-forming carbon atoms is selected from an aryl group of 6 to 14 carbon atoms or a heteroaryl group of 6 to 12 carbon atoms.

6. The nitrogen-containing compound according to claim 1, wherein $Ar_1$ and $Ar_2$ are each independently selected from the following substituents:

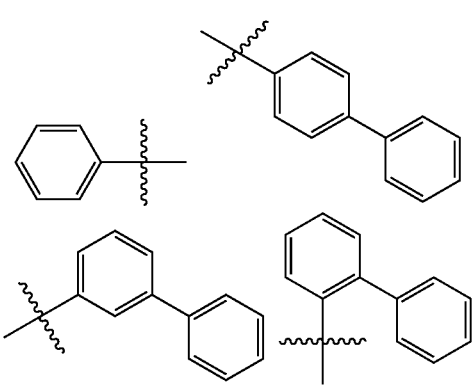

181
-continued
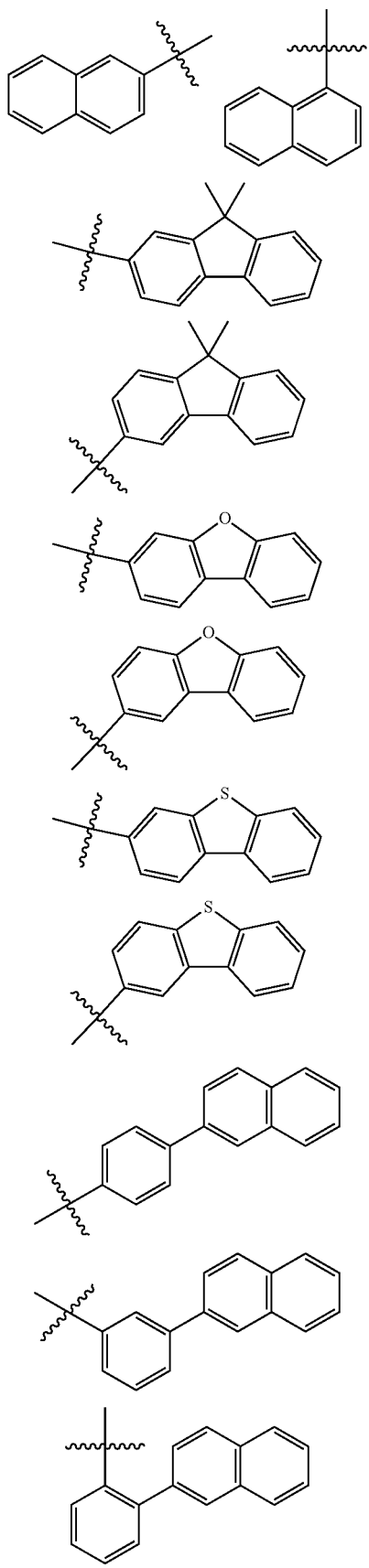
182
-continued
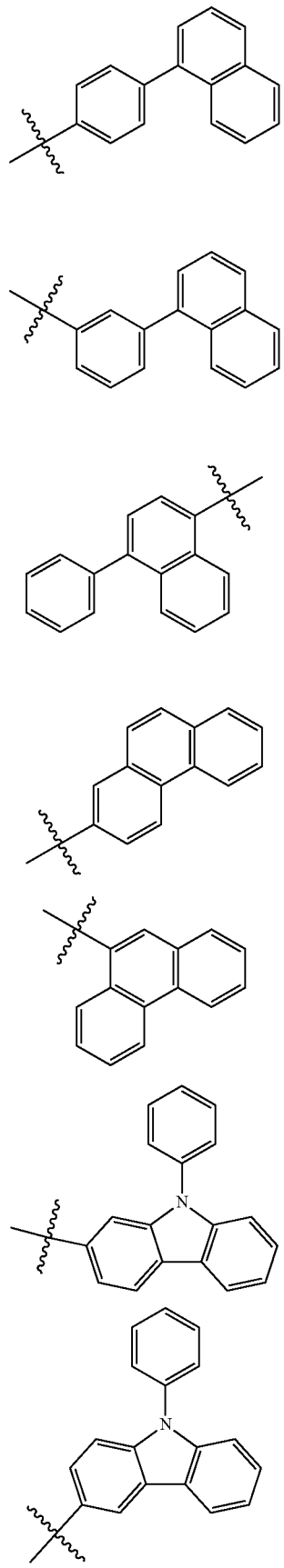

-continued
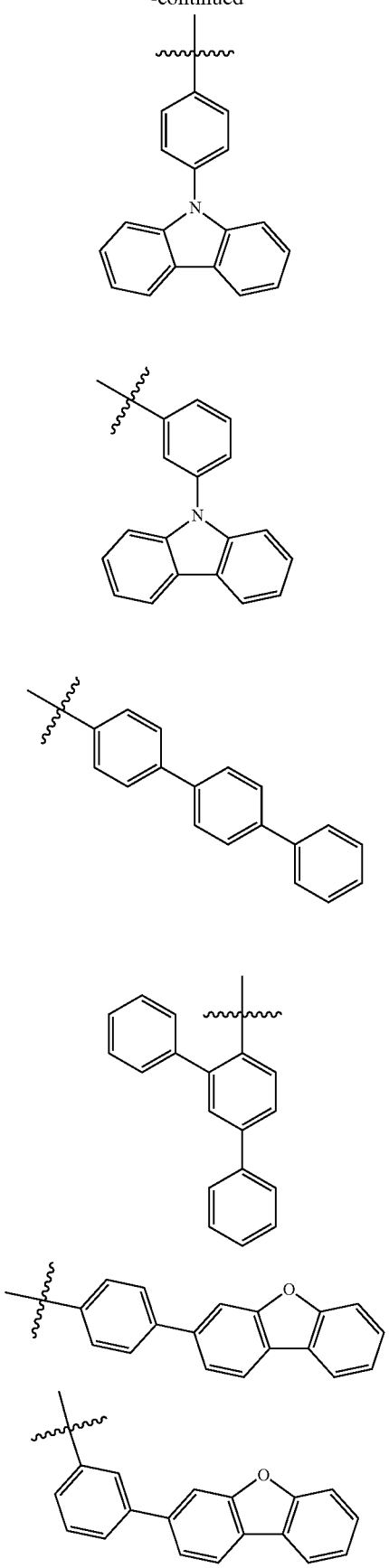
-continued
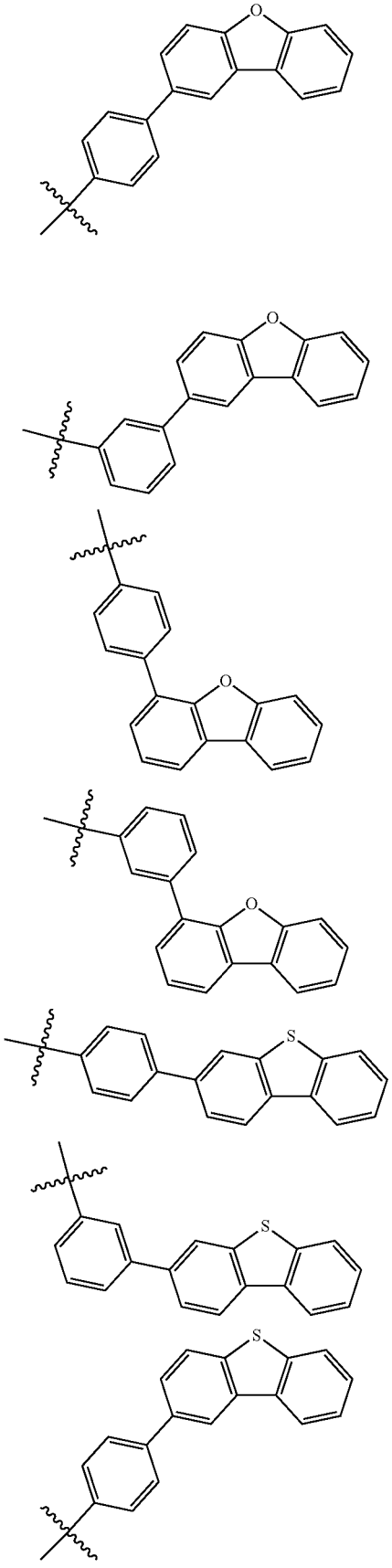

-continued
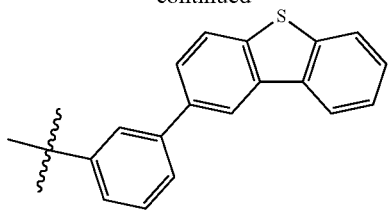
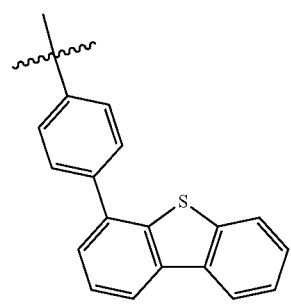
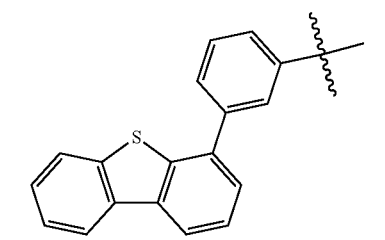
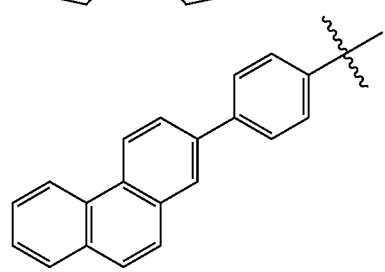
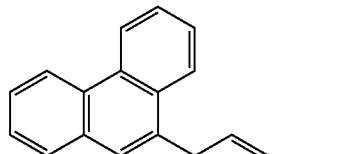
or
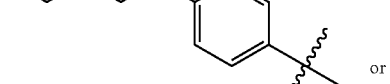
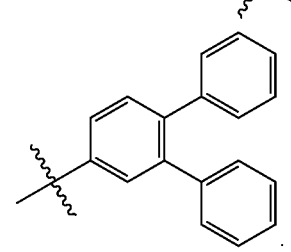
7. The nitrogen-containing compound according to claim 1, wherein the nitrogen-containing compound is selected from the following compounds:
Compound 1
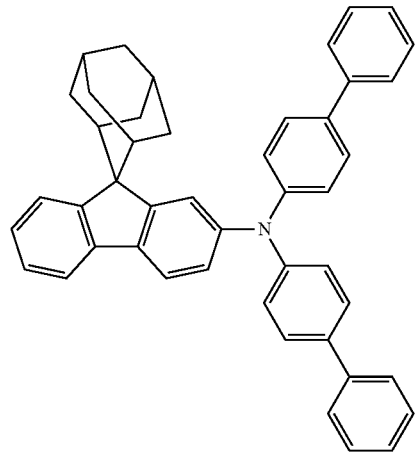
Compound 2
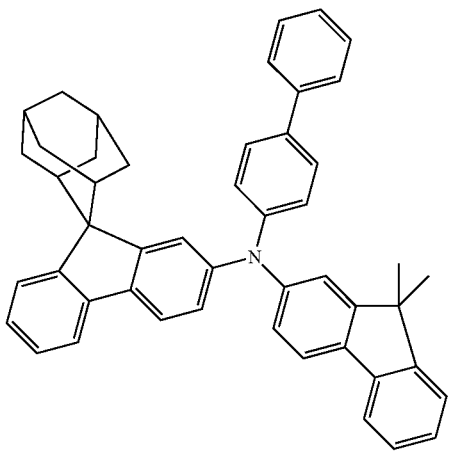
Compound 3
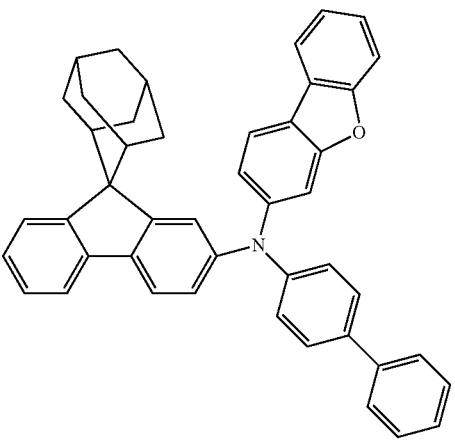

Compound 4
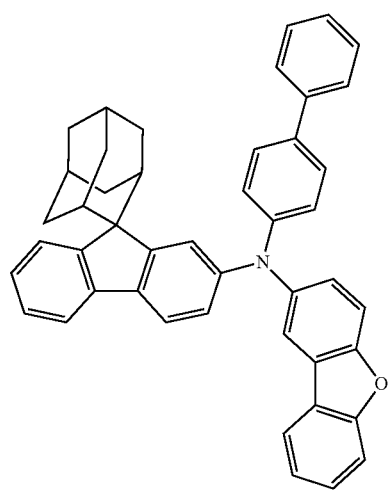
Compound 5
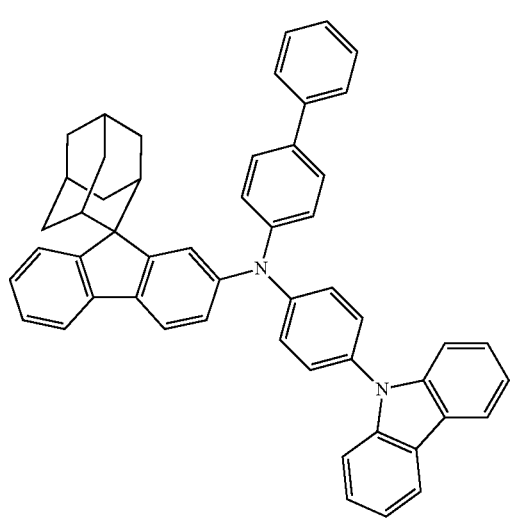
Compound 6
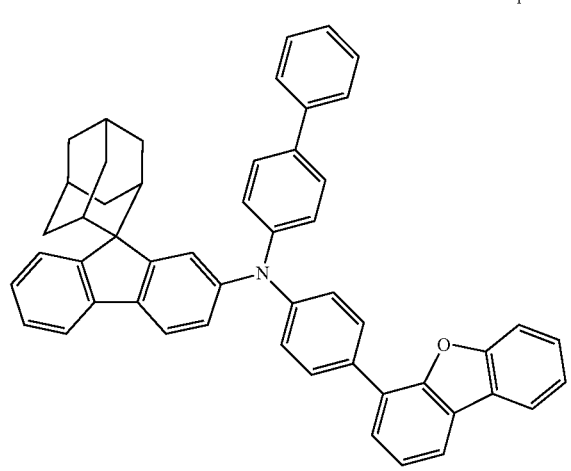
Compound 7
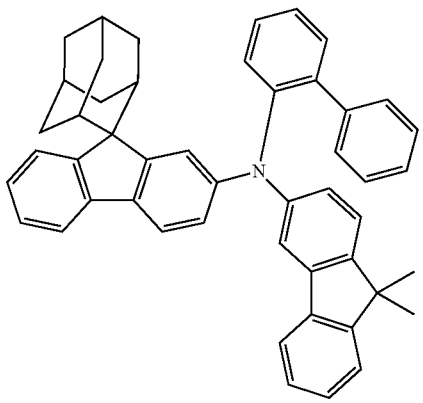
Compound 8
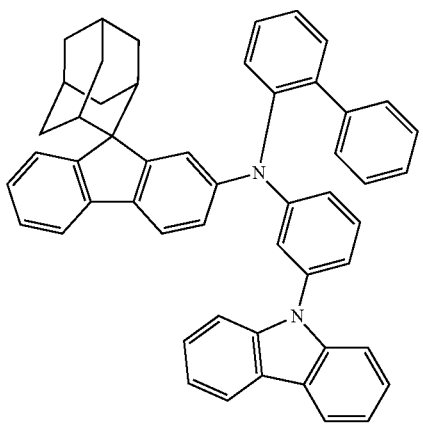
Compound 9
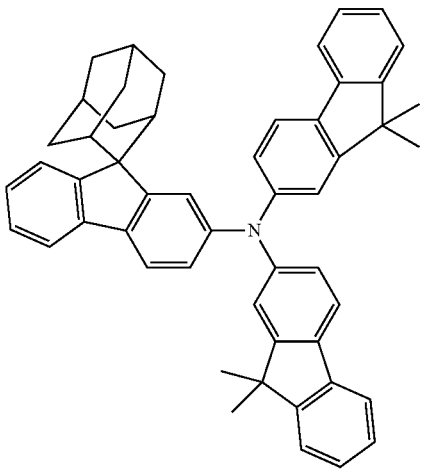

Compound 10
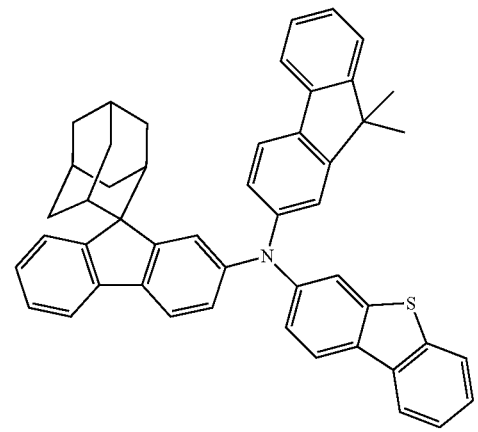
Compound 11
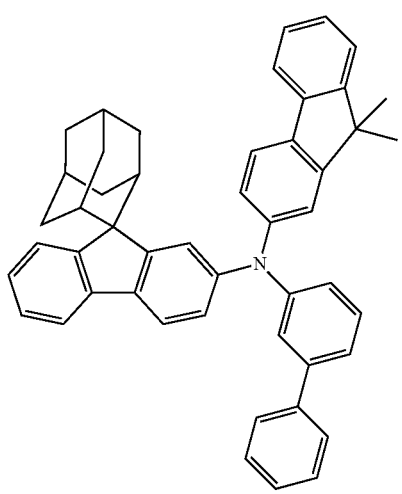
Compound 12
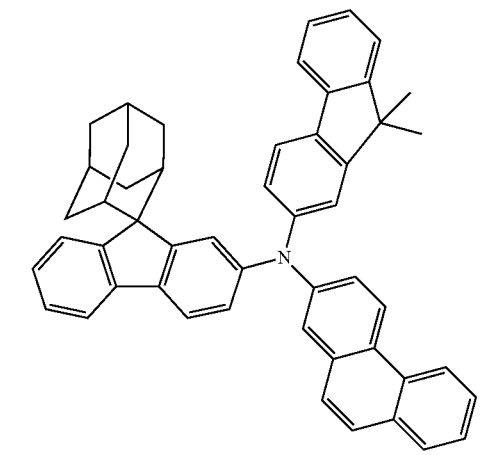
Compound 13
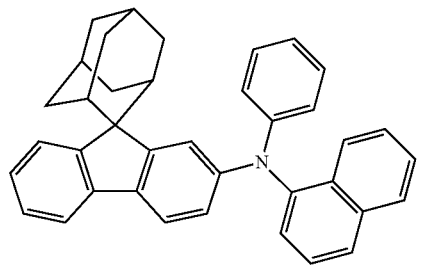
Compound 14
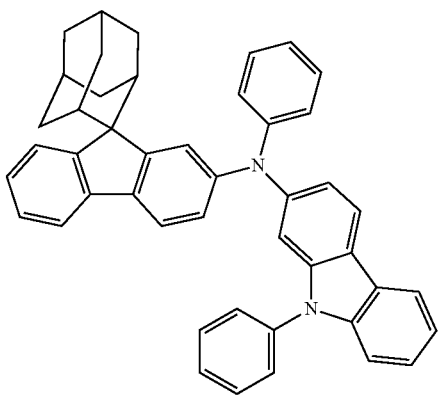
Compound 15
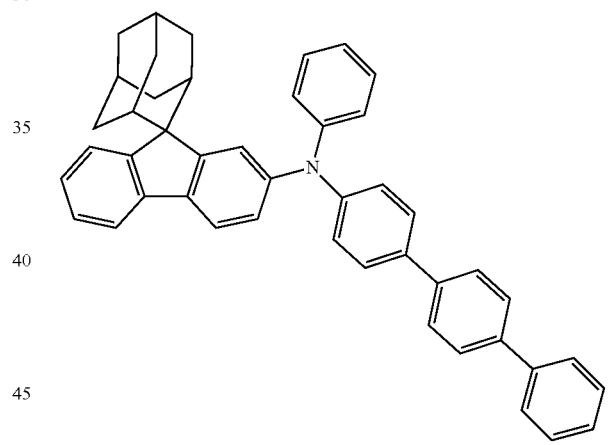
Compound 16
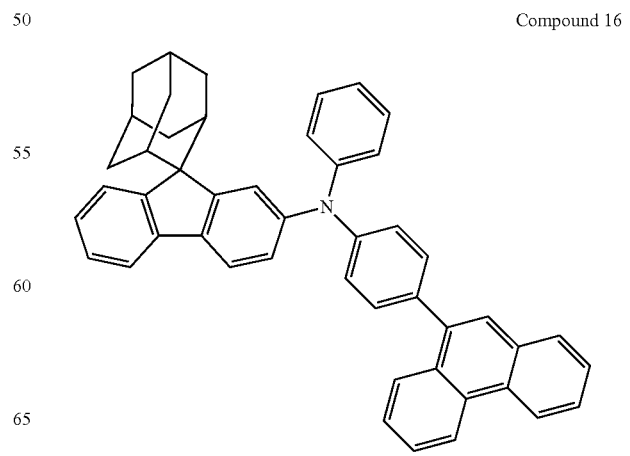

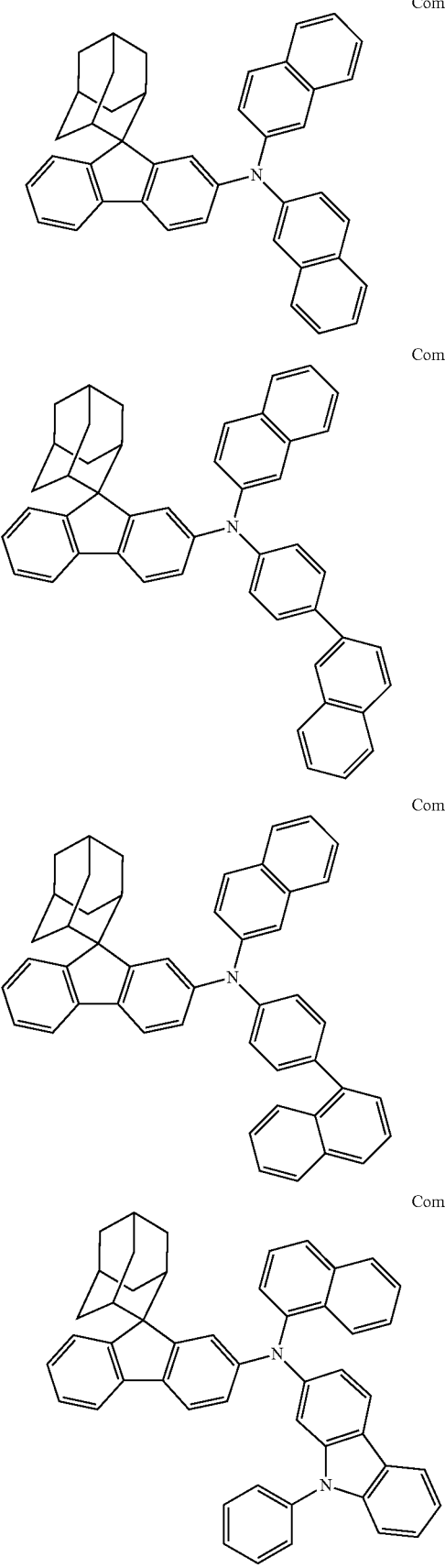
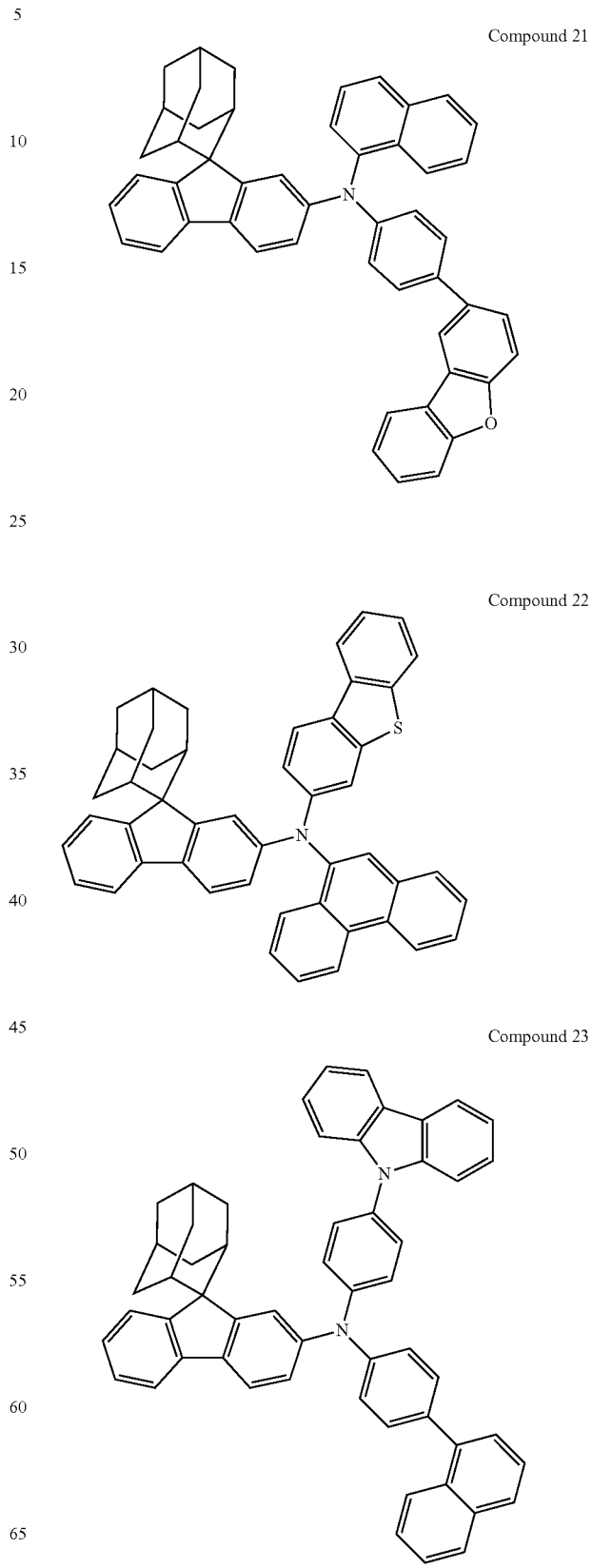

Compound 25
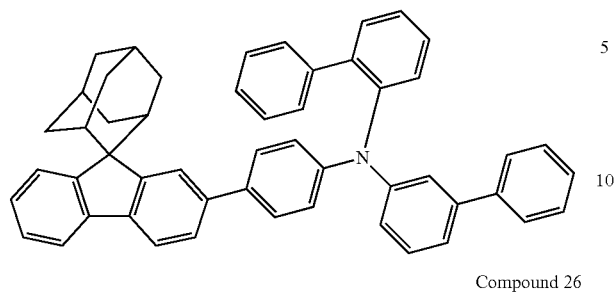
Compound 26
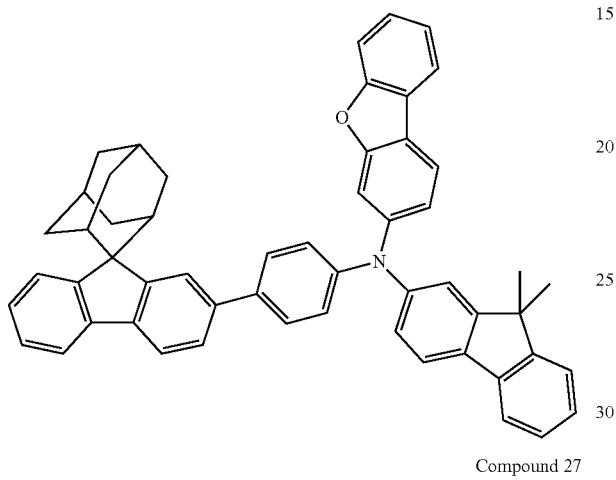
Compound 27
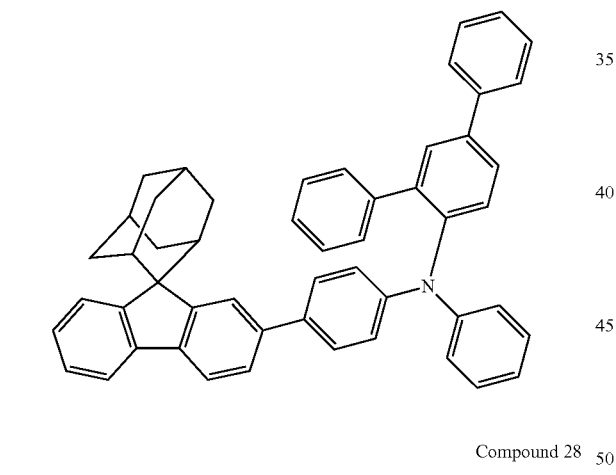
Compound 28
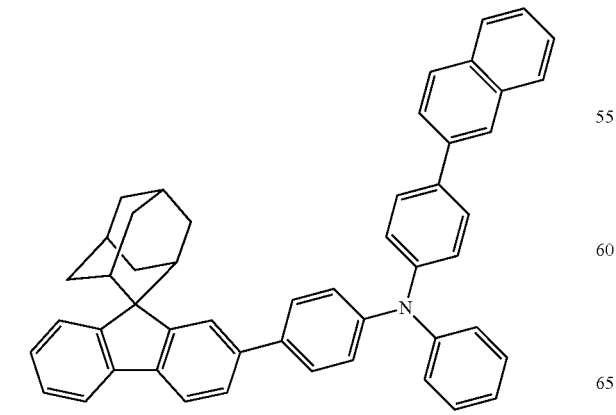
Compound 29
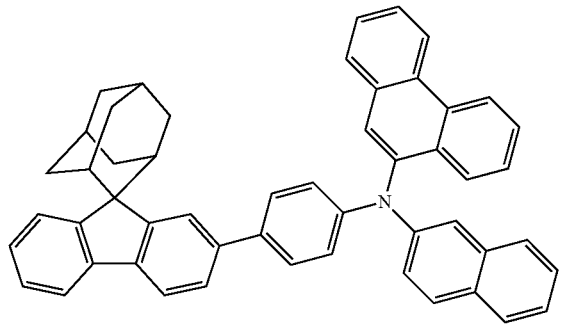
Compound 30
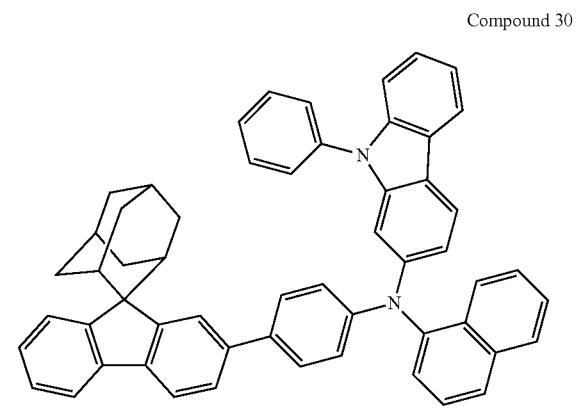
Compound 31
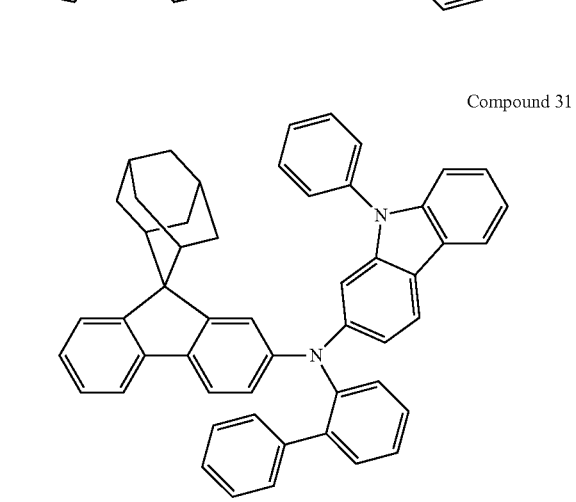
Compound 32
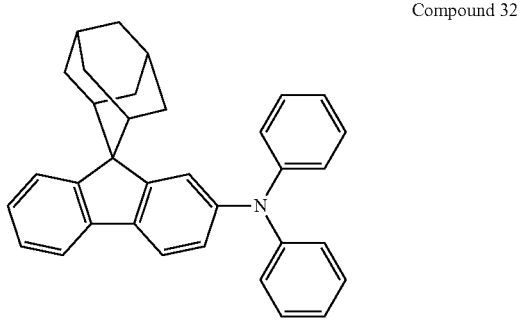

-continued
Compound 33
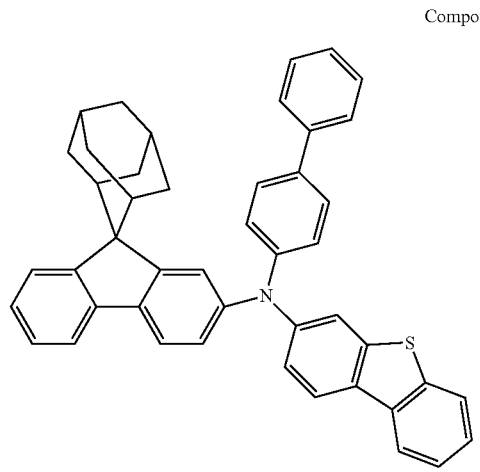
Compound 34
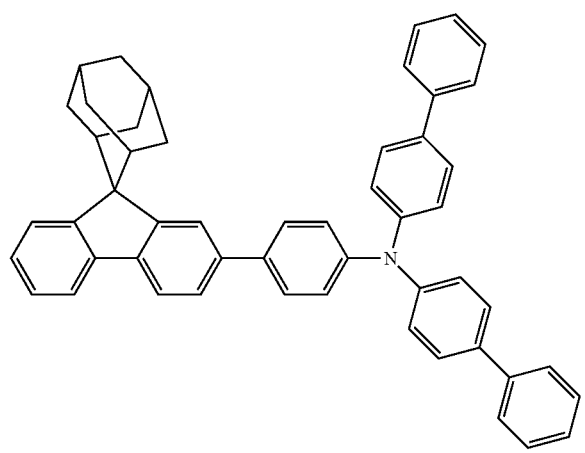
Compound 35
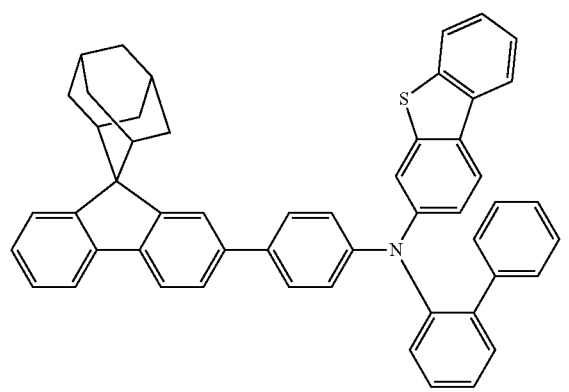
-continued
Compound 36
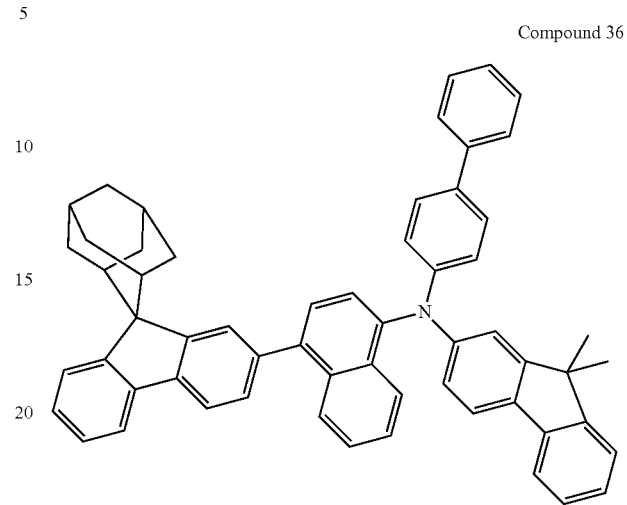
Compound 37
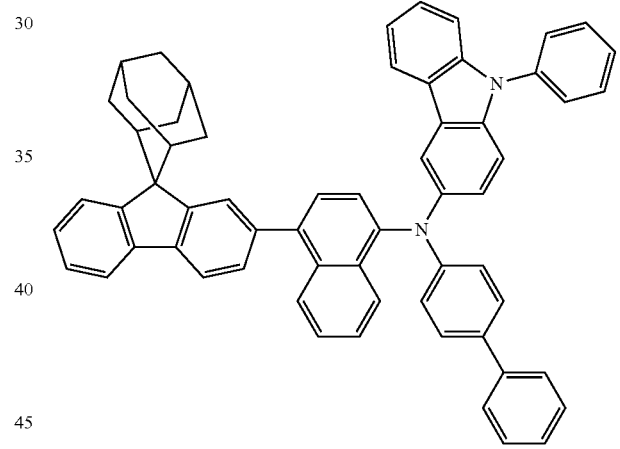
Compound 38
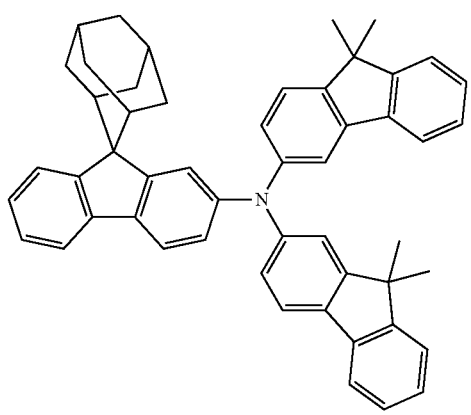

Compound 39
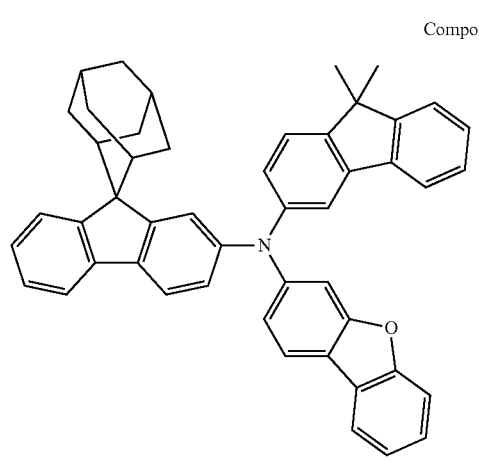
Compound 40
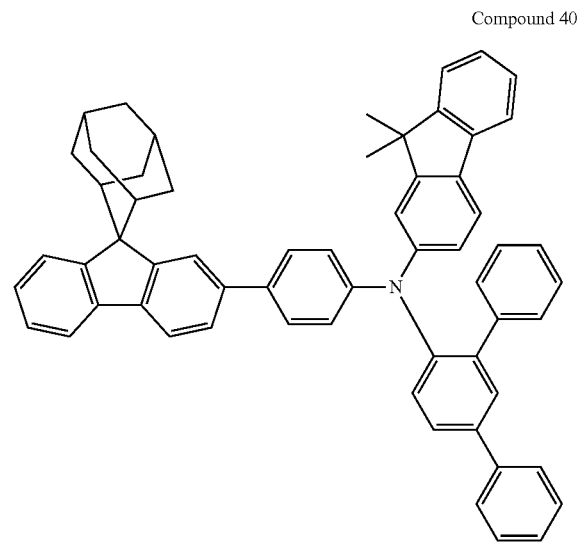
Compound 41
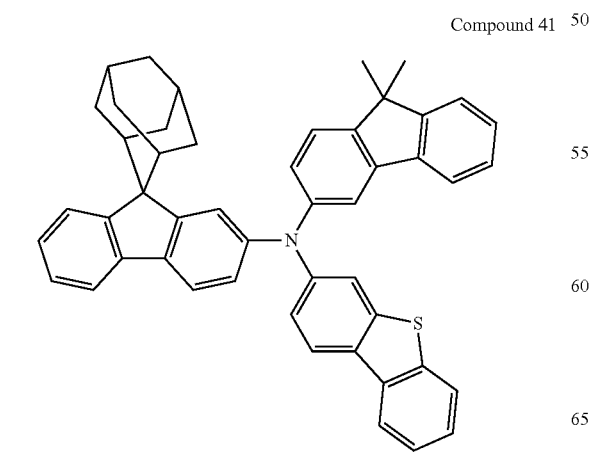
Compound 42
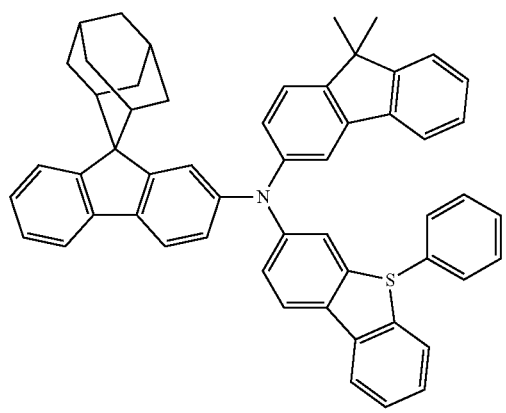
Compound 43
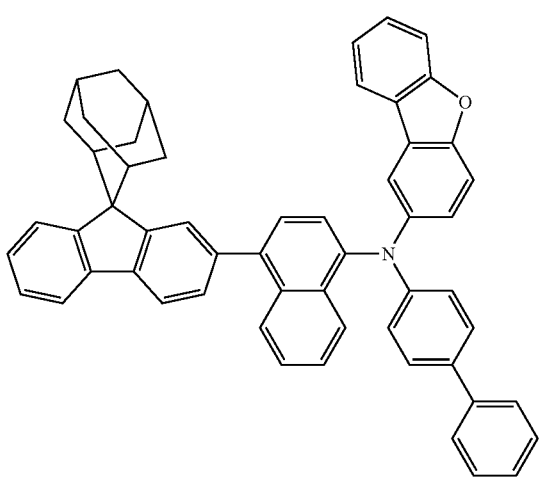
Compound 44
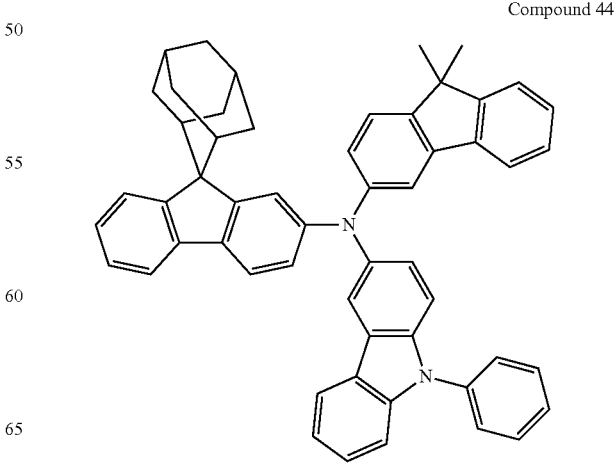

Compound 45
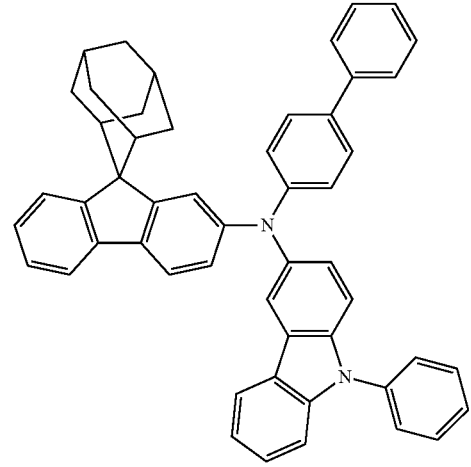
Compound 48
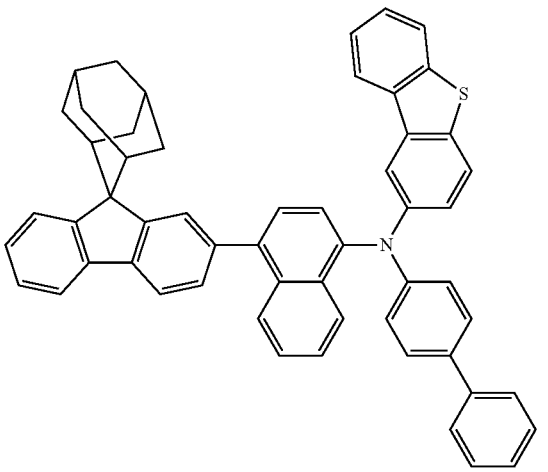
Compound 46
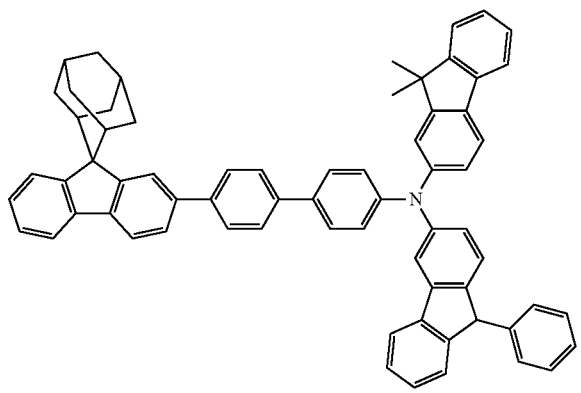
Compound 49
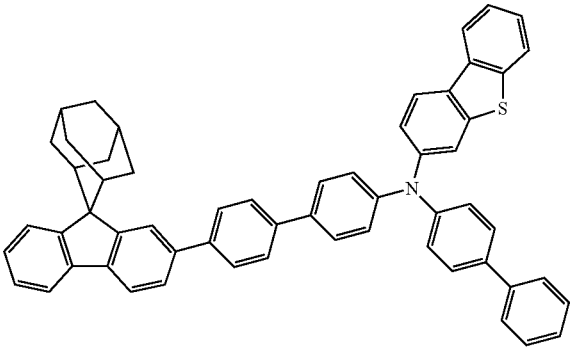
Compound 50
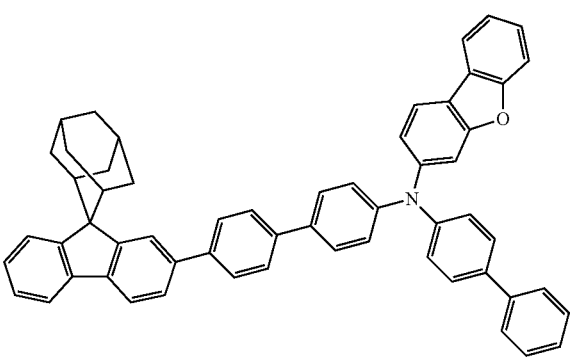
Compound 47
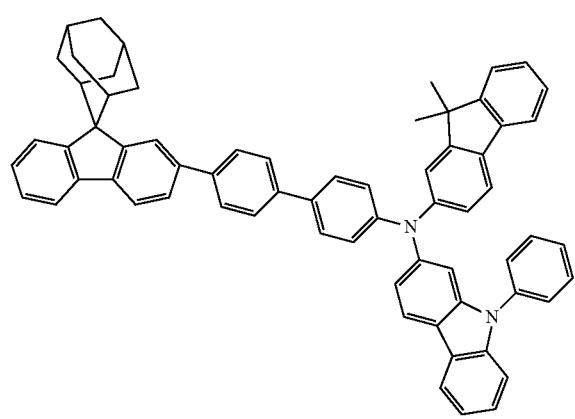
Compound 51
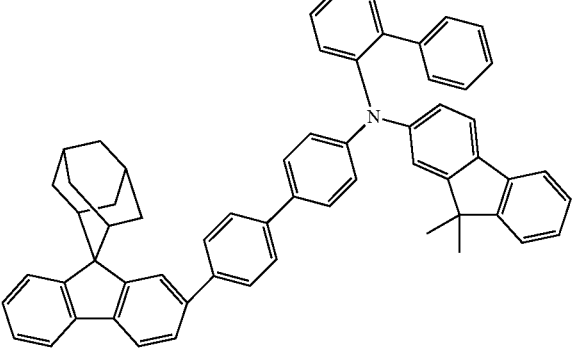

Compound 52
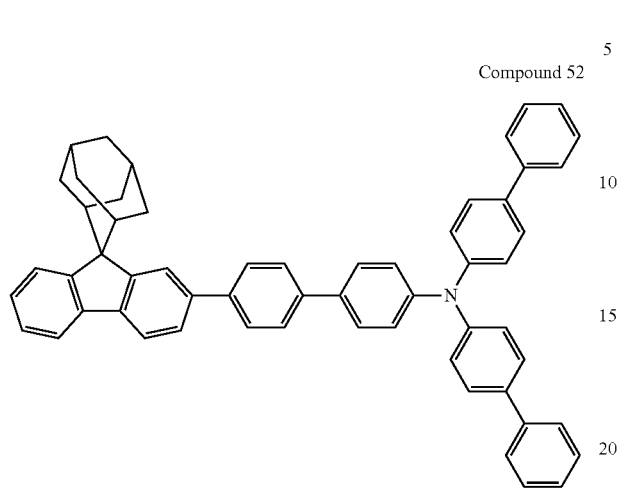
Compound 53
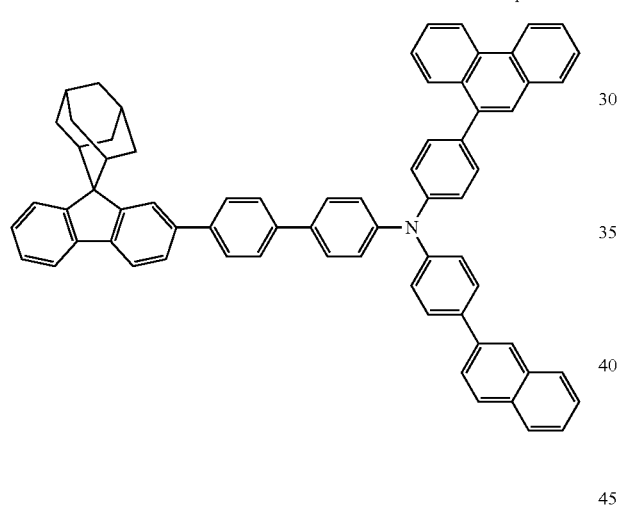
Compound 54
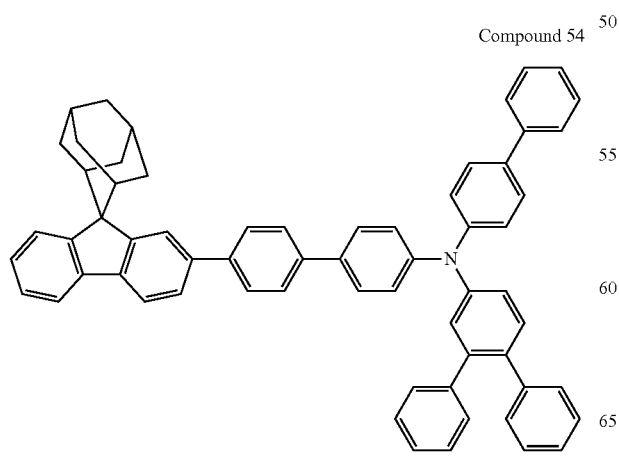
Compount 55
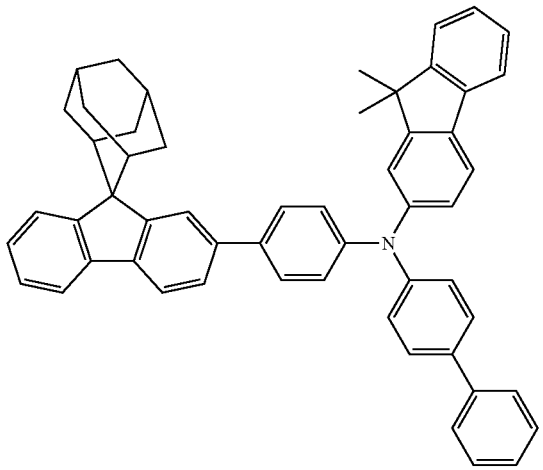
Compount 56
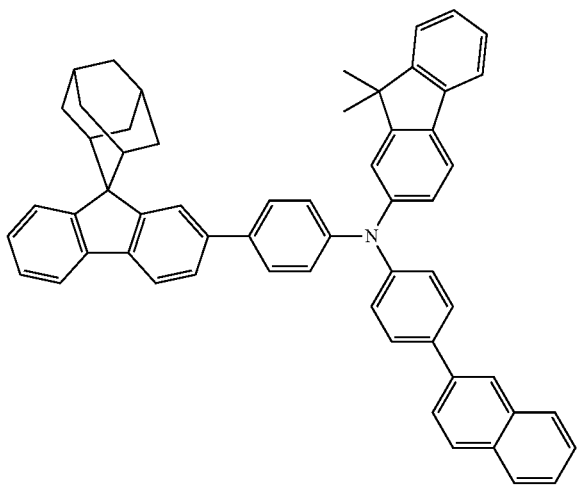
Compound 57
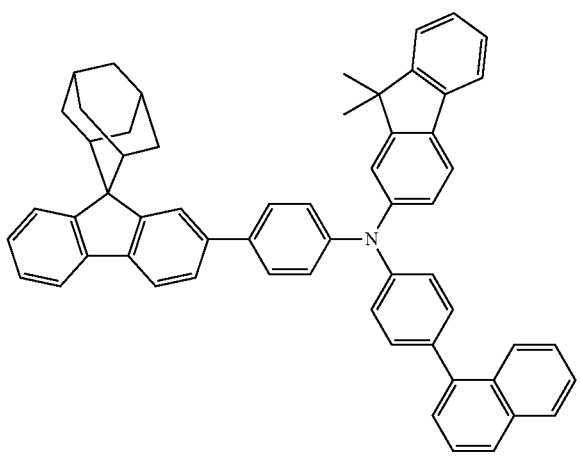

-continued
Compound 58
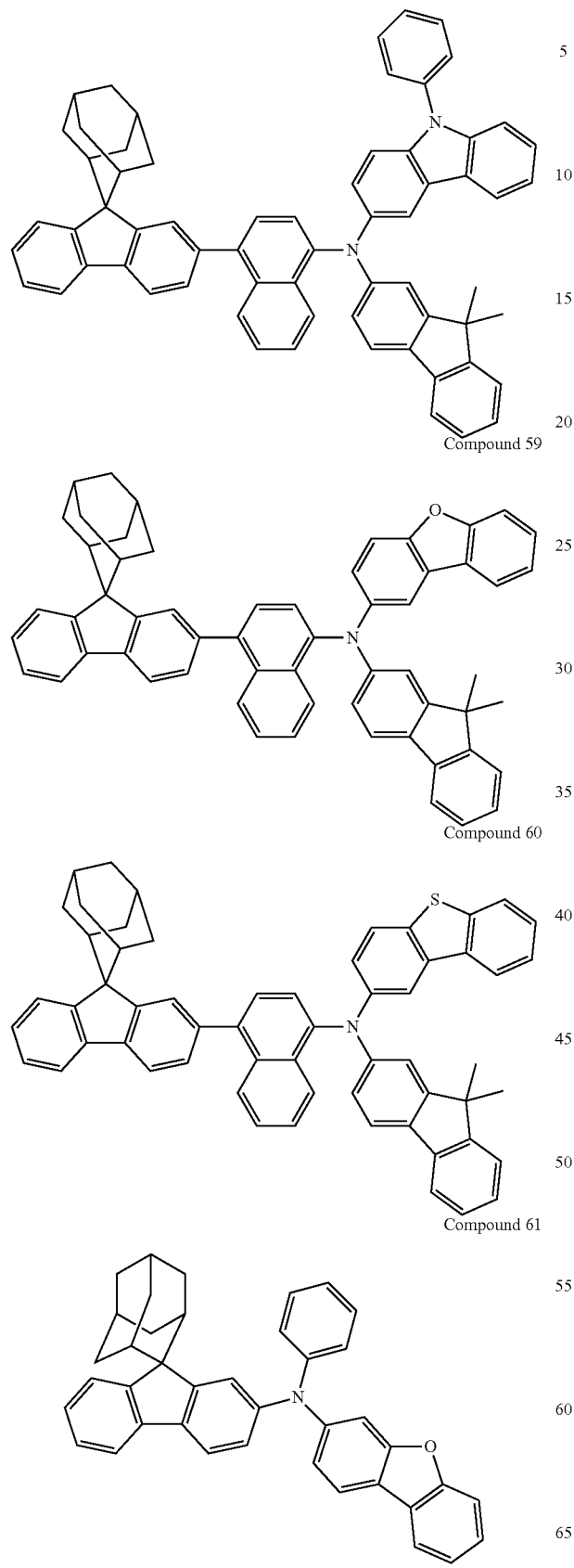
Compound 59
Compound 60
Compound 61
-continued
Compound 62
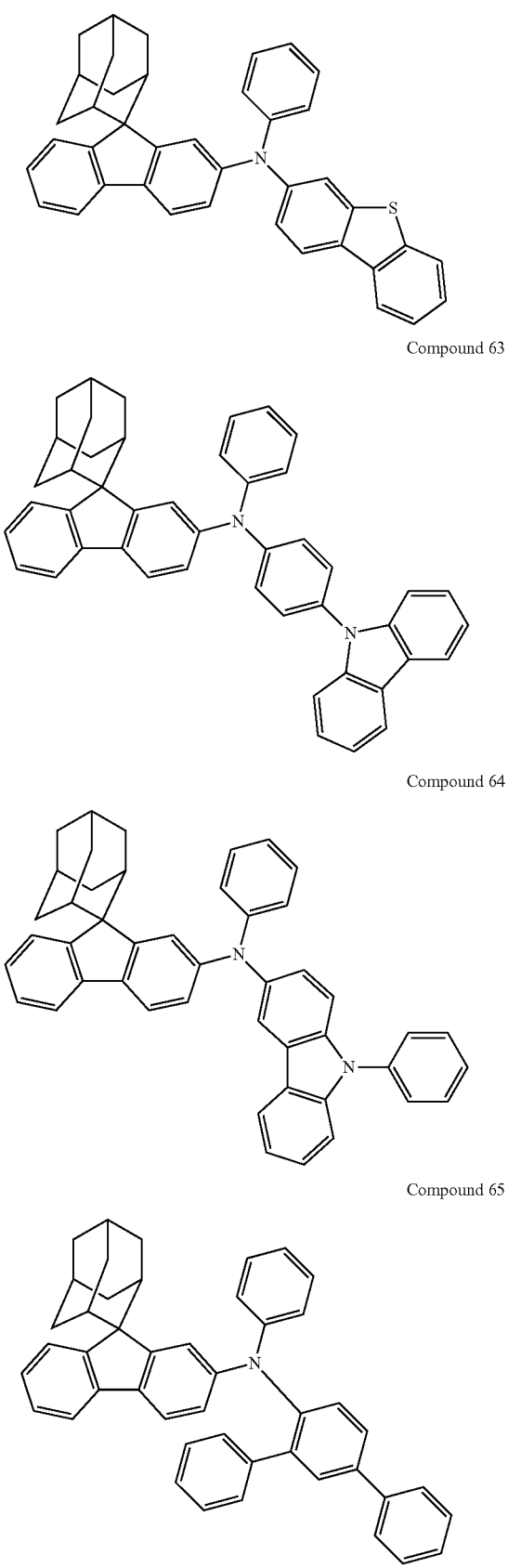
Compound 63
Compound 64
Compound 65

Compound 66
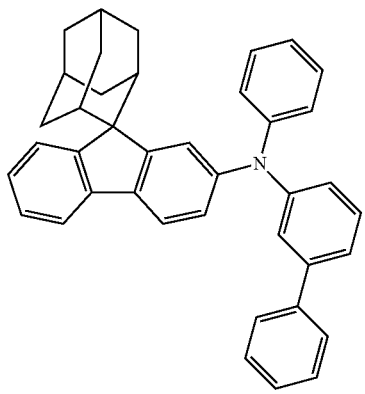
Compound 67
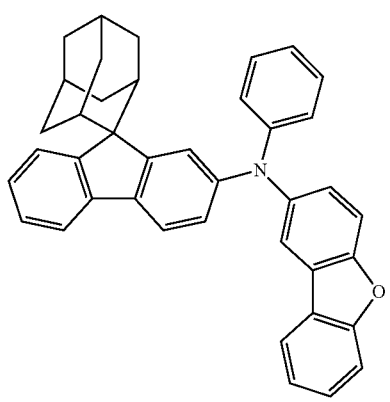
Compound 68
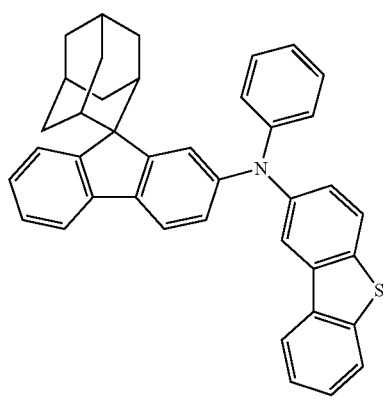
Compound 69
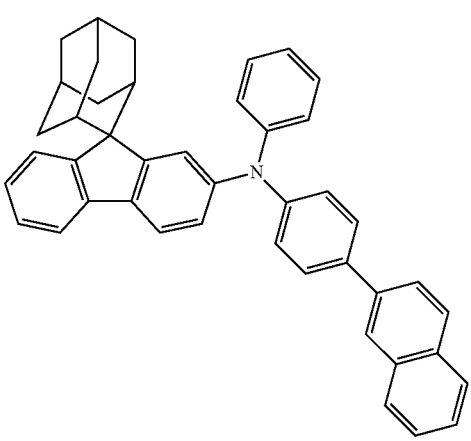
Compound 70
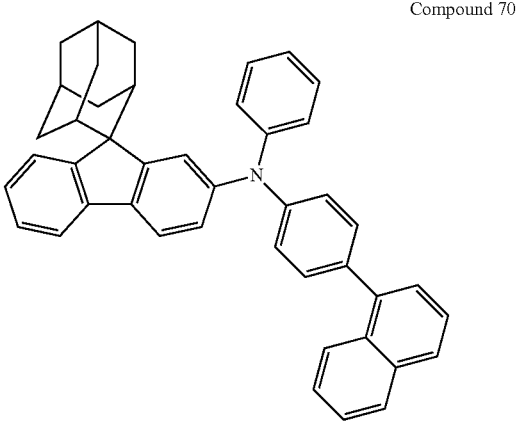
Compound 71
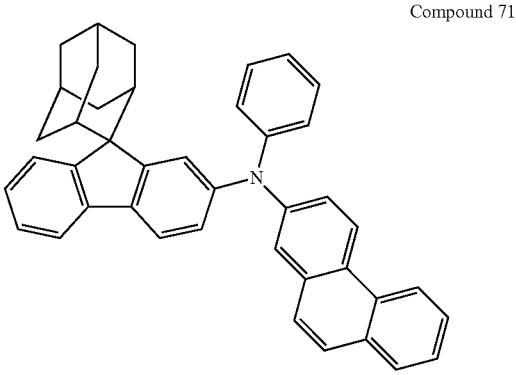
Compound 72
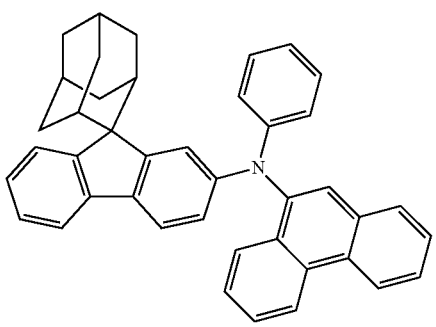
Compound 73
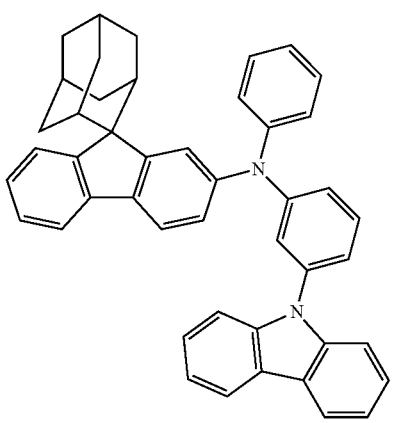

Compound 74
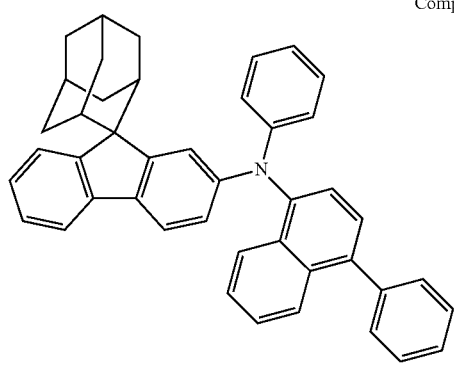
Compound 75
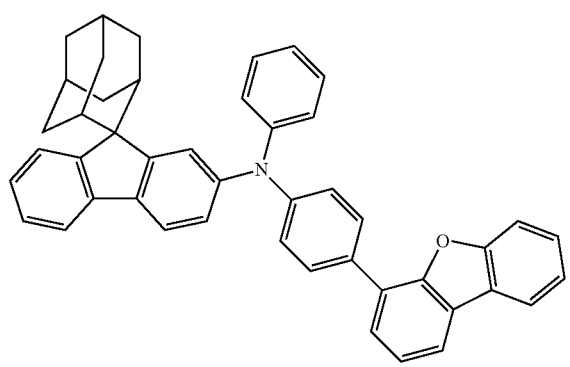
Compound 76
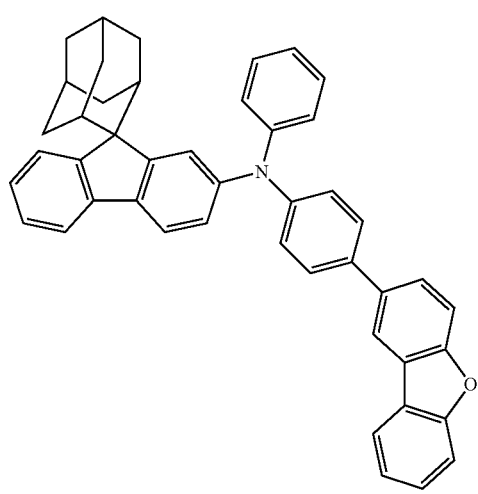
Compound 77
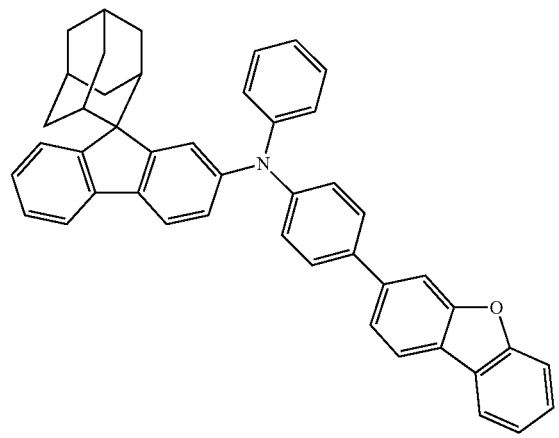
Compound 78
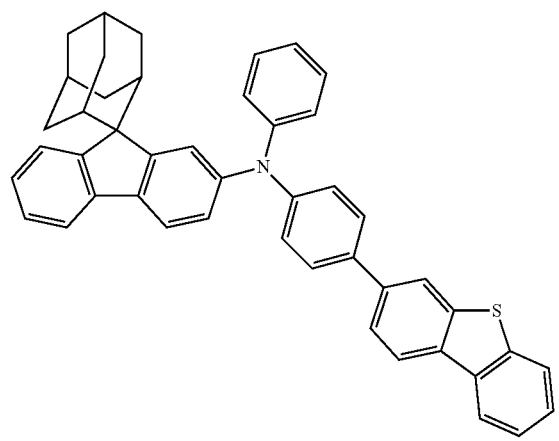
Compound 79
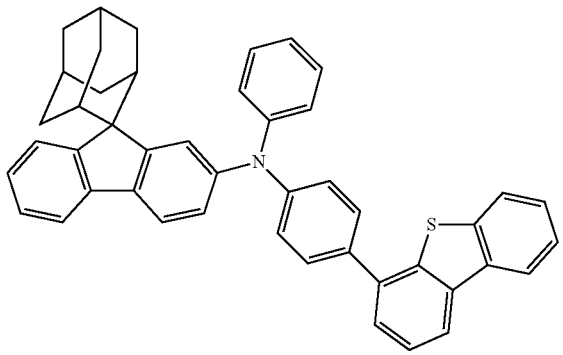

-continued
Compound 80
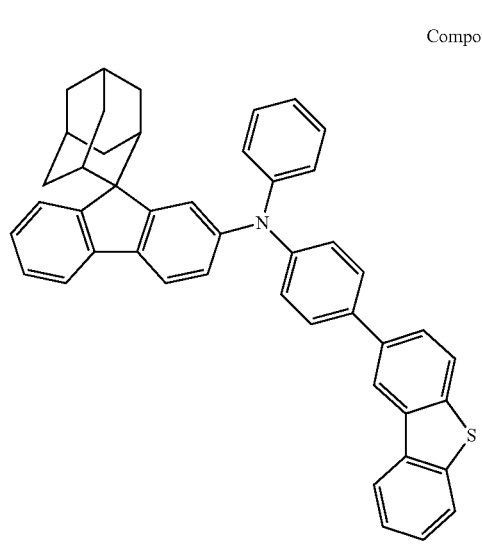
Compound 83
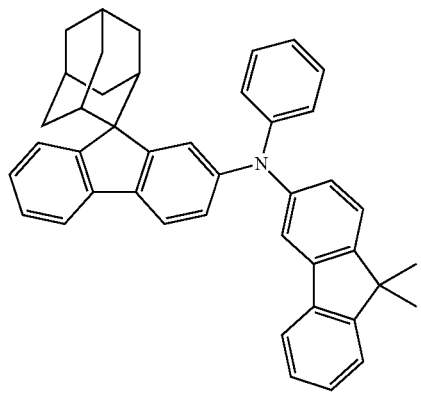
Compound 81
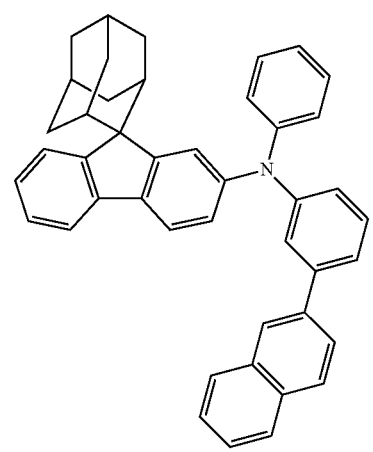
Compound 84
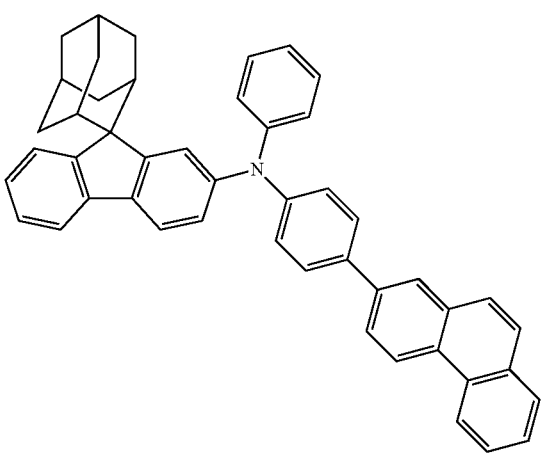
Compound 82
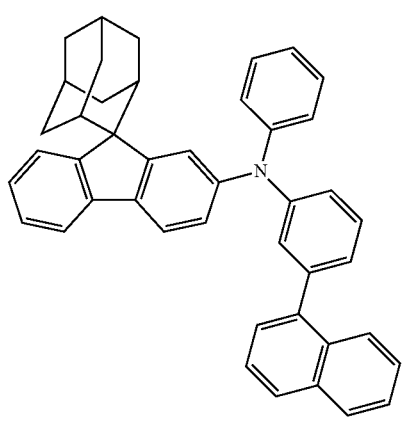
Compound 85
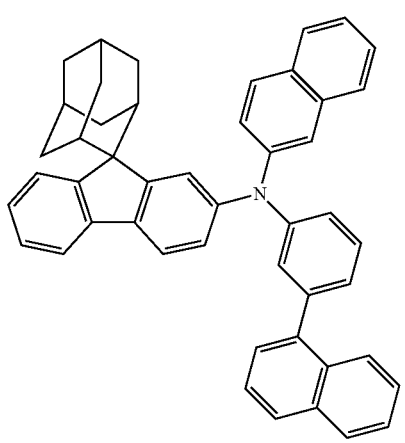

-continued
Compound 86
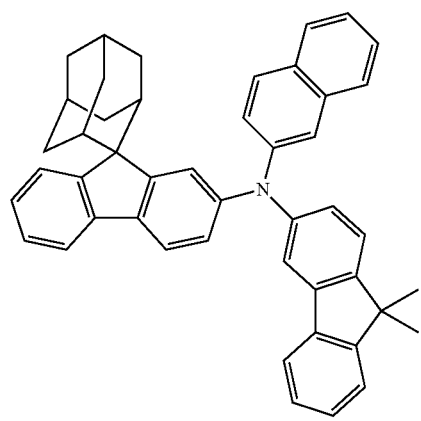
Compound 87
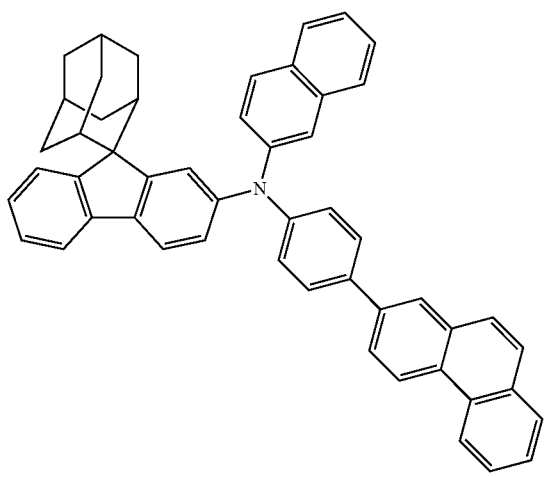
Compound 88
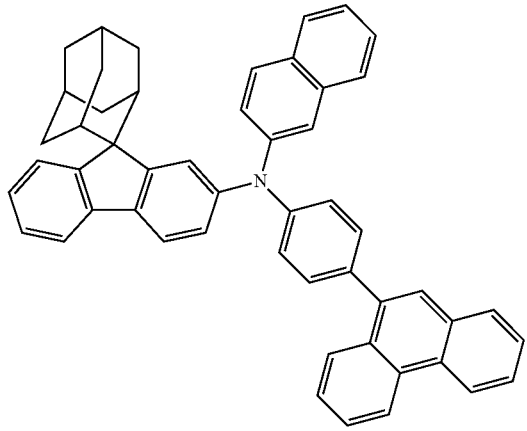
-continued
Compound 89
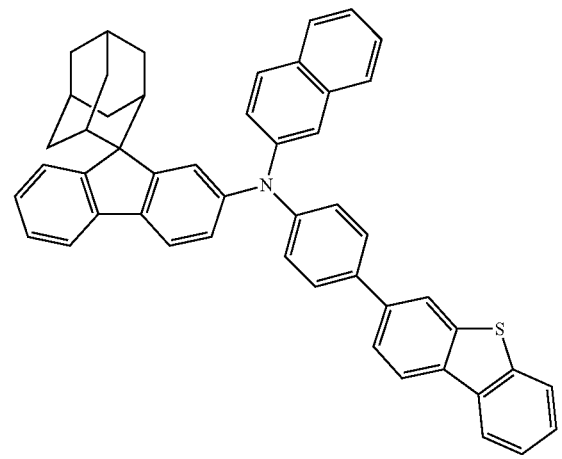
Compound 90
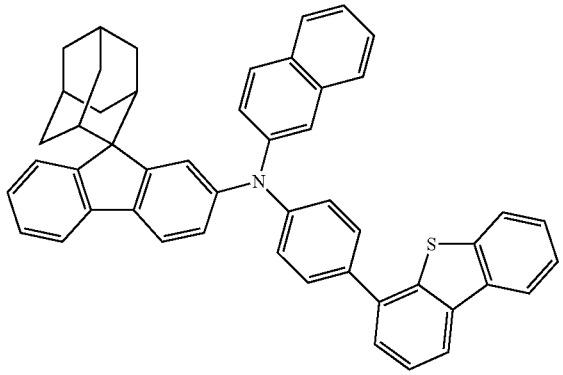
Compound 91
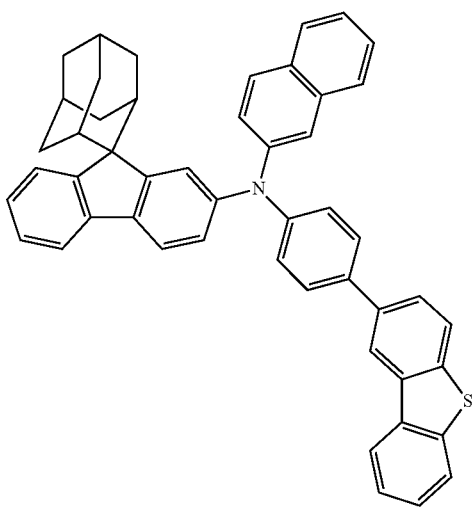

Compound 92
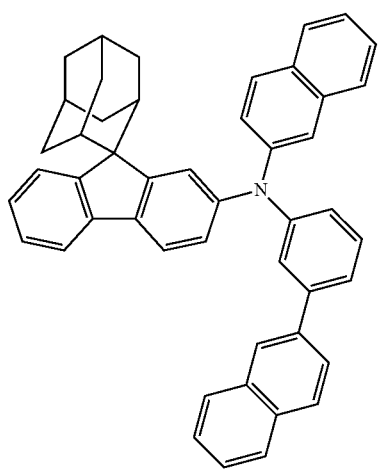
Compound 93
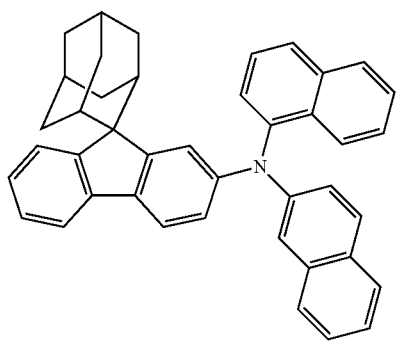
Compound 94
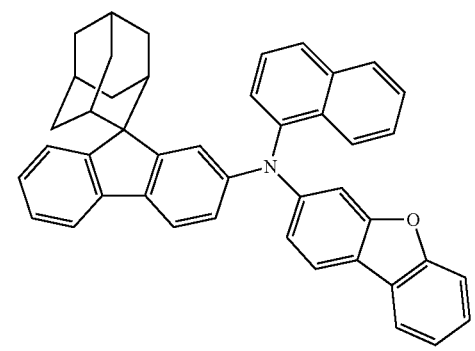
Compound 95
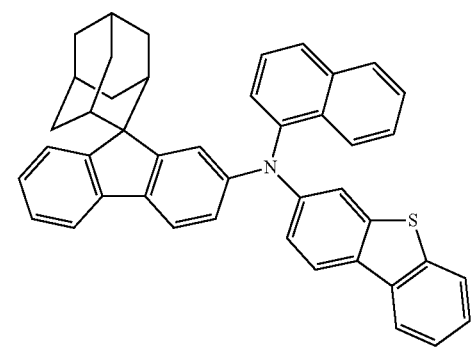
Compound 96
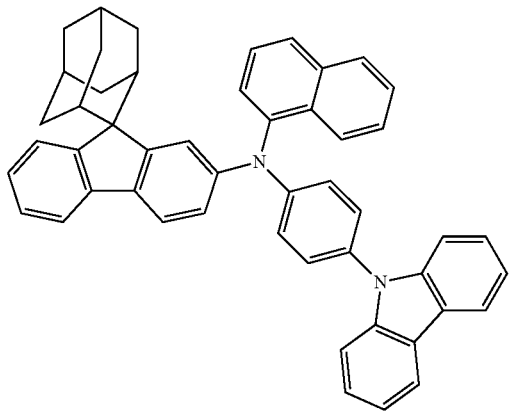
Compound 97
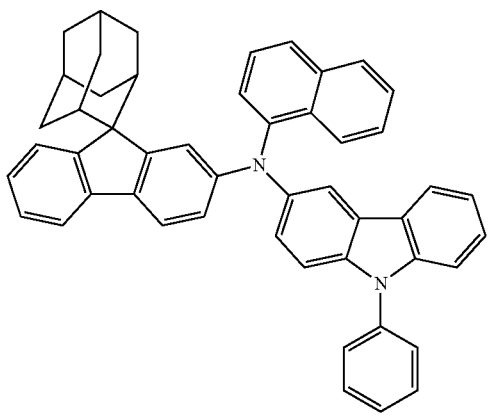
Compound 98
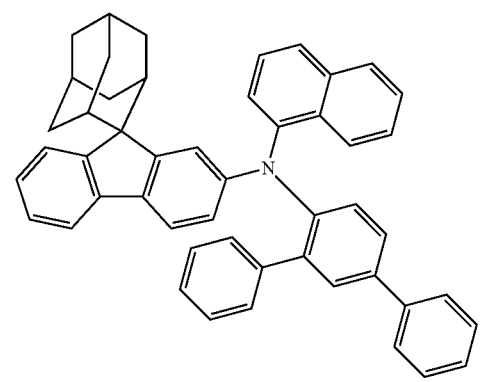

Compound 99
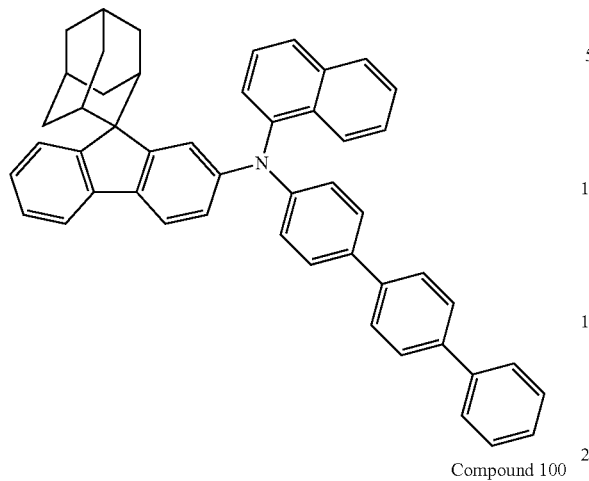
Compound 100
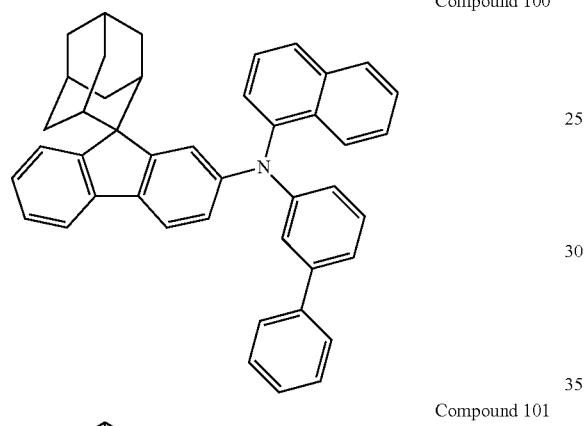
Compound 101
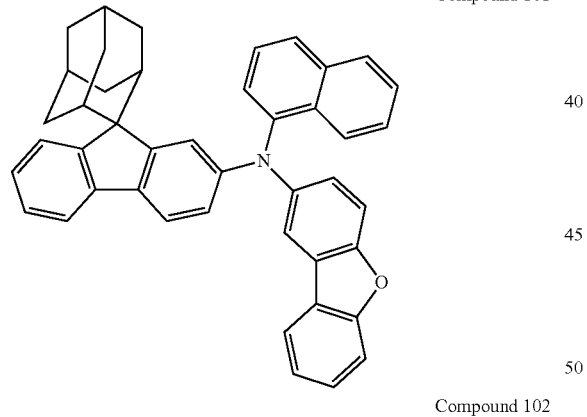
Compound 102
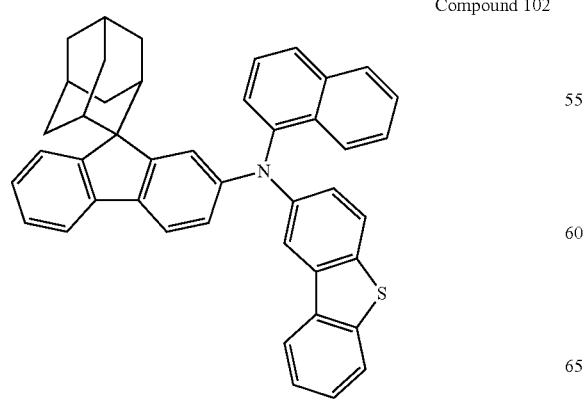
Compound 103
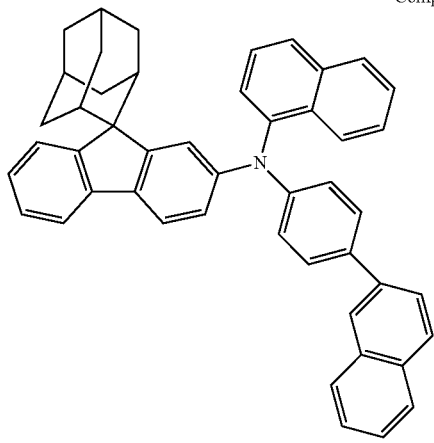
Compound 104
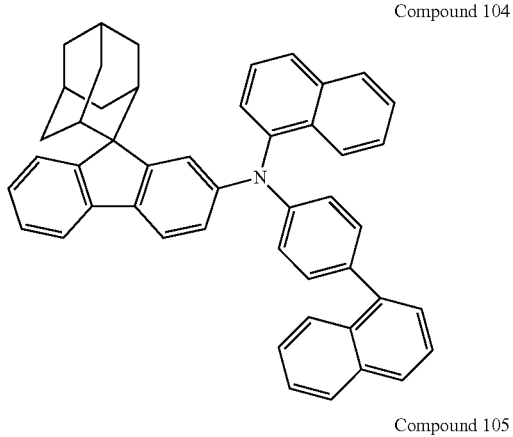
Compound 105
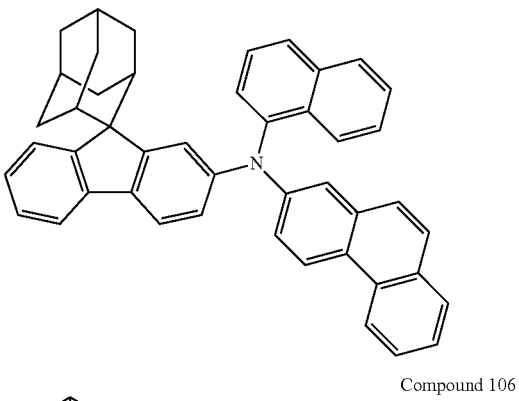
Compound 106
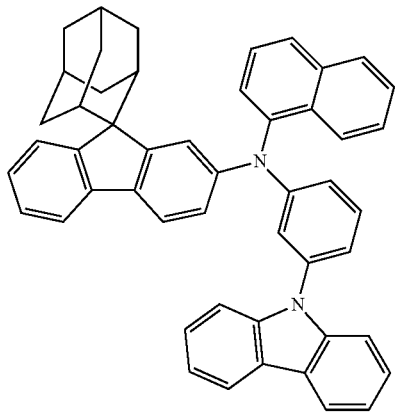

Compound 107
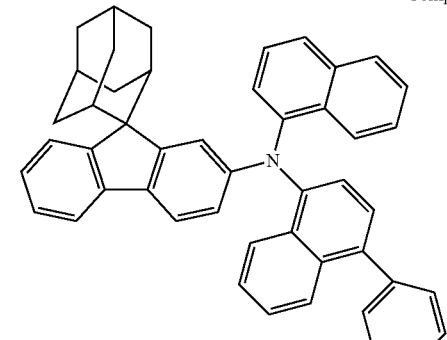
Compound 108
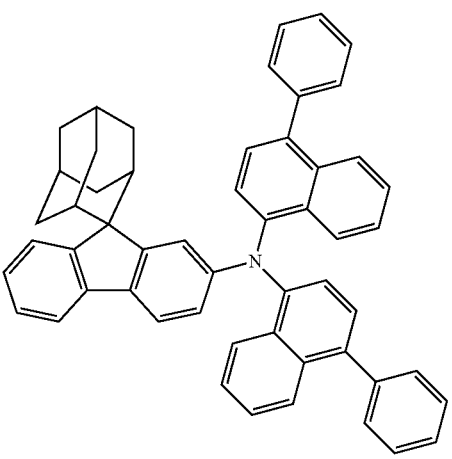
Compound 109
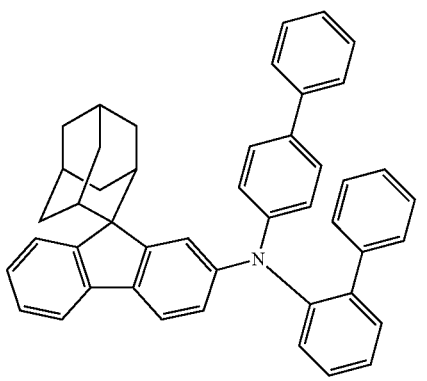
Compound 110
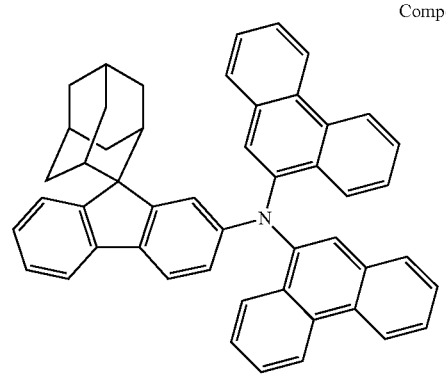
Compound 111
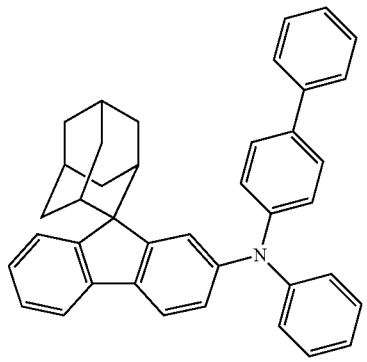
Compound 112
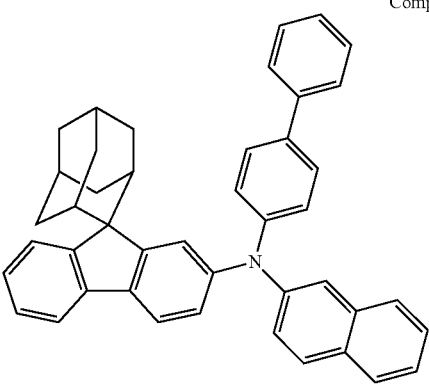
Compound 114
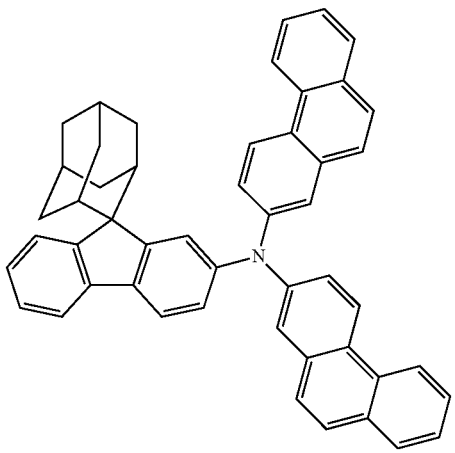

Compound 115
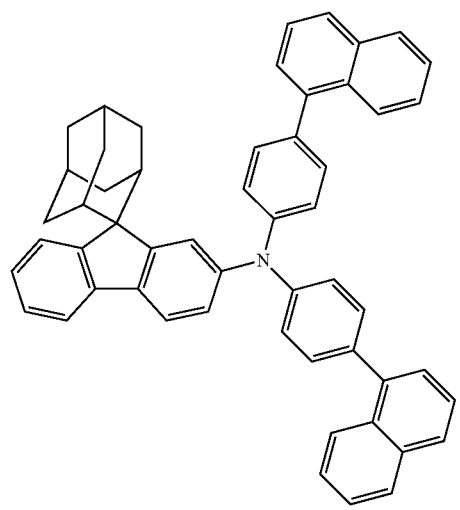
Compound 116
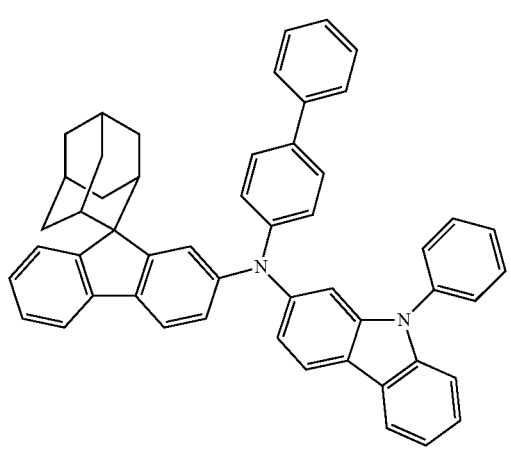
Compound 117
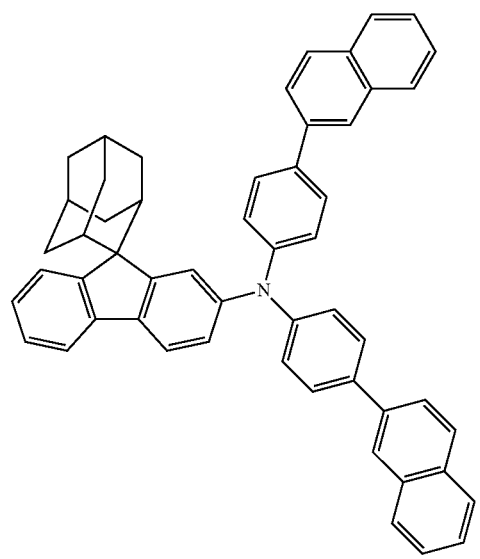
Compound 118
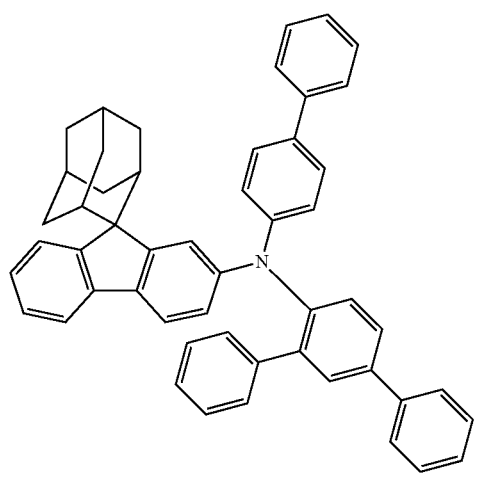
Compound 119
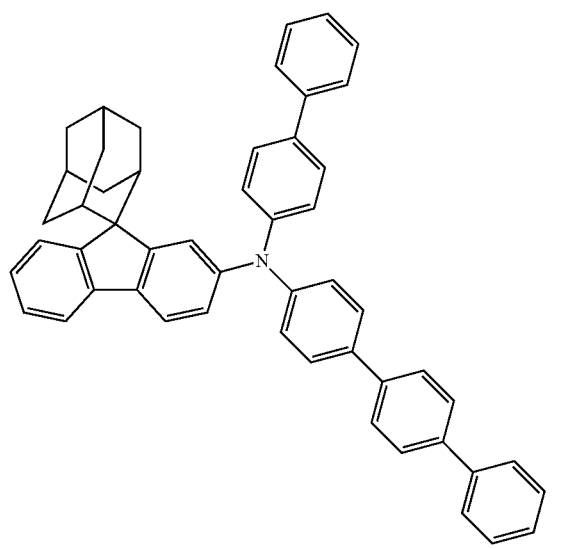
Compound 120

Compound 121
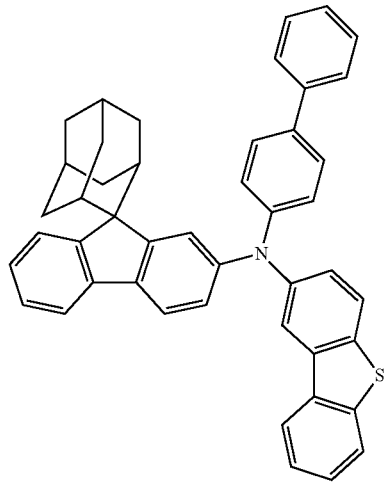
Compound 122
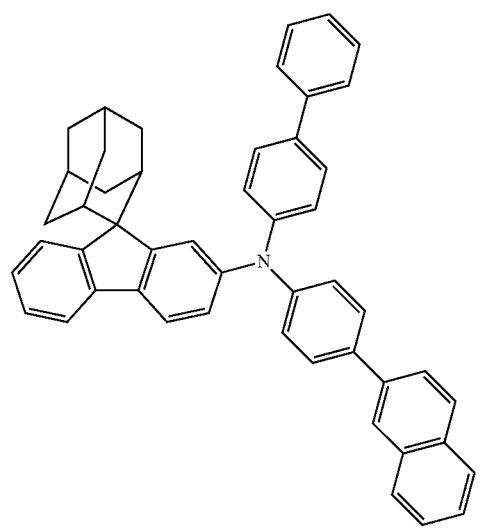
Compound 123
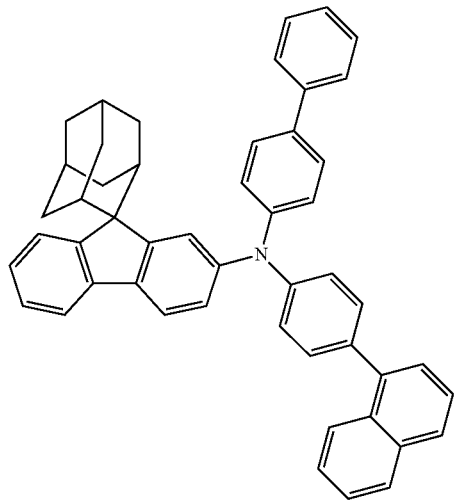
Compound 124
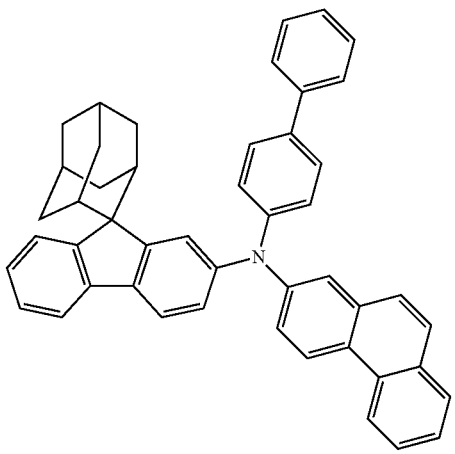
Compound 125
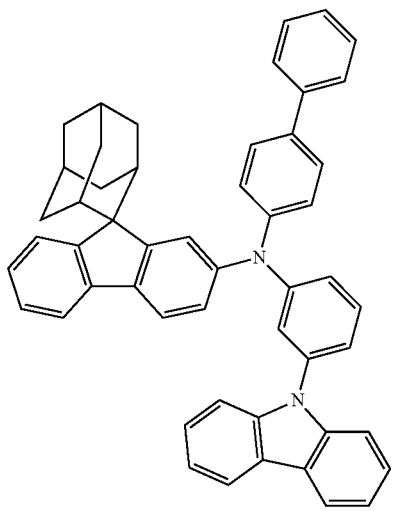
Compound 126
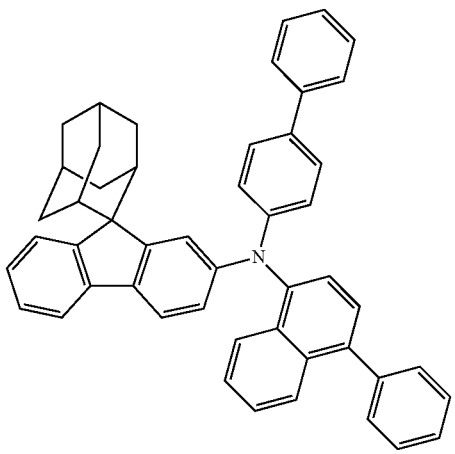

Compound 127
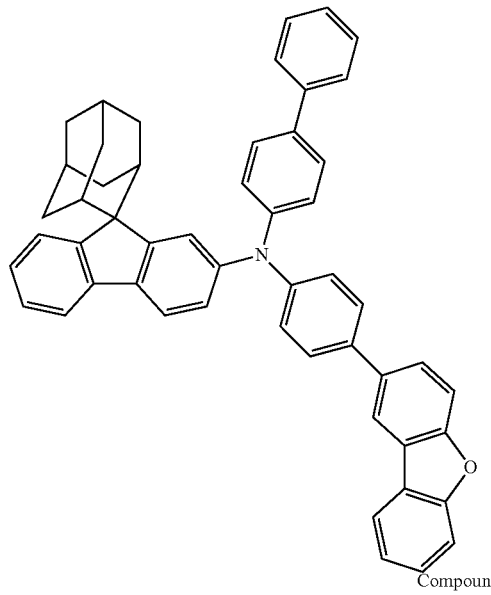
Compound 128
Compound 130
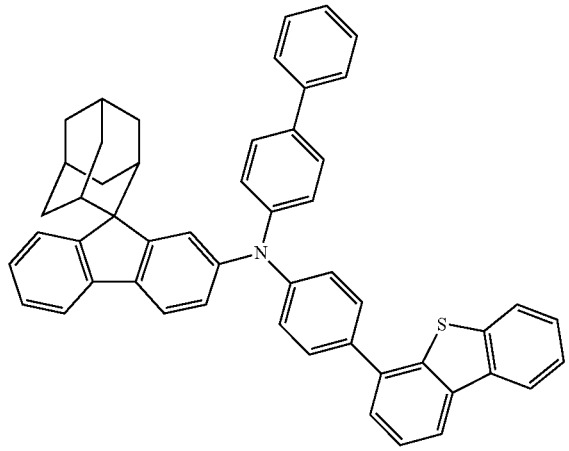
Compound 131
Compound 129
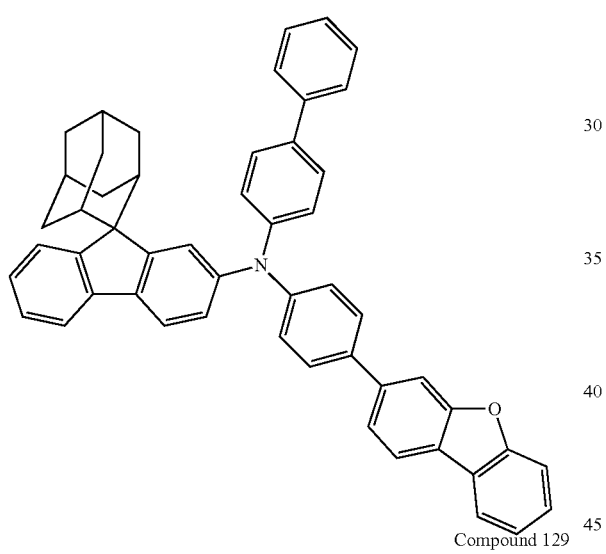
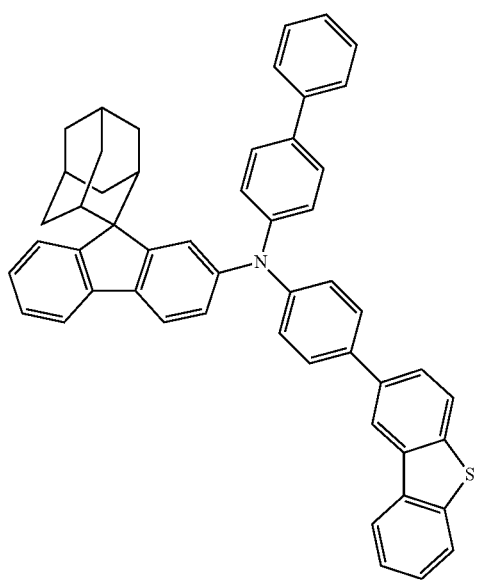
Compound 132
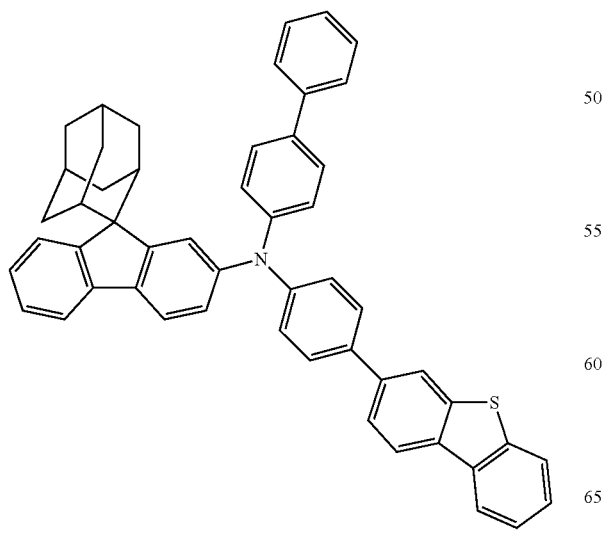

Compound 133
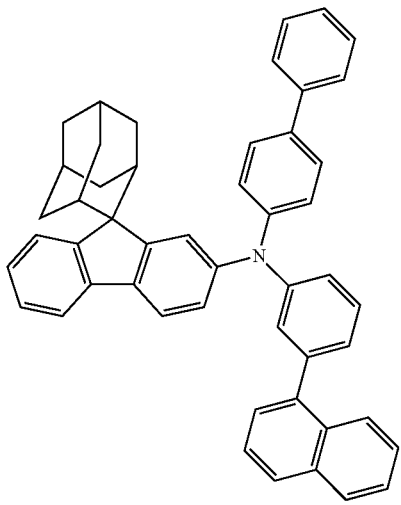
Compound 136
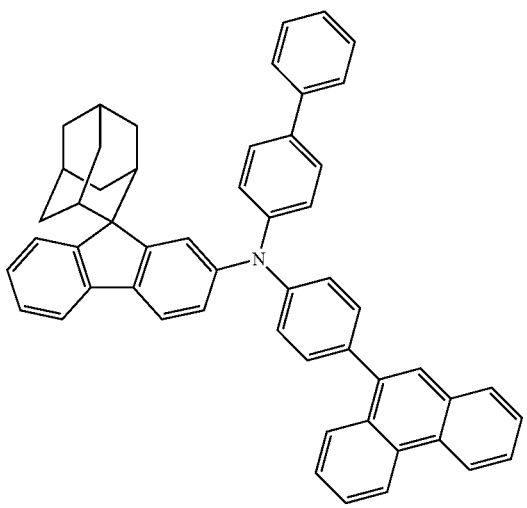
Compound 134
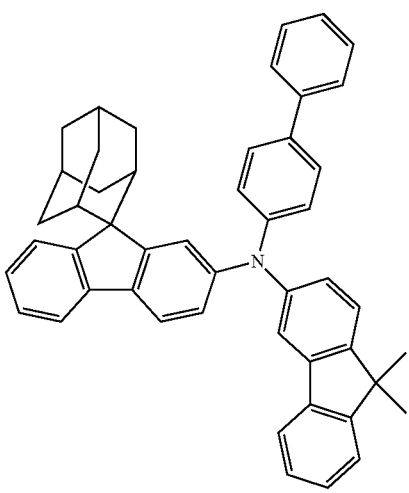
Compound 137
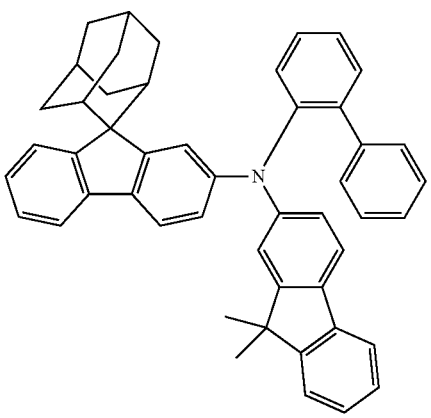
Compound 135
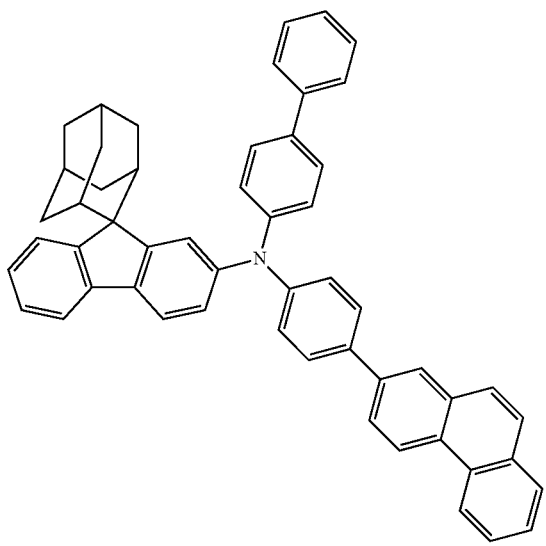
Compound 138
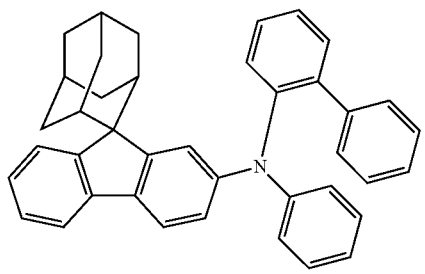
Compound 139
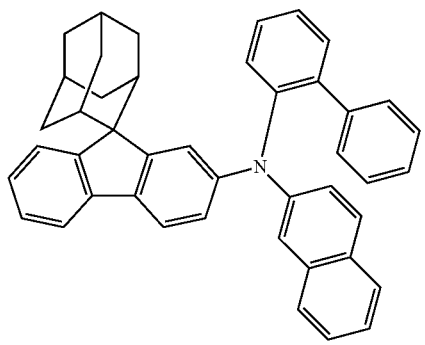

Compound 140
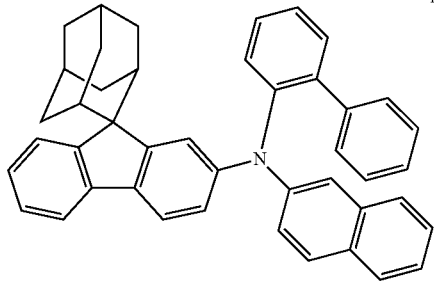
Compound 141
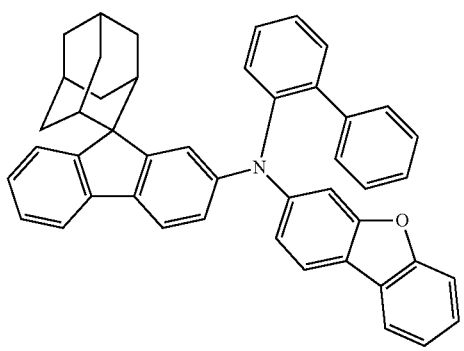
Compound 142
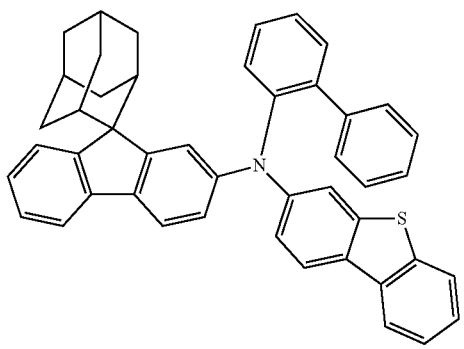
Compound 143
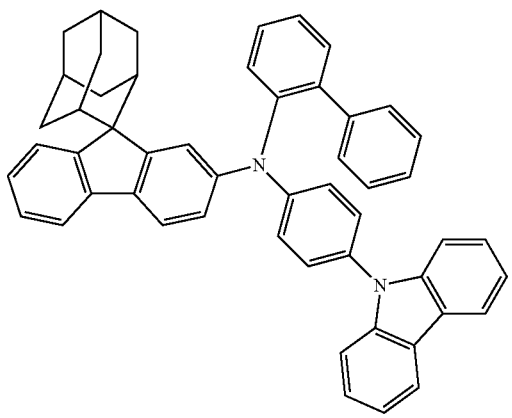
Compound 144
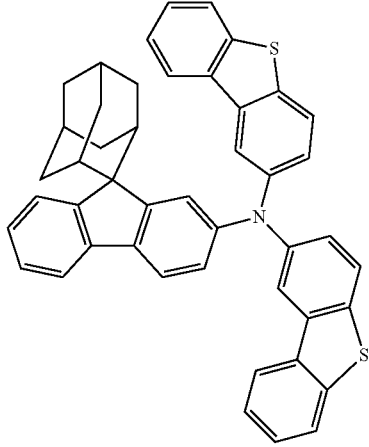
Compound 145
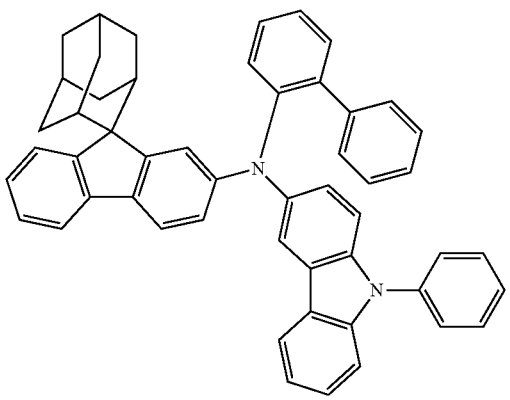
Compound 146
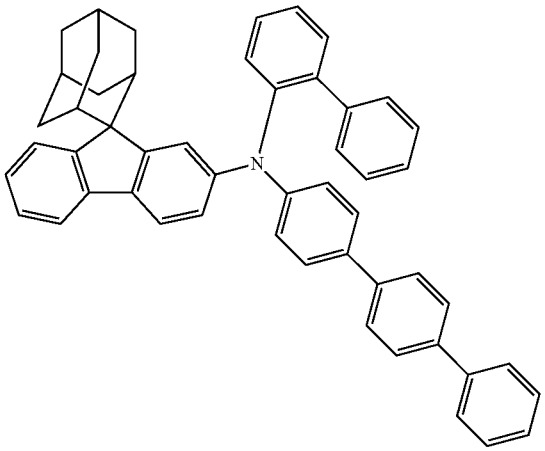

Compound 147
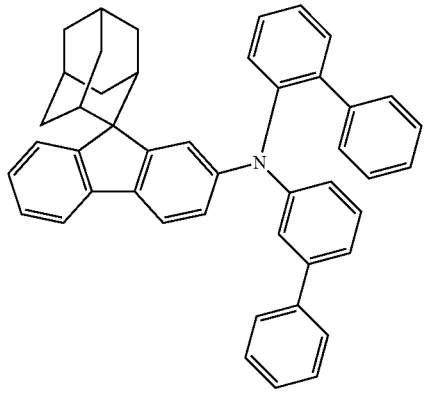
Compound 148
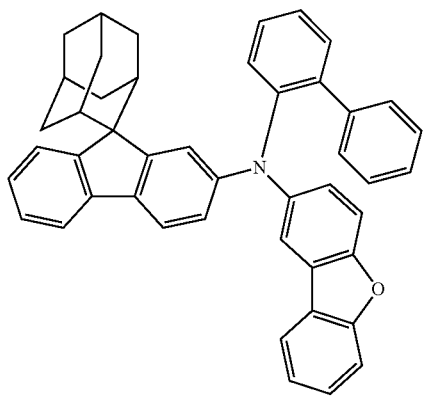
Compound 149
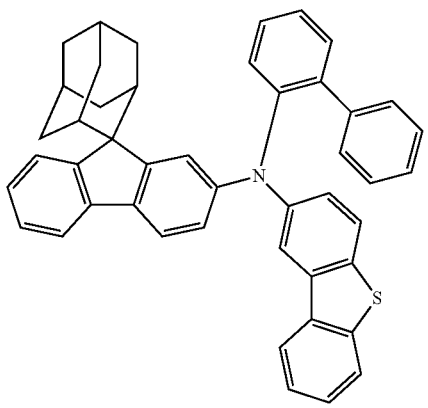
Compound 150
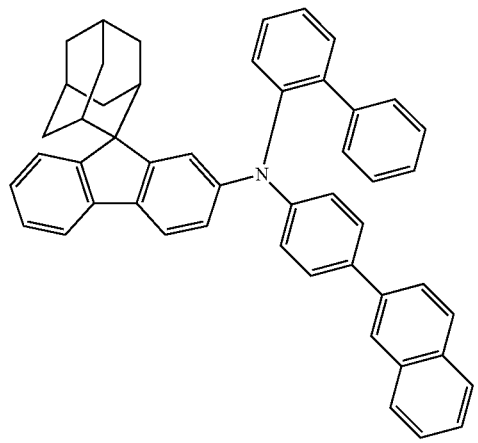
Compound 151
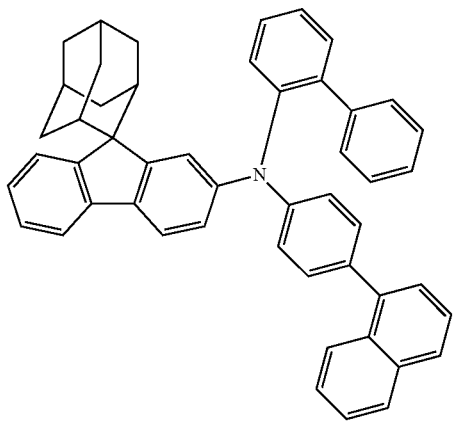
Compound 152
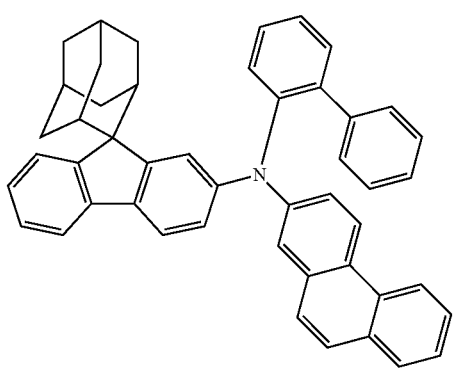
Compound 153

Compound 154
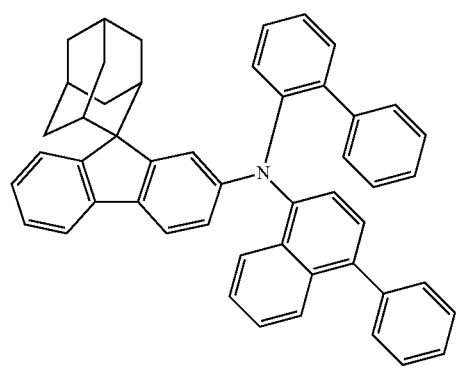
Compound 157
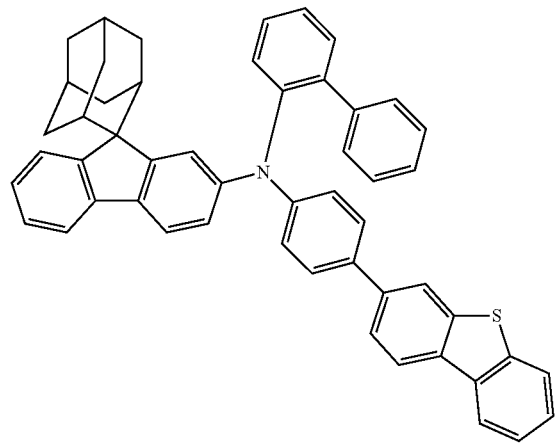
Compound 155
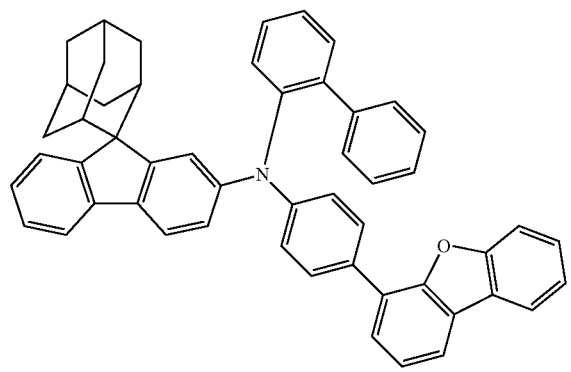
Compound 158
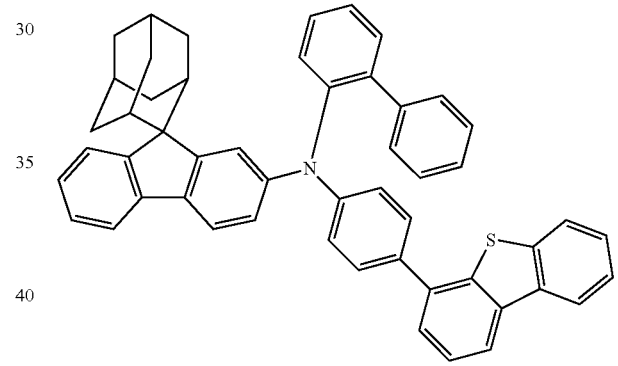
Compound 156
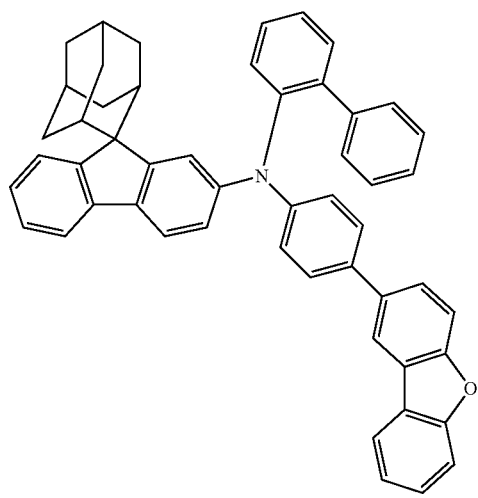
Compound 159
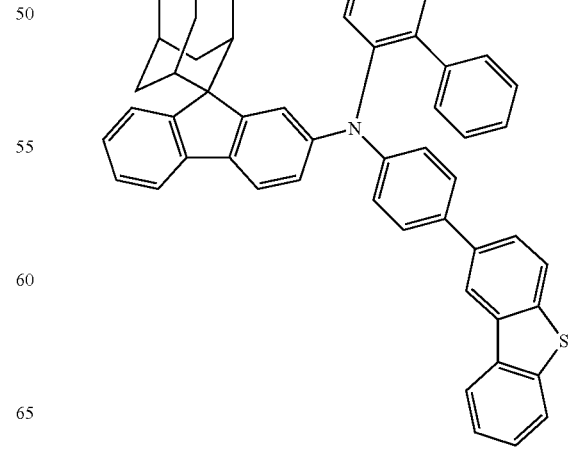

Compound 160
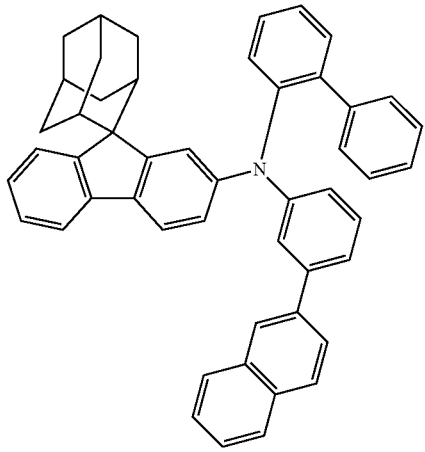
Compound 161
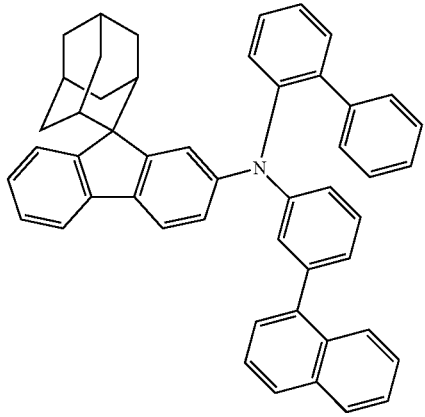
Compound 162
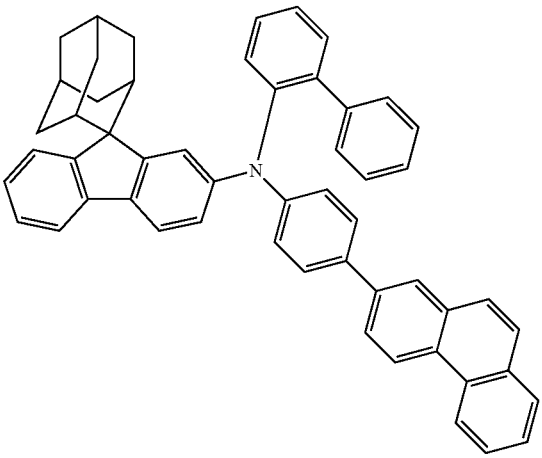
Compound 163
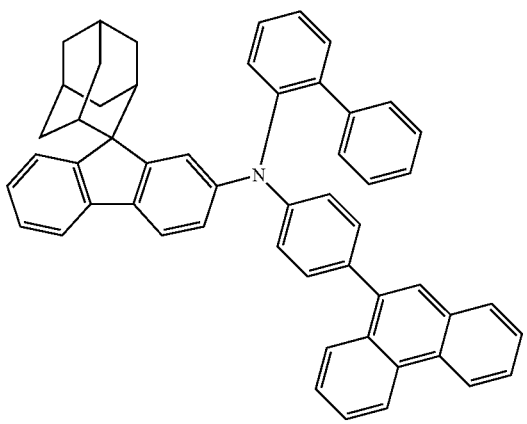
Compound 164
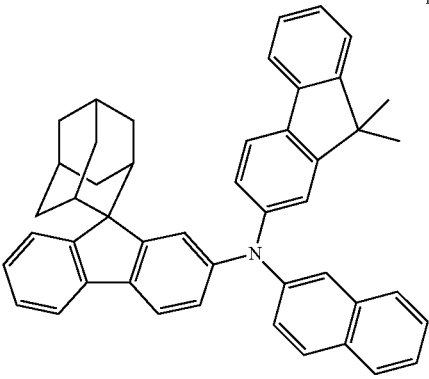
Compound 165
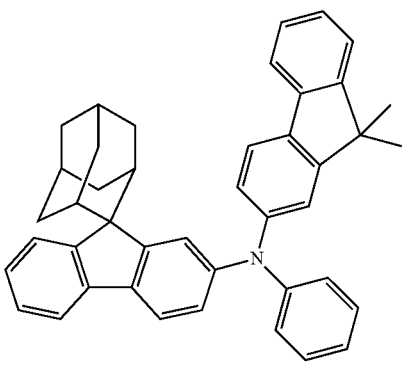
Compound 166
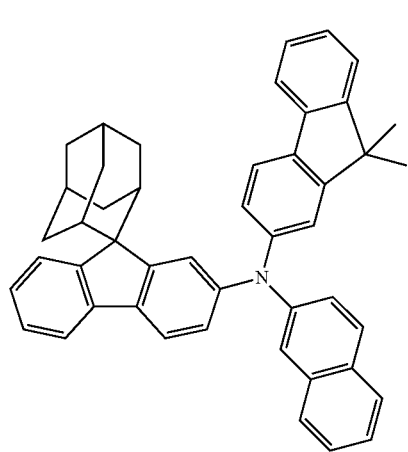

Compound 167
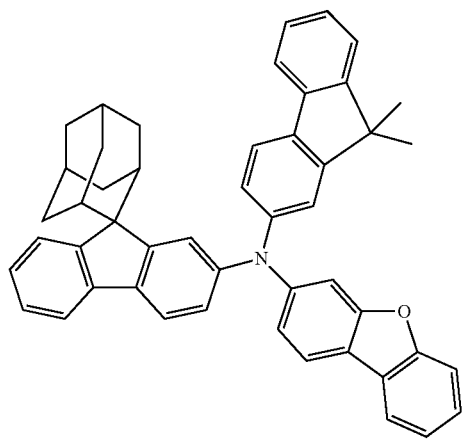
Compound 168
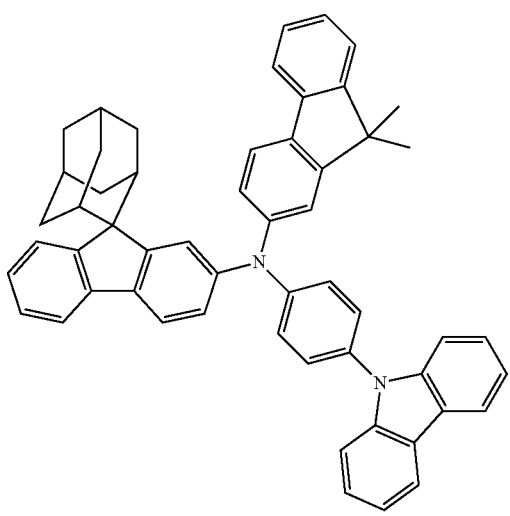
Compound 169
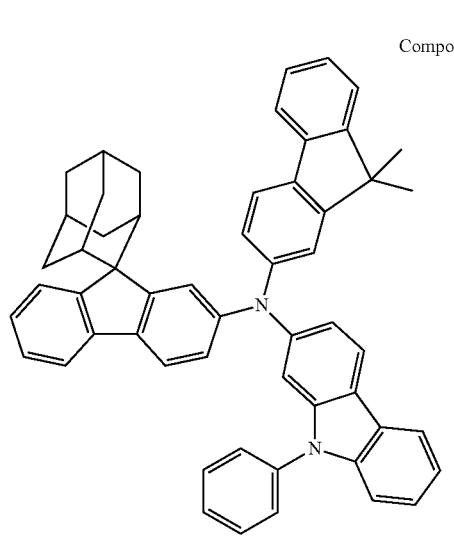
Compound 170
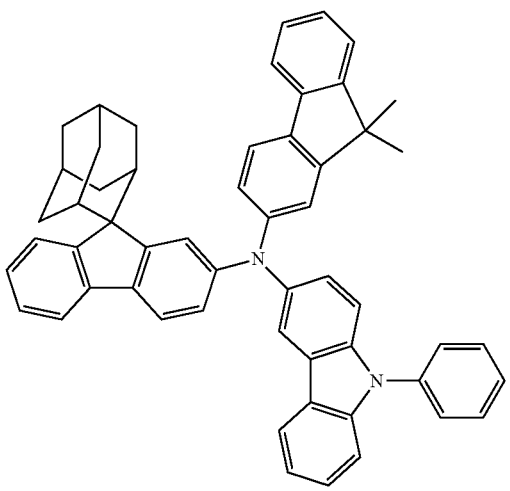
Compound 171
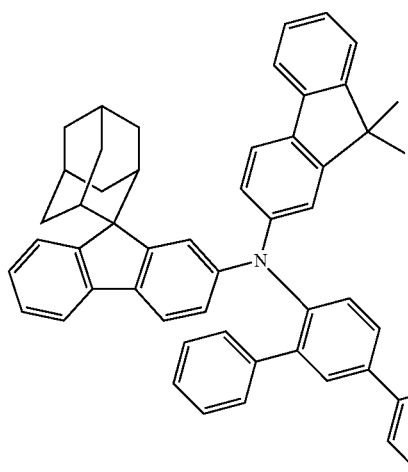
Compound 172
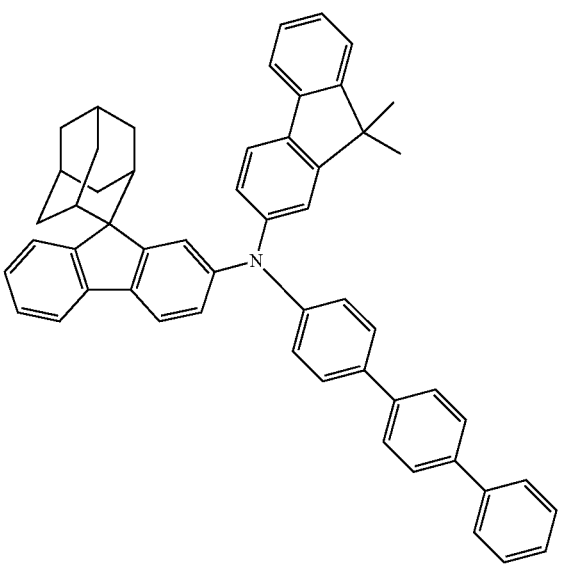

Compound 173
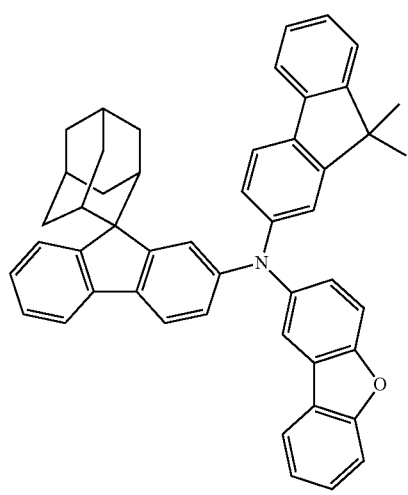
Compound 174
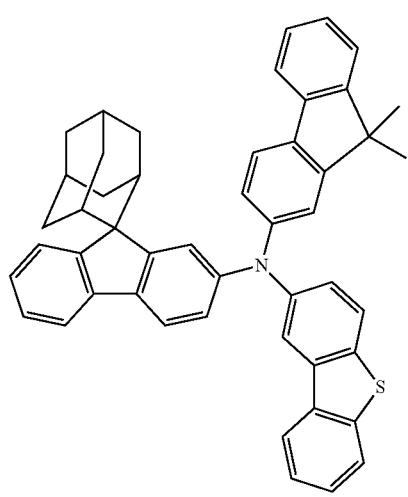
Compound 175
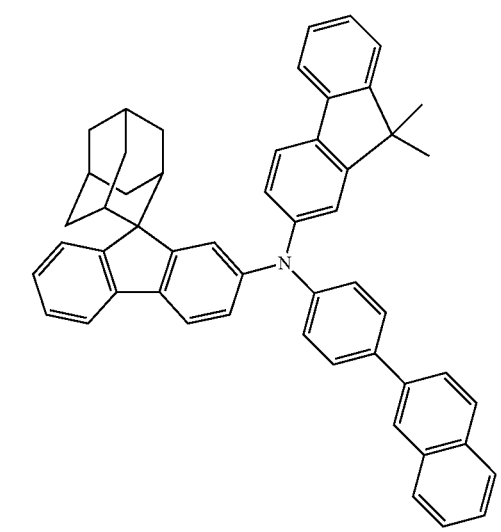
Compound 176
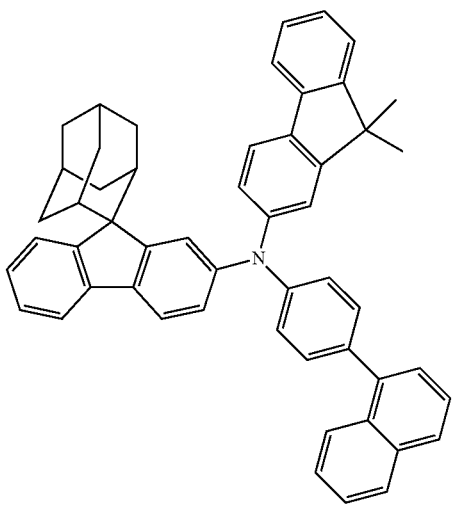
Compound 177
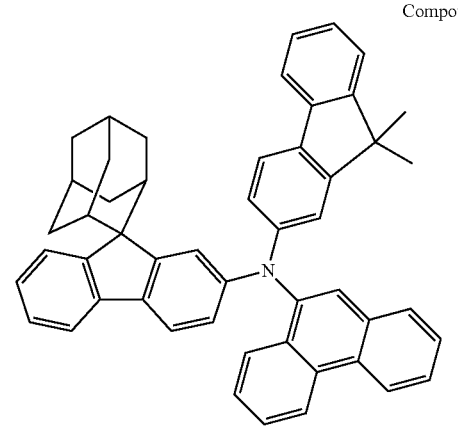
Compound 178
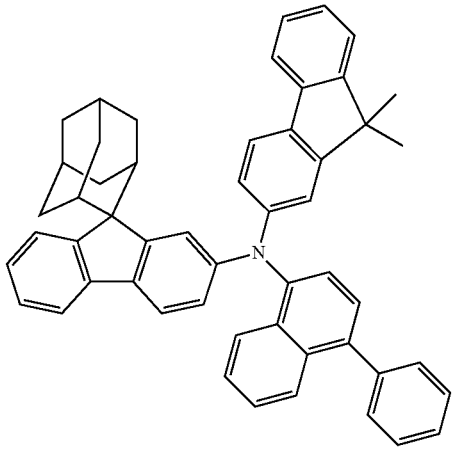

Compound 179
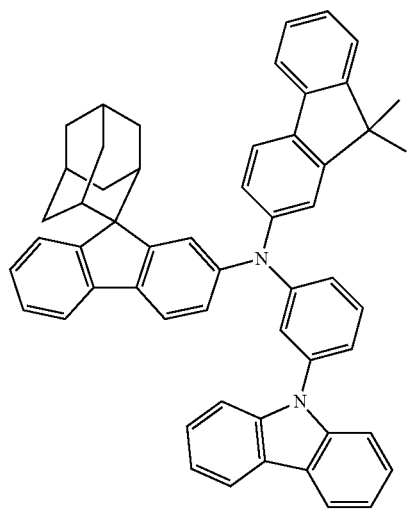
Compound 180
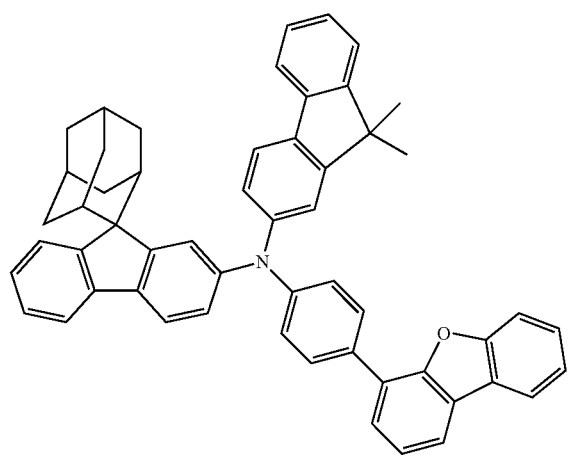
Compound 181
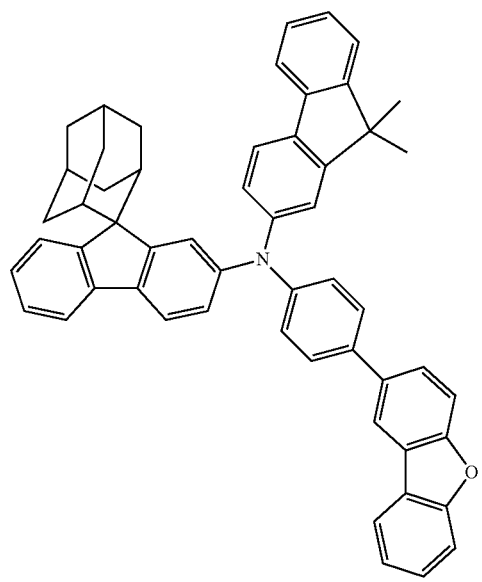
Compound 182
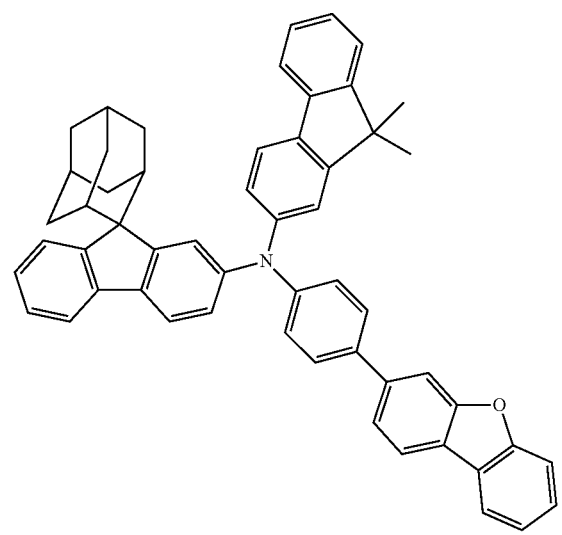
Compound 183
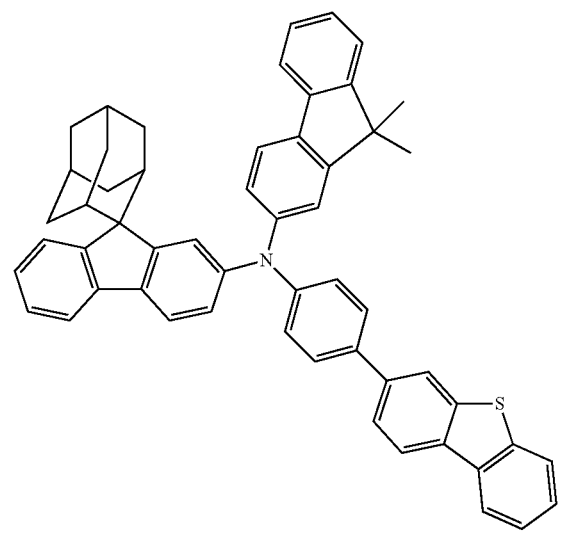
Compound 184
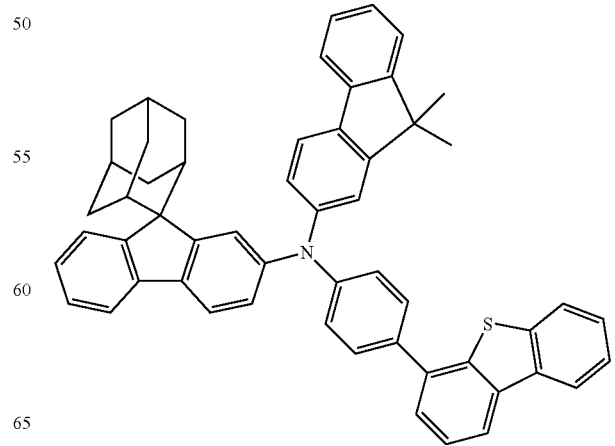

Compound 185
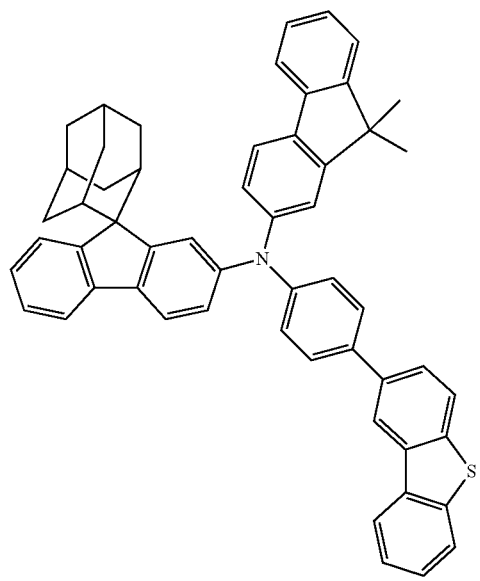
Compound 186
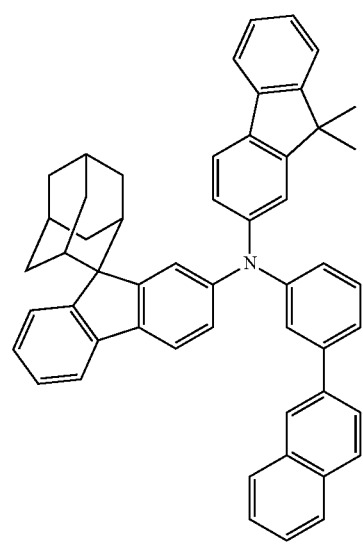
Compound 187
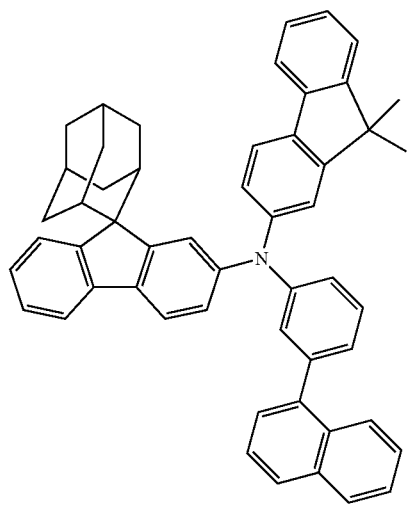
Compound 188
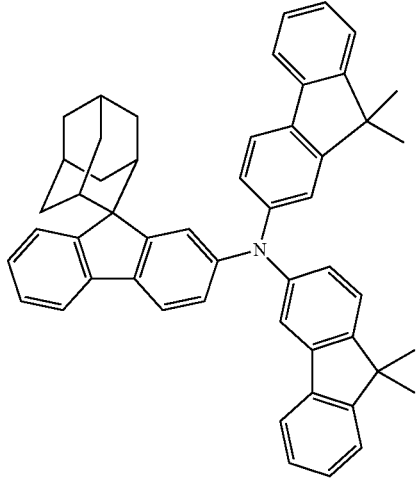
Compound 190
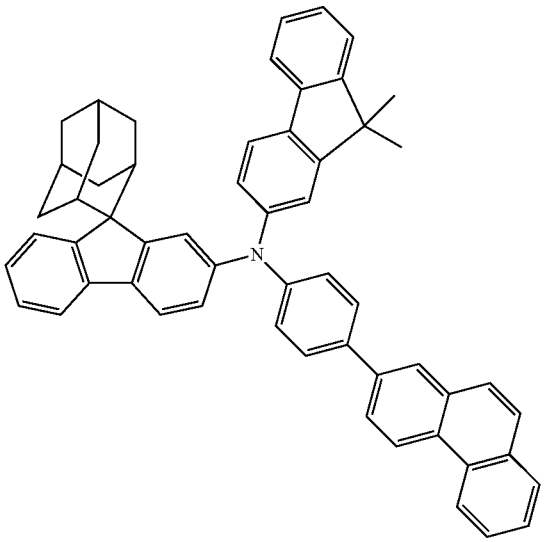
Compound 191
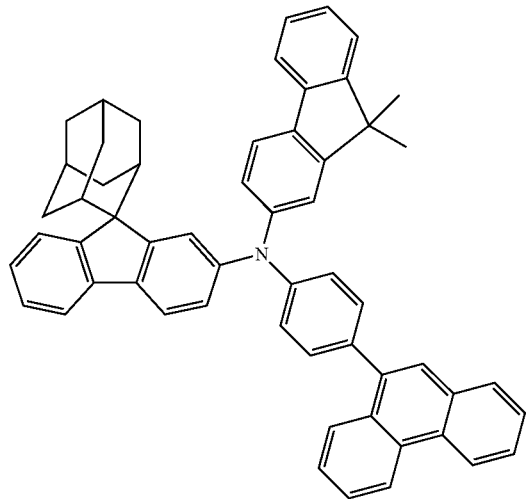

Compound 193
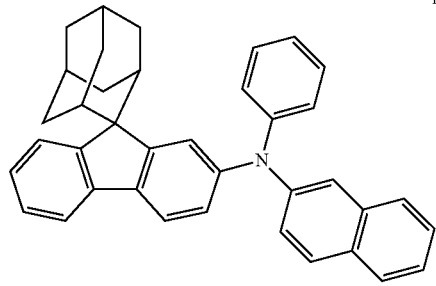
Compound 195
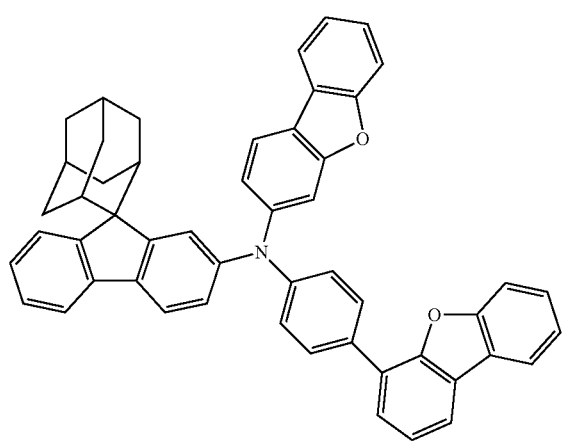
Compound 196
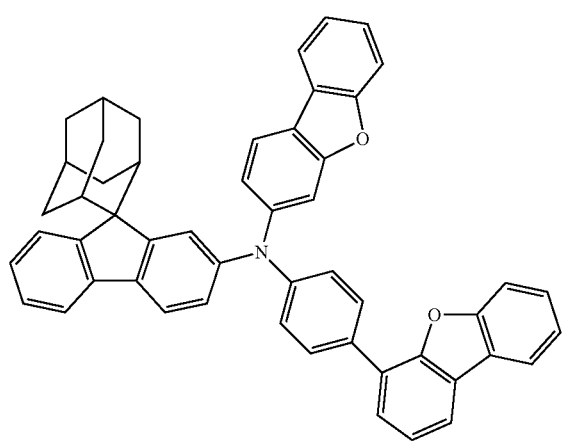
Compound 197
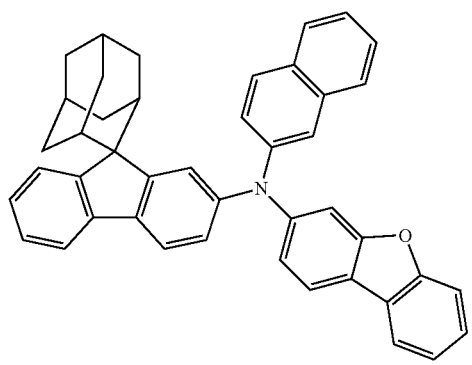
Compound 198
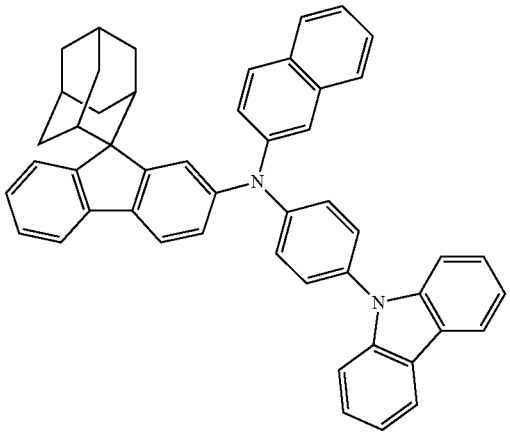
Compound 199
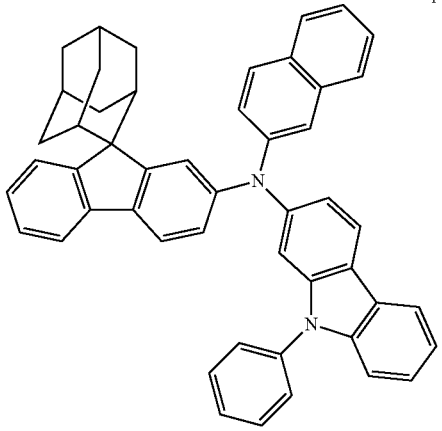
Compound 200
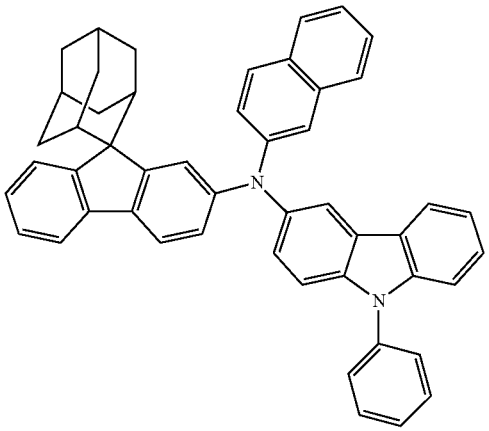

Compound 201
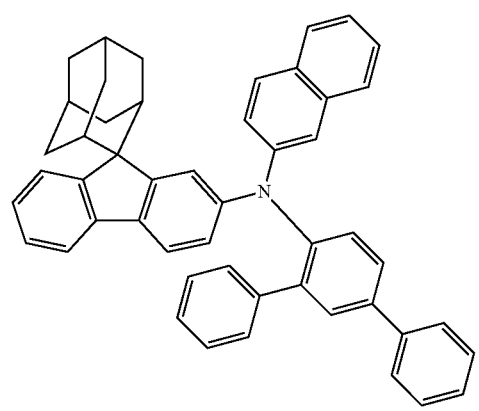
Compound 202
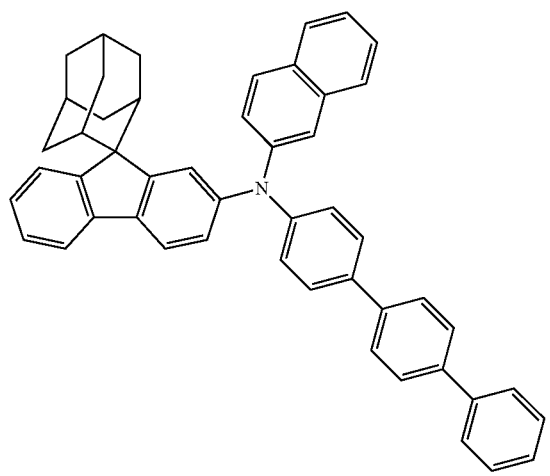
Compound 203
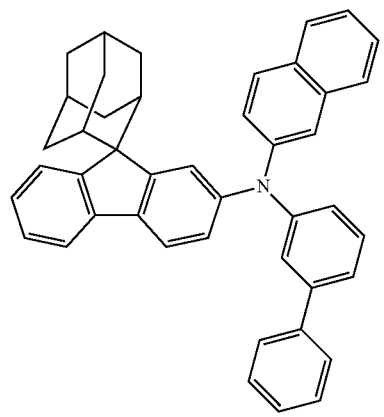
Compound 204
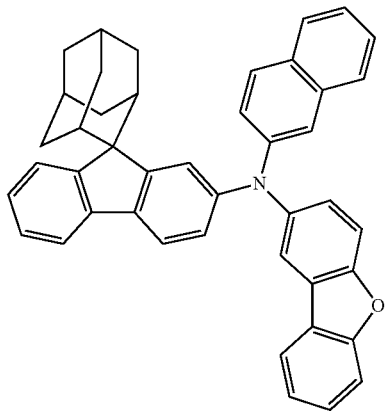
Compound 205
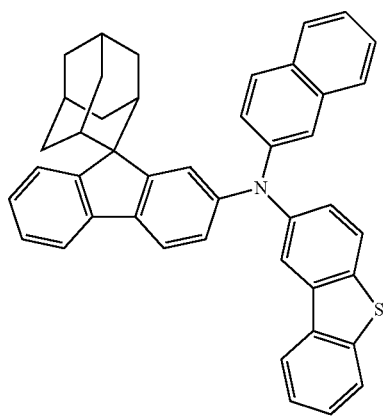
Compound 206
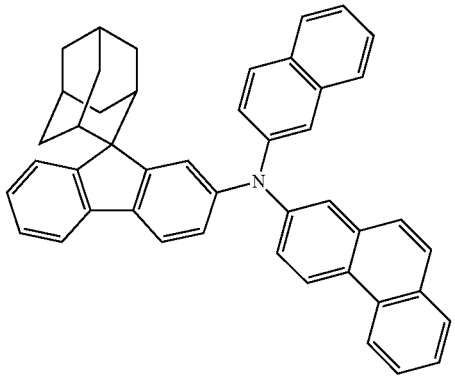

Compound 207
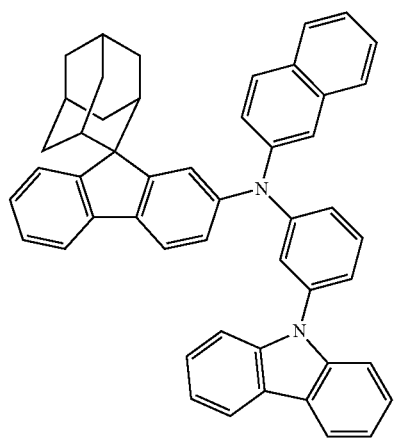
Compound 208
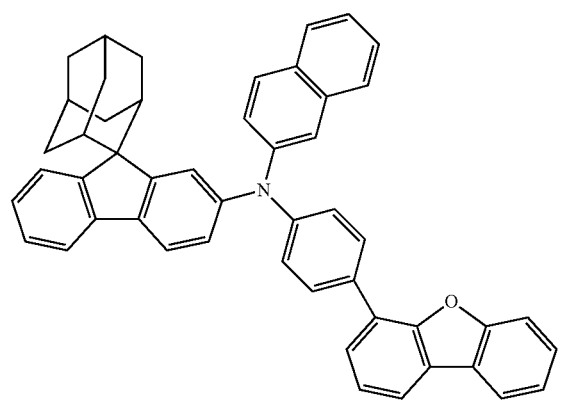
Compound 209
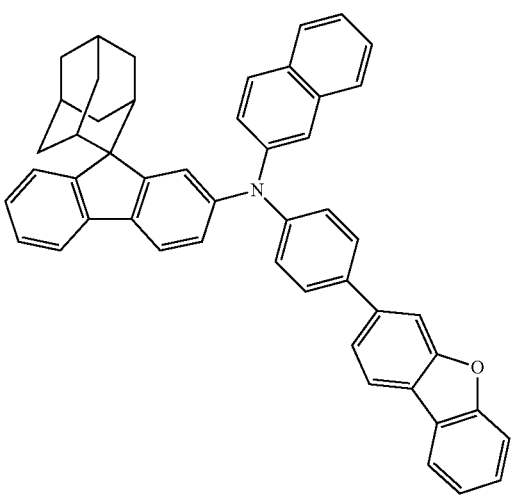
Compound 210
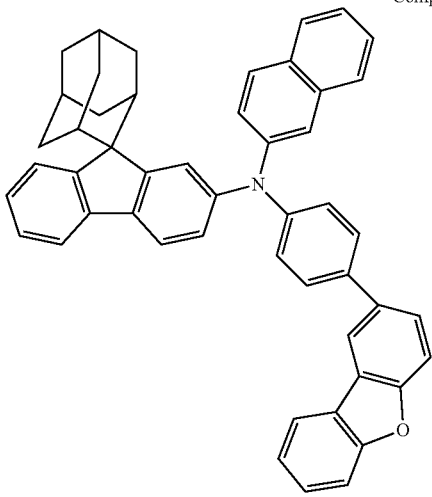
Compound 211
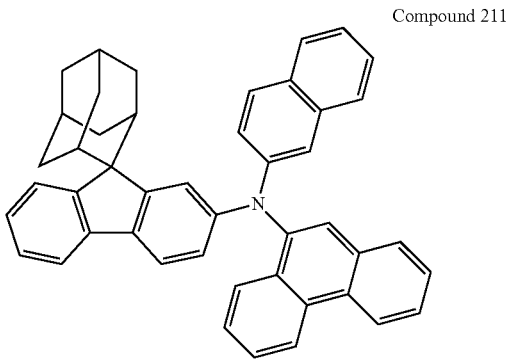
Compound 212
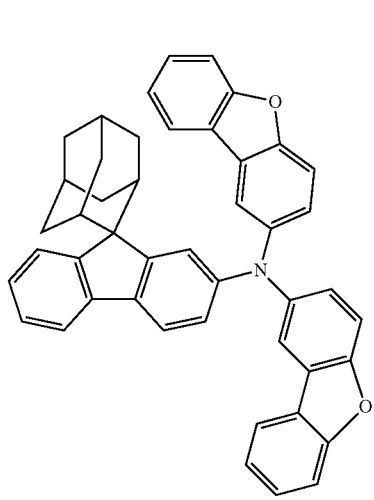

Compound 213
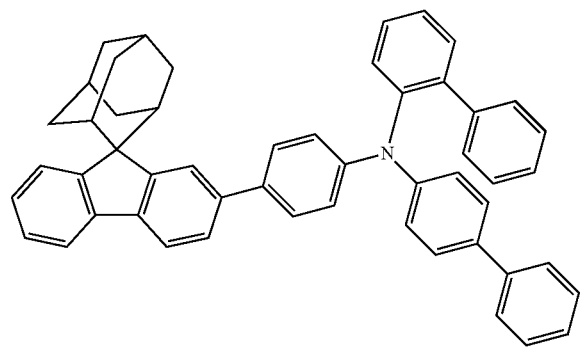
Compound 214
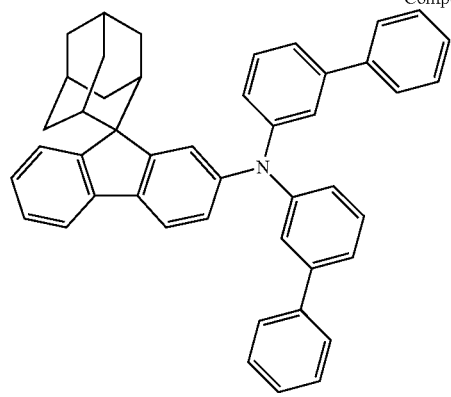
Compound 215
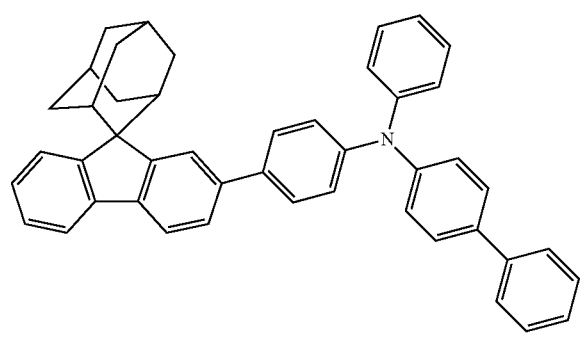
Compound 216
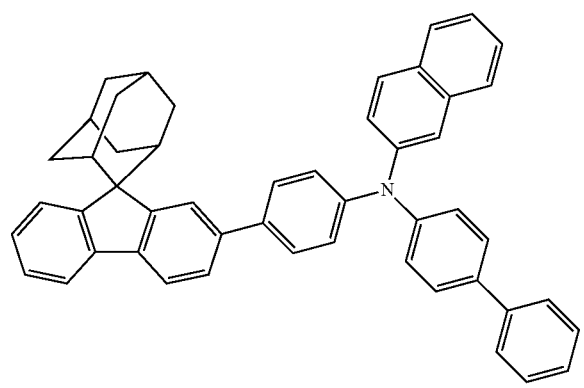
Compound 217
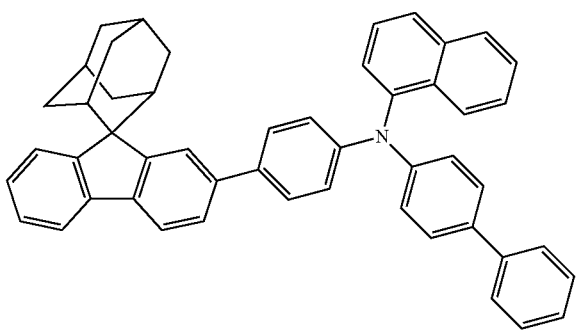
Compound 218
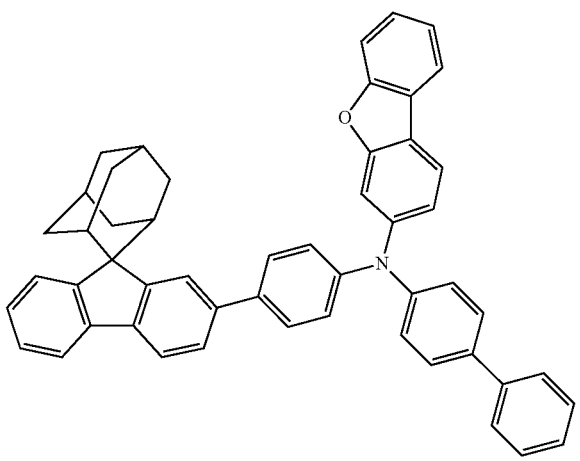
Compound 219
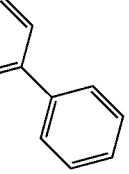

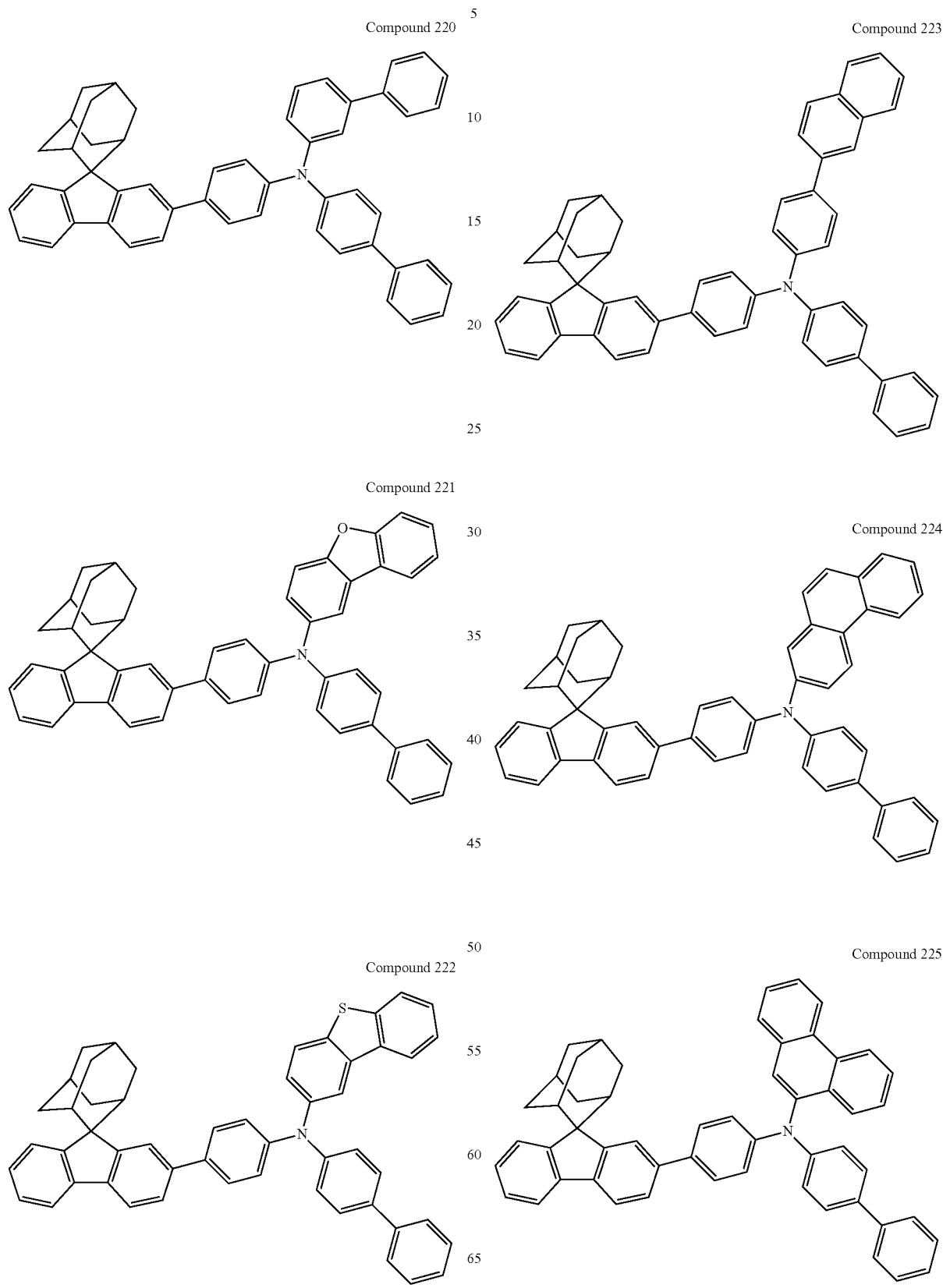

Compound 226
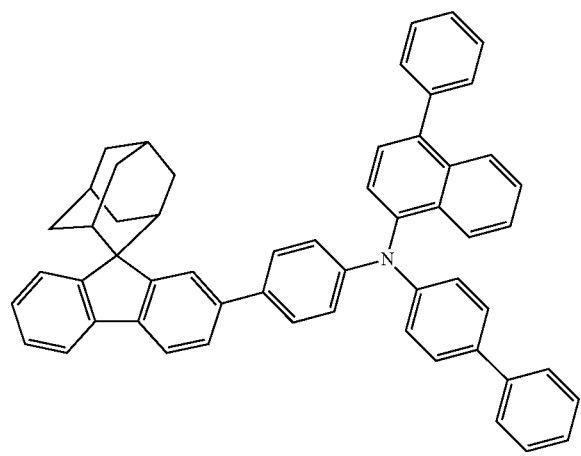
Compound 227
Compound 228
Compound 229
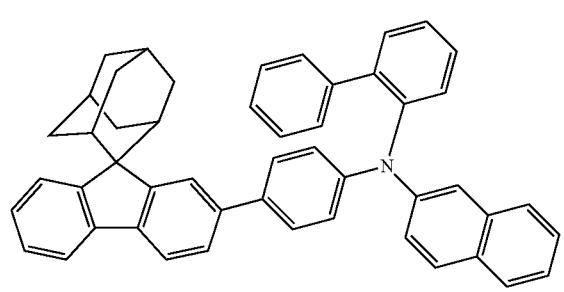
Compound 230
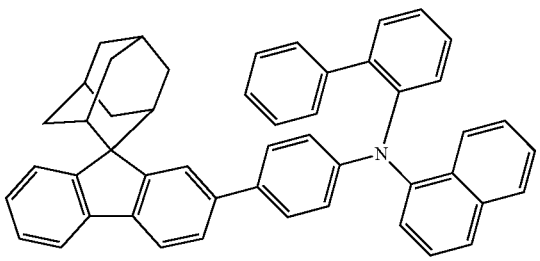
Compound 231
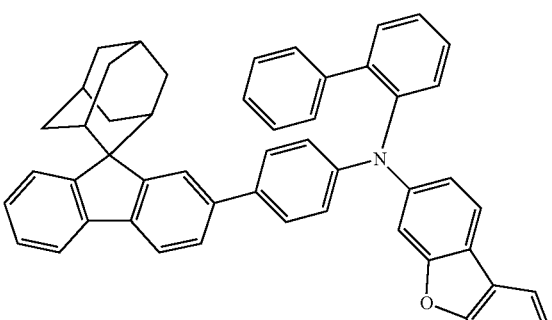
Compound 232
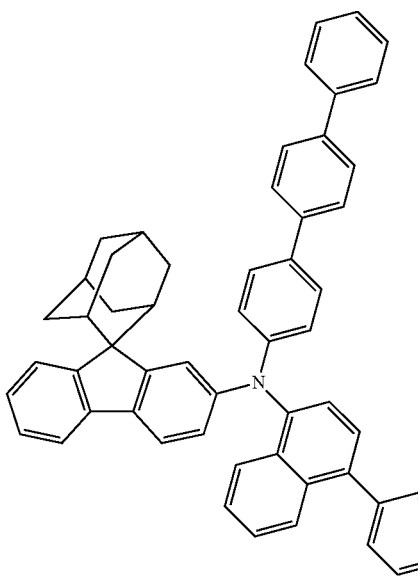
Compound 233
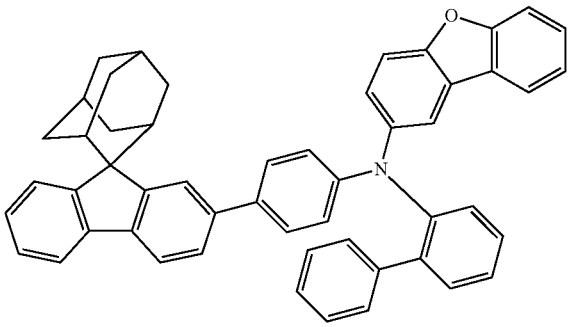

Compound 234
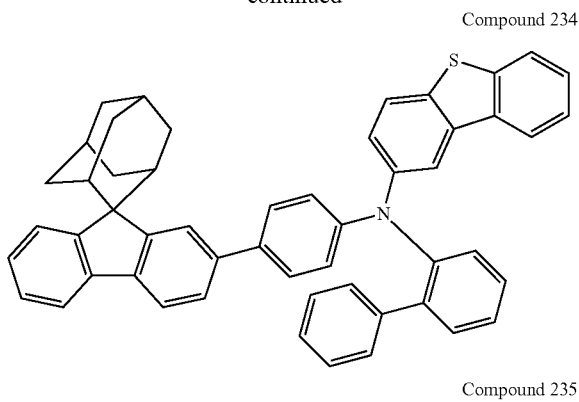
Compound 235
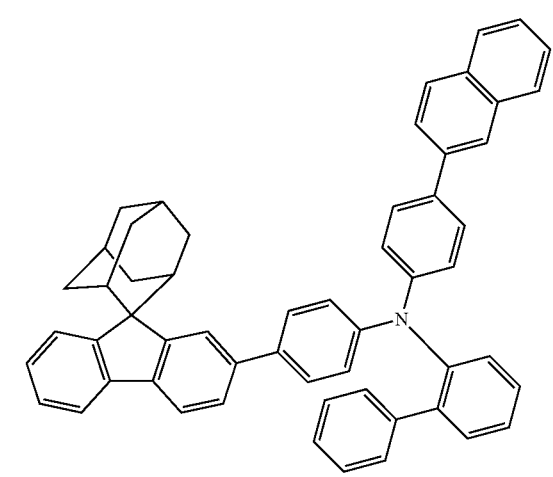
Compound 236
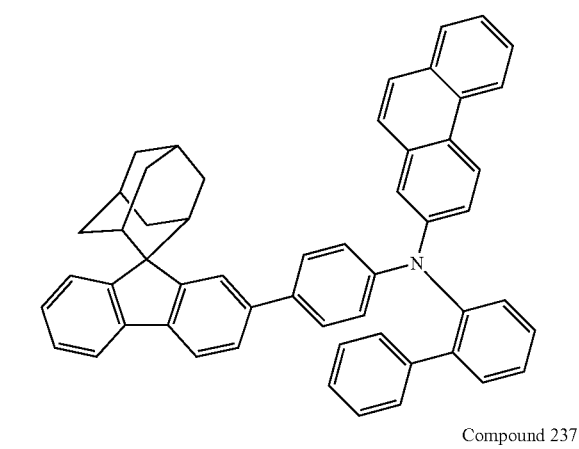
Compound 237
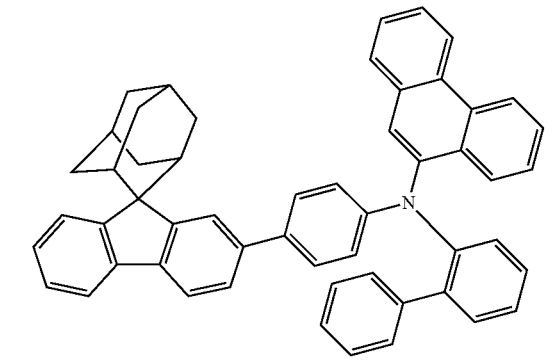
Compound 238
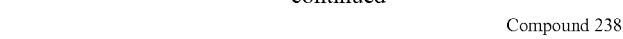
Compound 239
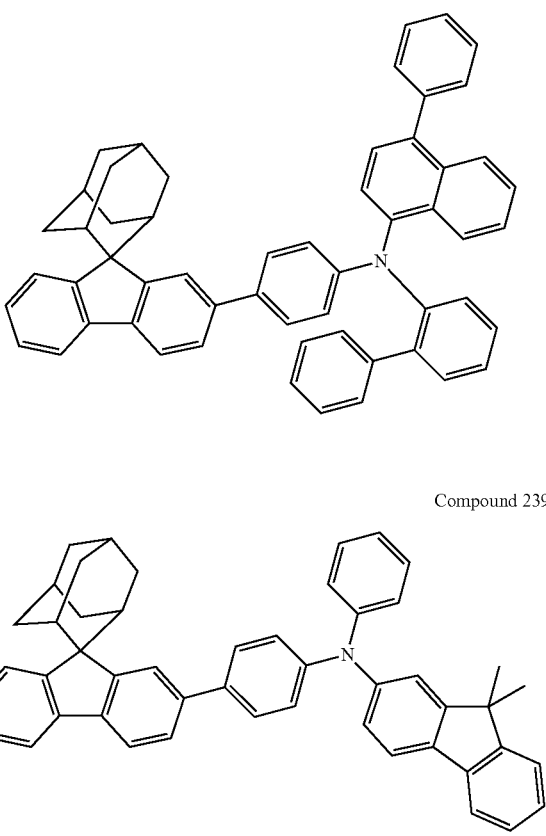
Compound 240
Compound 241
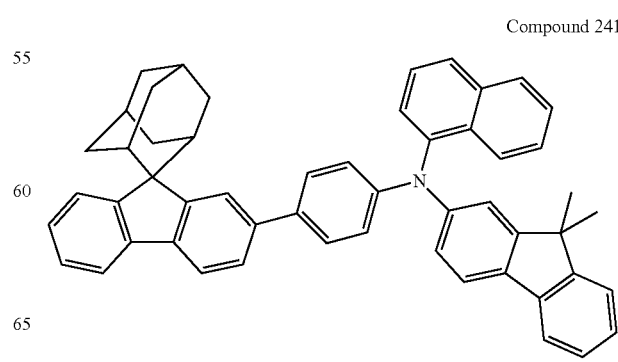

Compound 242
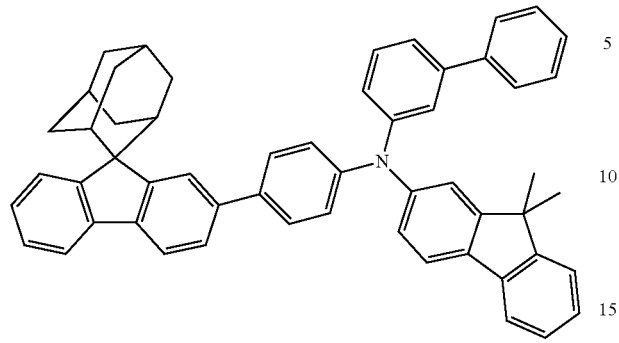
Compound 243
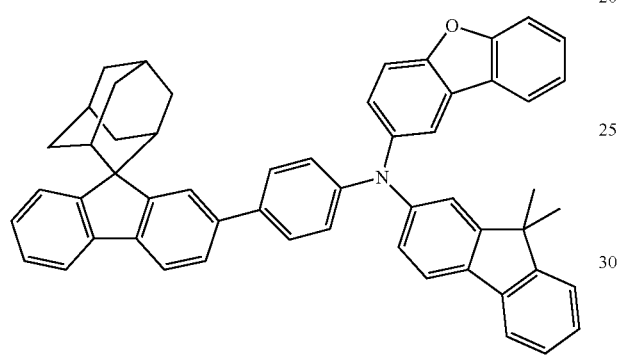
Compound 244
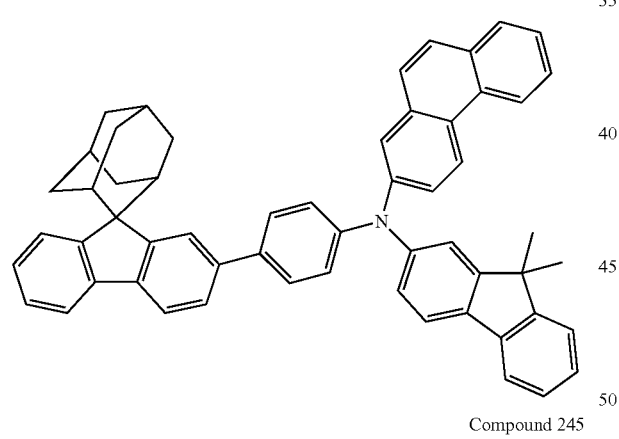
Compound 245
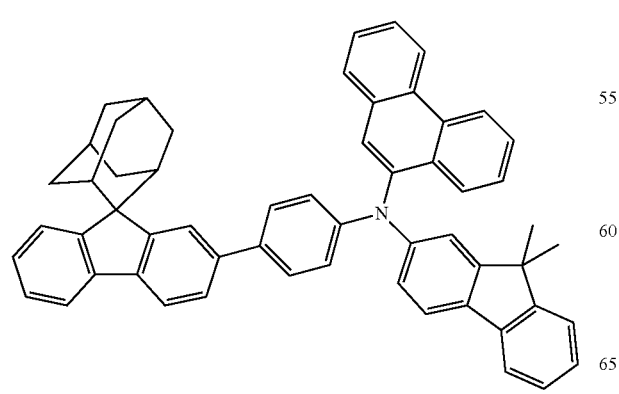
Compound 246
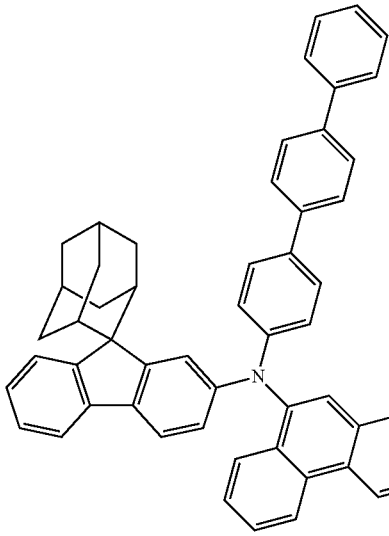
Compound 247
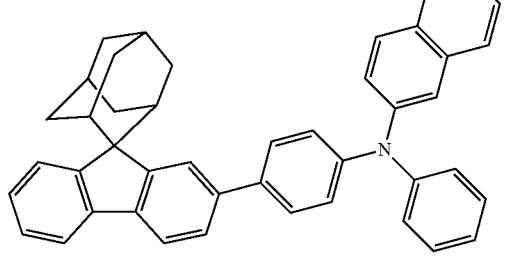
Compound 248
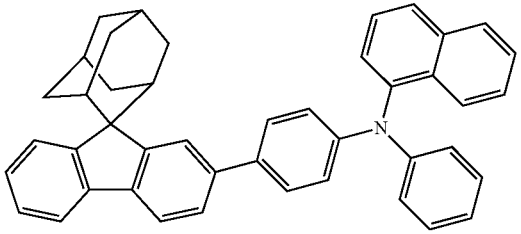
Compound 249
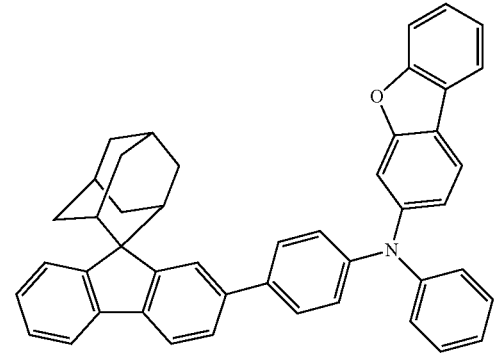

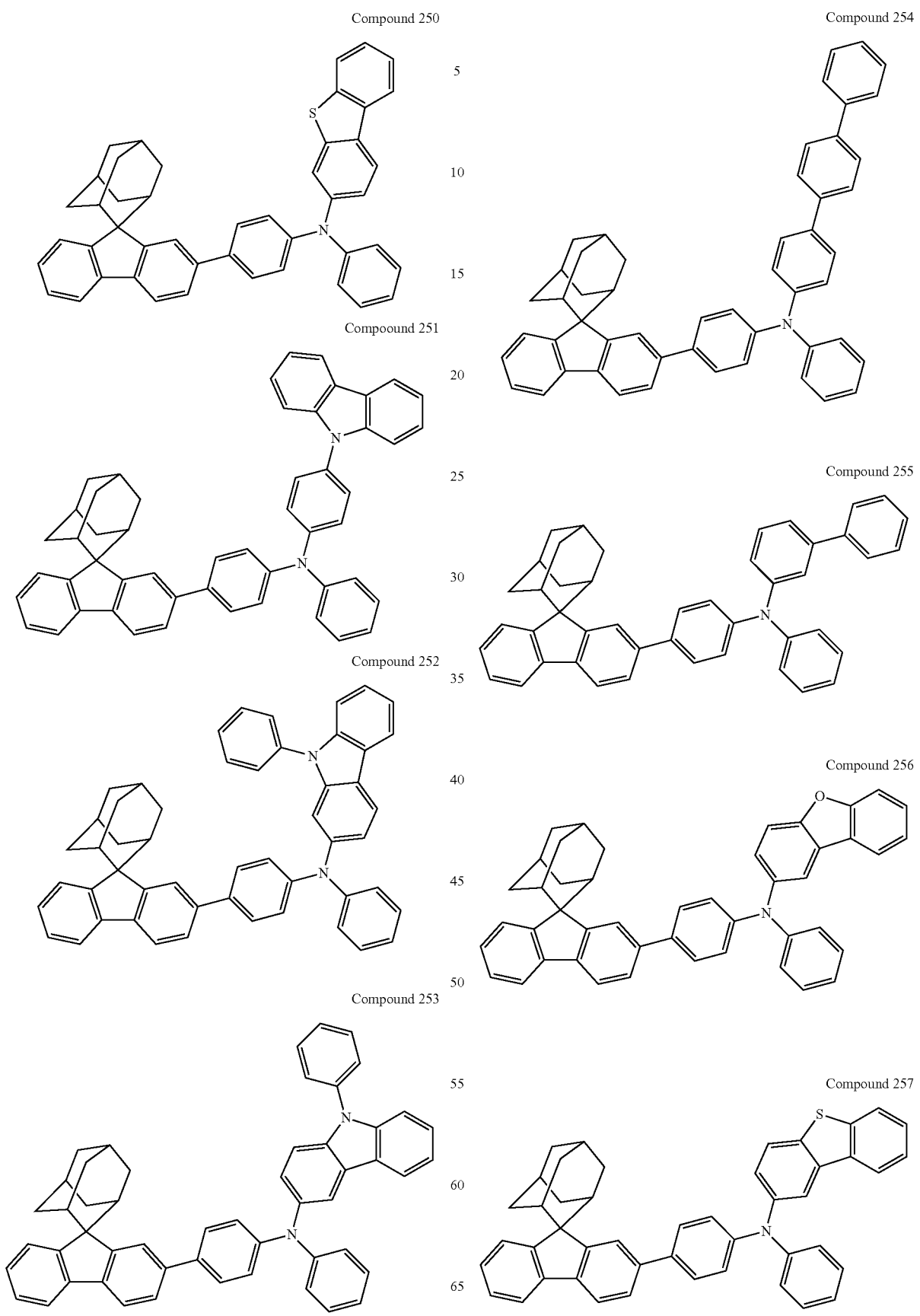

Compound 258
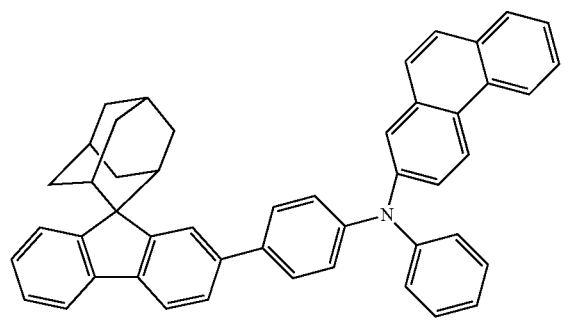
Compound 259
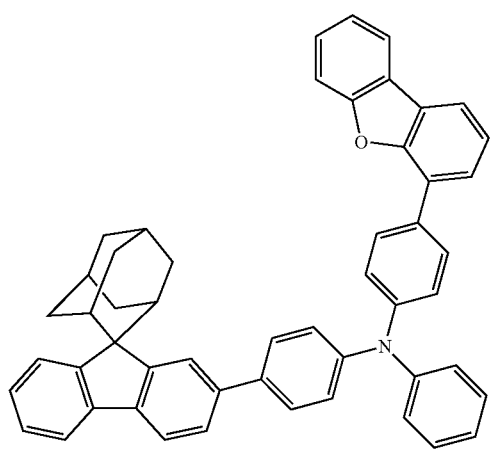
Compound 260
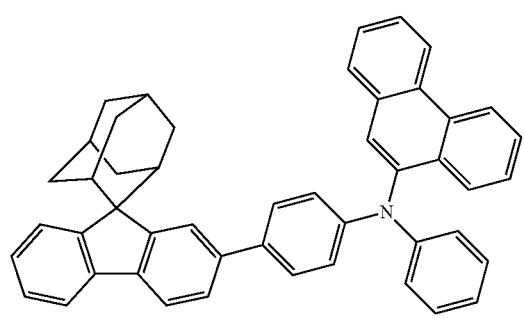
Compound 261
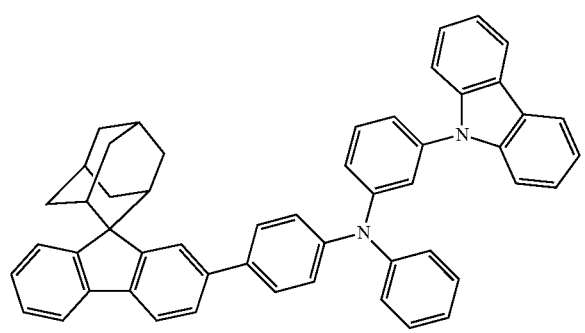
Compound 262
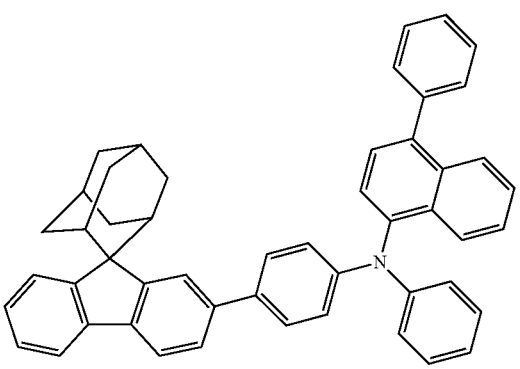
Compound 263
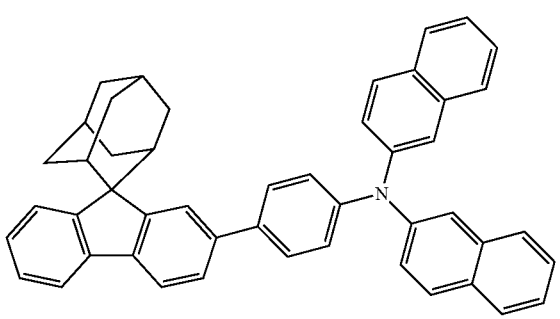
Compound 264
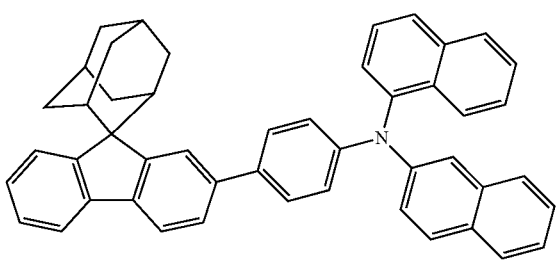
Compound 265
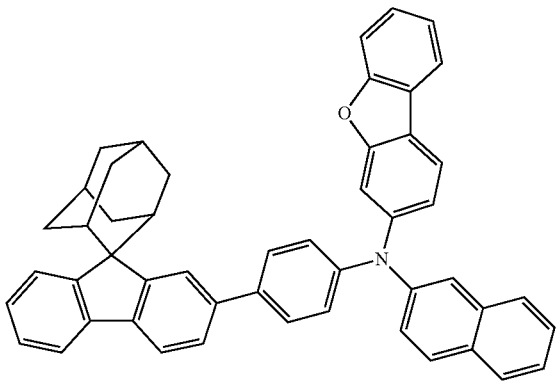

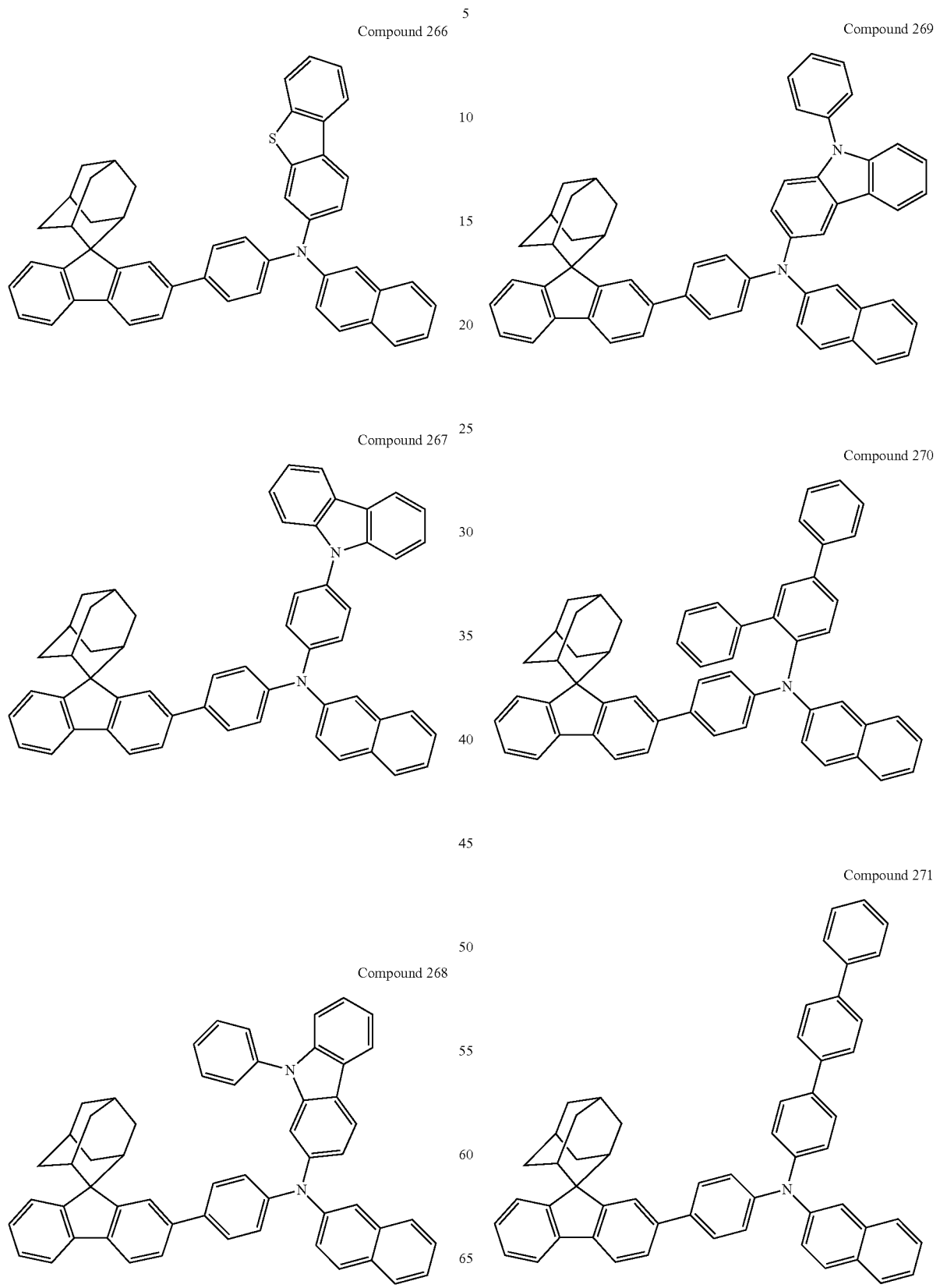

Compound 272
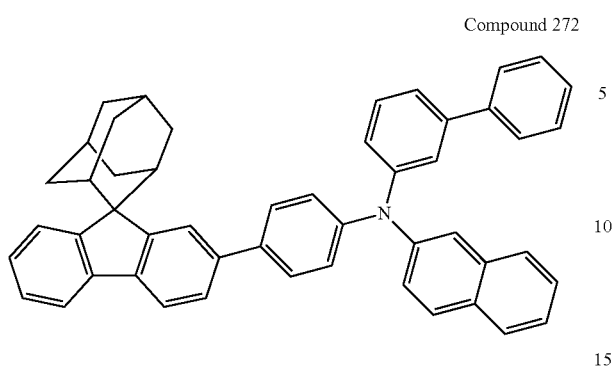
Compound 273
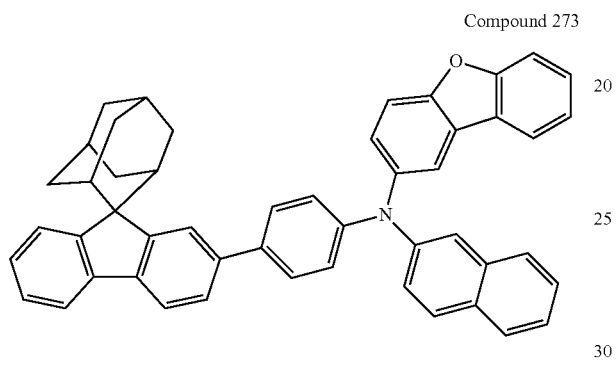
Compound 274
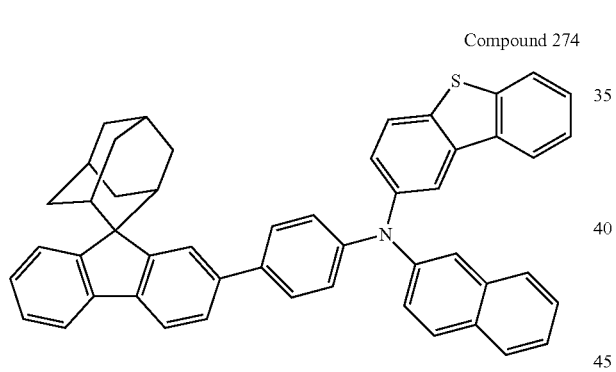
Compound 275
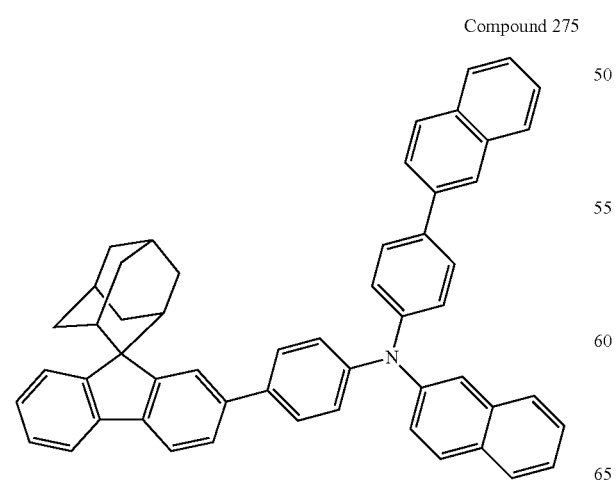
Compound 276
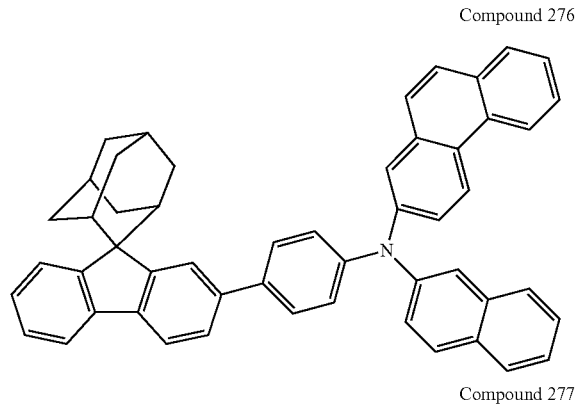
Compound 277
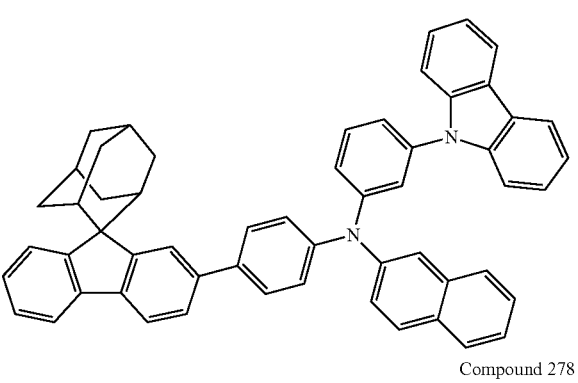
Compound 278
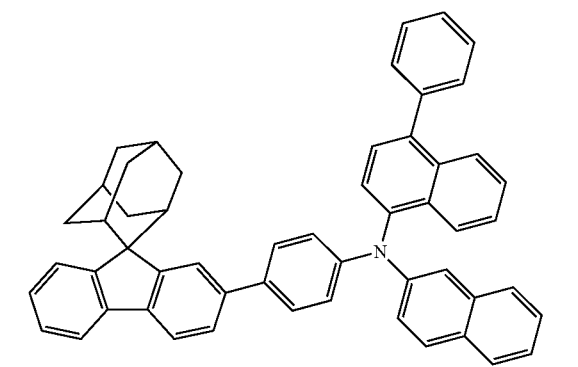
Compound 279
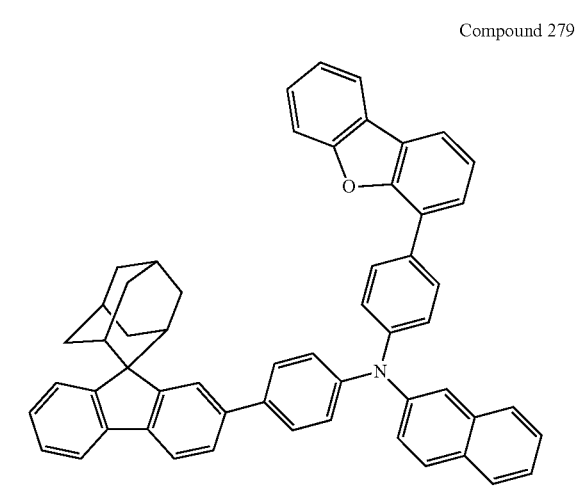

Compound 281
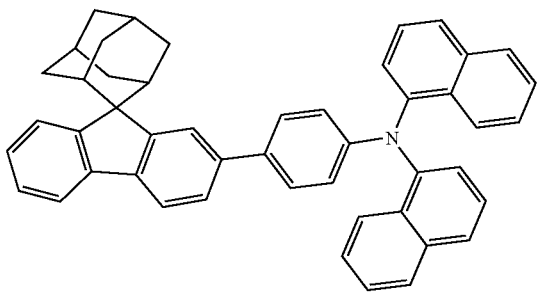
Compound 282
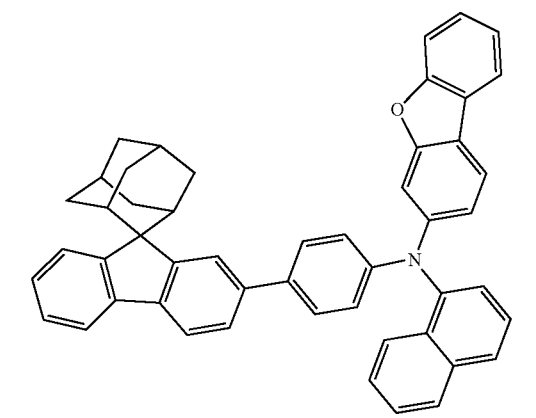
Compound 283
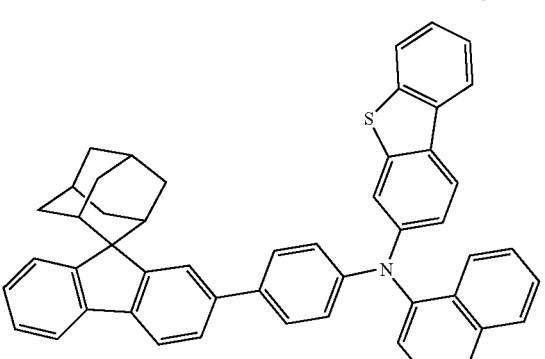
Compound 284
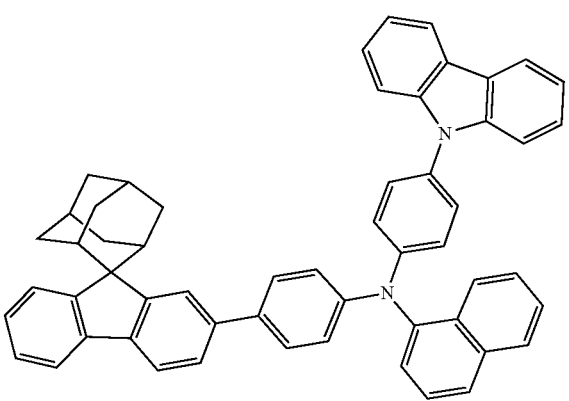
Compound 285
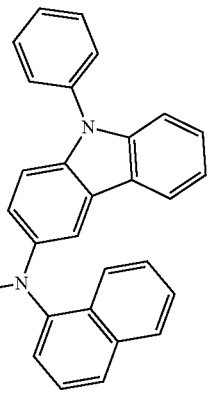
Compound 286
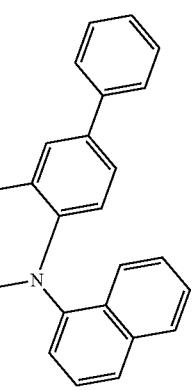
Compound 287
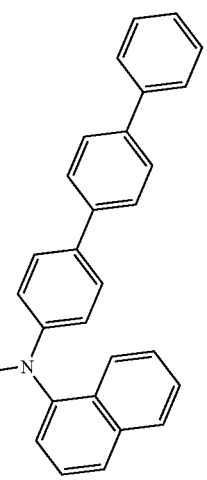
Compound 288

Compound 289
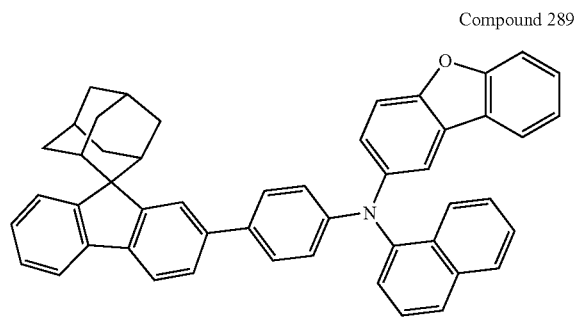
Compound 290
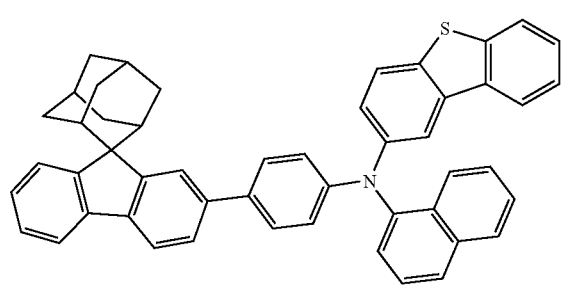
Compound 291
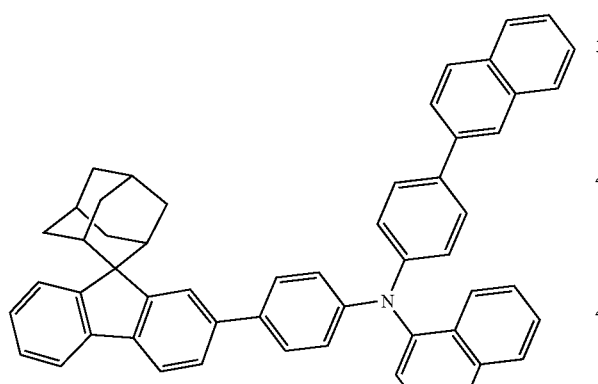
Compound 292
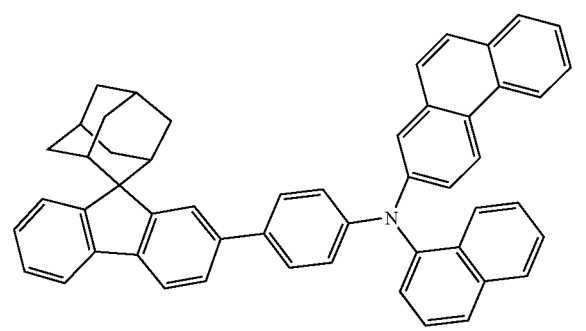
Compound 293
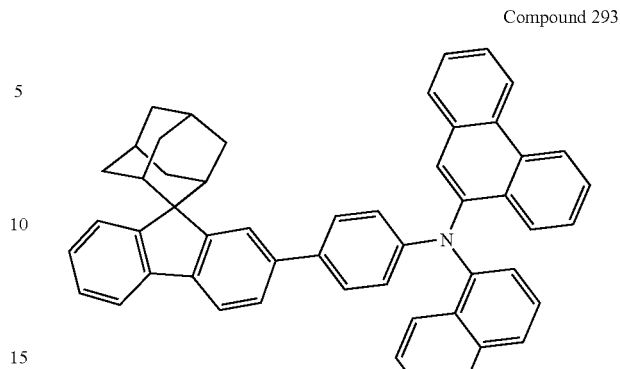
Compound 294
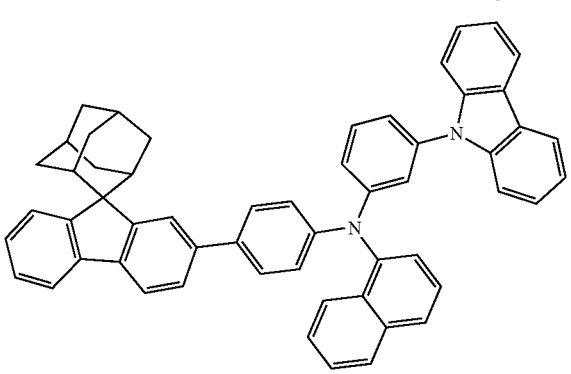
Compound 295
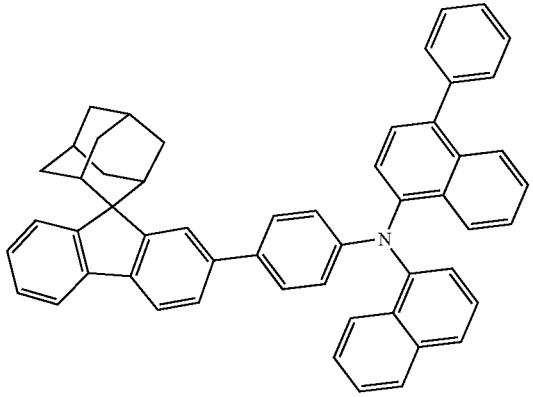
Compound 296
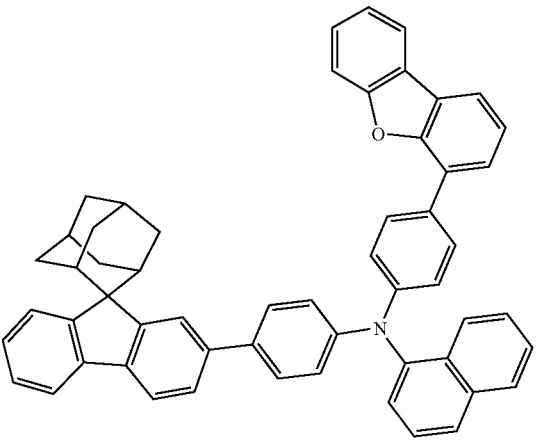

271
-continued
272
-continued
Compound 298
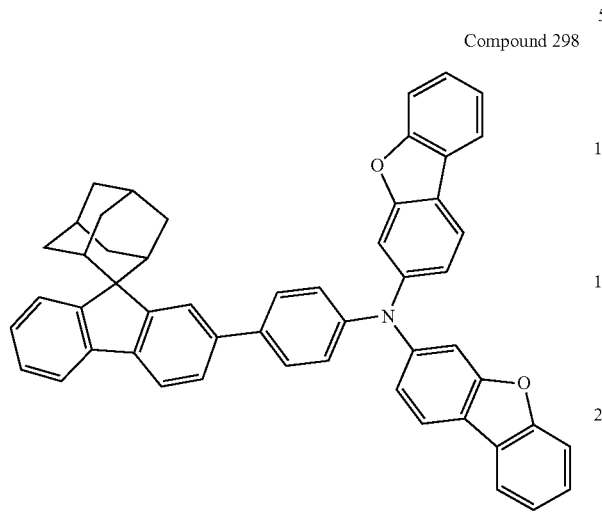
Compound 301
Compound 299
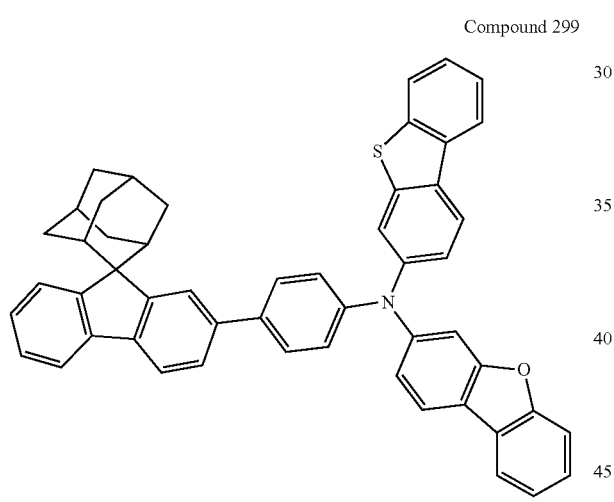
Compound 302
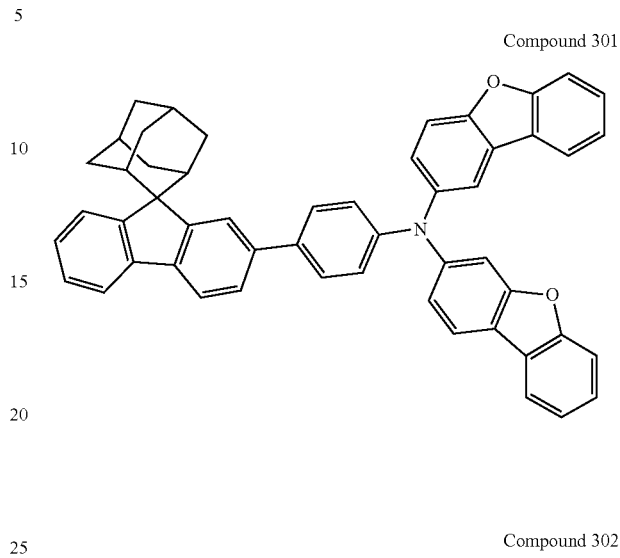
Compound 300
Compound 303
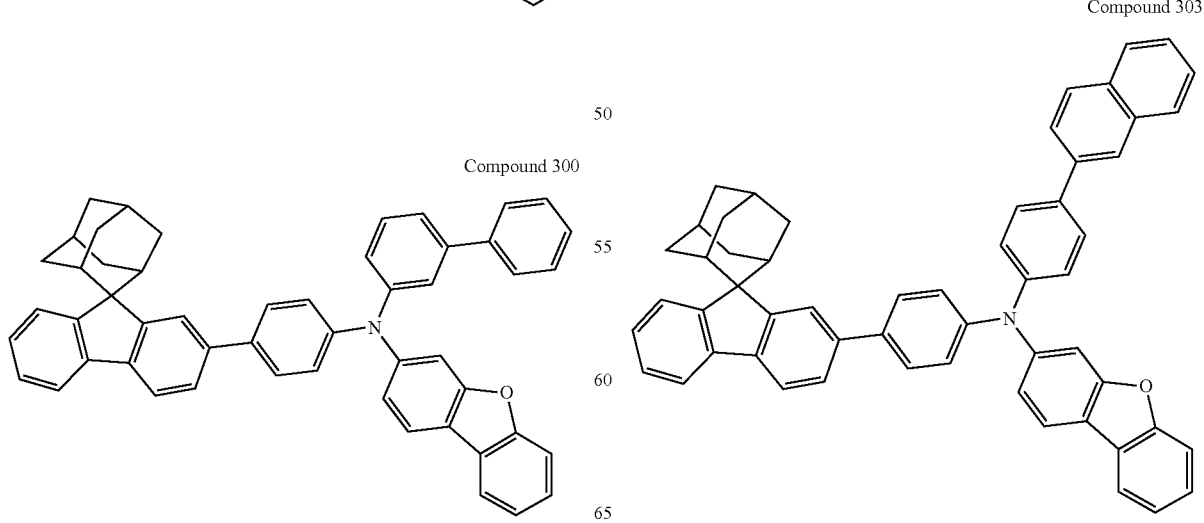

Compound 304
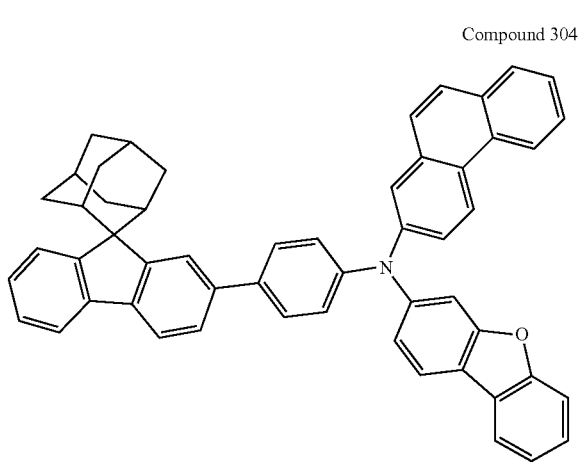
Compound 305
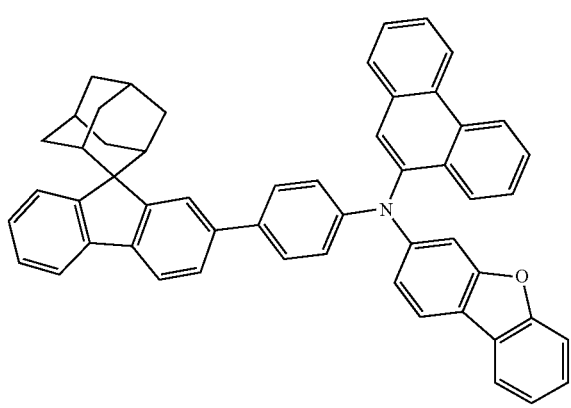
Compound 306
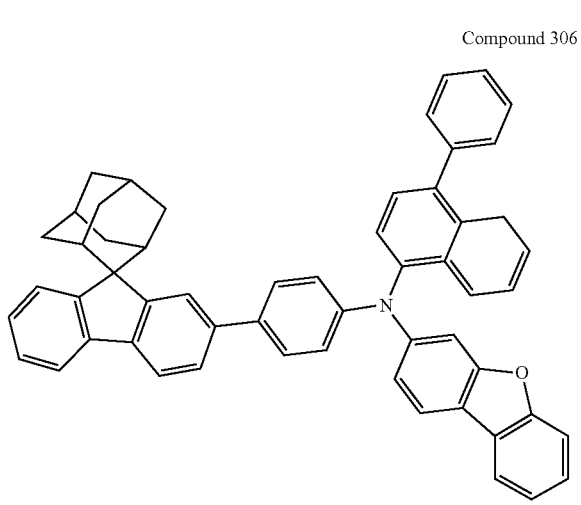
Compound 309
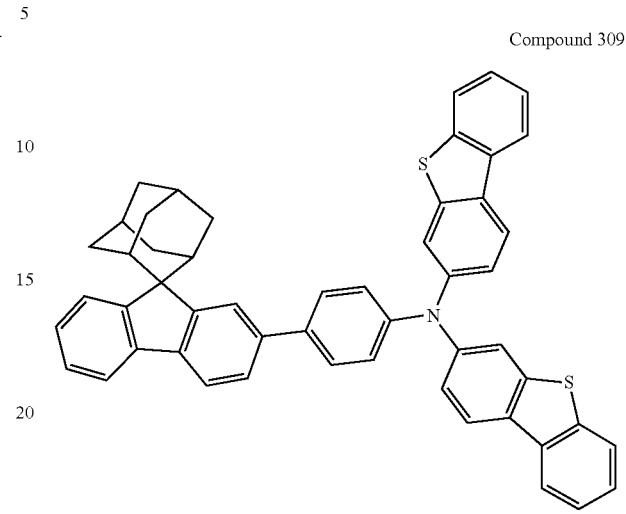
Compound 310
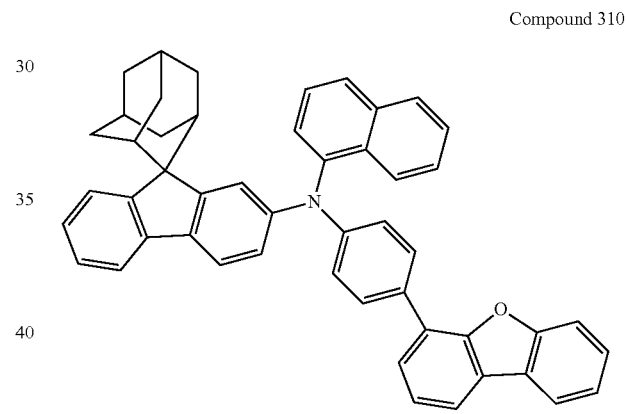
Compound 311
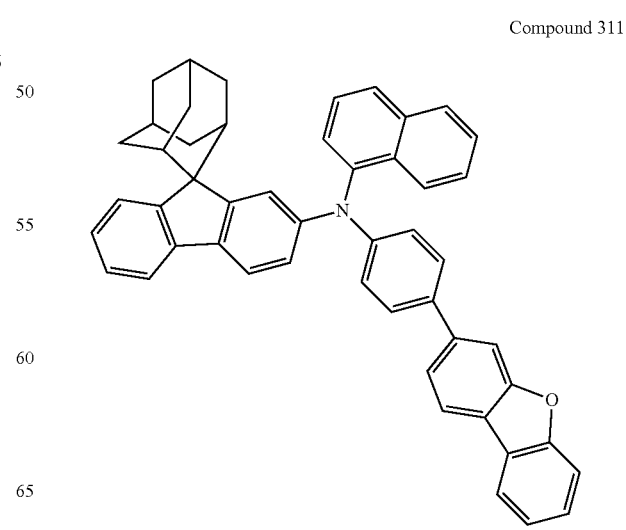

Compound 312
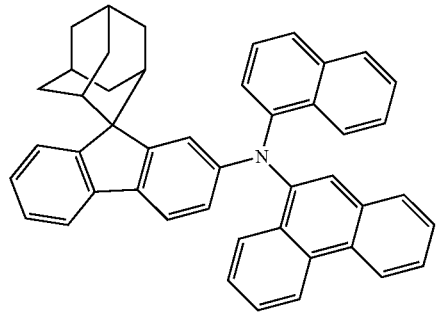
Compound 313
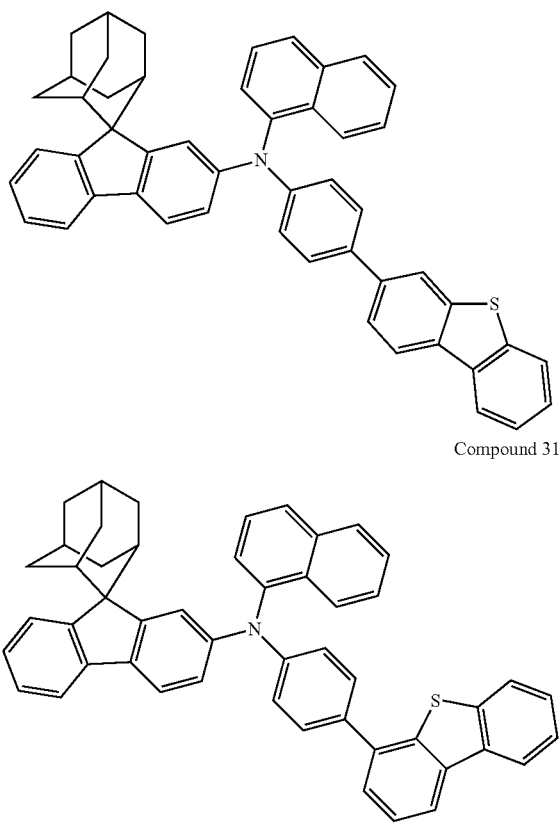
Compound 314
Compound 315
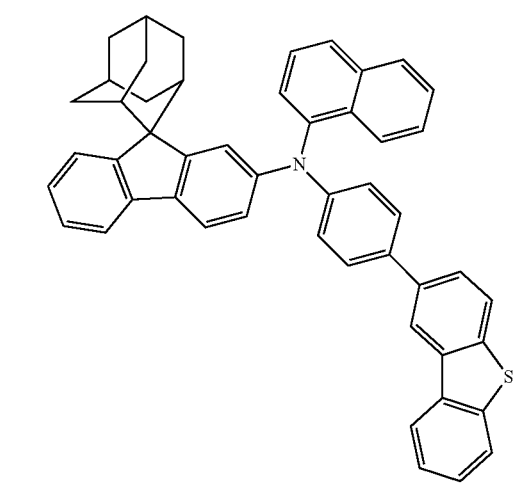
Compound 316
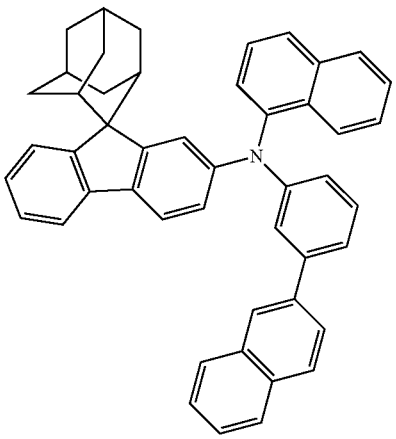
Compound 317
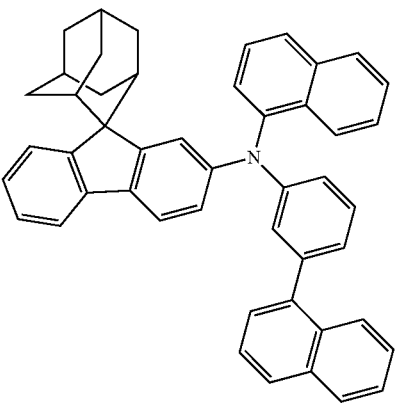
Compound 318
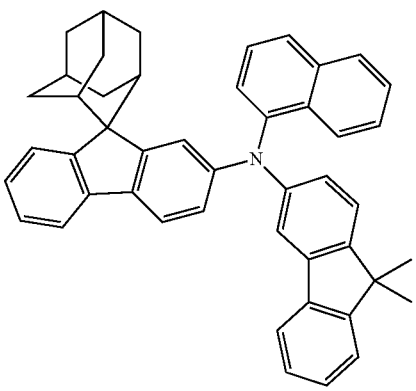

Compound 319
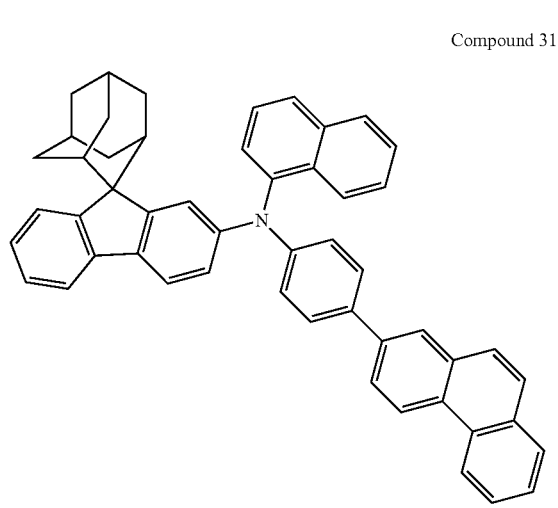
Compound 320
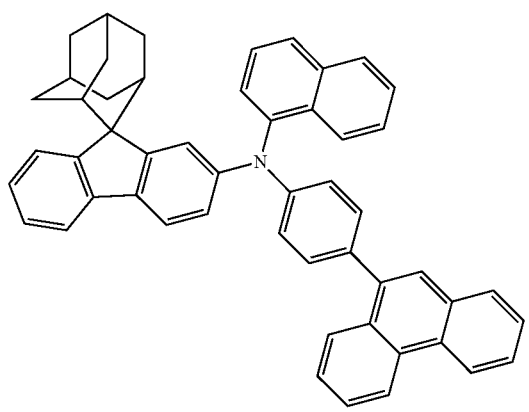
Compound 321
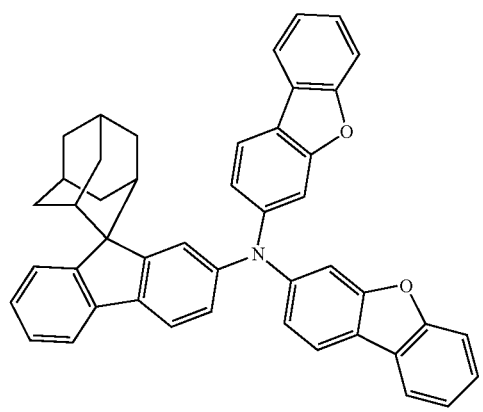
Compound 322
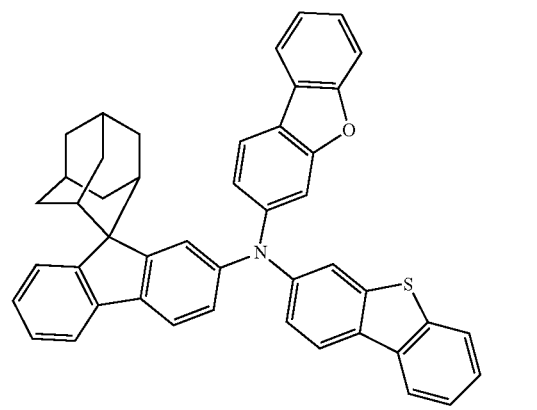
Compound 323
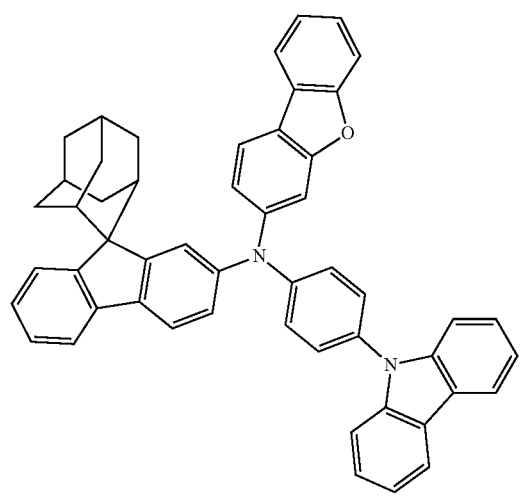
Compound 324
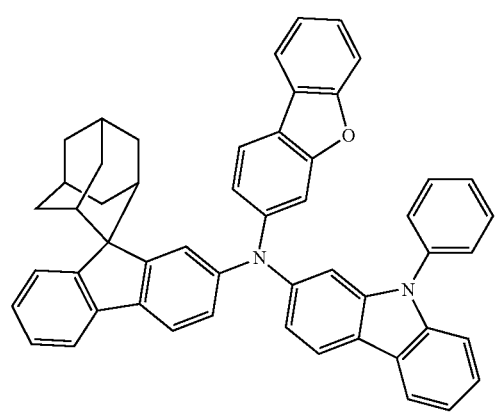

Compound 325
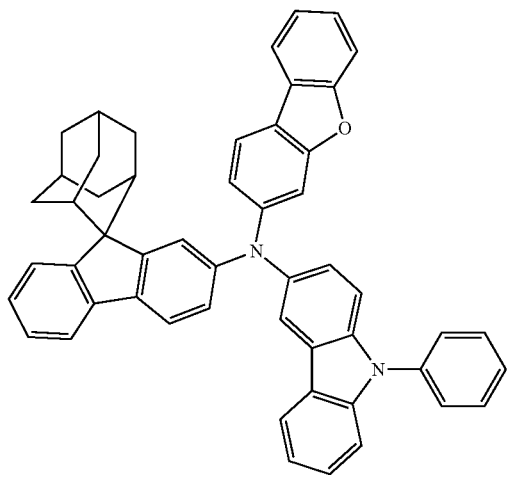
Compound 328
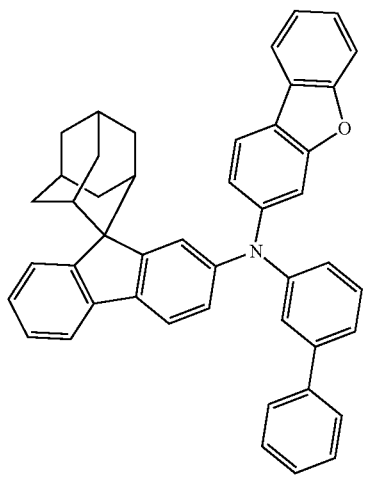
Compound 326
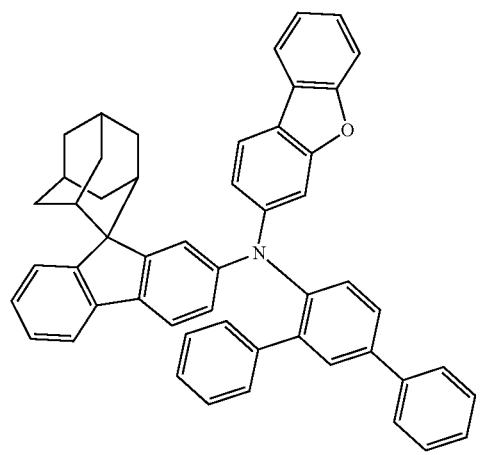
Compound 329
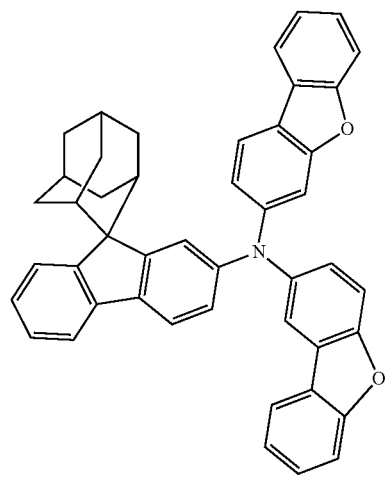
Compound 327
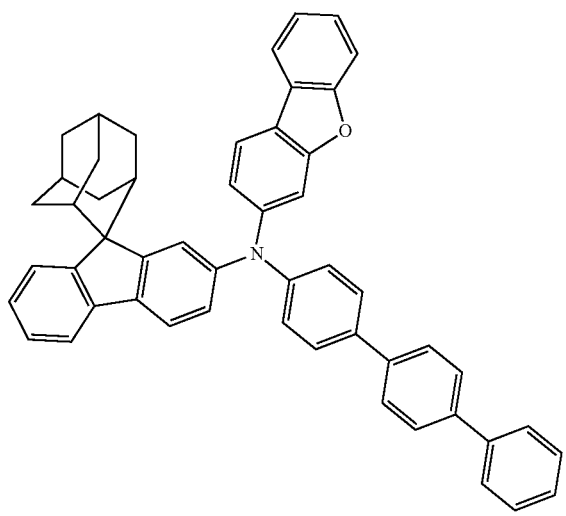
Compound 330
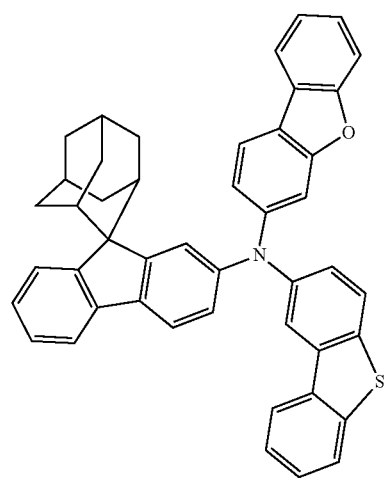

Compound 331
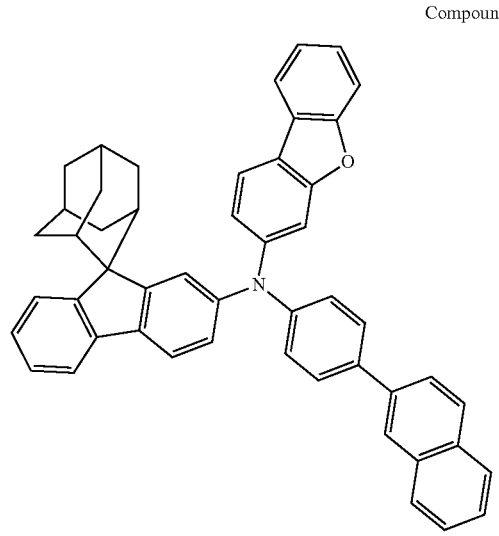
Compound 332
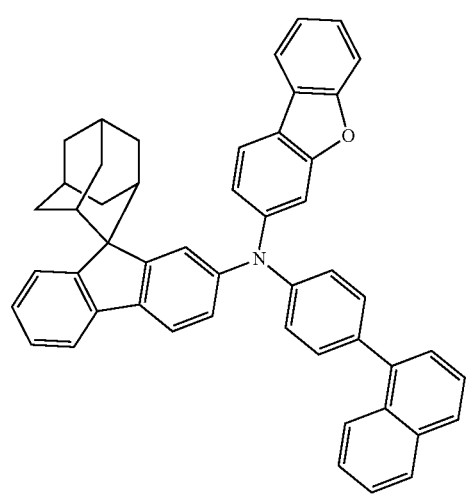
Compound 333
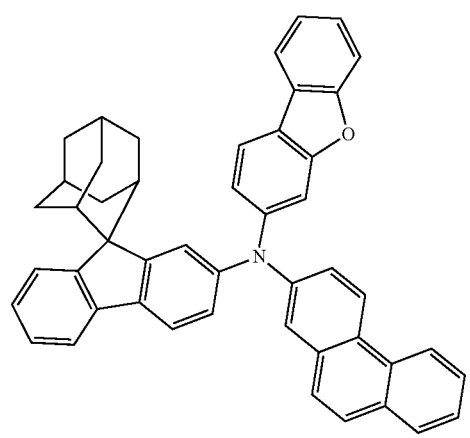
Compound 334
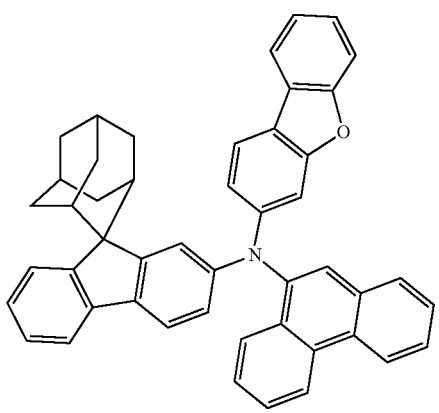
Compound 335
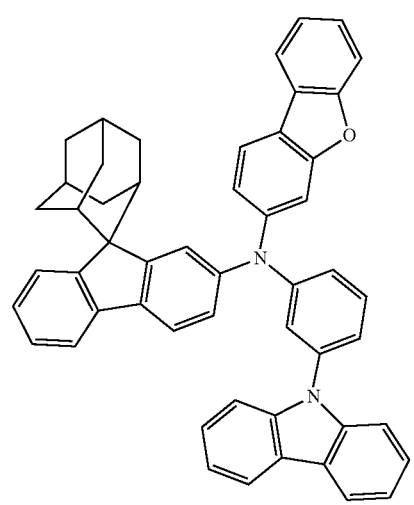
Compound 336
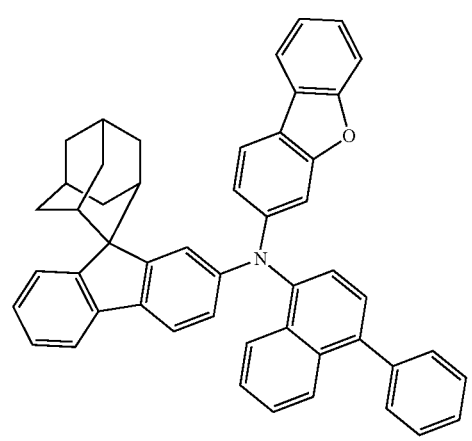

Compound 337
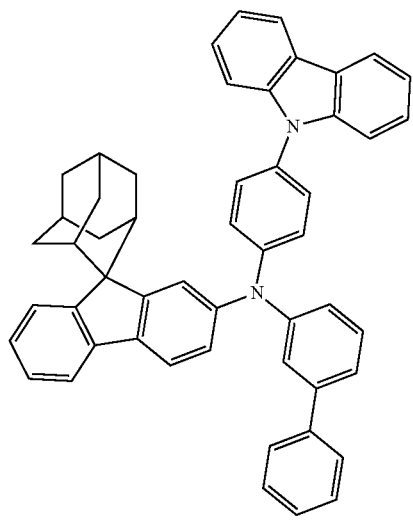
Compound 338
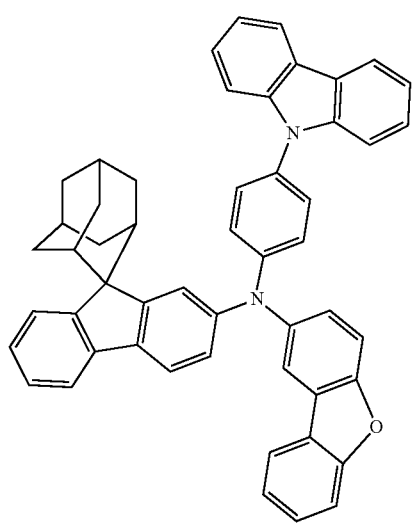
Compound 339
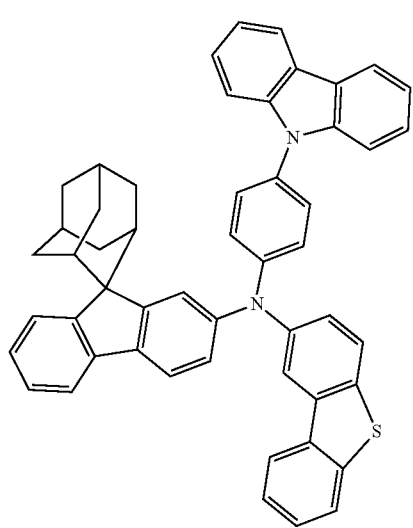
Compound 340
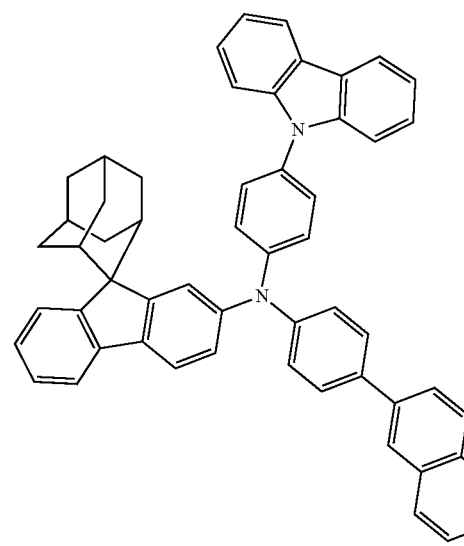
Compound 341
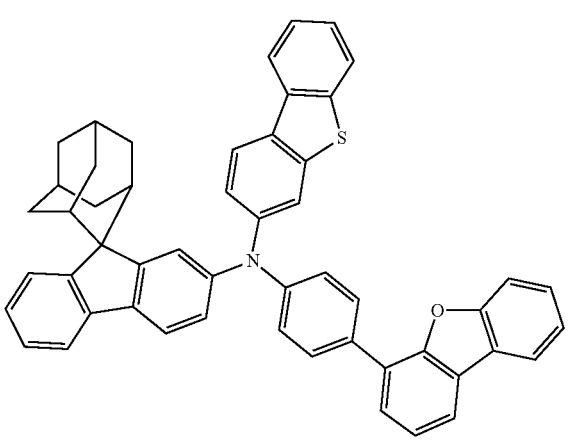
Compound 342
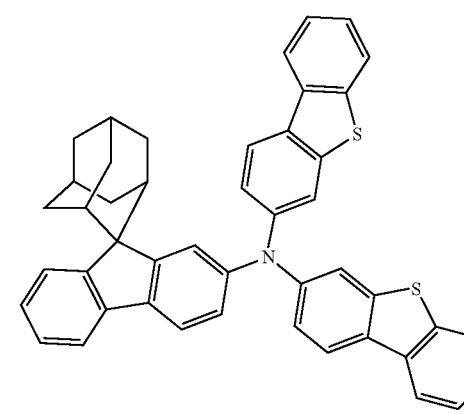

Compound 343
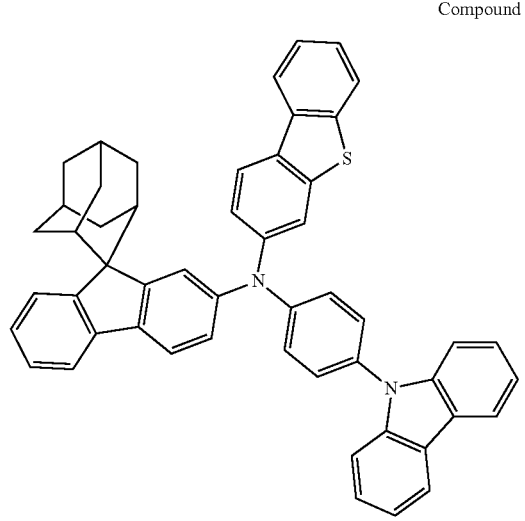
Compound 344
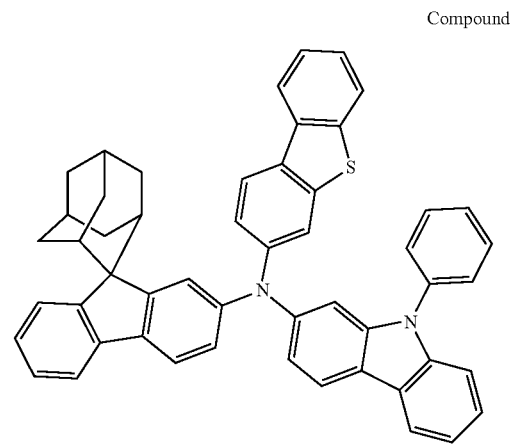
Compound 345
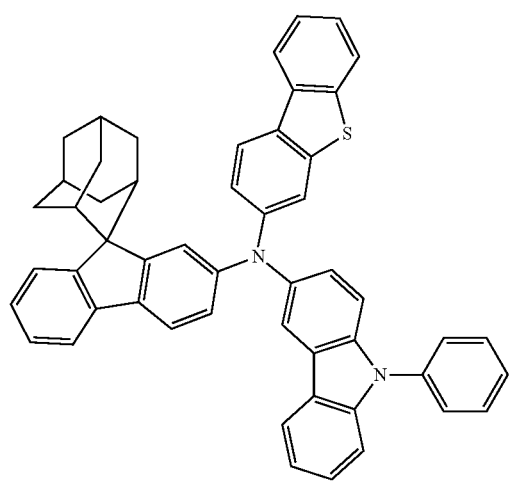
Compound 346
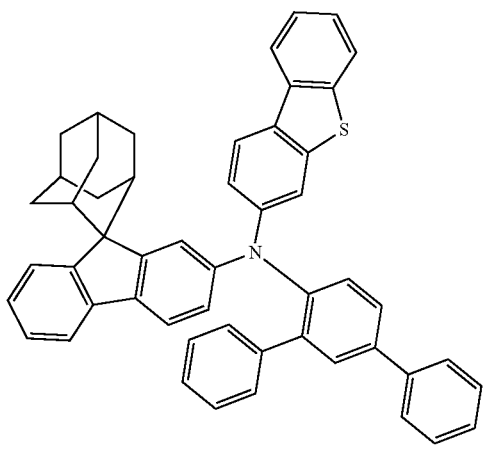
Compound 347
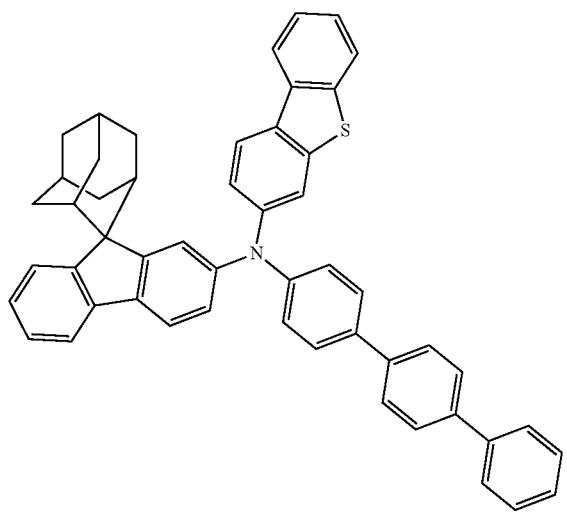
Compound 348
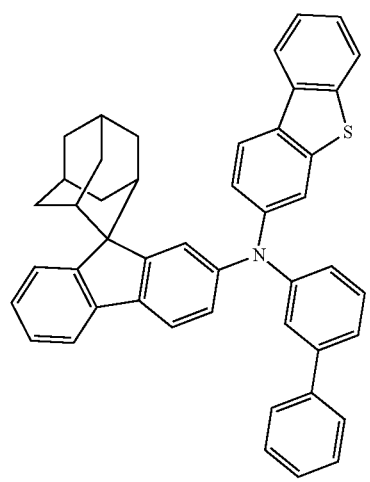

Compound 349
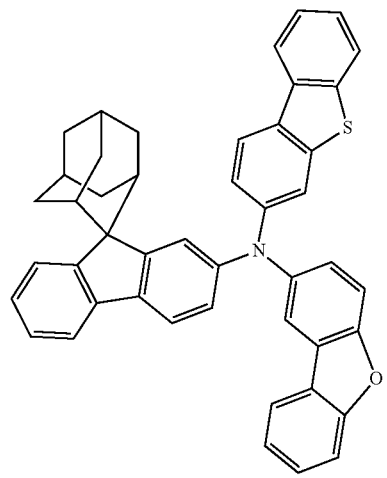
Compound 350
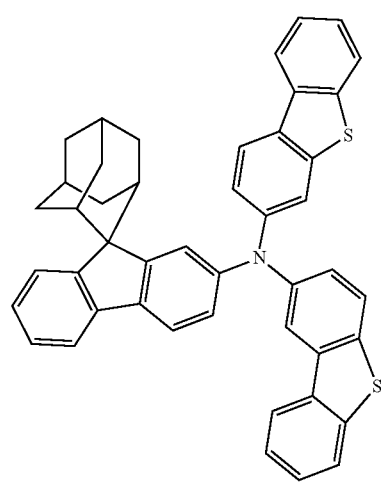
Compound 351
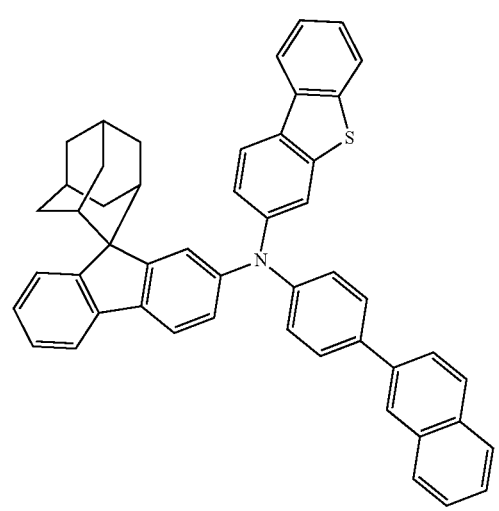
Compound 352
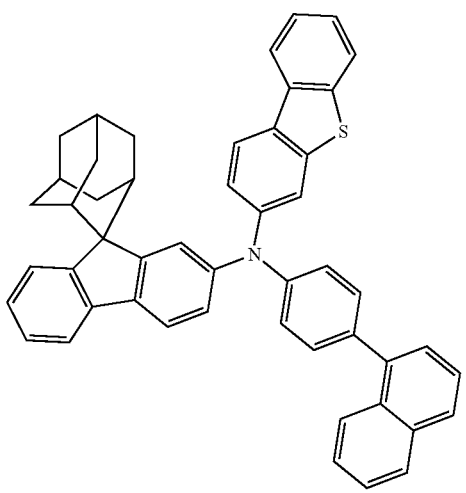
Compound 353
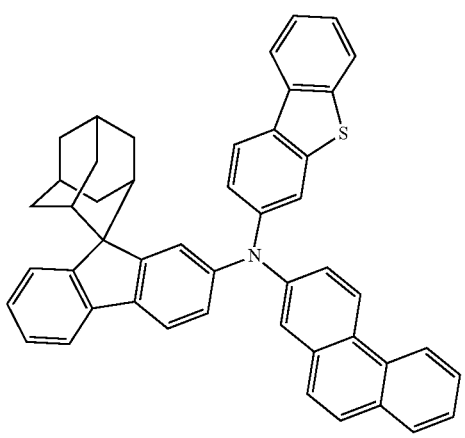
Compound 354
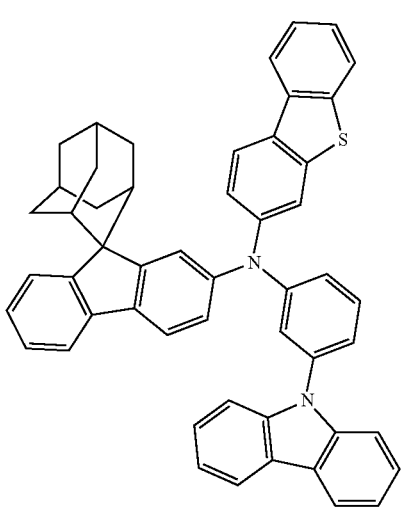

Compound 355
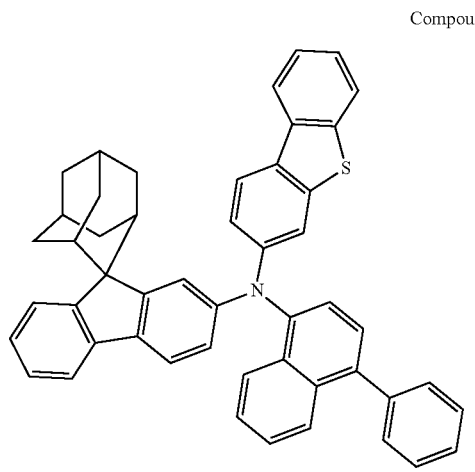
Compound 358
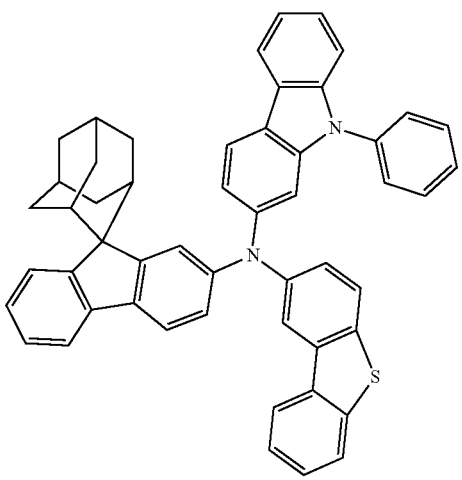
Compound 356
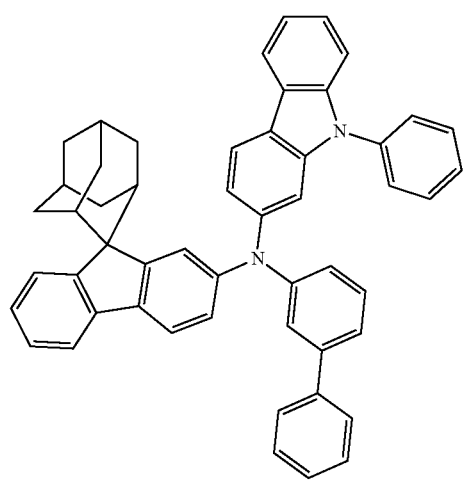
Compound 359
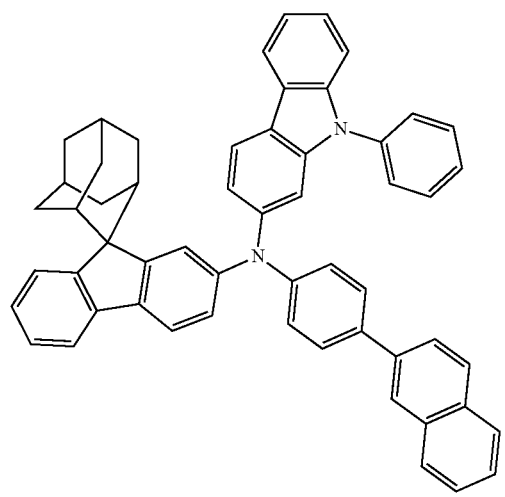
Compound 357
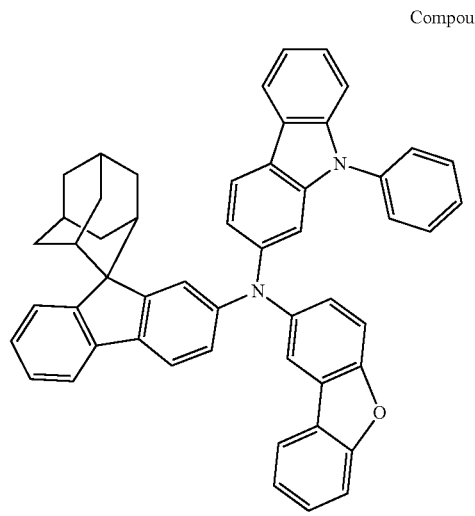
Compound 360
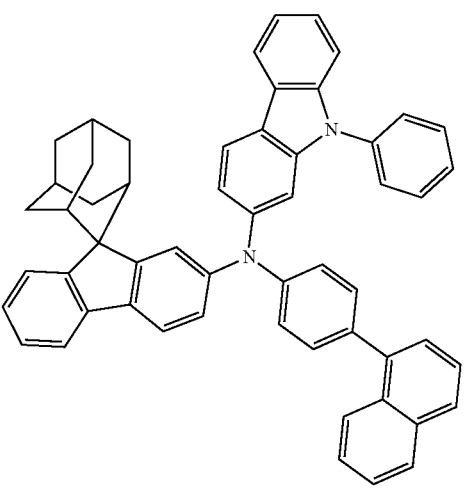

Compound 361
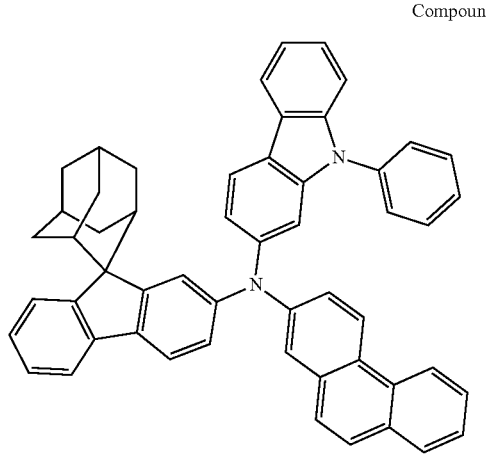
Compound 362
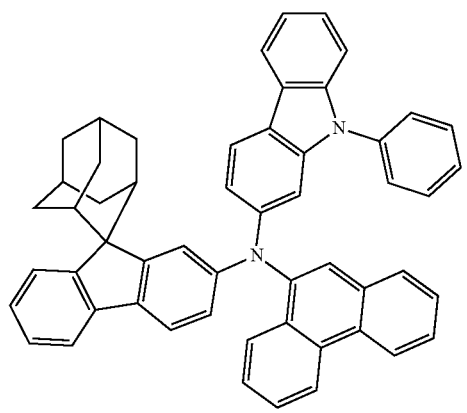
Compound 363
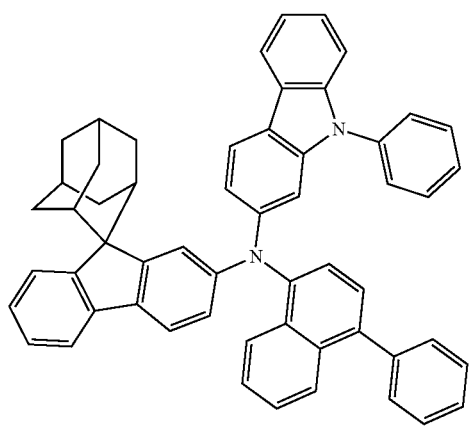
Compound 364
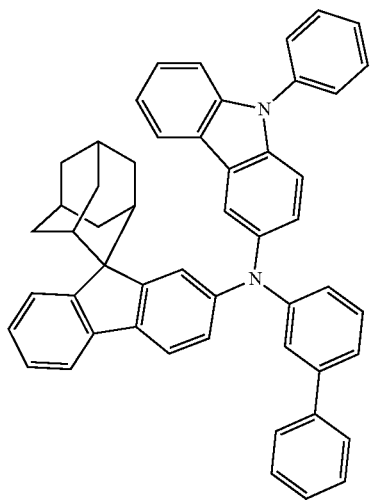
Compound 365
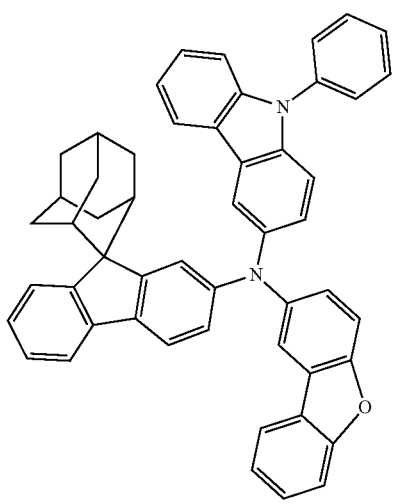
Compound 366
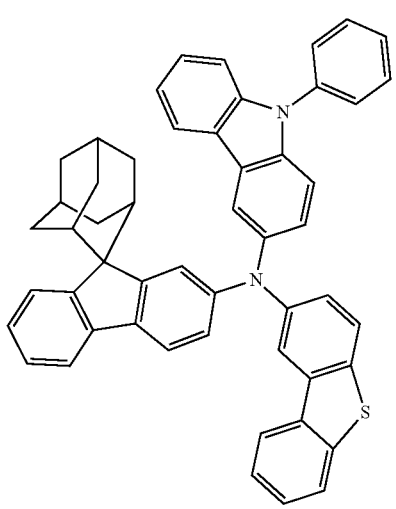

Compound 367
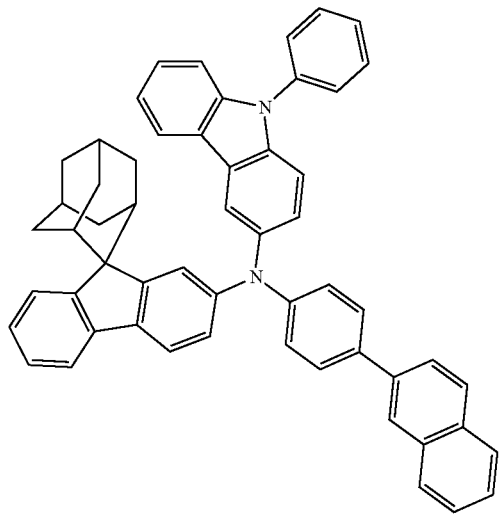
Compound 368
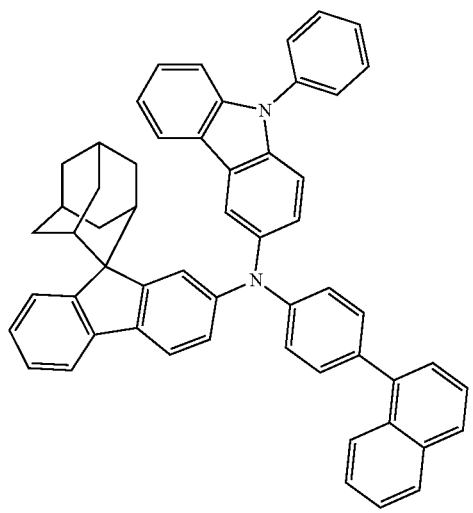
Compound 369
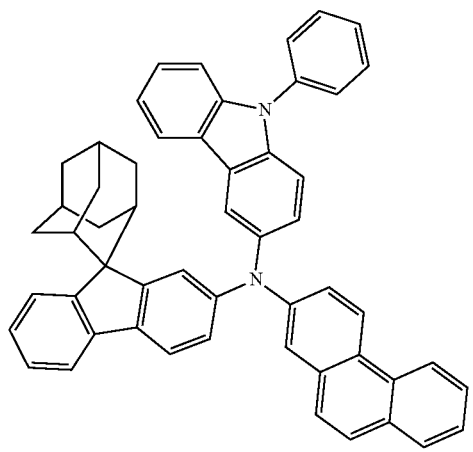
Compound 370
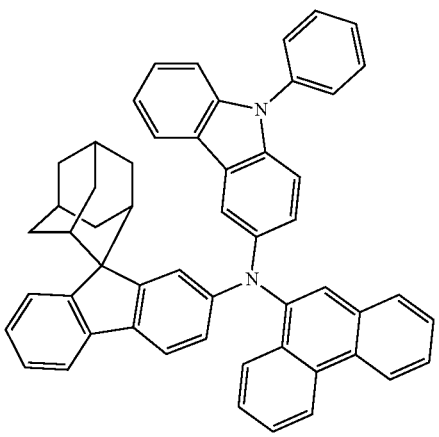
Compound 371
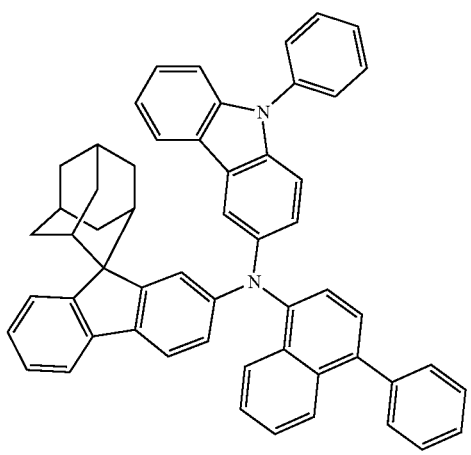
Compound 372
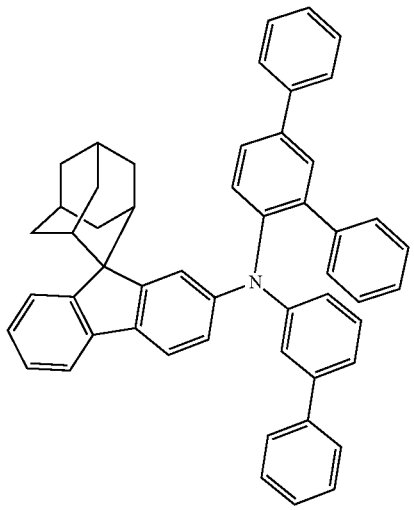

Compound 373
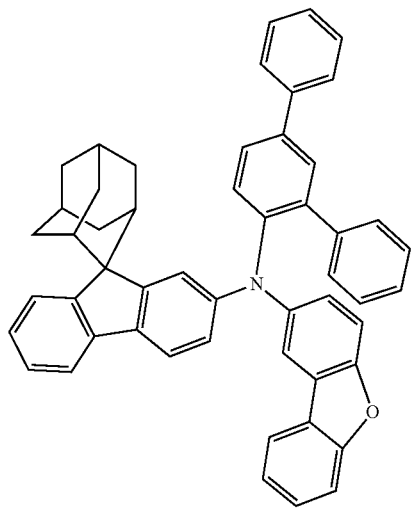
Compound 374
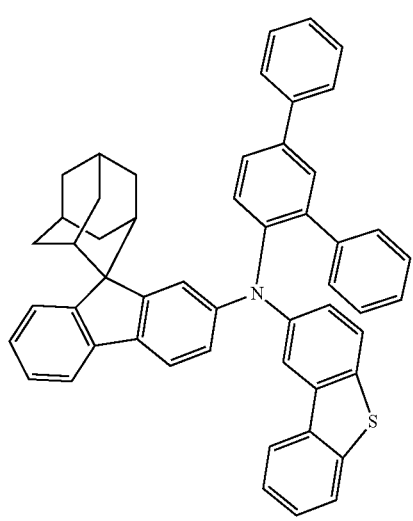
Compound 375
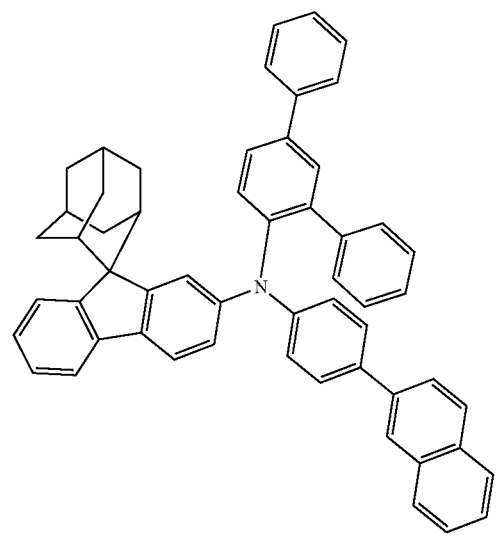
Compound 376
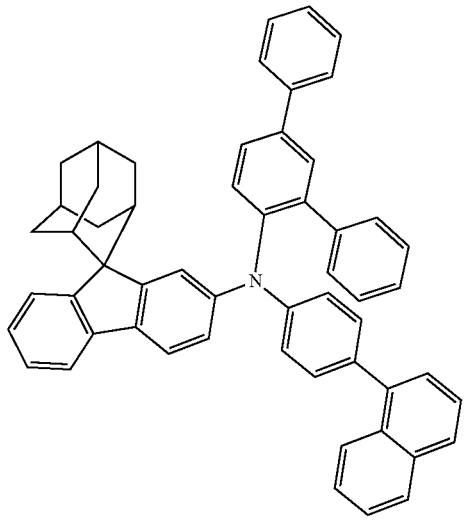
Compound 377
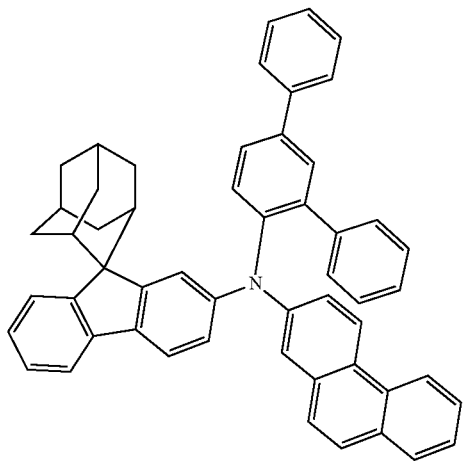
Compound 378
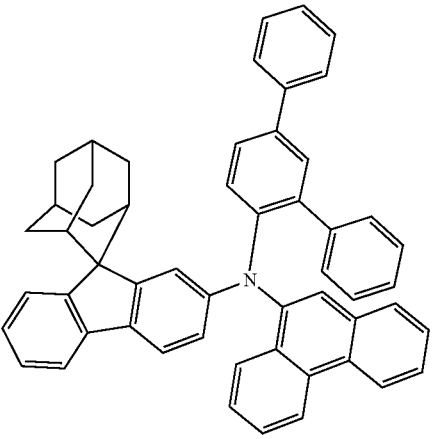

Compound 379
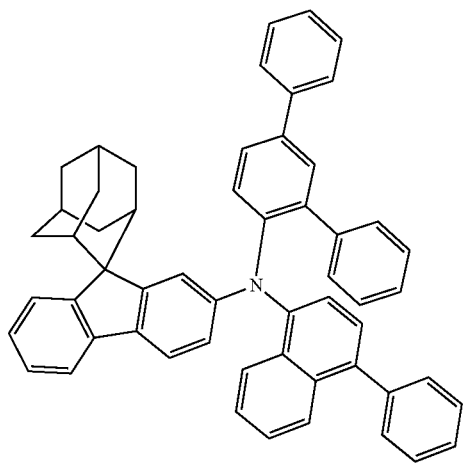
Compound 380
Compound 381
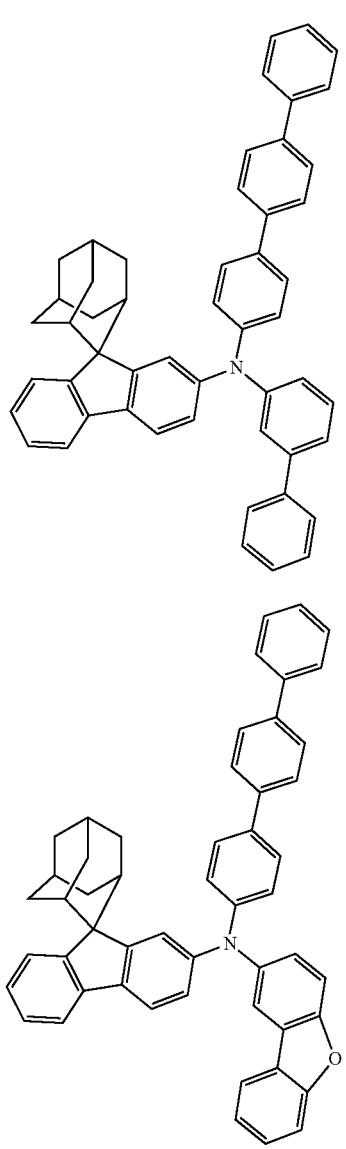
Compound 382
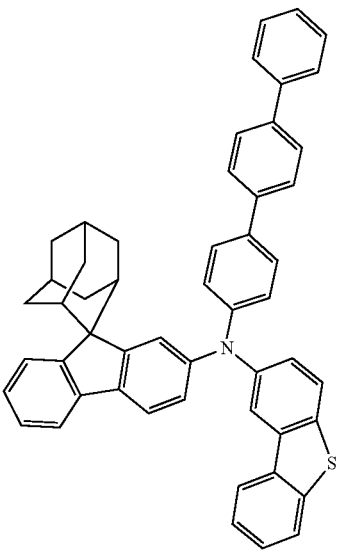
Compound 383
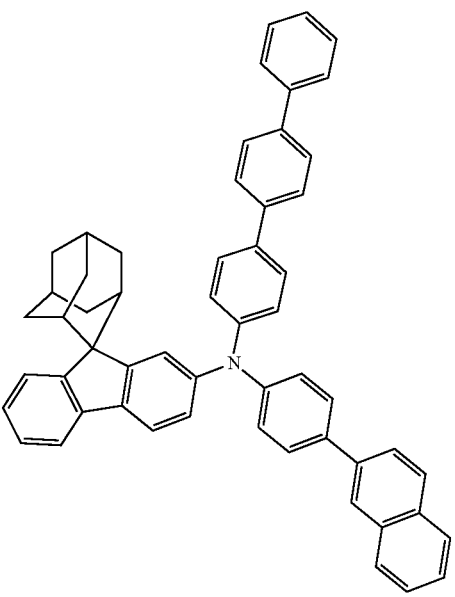

Compound 384

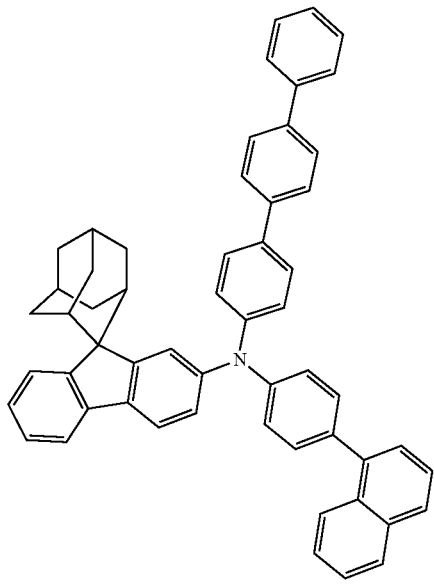

Compound 385

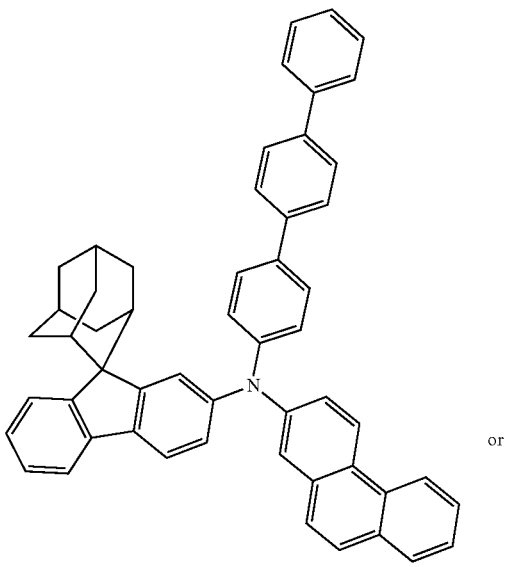

or

Compound 389

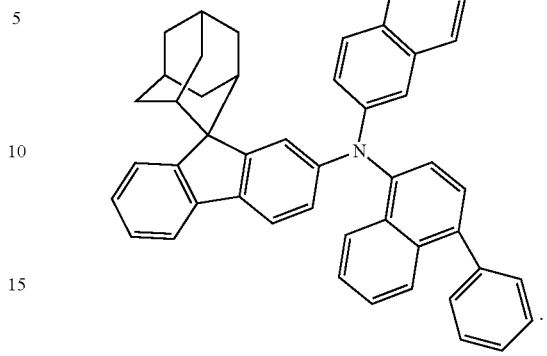

8. An organic electroluminescent device, comprising an anode and a cathode disposed opposite to each other, and a functional layer disposed between the anode and the cathode,
wherein the functional layer comprises the nitrogen-containing compound according to claim 1.

9. The organic electroluminescent device according to claim 8, wherein the functional layer comprises a hole transport layer, and the hole transport layer comprises the nitrogen-containing compound.

10. The organic electroluminescent device according to claim 9, wherein the hole transport layer comprises a first hole transport layer and a second hole transport layer, and the first hole transport layer is disposed on the surface of the second hole transport layer close to the anode;
the first hole transport layer or the second hole transport layer comprises the nitrogen-containing compound.

11. The organic electroluminescent device according to claim 8, wherein the functional layer comprises a hole injection layer, and the hole injection comprises the nitrogen-containing compound provided.

12. A photoelectric conversion device, comprising an anode and a cathode disposed opposite to each other, and a functional layer disposed between the anode and the cathode,
wherein the functional layer comprises the nitrogen-containing compound according to claim 1.

13. The photoelectric conversion device according to claim 12, wherein the functional layer comprises a hole transport layer, and the hole transport layer comprises the nitrogen-containing compound.

14. The photoelectric conversion device according to claim 12, wherein the photoelectric conversion device is a solar cell.

* * * * *